US012618008B2

(12) United States Patent
Wang et al.

(10) Patent No.: US 12,618,008 B2
(45) Date of Patent: May 5, 2026

(54) LIQUID CRYSTAL MEDIUM

(71) Applicant: MERCK PATENT GmbH, Darmstadt (DE)

(72) Inventors: Jing Wang, Shanghai (CN); Hee-Kyu Lee, Shanghai (CN); Sven Christian Laut, Darmstadt (DE); Aaron Lackner, Darmstadt (DE); Dmitry Ushakov, Darmstadt (DE); Rocco Fortte, Darmstadt (DE); Philipp Wucher, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 19/191,286

(22) Filed: Apr. 28, 2025

(65) Prior Publication Data

US 2025/0361444 A1 Nov. 27, 2025

(30) Foreign Application Priority Data

May 22, 2024 (WO) ................ PCT/CN2024/094658

(51) Int. Cl.

| | |
|---|---|
| ***G02F 1/1333*** | (2006.01) |
| ***C07C 39/23*** | (2006.01) |
| ***C07D 211/46*** | (2006.01) |
| ***C09K 19/34*** | (2006.01) |
| *C09K 19/04* | (2006.01) |

(52) U.S. Cl.

CPC .......... *C09K 19/3491* (2013.01); *C07C 39/23* (2013.01); *C07D 211/46* (2013.01); *C09K 19/3402* (2013.01); *C09K 2019/0466* (2013.01); *C09K 2019/3422* (2013.01)

(58) Field of Classification Search

CPC ...... C07C 5/00; C09K 19/3001; G02F 1/1333

See application file for complete search history.

(56) References Cited

U.S. PATENT DOCUMENTS

| | | | | |
|---|---|---|---|---|
| 5,576,867 | A | 11/1996 | Baur et al. | |
| 5,993,691 | A | 11/1999 | Pausch et al. | |
| 6,027,665 | A | 2/2000 | Pausch et al. | |
| 6,233,034 | B1 | 5/2001 | Lee et al. | |
| 7,695,777 | B2 * | 4/2010 | Goto | C09K 19/54 252/299.61 |
| 2006/0066793 | A1 | 3/2006 | Ohmuro et al. | |

FOREIGN PATENT DOCUMENTS

| | | | | |
|---|---|---|---|---|
| CN | 112079687 | A * | 12/2020 | C09K 19/44 |
| DE | 19528106 | A1 | 8/1996 | |
| DE | 19509410 | A1 | 9/1996 | |
| DE | 19528107 | A1 | 9/1996 | |
| DE | 19528104 | A1 | 2/1997 | |
| DE | 19824137 | A1 | 7/1999 | |
| EP | 0588568 | A2 | 3/1994 | |
| EP | 0667555 | A1 | 8/1995 | |
| EP | 0673986 | A2 | 9/1995 | |
| EP | 4538349 | A1 | 4/2025 | |
| JP | H07181439 | A | 7/1995 | |
| WO | 9110936 | A1 | 7/1991 | |
| WO | 9623851 | A1 | 8/1996 | |
| WO | 9628521 | A1 | 9/1996 | |
| WO | WO-2016152405 | A1 * | 9/2016 | C09K 19/30 |

OTHER PUBLICATIONS

PE2E text for WO 2016/152405 (Year: 2016).*

PE2E text for CN 112079687 A (Year: 2020).*

Jung et al., "Analysis of Optimal Phase Retardation of a Fringe Field-Driven Homogeneously Aligned Nematic Liquid Crystal Cell", Japanese Journal of Applied Physics, vol. 43, No. 3, month unknown, 2004, pp. 1027-1031.

Soref, "Field effects in nematic liquid crystal obtained with interdigital electrodes", Journal of Applied Physics, vol. 45, No. 12, May 13, 1974, pp. 5465-5468.

European Search Report dated Sep. 23, 2025, issued by the European Patent Office in corresponding European Application No. 25177260, (2 pages).

* cited by examiner

*Primary Examiner* — Geraldina Visconti

(74) *Attorney, Agent, or Firm* — Buchanan Ingersoll & Rooney PC

(57) ABSTRACT

Liquid-crystalline (LC) media having positive dielectric anisotropy and liquid-crystal displays (LCDs) containing these media. Also, displays addressed by an active matrix and LC displays of the TN, PS-TN, STN, TN-TFT, OCB, IPS, PS-IPS, FFS, HB-FFS, XB-FFS, PS-FFS, SA-HB-FFS, SA-XB-FFS, polymer-stabilized SA-HB-FFS, polymer-stabilized SA-XB-FFS, positive VA, or positive PS-VA type.

12 Claims, No Drawings

LIQUID CRYSTAL MEDIUM

CROSS-REFERENCE TO RELATED APPLICATIONS

This is a U.S. nonprovisional patent application filed under 35 U.S.C. § 111 (a), claiming priority benefit under 35 U.S.C. § 119 (a) of and to PCT International Application No. PCT/CN2024/094658, filed May 22, 2024, the contents of which documents are incorporated herein by reference in their entirety and for all purposes.

FIELD OF INVENTION

The present invention relates to liquid-crystalline (LC) media having positive dielectric anisotropy and to liquid-crystal displays (LCDs) containing these media, especially to displays addressed by an active matrix and in particular to LC displays of the TN, PS-TN, STN, TN-TFT, OCB, IPS, PS-IPS, FFS, HB-FFS, PS-HB-FFS, SA-HB-FFS, polymer-stabilized SA-HB-FFS, positive VA, or positive PS-VA type.

BACKGROUND

Liquid crystal displays (LCDs) are used in many areas for the display of information. LCDs are used both for direct-view displays and for projection-type displays. The electro-optical modes used are, for example, the twisted nematic (TN), super twisted nematic (STN), optically compensated bend (OCB), and electrically controlled birefringence (ECB) modes, together with their various modifications, as well as others. All these modes utilize an electric field which is generated substantially perpendicular to the substrates and the liquid-crystal layer.

Besides these modes, there are also electro-optical modes that utilize an electric field which is substantially parallel to the substrates or the liquid-crystal layer. For example, WO 91/10936 discloses a liquid-crystal display in which the electric signals are generated in such a way that the electric fields have a significant component parallel to the liquid-crystal layer, and which has since then become known as in-plane switching IPS) display. The principles of operating such a display are described, for example, by R. A. Soref in Journal of Applied Physics, Vol. 45, No. 12, pp. 5466-5468 (1974).

IPS displays contain an LC layer between two substrates with a planar orientation, where the two electrodes are arranged on only one of the two substrates and preferably have interdigitated, comb-shaped structures. Upon application of a voltage to the electrodes, an electric field with a significant component parallel to the LC layer is generated between them. This applied voltage causes realignment of the LC molecules in the layer plane.

EP 0 588 568, for example, discloses various possibilities for the design of the electrodes and for addressing an IPS display. DE 198 24 137 likewise describes various embodiments of such IPS displays.

Liquid-crystalline materials for IPS displays of this type are described, for example, in DE 195 28 104.

Furthermore, so-called "fringe-field switching" (FFS) displays have been reported (see, inter alia, S. H. Jung et al., Jpn. J. Appl. Phys., Volume 43, No. 3, 2004, 1028), which contain two electrodes on the same substrate, one of which is structured in a comb-shaped manner and the other is unstructured. A strong, so-called "fringe field" is thereby generated, i.e., a strong electric field close to the edge of the electrodes, and, throughout the cell, an electric field which has both a strong vertical component and a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

Liquid-crystal displays of the IPS and FFS electro-optical modes are in particular suitable for use in not only modern desktop monitors, TV sets, and multimedia applications, but also for mobile phones, tablet PCs, and the like. The liquid-crystalline media according to the present invention are preferably used in displays of this type. In general, dielectrically positive liquid-crystalline media having rather lower values of the dielectric anisotropy are used in FFS displays, but in some cases, liquid-crystalline media having a dielectric anisotropy of only about 3 or even less are also used in IPS displays.

A further improvement has been achieved by the so-called HB-FFS mode. One of the unique features of the HB-FFS mode in contrast to the traditional FFS technology is that it enables higher transmittance, which allows operation of the panel with less energy consumption.

Liquid-crystal compositions which are suitable for LCDs and especially for FFS and IPS displays are known in prior art, for example, from JP 07-181 439 (A), EP 0 667 555, EP 0 673 986, DE 195 09 410, DE 195 28 106, DE 195 28 107, WO 96/23 851, and WO 96/28 521. However, these compositions have certain disadvantages. Amongst other deficiencies, most of them result in disadvantageously long addressing times, have inadequate values of the resistivity, and/or require excessively high operating voltages.

FFS and IPS displays can be operated as active-matrix displays (AMD) or passive-matrix displays (PMD). In the case of active-matrix displays, individual pixels are usually addressed by integrated, non-linear active elements such as, for example, thin-film transistors (TFTs), while in the case of passive-matrix displays, individual pixels are usually addressed by the multiplex method as known from the prior art.

The displays according to the present invention are preferably addressed by an active matrix, preferably by a matrix of TFT. However, the liquid crystals according to the invention can also advantageously be used in displays having other known addressing means.

Both the IPS and the FFS technology have certain advantages over other LCD technologies, such as, for example, the vertical alignment (VA) technology, e.g., a broad viewing-angle dependency of the contrast.

The provision of further liquid-crystalline media and the use thereof in a display having high transmission, a good black state and a high contrast ratio is a central challenge for modern FFS and IPS applications. In addition, modern applications also require good low-temperature stability and fast addressing times. The contrast can be improved by a higher transmittance in the bright state and a better dark state. One solution to improve the dark state is to lower the scattering parameter of the LC mixture by developing mixtures with a higher $K_{Avg.}$, but this normally has the drawback of reduced response time.

It was observed that a high brightness in displays like those of the HB-FFS mode can be achieved by using liquid-crystalline media having positive dielectric anisotropy and an increased dielectric constant $\varepsilon_\perp$ perpendicular to the longitudinal axes of the liquid-crystalline molecules. This can be achieved by adding a limited amount of liquid-crystalline compounds with negative dielectric anisotropy, which have high $\varepsilon_\perp$ properties, to the liquid-crystalline medium whilst maintaining a positive dielectric anisotropy of the entire medium. However, the addition of compounds with high $\varepsilon_\perp$ has some drawbacks. For example, such compounds can lead to higher values of the rotational viscosity $\gamma_1$, and consequently to higher values of the $\gamma_1/K_2$ ratio between the rotational viscosity $\gamma_1$ and the elastic constant $K_2$ for twist deformation, which leads to higher response times. Since $K_2$ is approximately proportional to the elastic constant $K_1$ for splay deformation (the value of $K_2$ is typically about half the value of $K_1$), this ratio can easily be determined by measuring $\gamma_1$ and $K_1$.

Another disadvantage is that the reliability (VHR) of HB-FFS mixtures can be inferior compared to conventional FFS mixtures.

It is also important to maintain a good low-temperature stability (LTS) of the medium. In particular, for car navigation systems, a good LTS even at −40° C. is necessary. Due to this requirement, it is challenging to further improve the optical performance.

SUMMARY OF THE INVENTION

There is an unmet need for improvement in both operating properties and shelf life of LCDs. The invention described herein has the objective of providing new compounds and liquid-crystalline media, preferably for FFS and IPS displays, in particular for HB-FFS displays, but also for TN, positive VA, or STN displays, and in particular for active-matrix displays like those addressed by TFTs, which do not exhibit the disadvantages indicated above or only do so to a lesser extent, and in particular to provide a medium that enables a display with improved contrast, preferably without deterioration of other display parameters.

To solve the problem, the present invention provides a compound of the formula I and a liquid-crystalline medium comprising a compound of the formula I.

Advantageous embodiments of the invention are subject of the claims or can also be taken from the description.

The invention relates to a compound of the formula I:

I

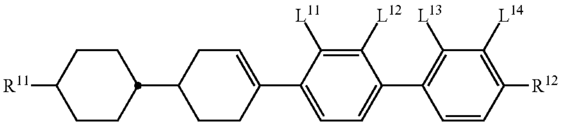

in which $R^{11}$ and $R^{12}$ identically or differently, denote H, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group each having 3 to 15 C atoms, where one or more $CH_2$ groups in these radicals may each be replaced, independently of one another, by

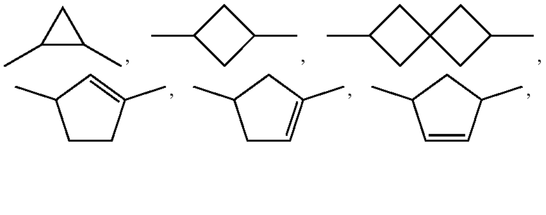

—CH═CH—, —C≡C—, $—CF_2O—$, $—OCF_2—$, —O—, —CO—O—, or —O—CO— in such a way that O atoms are not linked directly to one another, and in which one or more H atoms may be replaced by halogen;

$L^{11}$, $L^{12}$, $L^{13}$, and $L^{14}$ identically or differently, denote H, F, Cl, $CH_3$, $CF_3$, or $CHF_2$, wherein at least one of $L^{11}$, $L^{12}$, $L^{13}$, or $L^{14}$ denotes F, Cl, $CH_3$, $CF_3$, or $CHF_2$.

The present invention further relates to a liquid-crystal medium with positive dielectric anisotropy comprising:

a) one or more compounds of the formula I; and preferably b) one or more compounds selected from the group of compounds of the formulae II and III:

II

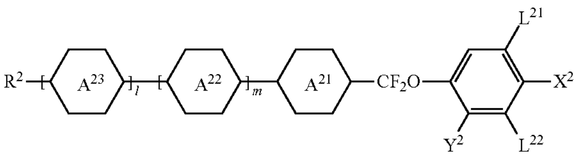

III

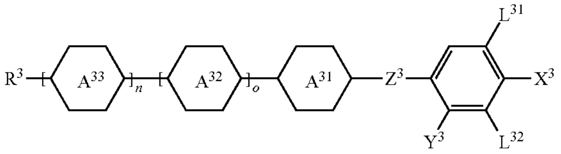

in which $R^2$ and $R^3$ have the meanings given above for $R^{11}$, preferably denote alkyl having 1 to 7 C atoms or alkenyl having 2 to 7 C atoms;

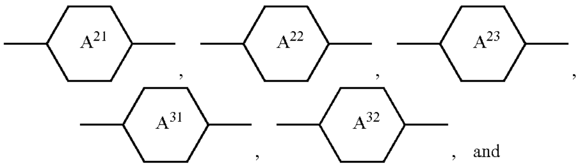

, and

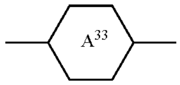

independently of one another, denote

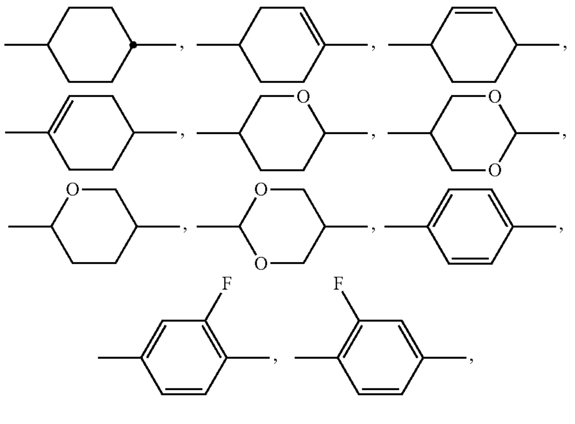

-continued

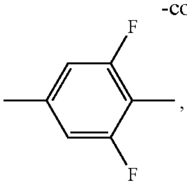

, or

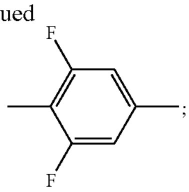

;

$L^{21}$, $L^{22}$, $L^{31}$, and $L^{32}$ independently of each other, denote H or F;

$Y^2$ and $Y^3$ identically or differently, denote H or $CH_3$, preferably H;

$X^2$ and $X^3$ independently of each other, denote halogen, a halogenated alkyl or halogenated alkoxy with 1 to 3 C atoms, or a halogenated alkenyl or halogenated alkenyloxy with 2 or 3 C atoms, preferably F, Cl, $CF_3$, $OCF_3$, or $OCHF_2$, more preferably F or $OCF_3$;

$Z^3$ denotes —$CH_2CH_2$—, —$CF_2CF_2$—, —COO—, trans-—CH═CH—, trans-—CF═CF—, —$CH_2O$—, or a single bond, preferably a single bond; and l, m, n, and o are, independently of each other, 0 or 1.

The compounds of formula I, preferably in combination with compounds of the formula II and/or III, enable liquid-crystalline media that show a low rotational viscosity and a low value of the ratios of $\gamma_1/K_2$ and $\gamma_1/K_1$. This feature enables liquid crystal displays, especially of the IPS and FFS mode, with high brightness, high transmission, and fast response times. In addition, a higher average elastic constant ($K_{av}$) can be achieved while keeping all other relevant physical properties, which leads to a lower scattering parameter that improves the dark state of a display and therefore, improves the contrast.

In particular, the low-temperature stability (LTS) of the medium according to the invention is remarkably high. The medium is sufficiently stable at temperatures as low as −40° C., which is one the reasons why the medium is particularly suitable for mobile applications, for example in automotive applications.

The liquid-crystalline media according to the invention are suitable for mobile applications and TFT applications, such as, for example, mobile telephones and PDAs. Furthermore, the liquid-crystalline media according to the invention are particularly suitably for use in FFS, HB-FFS, and IPS displays based on dielectrically positive liquid crystals.

The liquid-crystal media according to the present invention are likewise suitable for use in liquid-crystal displays of the FFS, HB-FFS, and IPS mode, based on dielectrically positive liquid crystals, and polymer-stabilized variants thereof, for large-size TV applications.

The invention further relates to the use of a liquid-crystalline medium as described above and below for electro-optical purposes, in particular for the use in liquid-crystal displays, shutter glasses, LC windows, or 3D applications, preferably in TN, PS-TN, STN, TN-TFT, OCB, IPS, PS-IPS, FFS, HB-FFS, PS-HB-FFS, SA-HB-FFS, polymer-stabilized SA-HB-FFS, positive VA, and positive PS-VA displays, very preferably in FFS, HB-FFS, IPS, PS-HB-FFS, and PS-IPS displays.

The invention further relates to an electro-optical liquid-crystal display containing a liquid-crystalline medium as described above and below, in particular a TN, PS-TN, STN, TN-TFT, OCB, IPS, PS-IPS, FFS, HB-FFS, PS-HB-FFS, SA-HB-FFS, polymer-stabilized SA-HB-FFS, positive VA, or positive PS-VA display, preferably a FFS, HB-FFS, IPS, PS-HB-FFS, or PS-IPS display.

According to another aspect of the present invention, provided herein is a compound of the formula (3) defined below in scheme 1.

A preferred synthetic pathway towards compounds of formula I is shown in scheme 1.

Scheme 1

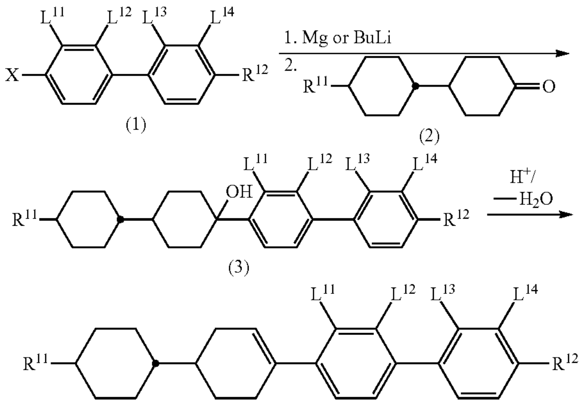

(1) (2) (3)

in which X denotes Br or I and the other occurring groups have the meanings given above.

Herein, an alkyl radical and/or an alkoxy radical is taken to mean a straight-chain, branched, or cyclic alkyl group. It is preferably a straight chain, has 2, 3, 4, 5, 6, or 7 C atoms, and accordingly preferably denotes an ethyl, propyl, butyl, pentyl, hexyl, heptyl, ethoxy, propoxy, butoxy, pentoxy, hexyloxy, or heptyloxy group, furthermore a methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy, or tetradecyloxy group.

Herein, a branched alkyl group is preferably an isopropyl, s-butyl, isobutyl, isopentyl, 2-methylbutyl, 2-methylhexyl, or 2-ethylhexyl group.

As used herein, a cyclic alkyl group is taken to mean a straight-chain or branched alkyl or alkenyl group having up to 12 C atoms, preferably an alkyl group having 1 to 7 C atoms, in which a group $CH_2$ is replaced with a carbocyclic ring having 3 to 5 C atoms, very preferably selected from the group consisting of a cyclopropylalkyl group, cyclobutylalkyl group, a cyclopentylalkyl group, and a cyclopentenylalkyl group, wherein the alkyl is straight-chain alkyl having 1 to 5 C atoms.

Herein, oxaalkyl preferably denotes a straight-chain 2-oxapropyl (=methoxymethyl) group, 2-oxabutyl (=ethoxymethyl) group, 3-oxabutyl (=2-methoxyethyl) group, 2-, 3-, or 4-oxapentyl group, 2-, 3-, 4-, or 5-oxahexyl group, 2-, 3-, 4-, 5-, or 6-oxaheptyl group, 2-, 3-, 4-, 5-, 6-, or 7-oxaoctyl group, 2-, 3-, 4-, 5-, 6-, 7-, or 8-oxanonyl group, or 2-, 3-, 4-, 5-, 6-, 7-, 8-, or 9-oxadecyl group.

Herein, an alkenyl group, i.e., an alkyl radical in which one $CH_2$ group has been replaced by —CH═CH—, may be straight-chain or branched. It is preferably straight-chain and has 2 to 10 C atoms. Accordingly, it denotes, in particular, a vinyl group, a prop-1- or -2-enyl group, a but-1-, -2-, or -3-enyl group, a pent-1-, -2-, -3-, or -4-enyl group, a hex-1-, -2-, -3-, -4-, or -5-enyl group, a hept-1-, -2-, -3-, -4-, -5-, or -6-enyl group, an oct-1-, -2-, -3-, -4-, -5-, -6-, or -7-enyl group, a non-1-, -2-, -3-, -4-, -5-, -6-, -7-, or -8-enyl group, or a dec-1-, -2-, -3-, -4-, -5-, -6-, -7-, -8-, or -9-enyl group.

Herein, an alkyl or alkenyl radical which is at least monosubstituted by halogen, is preferably straight-chain, and halogen is preferably F or Cl. In the case of polysubstitution, halogen is preferably F. The resultant radicals also include perfluorinated radicals. In the case of mono-substitution, the fluorine or chlorine substituent may be in any desired position, but is preferably in the @-position.

Herein, a mono- or polyfluorinated alkyl or alkoxy radical having 1, 2, or 3 C atoms or a mono- or polyfluorinated alkenyl radical having 2 or 3 C atoms is particularly preferably F, Cl, $CF_3$, $CHF_2$, $OCF_3$, $OCHF_2$, $OCFHCF_3$, $OCFHCHF_2$, $OCFHCHF_2$, $OCF_2CH_3$, $OCF_2CHF_2$, $OCF_2CHF_2$, $OCF_2CF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$, $OCH{=}CF_2$, or $CH{=}CF_2$, very particularly preferably F or $OCF_3$, furthermore $CF_3$, $OCF{=}CF_2$, $OCHF_2$, or $OCH{=}CF_2$.

In the compounds of the formula I, preferably one or two, more preferably one, of the radicals $L^{11}$, $L^{12}$, $L^{13}$, and $L^{14}$ denote(s) F and the remaining radicals $L^{11}$, $L^{12}$, $L^{13}$, and/or $L^{14}$ denote H.

The compounds of the formula I are preferably selected from the compounds of the formulae I-1 to I-6, more preferably selected from the compounds of the formulae I-1 to I-4, very preferably selected from the compounds of the formulae I-1 and I-2, and in particular from the compounds of the formula I-1:

I-1

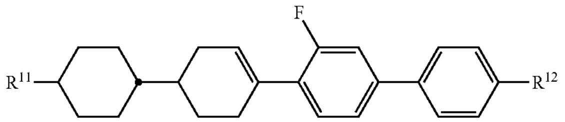

I-2

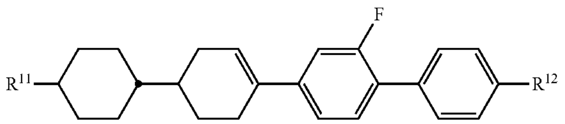

I-3

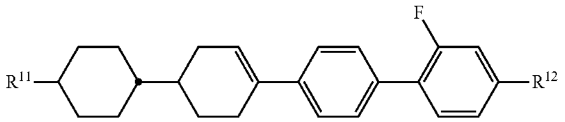

-continued

I-4

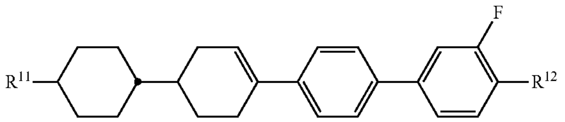

I-5

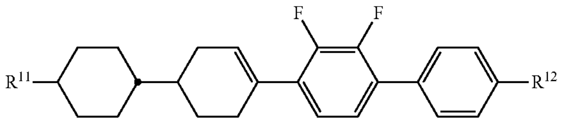

I-6

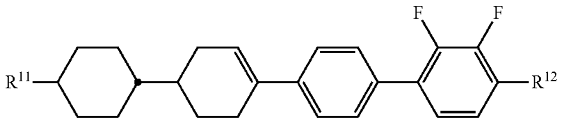

in which $R^{11}$ and $R^{12}$ have the meanings defined above for formula I and preferably denote straight-chain alkyl or alkoxy each having 1 to 9 C atoms, or straight-chain alkenyl having 2 to 9 C atoms where one or more $CH_2$ groups in these radicals may each be replaced, independently of one another, by

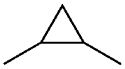,
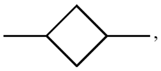,
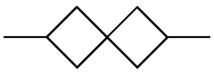,
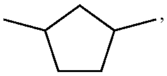,
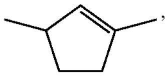,
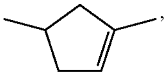, or
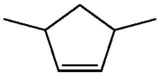, and very preferably denote straight-chain alkyl having 1 to 7 C atoms or straight-chain alkenyl having 1 to 7 C atoms.

The medium according to the invention particularly preferably comprises one or more compounds of formula I-1, preferably selected from the compounds of the formula I-1-1 to I-1-23:

I-1-1

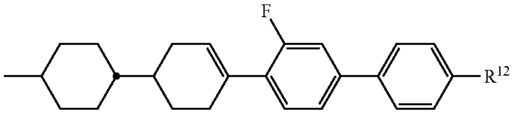

I-1-2

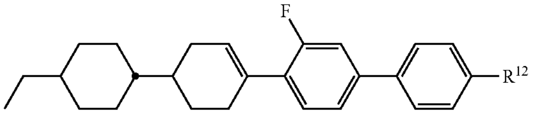

I-1-3

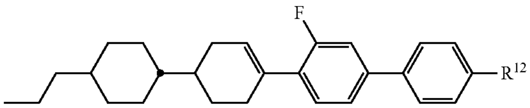

I-1-4

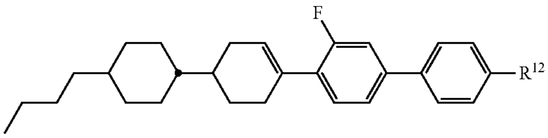

I-1-5

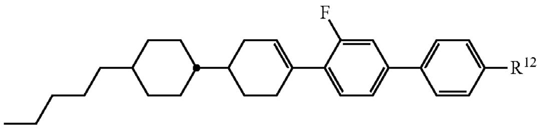

I-1-6

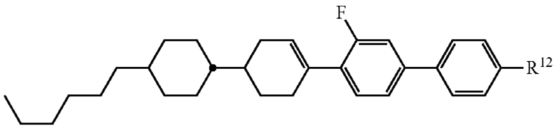

-continued
I-1-7
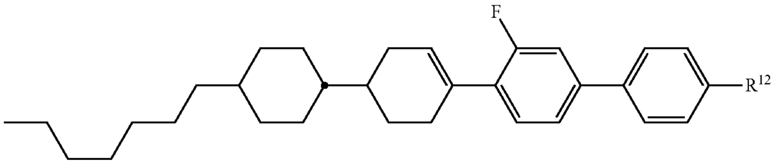
I-1-8
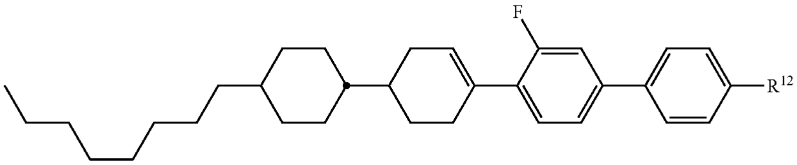
I-1-9
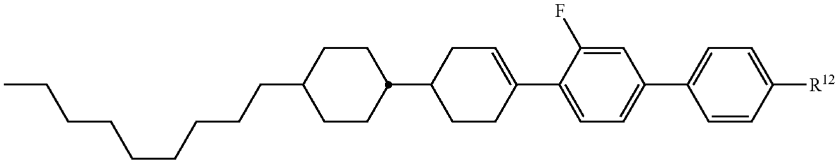
I-1-10
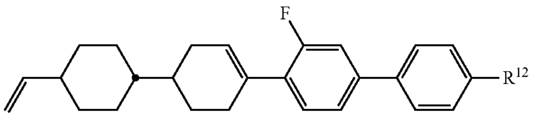
I-1-11
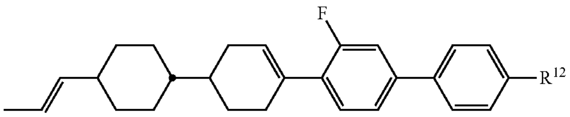
I-1-12
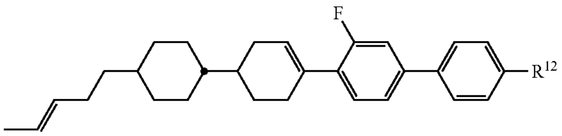
I-1-13
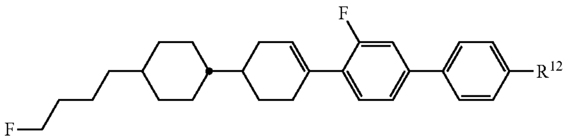
I-1-14
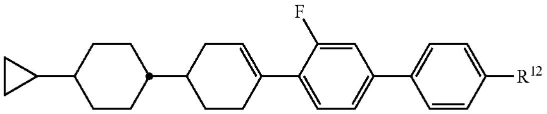
I-1-15
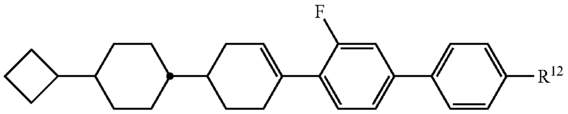
I-1-16
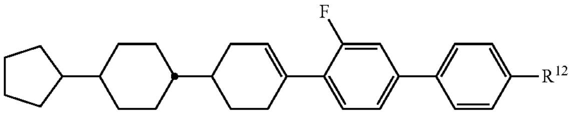
I-1-17
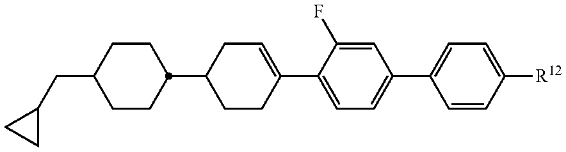
I-1-18
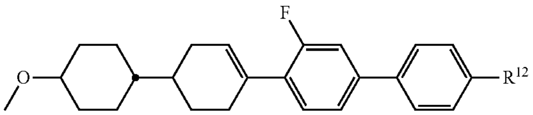
I-1-19
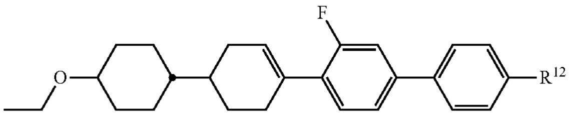
I-1-20
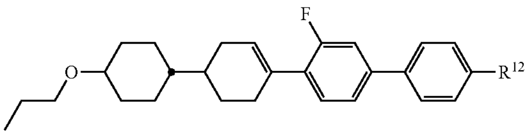
I-1-21
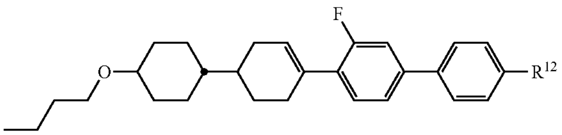

-continued

I-1-22

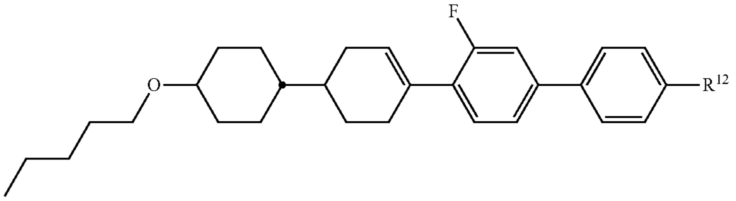

I-1-23

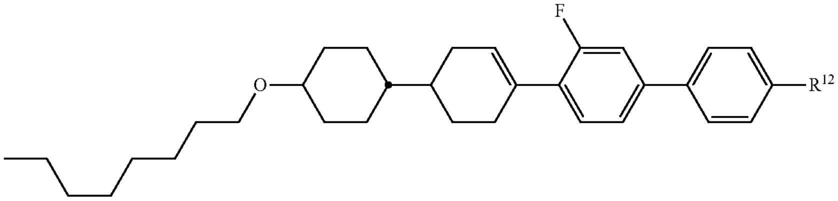

in which $R^{12}$ has the meanings given above for formula I and its sub-formulae and preferably denotes a methyl, ethyl, n-propyl, n-butyl, n-pentyl, n-hexyl, n-heptyl, n-octyl, n-nonyl, methoxy, ethoxy, n-propoxy, n-butoxy, n-pentoxy, n-hexoxy, n-heptoxy, n-octyloxy, n-nonyloxy, but-3-en-1yl, trans-pent-3-en-1-yl, cyclopropyl, cyclobutyl, cyclopentyl, cyclopropylmethyl, cyclobutylmethyl, cyclopentylmethyl, cyclopropylmethoxy, cyclopentyloxy, or cyclopentylmethoxy group.

Preferably, the medium comprises one or more compounds of formula II, preferably selected from the group of compounds of formulae II-1 to II-3, very preferably from the group of compounds of the formulae II-1 and II-3:

II-1

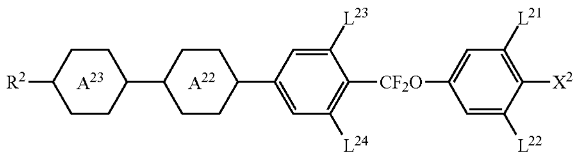

II-2

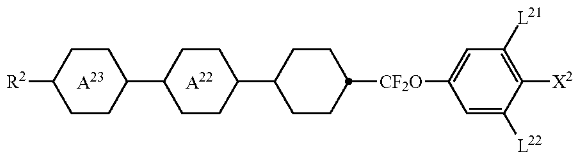

II-3

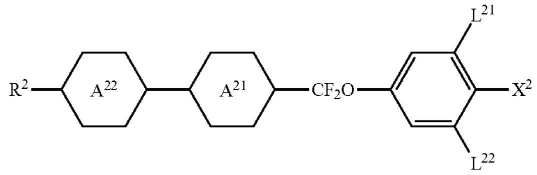

in which the occurring groups have the respective meanings given under formula II above.

In formula II-1, the radicals $L^{23}$ and $L^{24}$ denote, independently of each other, H or F.

In formula II-2, preferably,

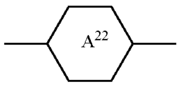

and

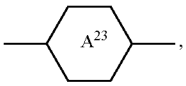

, independently of each other, denote

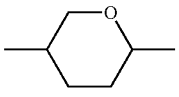

or

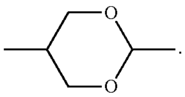

.

In formulae II-1, 11-2, and II-3, $L^{21}$ and $L^{22}$ or $L^{23}$ and $L^{24}$ are preferably both F.

In another preferred embodiment, in formulae II-1 and II-2, all of $L^{21}$, $L^{22}$, $L^{23}$, and $L^{24}$ denote F.

The compounds of formula II-1 are preferably selected from the group of compounds of the formulae II-1a to II-1h:

II-1a

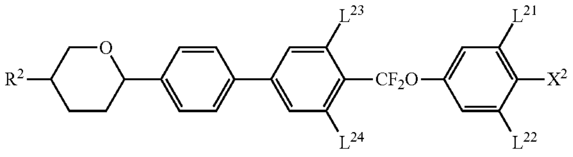

II-1b

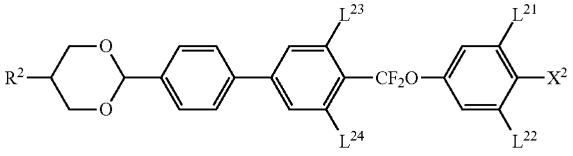

II-1c

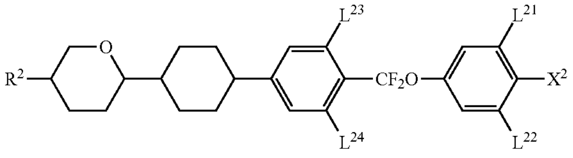

-continued

II-1d

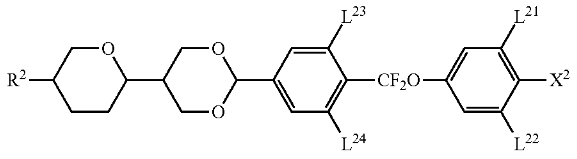

II-1e

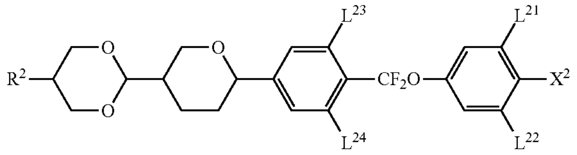

II-1f

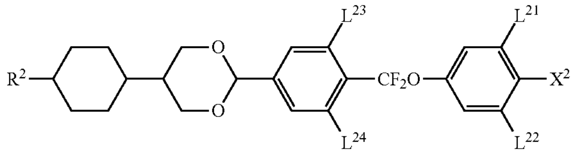

II-1g

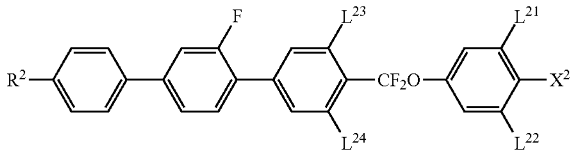

II-1h

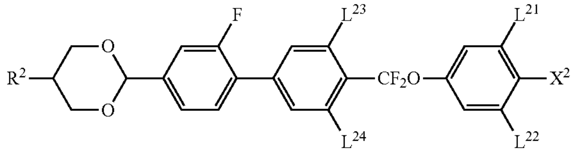

in which the occurring groups have the respective meanings given above.

In a preferred embodiment of the present invention the medium comprises one or more compounds selected from the group of compounds of the formulae II-1a to II-1h wherein $L^{21}$ and $L^{22}$, and/or $L^{23}$ and $L^{24}$ are both F, respectively.

In another preferred embodiment, the medium comprises compounds selected from the group of compounds of formulae II-1a to II-1h, wherein $L^{21}$, $L^{22}$, $L^{23}$, and $L^{24}$ all are F.

Especially preferred compounds of formula II-1 are:

II-1a-1

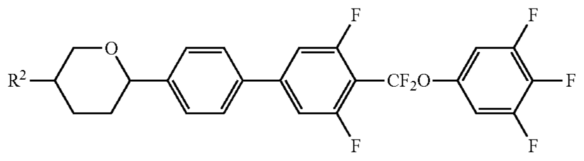

-continued

II-1f-1

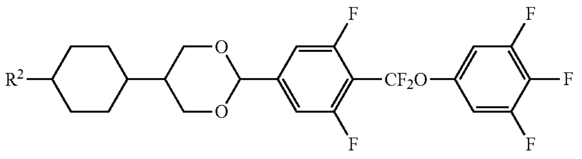

II-1g-1

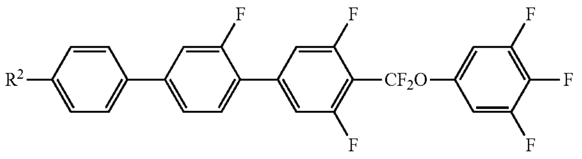

II-1h-1

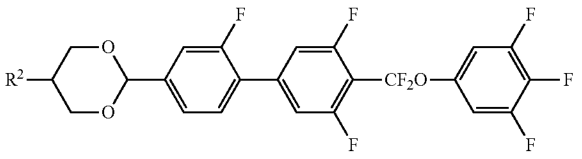

in which $R^2$ has the meaning given above.

Preferably the compounds of formula II-2 are selected from the group of compounds of formulae II-2a to II-2c:

II-2a

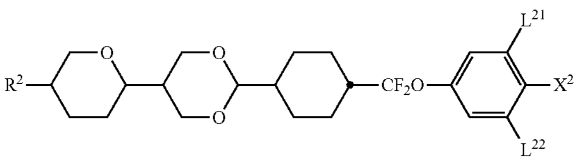

II-2b

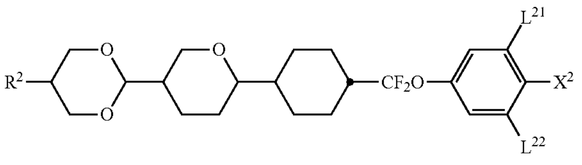

II-2c

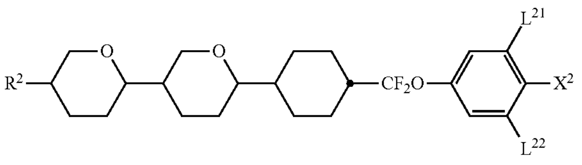

in which the occurring groups have the respective meanings given above and preferably $L^{21}$ and $L^{22}$ are both F.

Preferably, the compounds of formula II-3 are selected from the group of compounds of formulae II-3a to II-3e:

II-3a

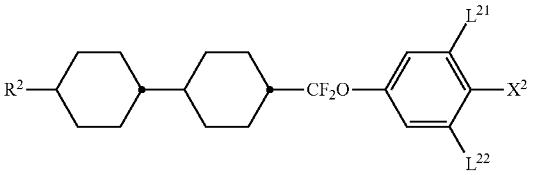

II-3b

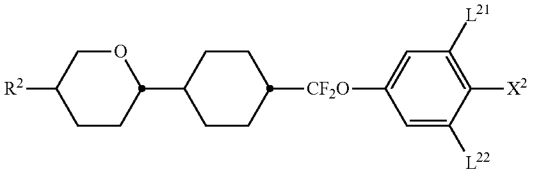

II-3c

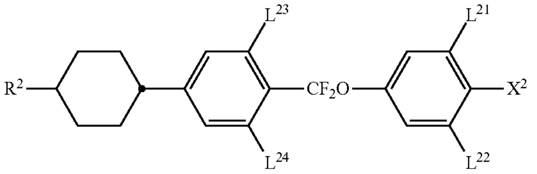

II-3d

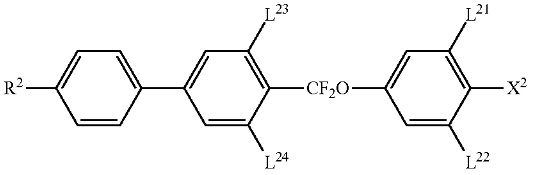

II-3e

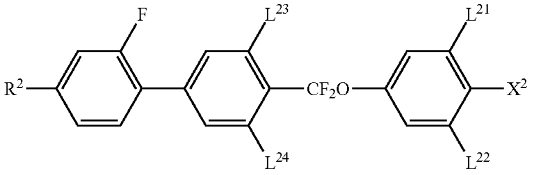

in which the occurring groups have the respective meanings given above, and preferably $L^{21}$ and $L^{22}$ are both F and $L^{23}$ and $L^{24}$ are both H or $L^{21}$, $L^{22}$, $L^{23}$ and $L^{24}$ are all F.

Especially preferred compounds of formula II-3 are:

II-3a-1

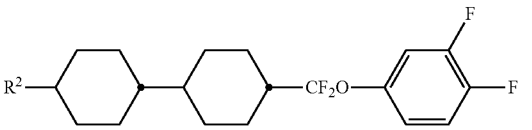

II-3a-2

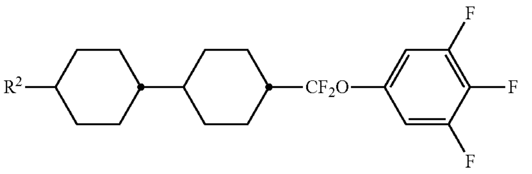

-continued

II-3b-1

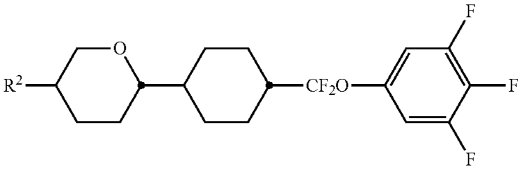

II-3d-1

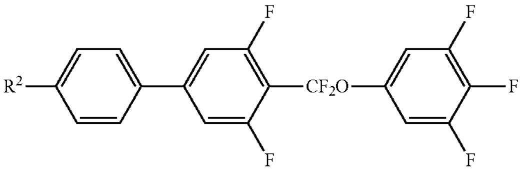

II-3e-1

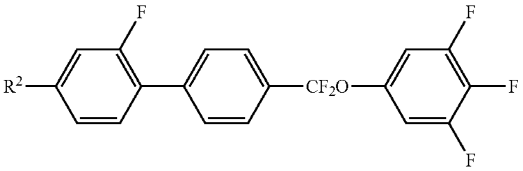

in which $R^2$ has the meaning given above.

In addition to the preferred compounds of formula II above the medium optionally comprises one or more compounds of formula II selected from the compounds of the formulae IIA1 to IIA7:

IIA1

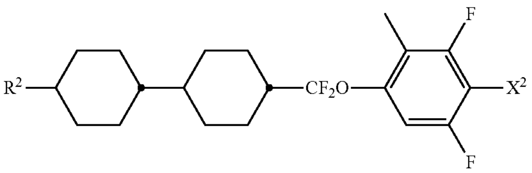

IIA1

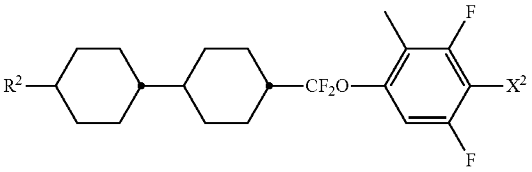

IIA2

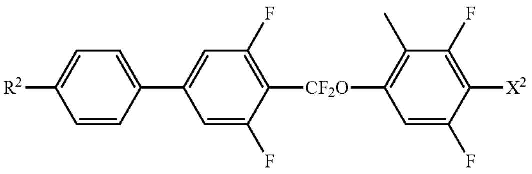

IIA3

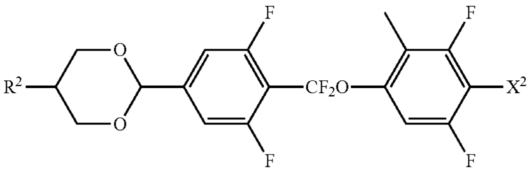

-continued

IIA4

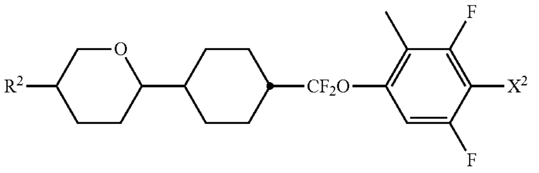

IIA5

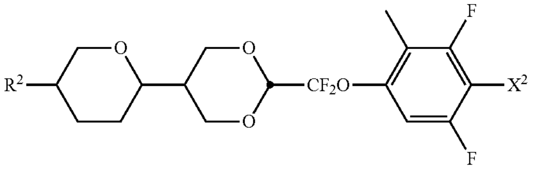

IIA6

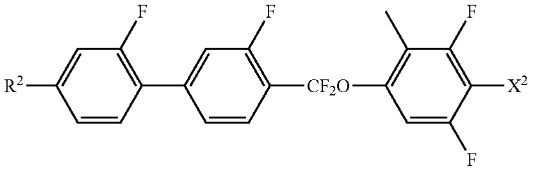

IIA1

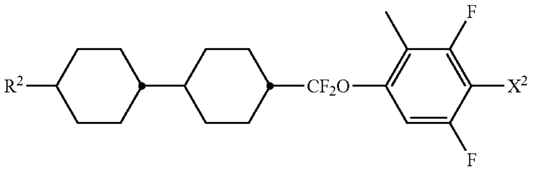

IIA7

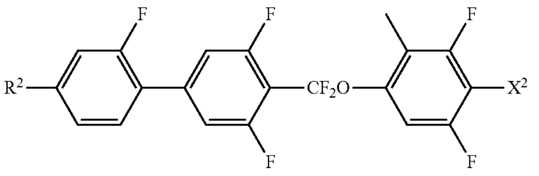

in which $R^2$ and $X^2$ have the meanings given in formula II or one of the preferred meanings given above and below.

Preferred compounds are those of formulae IIA1, IIA2, and IIA3, very preferred compounds are those of formulae IIA1 and IIA2.

In the compounds of formulae IIA1 to IIA7, $R^2$ preferably denotes an alkyl group having 1 to 6 C atoms, very preferably an ethyl or n-propyl group, and $X^2$ preferably denotes F or $OCF_3$, very preferably F.

In another preferred embodiment of the present invention the medium comprises one or more compounds of formula III, preferably selected from the group of formulae III-1 and III-2, or more preferably of formula III-2:

III-1

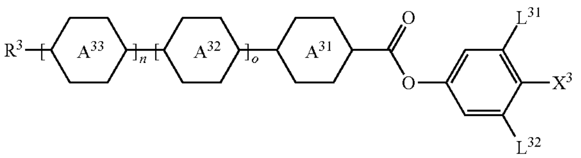

-continued

III-2

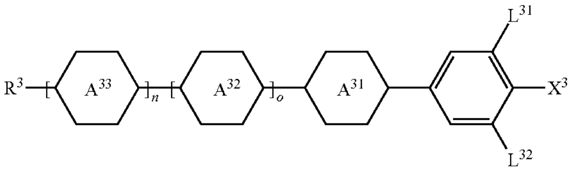

in which the occurring groups and parameters have the respective meanings given under formula III above.

$R^3$ preferably denotes an alkyl group having 1 to 7 C atoms or an alkenyl group having 2 to 7 C atoms.

Preferably the compounds of formula III-1 are selected from the group of compounds of formulae III-1a and III-1b:

III-1a

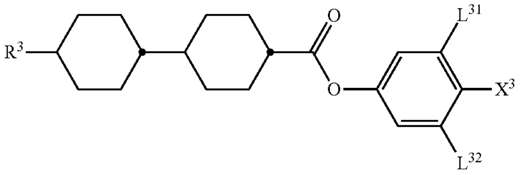

III-1b

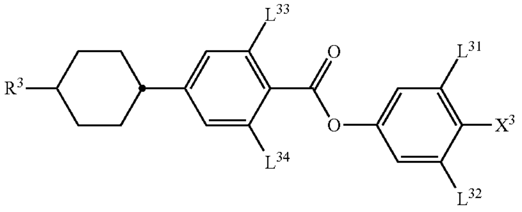

in which the occurring groups have the respective meanings given above and $L^{33}$ and $L^{34}$, independently of each other, denote H or F.

The compounds of formula III-1a are preferably selected from the group of compounds of formulae III-1a-1 to III-1a-6:

III-1a-1

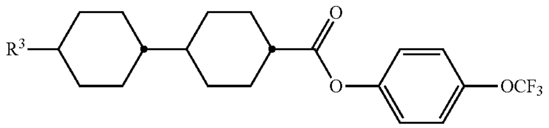

III-1a-2

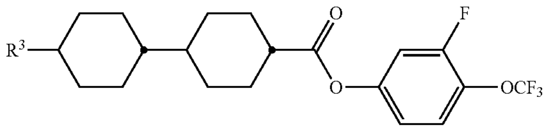

III-1a-3

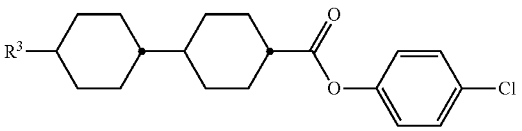

-continued
III-1a-4
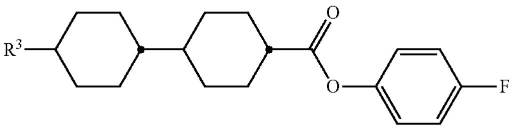
III-1a-5
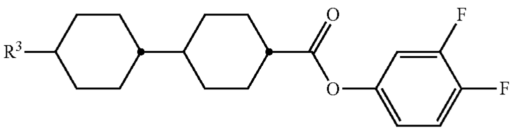
III-1a-6
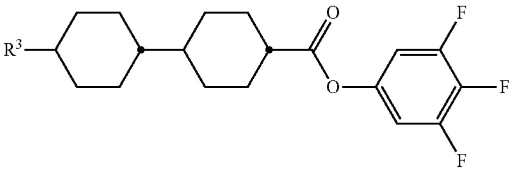
in which $R^3$ has the meaning given above.
Preferably, the compounds of formula III-2 are selected from the group of compounds of formulae III-2a to III-2n:
III-2a
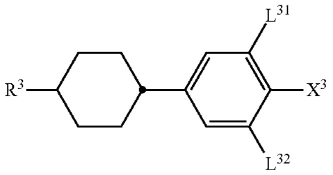
III-2b
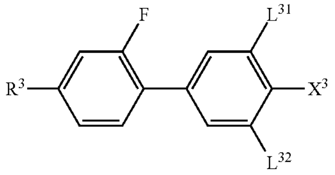
III-2c
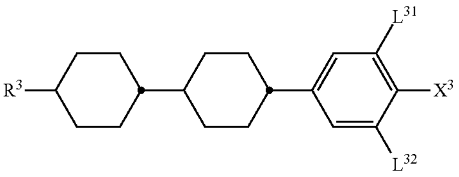
III-2d
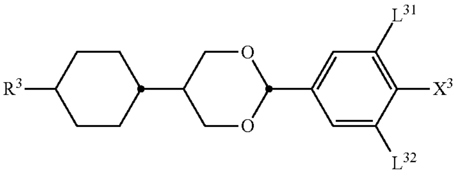
III-2e
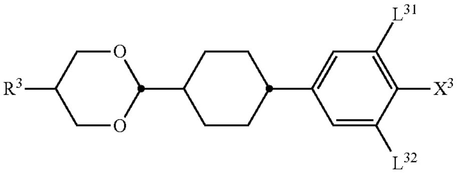
-continued
III-2f
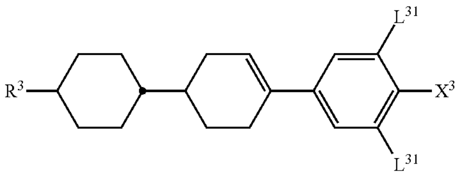
III-2g
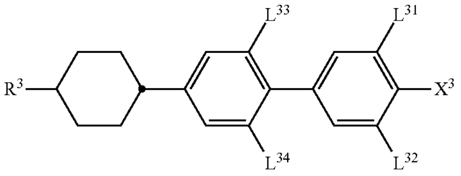
III-2h
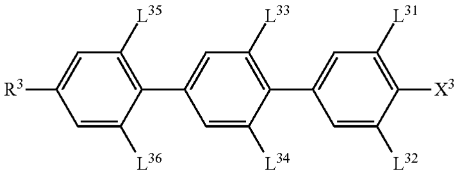
III-2i
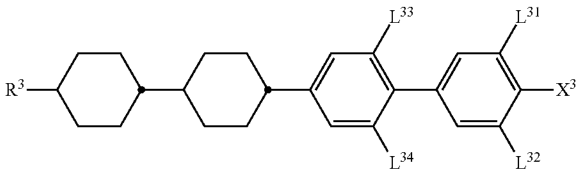
III-2j
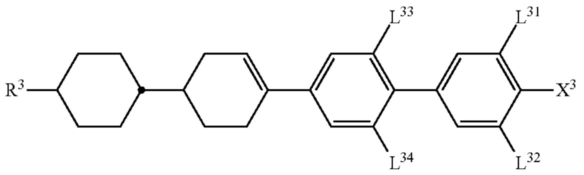
III-2k
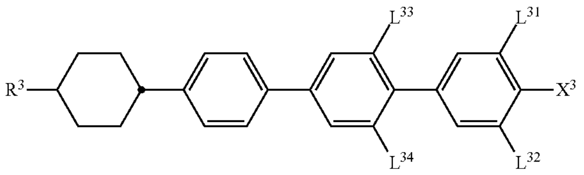
III-2l
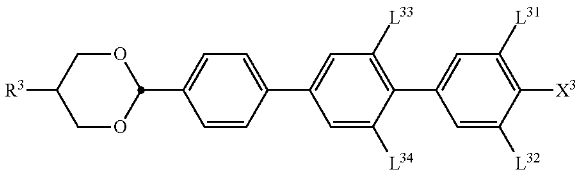
III-2m
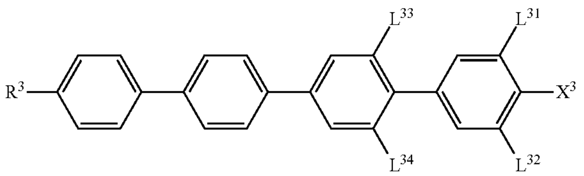

-continued

III-2n

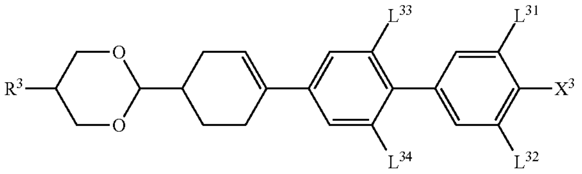

in which the occurring groups have the respective meanings given above and $L^{35}$ and $L^{36}$, independently of one another, denote H or F.

Preferably, the compounds of formula II-2a are selected from the group of compounds of formulae III-2a-1 to III-2a-4:

III-2a-1

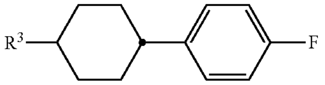

III-2a-2

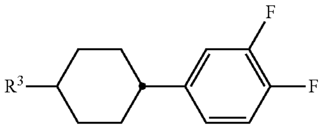

III-2a-3

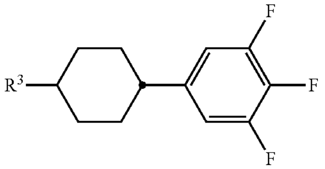

III-2a-4

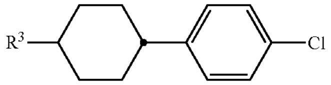

in which $R^3$ has the meaning given above.

The compounds of formula III-2b are preferably selected from the group of compounds of formulae III-2b-1 and III-2b-2, preferably III-2b-2:

III-2b-1

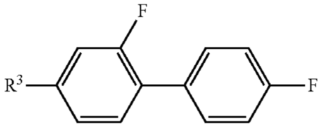

III-2b-2

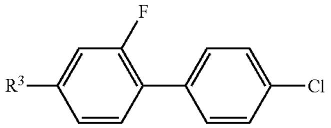

in which $R^3$ has the meaning given above.

The compounds of formula II-2c, are preferably selected from the group of compounds of formulae III-2c-1 to III-2c-5:

III-2c-1

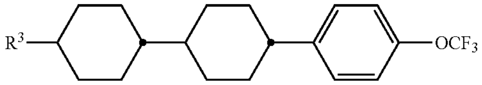

III-2c-2

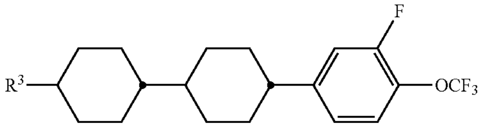

III-2c-3

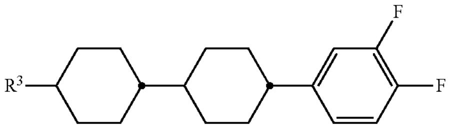

III-2c-4

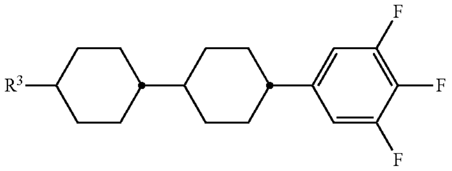

III-2c-5

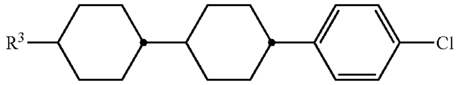

in which $R^3$ has the meaning given above.

The compounds of formulae III-2d and III-2e are preferably selected from the group of compounds of formulae III-2d-1 and III-2e-1:

III-2d-1

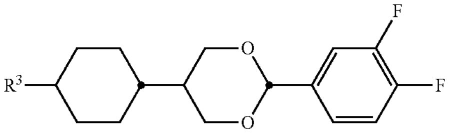

III-2e-1

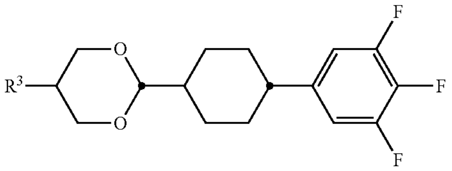

in which $R^3$ has the meaning given above.

The compounds of formula III-2f are preferably selected from the group of compounds of formulae III-2f-1 to III-2f-7:

III-2f-1

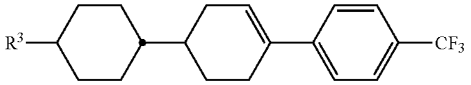

III-2f-2

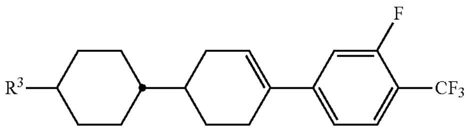

-continued

III-2f-3

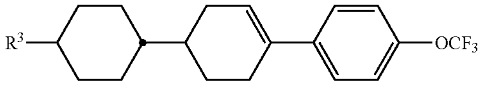

III-2f-4

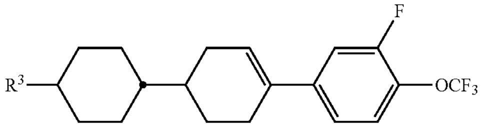

III-2f-5

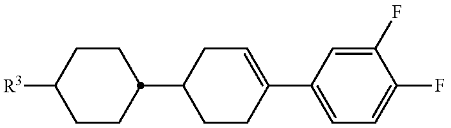

III-2f-6

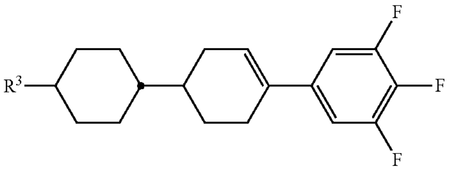

III-2f-7

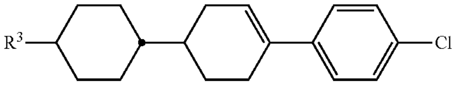

in which $R^3$ has the meaning given above.

The compounds of formula III-2g are preferably selected from the group of compounds of formulae III-2g-1 to III-2g-7:

III-2g-1

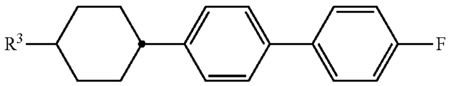

III-2g-2

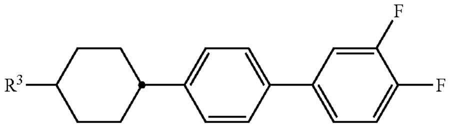

III-2g-3

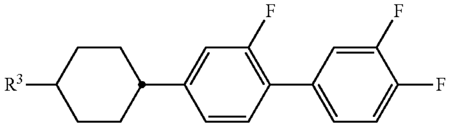

III-2g-4

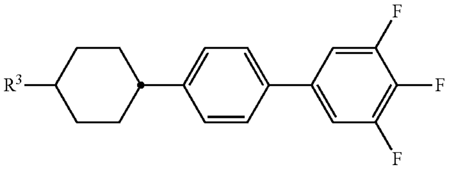

-continued

III-2g-5

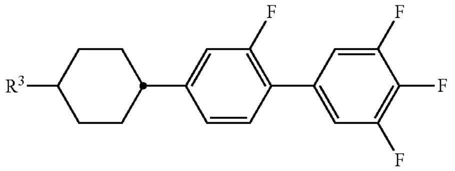

III-2g-6

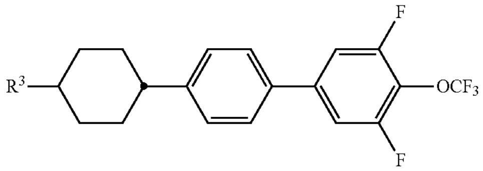

III-2g-7

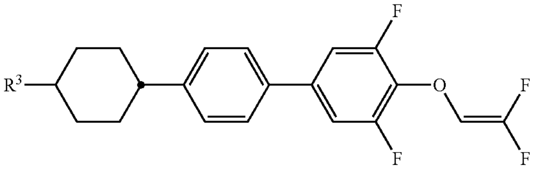

in which $R^3$ has the meaning given above.

The compounds of formula III-2h are preferably selected from the group of compounds of formulae III-2h-1 to III-2h-5:

III-2h-1

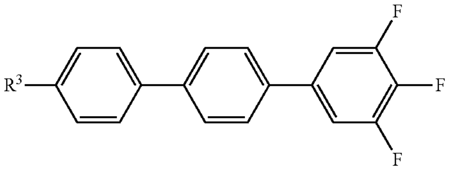

III-2h-2

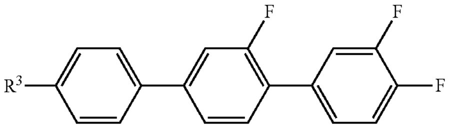

III-2h-3

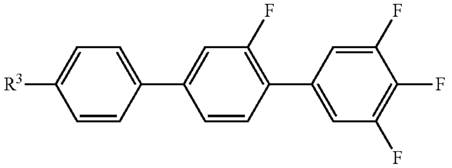

III-2h-4

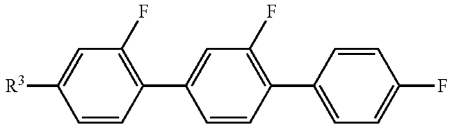

III-2h-5

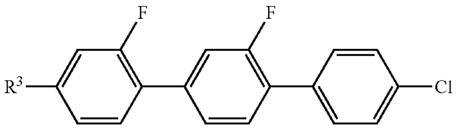

in which $R^3$ has the meaning given above.

The compounds of formula III-2i are preferably selected from the group of compounds of formulae III-2i-1 to III-2i-3:

III-2i-1

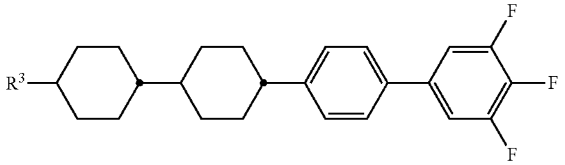

III-2i-2

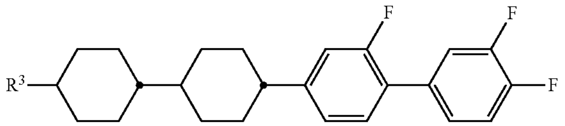

III-2i-3

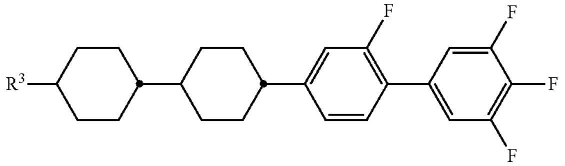

in which $R^3$ has the meaning given above.

The compounds of formula III-2j are preferably selected from the group of compounds of formulae III-2j-1 to III-2j-3:

III-2j-1

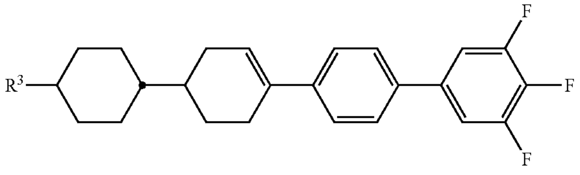

III-2j-2

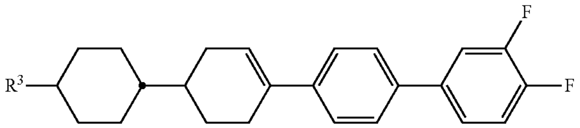

III-2j-3

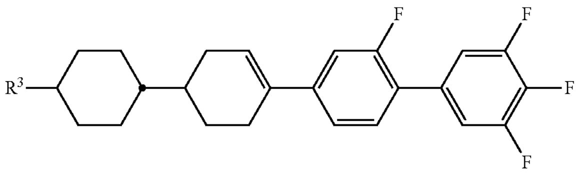

in which $R^3$ has the meaning given above.

The compounds of formula III-2k are preferably selected from the group of compounds of formulae III-2k-1 to III-2k-6:

III-2k-1

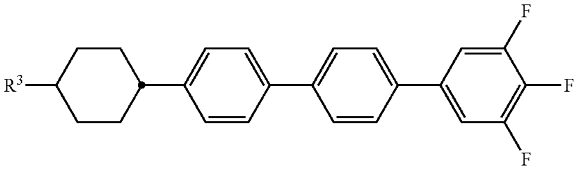

III-2k-2

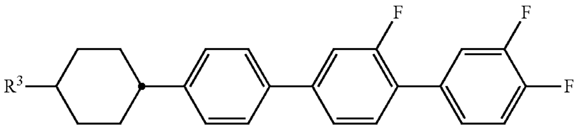

III-2k-3

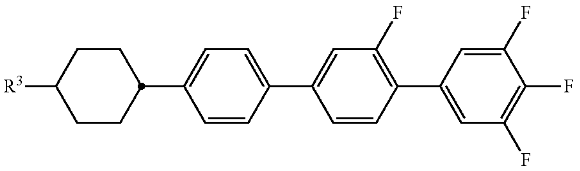

III-2k-4

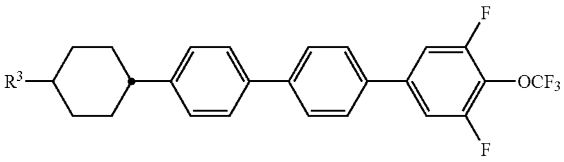

III-2k-5

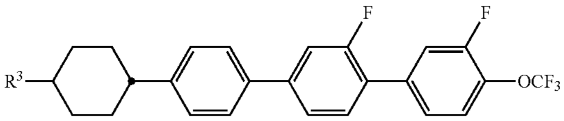

III-2k-6

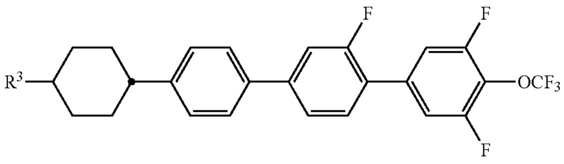

in which $R^3$ has the meaning given above.

The compounds of formula III-21 are preferably selected from the group of compounds of formulae III-21-1 to III-21-6:

III-2l-1

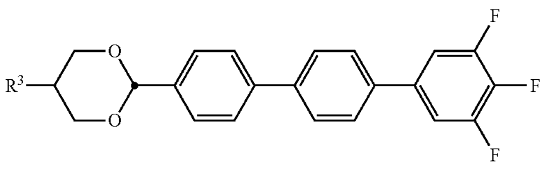

III-2l-2

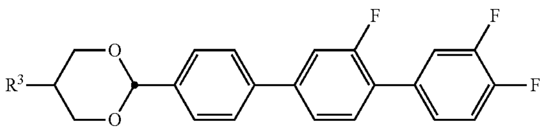

-continued

III-2l-3

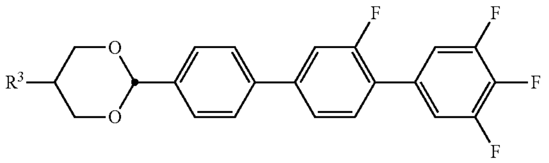

III-2l-4

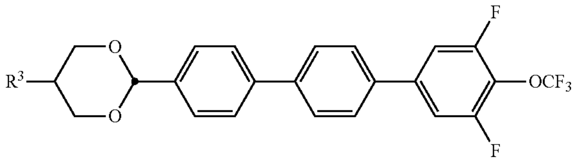

III-2l-5

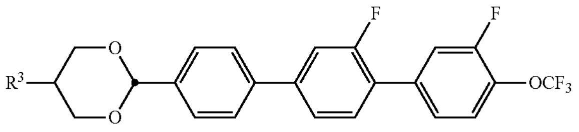

III-2l-6

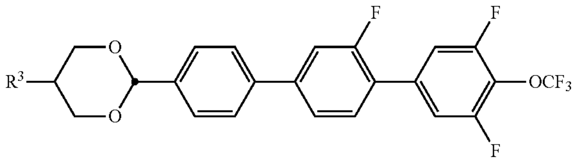

in which $R^3$ has the meaning given above.

The compounds of formula III-2m are preferably selected from the compounds of formula III-2m-1:

III-2m-1

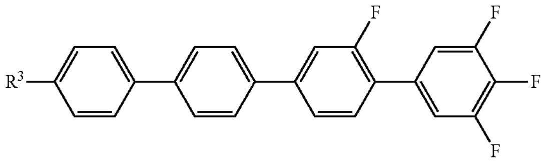

in which $R^3$ has the meaning given above.

The compounds of formula III-2n are preferably selected from the compounds of formula III-2n-1:

III-2n-1

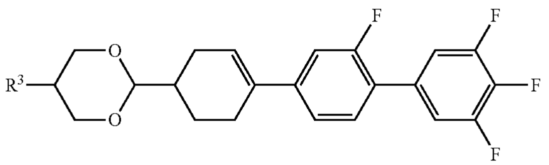

in which $R^3$ has the meaning given above.

Alternatively, or in addition to the compounds of the formulae III-1 and/or III-2, the media according to the present invention optionally comprise one or more compounds of formula III-3:

III-3

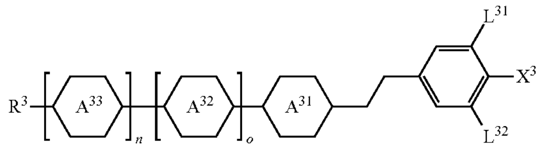

in which the groups and parameters have the respective meanings given under formula III above, preferably of formula III-3a:

III-3a

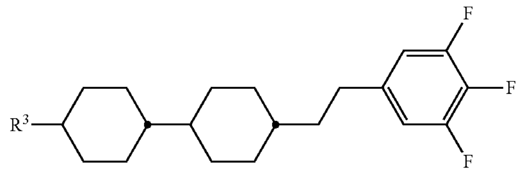

in which the $R^3$ has the meaning given above.

In addition to the preferred compounds of formula III above the medium optionally comprises one or more compounds selected from the group consisting of the formulae IIIA-1 to IIIA-21:

IIIA1

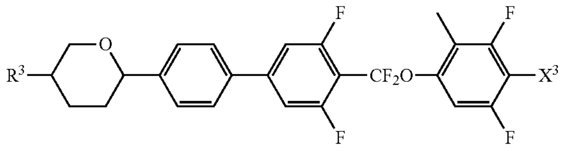

IIIA2

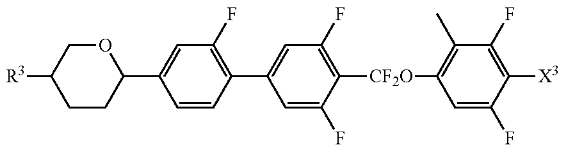

IIIA3

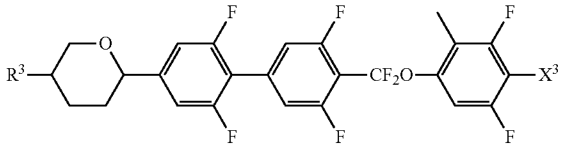

IIIA1

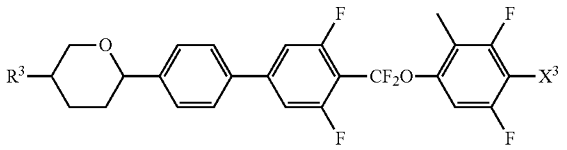

IIIA4

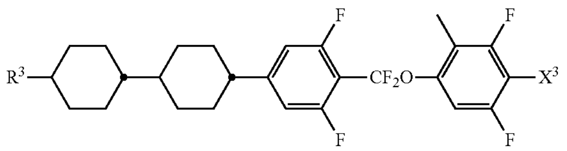

-continued
IIIA5
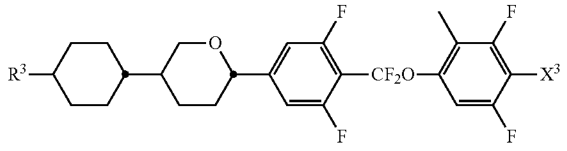
IIIA6
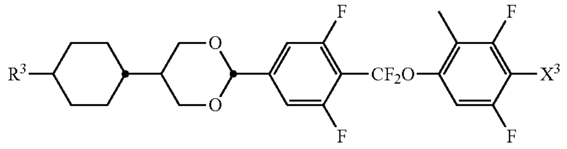
IIIA7
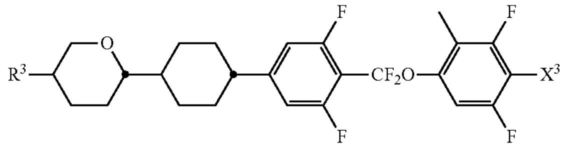
IIIA8
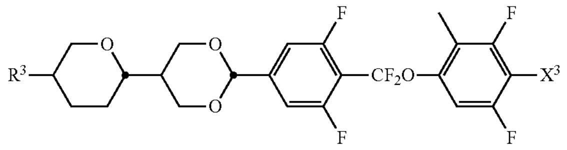
IIIA1
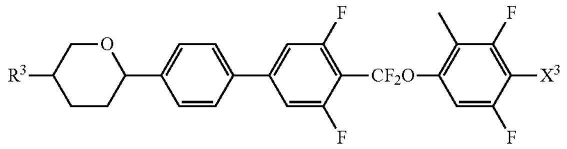
IIIA9
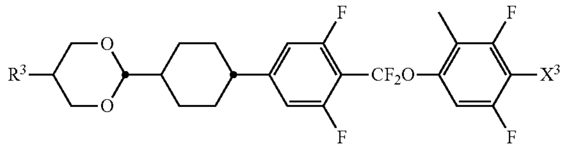
IIIA10
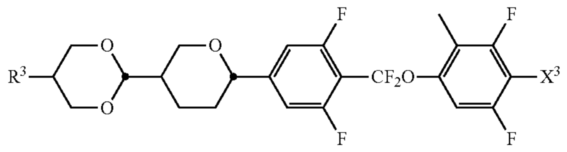
IIIA11
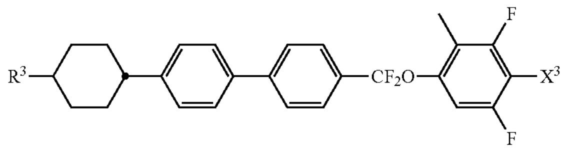
IIIA12
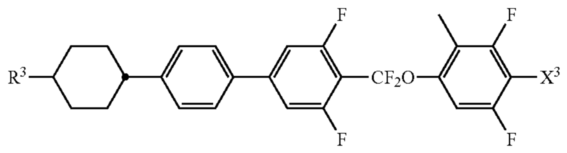
-continued
IIIA13
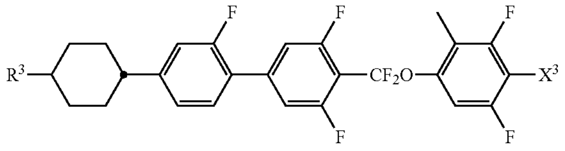
IIIA1
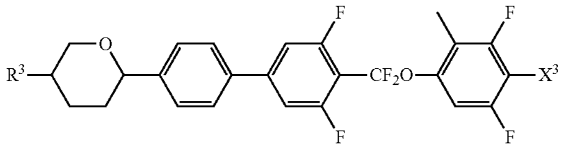
IIIA14
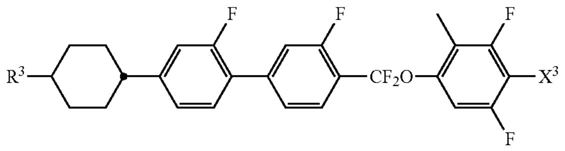
IIIA15
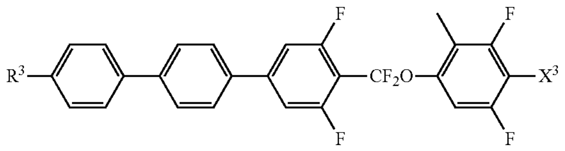
IIIA16
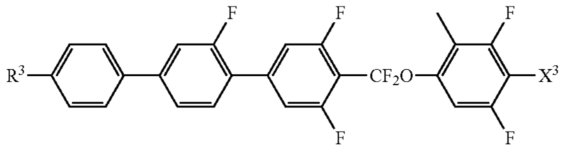
IIIA17
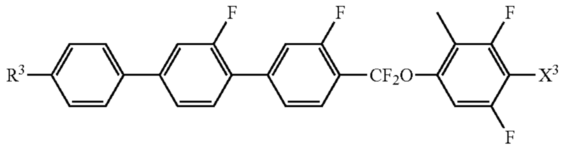
IIIA18
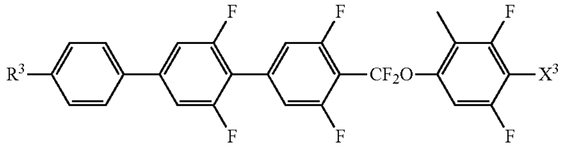
IIIA1
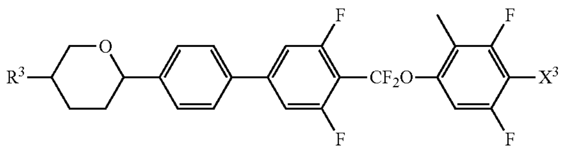
IIIA19
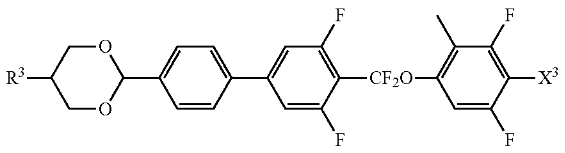

-continued

IIIA20

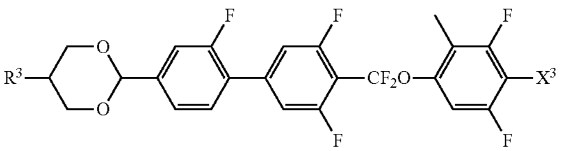

IIIA21

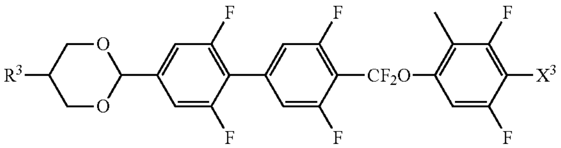

in which $R^3$ and $X^3$ have the meanings given in formula III or one of the preferred meanings given above and below. Preferred compounds are those of formulae IIIA1, IIIA4, IIIA6, IIIA16, IIIA19, and IIIA20.

In the compounds of formulae IIIA1 to IIIA21 $R^3$ preferably denotes alkyl having 1 to 6 C atoms, very preferably ethyl or propyl, and $X^3$ preferably denotes F or $OCF_3$, very preferably F.

Preferably, the medium according to the invention comprises one or more compounds of the formula IV:

IV

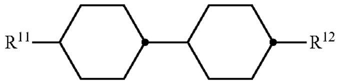

in which $R^{11}$ denotes a straight-chain alkyl or alkoxy radical having 1 to 12 C atoms, a branched or cyclic alkyl radical having 3 to 12 C atoms, a straight-chain alkenyl radical having 2 to 12 C atoms, a branched alkenyl radical having 3 to 12 C atoms, or a cyclic alkenyl radical having 5 to 12 C atoms, wherein one or more H atoms are optionally replaced by fluorine, preferably a straight-chain alkyl radical having 1 to 12 C atoms, very preferably having 1 to 7 C atoms; and $R^{12}$ denotes a straight-chain alkyl or alkoxy radical having 1 to 12 C atoms, a branched or cyclic alkyl or alkoxy radical having 3 to 12 C atoms, a straight-chain alkenyl radical having 2 to 12 C atoms, a branched alkenyl radical having 3 to 12 C atoms, or a cyclic alkenyl radical having 5 to 12 C atoms, wherein one or more H atoms are optionally replaced by fluorine, preferably a straight-chain alkenyl radical having 2 to 12 C atoms, very preferably having 2 to 7 C atoms.

The compounds of the formula IV are preferably selected from the group of the compounds of the formulae IV-1 to IV-4, very preferably of the formula IV-3:

IV-1

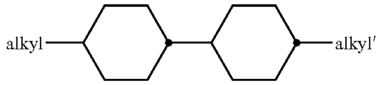

IV-2

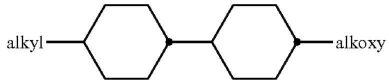

-continued

IV-3

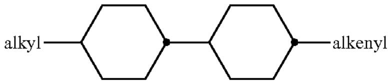

IV-4

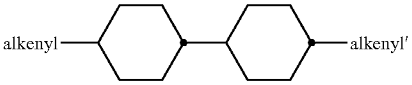

in which alkyl and alkyl' independently of one another, denote an alkyl radical having 1 to 7 C atoms, preferably having 2 to 5 C atoms;

alkoxy denotes an alkoxy radical having 1 to 5 C atoms, preferably having 2 to 4 C atoms;

alkenyl denotes an alkenyl radical having 2 to 5 C atoms, preferably having 2 to 4 C atoms, particularly preferably 2 C atoms; and alkenyl' denotes an alkenyl radical having 2 to 5 C atoms, preferably having 2 to 4 C atoms, or particularly preferably having 2 to 3 C atoms.

Preferably, the medium comprises one or more compounds of formula IV-1, preferably selected from the compounds of the formulae IV-1-1 to IV-1-6:

IV-1-1

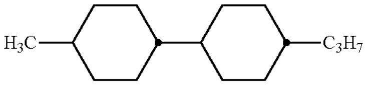

IV-1-2

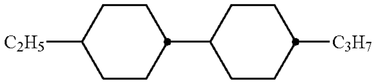

IV-1-3

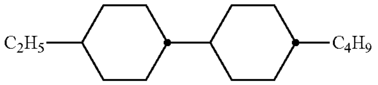

IV-1-4

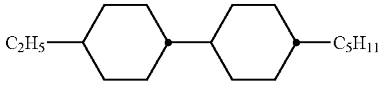

IV-1-5

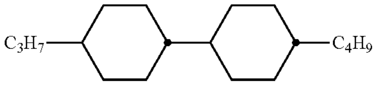

IV-1-1

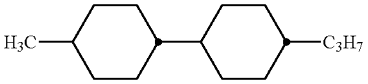

IV-1-6

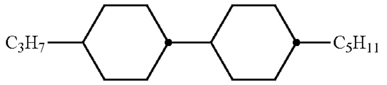

Preferably, the medium according to the invention comprises one or more compounds of the formulae IV-2-1 and/or IV-2-2:

IV-2-1

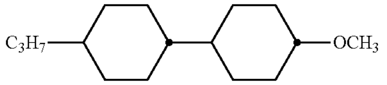

-continued

IV-2-2

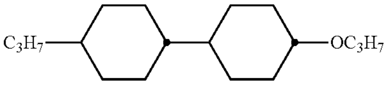

Preferably, the medium according to the invention comprises a compound of formula IV-3, very preferably selected from the compounds of the formulae IV-3-1 to IV-3-7, or in particular the compound of formulae IV-3-2 and/or IV-3-6:

IV-3-1

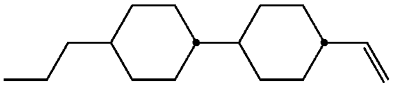

IV-3-2

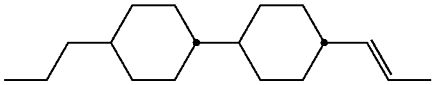

IV-3-3

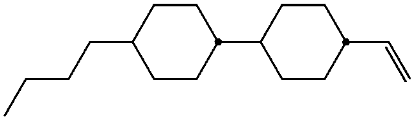

IV-3-4

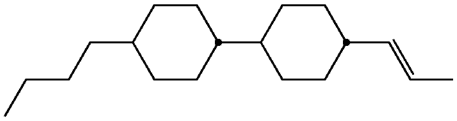

IV-3-5

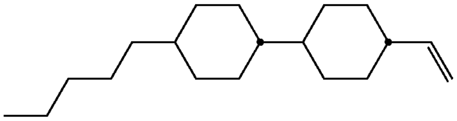

IV-3-6

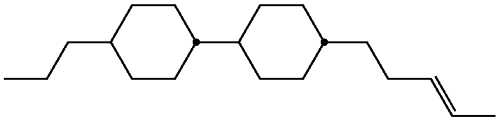

IV-3-7

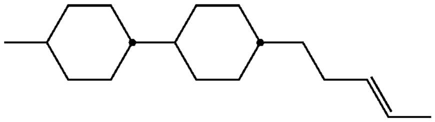

Preferably, the medium according to the invention comprises a compound of formula IV-4, in particular selected from the compounds of the formulae IV-4-1 and IV-4-2:

IV-4-1

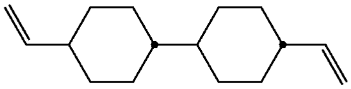

IV-4-2

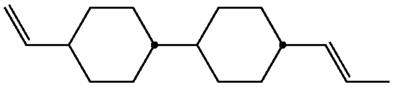

Preferably, the medium according to the invention comprises one or more compounds of the formulae IVa and/or IVb, very preferably IVb:

IVa

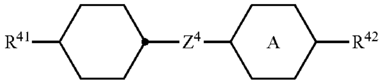

IVb

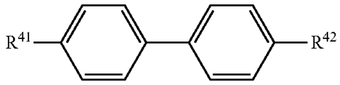

in which $R^{41}$ and $R^{42}$ each, independently of one another, denote a straight-chain alkyl, alkoxy, alkenyl, alkoxyalkyl, or alkenyloxy radical having up to 12 C atoms; and

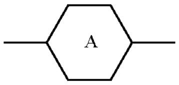 denotes 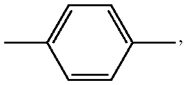,

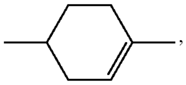, 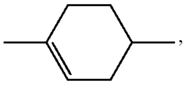,

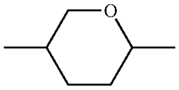 or 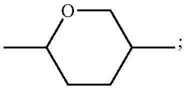;

and $Z^4$ denotes a single bond, $-CH_2CH_2-$, $-CH{=}CH-$, $-CF_2O-$, $-OCF_2-$, $-CH_2O-$, $-OCH_2-$, $-COO-$, $-OCO-$, $-C_2F_4-$0, $-C_4H_8-$, or $-CF{=}CF-$.

Preferred compounds of the formula IVa are selected from the compounds of the formulae IVa-1 to IVa-4:

IVa-1

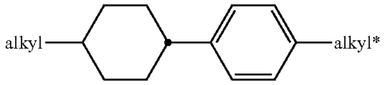

IVa-2

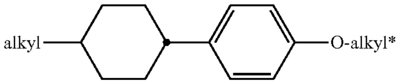

IVa-3

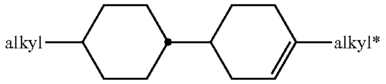

IVa-4

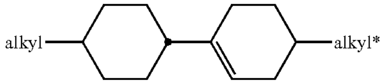

in which alkyl and alkyl* each, independently of one another, denote a straight-chain alkyl radical having 1 to 6 C atoms.

The medium according to the invention preferably comprises at least one compound of the formula IVa-2.

Preferred compounds of the formula IVb are selected from the compounds of the formulae IVb-1 to IVb-3:

IVb-1

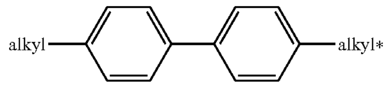

IVb-2

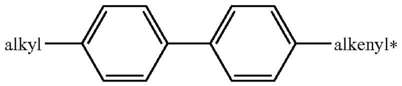

IVb-3

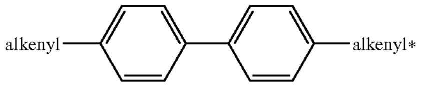

in which alkyl and alkyl* each, independently of one another, denote a straight-chain alkyl radical having 1 to 6 C atoms; and alkenyl and alkenyl* each, independently of one another, denote a straight-chain alkenyl radical having 2 to 6 C atoms.

Of the compounds of the formulae IVb-1 to IVb-3, the compounds of the formula IVb-2 are particularly preferred.

Very particularly preferred compounds of the formulae IVb are selected from the following compounds:

IVb-1-1

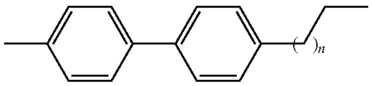

n = 1, 2 or 3

IVb-2-1

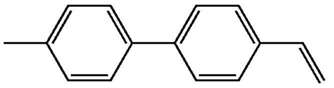

IVb-2-2

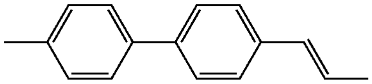

IVb-1-1

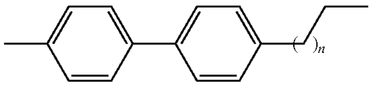

n = 1, 2 or 3

IVb-2-3

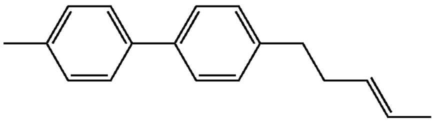

IVb-2-4

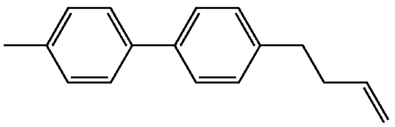

The medium according to the invention particularly preferably comprises the compound IVb-2-3.

In a preferred embodiment, the medium according to the invention comprises one or more compounds of formula V:

V

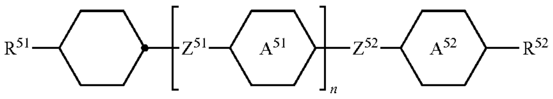

in which $R^{51}$, $R^{52}$ denote an alkyl group having 1 to 7 C atoms, an alkoxy group having 1 to 7 C atoms, or an alkoxyalkyl, alkenyl, or alkenyloxy group having 2 to 7 C atoms,

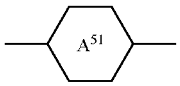 and 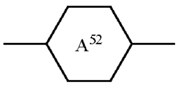

identically or differently, denote

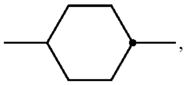, 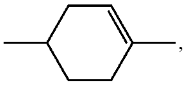, 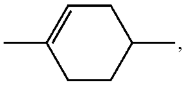,

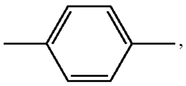, 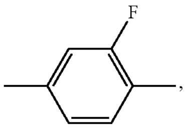, or

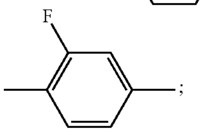;

$Z^{51}$, $Z^{52}$ each, independently of one another, denote $-CH_2-CH_2-$, $-CH_2-O-$, $-CH=CH-$, $-C\equiv C-$, $-COO-$ or a single bond; and n is 1 or 2, where the compounds of the formulae I and CL are excluded from formula V.

The compounds of formula V are preferably selected from the compounds of the formulae V-1, V-2, V-3 and V-4:

V-1

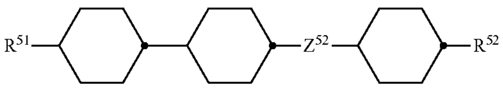

V-2

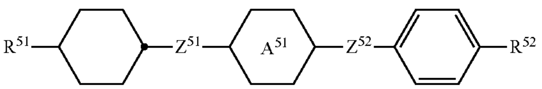

V-3

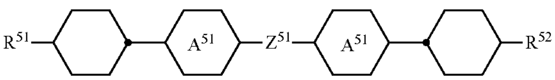

V-4

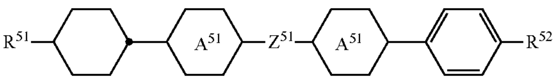

in which the groups occurring have the meanings given above for formula V.

The compounds of formula V-1 are preferably selected from the compounds of the formulae V-1-1 to V-1-8;

the compounds of formula V-2 are preferably selected from the compounds of the formulae V-2-1 to V-2-4;

the compounds of formula V-3 are preferably selected from the compounds of the formulae V-3-1 to V-3-6; and the compounds of formula V-4 are preferably selected from the compounds of the formula V-4-1:

V-1-1

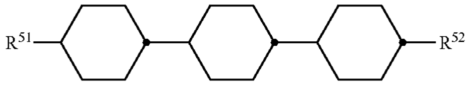

V-1-2

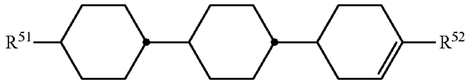

V-1-3

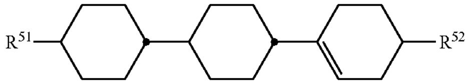

V-1-4

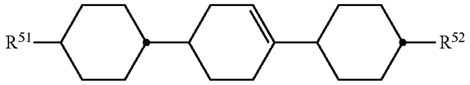

V-1-5

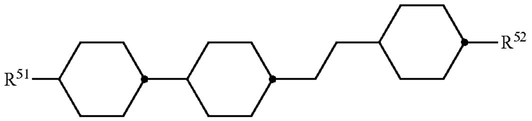

V-1-6

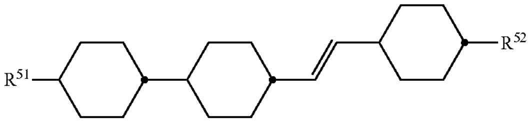

V-1-7

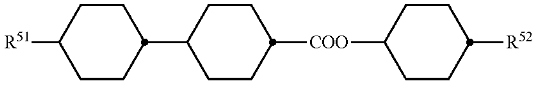

V-1-8

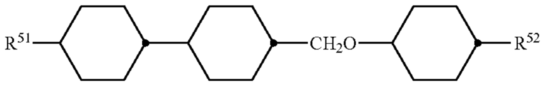

V-2-1

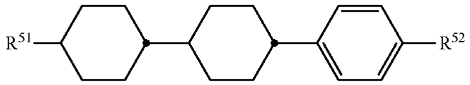

V-2-2

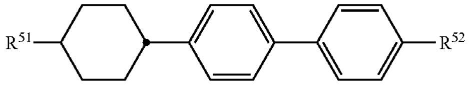

V-2-3

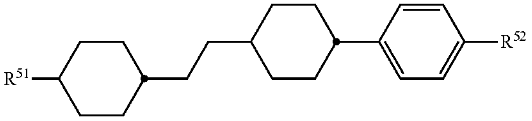

-continued

V-2-4

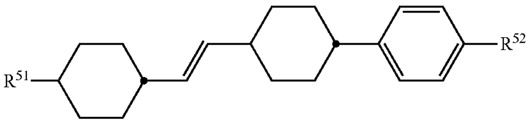

V-3-1

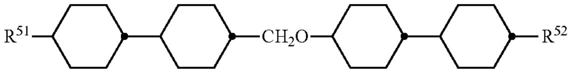

V-3-2

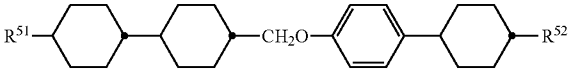

V-3-3

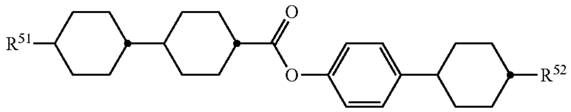

V-3-4

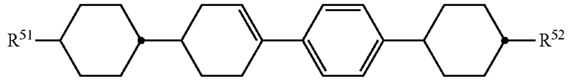

V-3-5

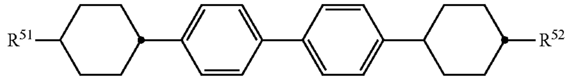

V-3-6

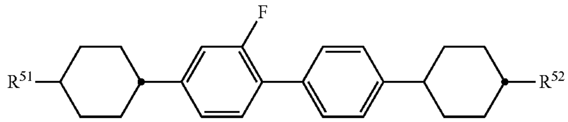

V-4-1

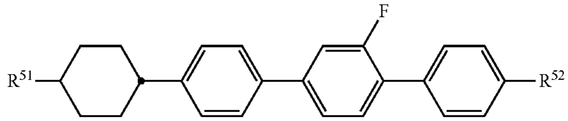

in which $R^{51}$ and $R^{52}$ have the meanings indicated for formula V above; and $R^{51}$ and $R^{52}$ preferably each, independently of one another, denote a straight-chain alkyl group having 1 to 7 C atoms or a straight-chain alkenyl group having 2 to 7 C atoms.

Very preferred compounds of the formula V-2-1 are selected from the compounds of the formulae V-2-1a to V-2-1g:

V-2-1a

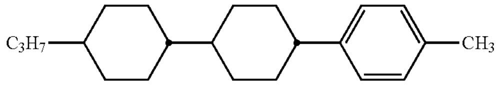

V-2-1b

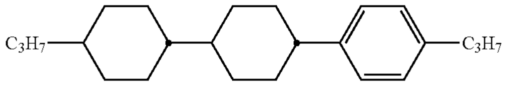

-continued

V-2-1c

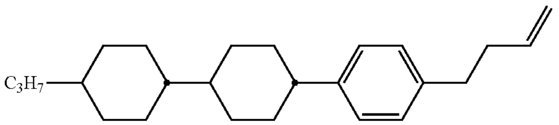

V-2-1d

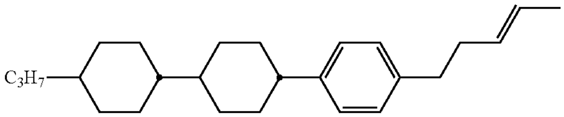

V-2-1e

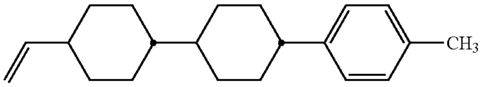

V-2-1f

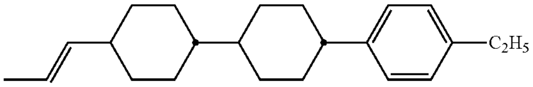

V-2-1g

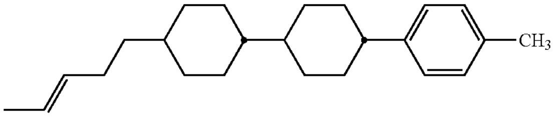

V-2-1h

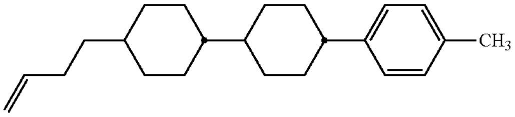

Very preferred compounds of the formula V-2-2 are selected from the compounds of the formulae V-2-2a to V-2-2i:

V-2-2a

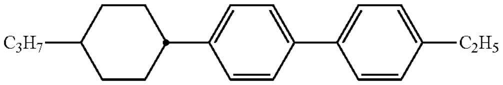

V-2-2b

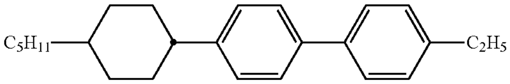

V-2-2c

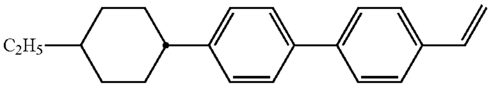

V-2-2d

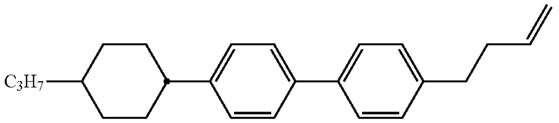

V-2-2e

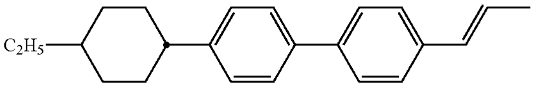

-continued

V-2-2f

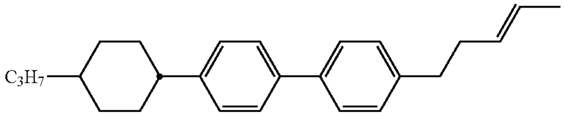

V-2-2g

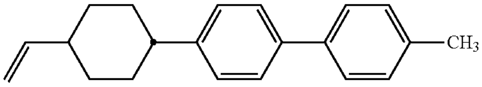

V-2-2h

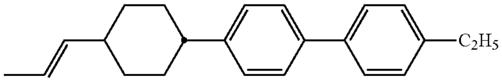

V-2-2i

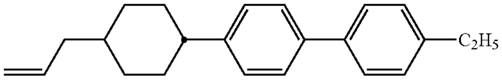

Preferably, the medium according to the invention comprises one or more compounds of the formula CL:

CL

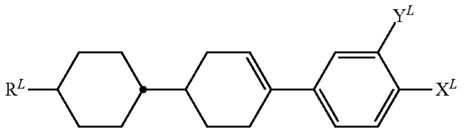

in which $R^L$ denotes H, a straight-chain or branched alkyl or alkoxy radical having 1 to 15 C atoms, or a straight-chain or branched alkenyl radical having 2 to 15 C atoms, where one or more $CH_2$ groups in these radicals may each be replaced, independently of one another, by

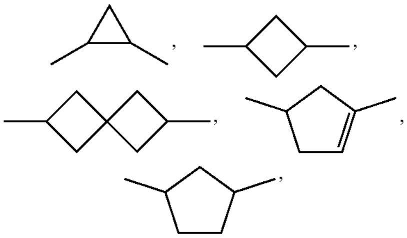

—C≡C—, —$CF_2O$—, —$OCF_2$—, —CH═CH—, —O—, —CO—O—, or —O—CO— in such a way that O atoms are not linked directly to one another, and in which, in addition, one or more H atoms may be replaced by halogen; and $X^L$ denotes F, Cl, CN, $CHF_2$, $CF_3$, $OCF_3$, or, identically or differently, has one of the meanings of $R^L$; and $Y^L$ denotes H, F, Cl, or $CH_3$.

The compounds of formula CL are preferably selected form the group of compounds of the formulae CL-1, CL-2 and CL-3:

CL-1

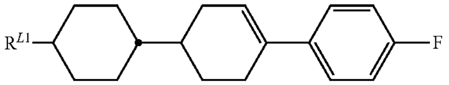

CL-2

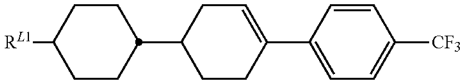

CL-3

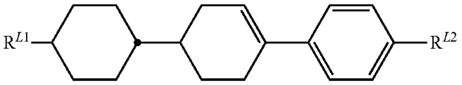

in which $R^{L1}$ and $R^{L2}$ identically or differently, have the meanings of $R^L$ and $X^L$ given above for formula CL and preferably denote an alkyl or alkenyl group having 1 to 7 C atoms or 2 to 7 C atoms, respectively, in which a $CH_2$ group may be replaced by cyclopropane-1,2-diyl, and $R^{L2}$ alternatively denotes an alkoxy group having 1 to 5 C atoms.

Very preferred compounds of the formula CL are selected from the compounds of the formulae CL-3-1 to CL-3-12:

CL-3-1

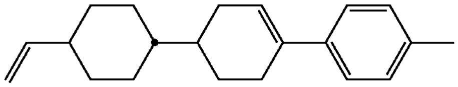

CL-3-2

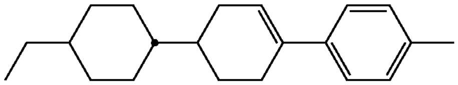

CL-3-3

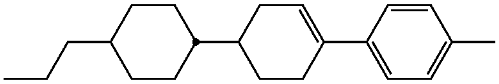

CL-3-4

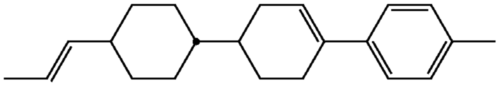

CL-3-5

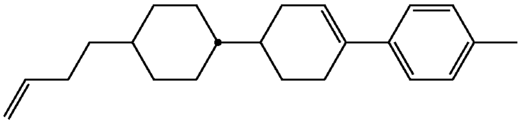

CL-3-6

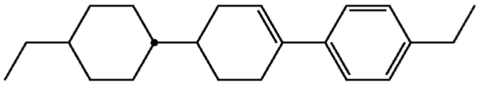

CL-3-7

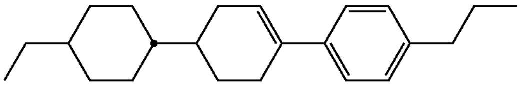

CL-3-1

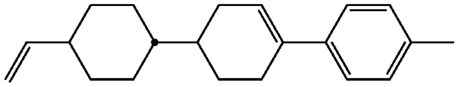

-continued

CL-3-8

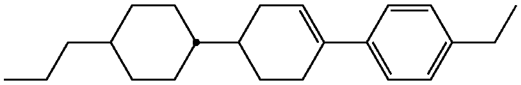

CL-3-9

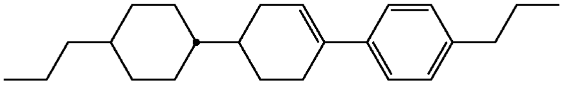

CL-3-10

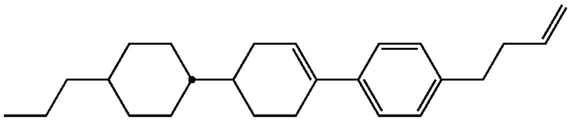

CL-3-11

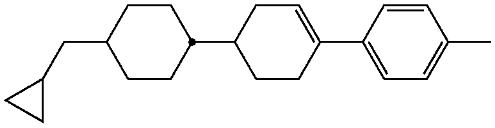

CL-3-12

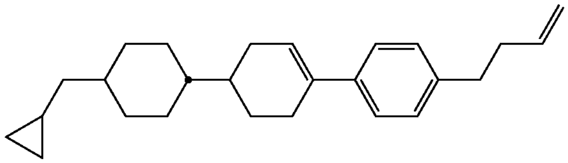

In a particularly preferred embodiment, the medium according to the invention comprises the compound CL-3-1 or CL-3-3.

In a preferred embodiment of the present invention the medium additionally comprises one or more compounds of the formulae VI-1 to VI-9:

VI-1

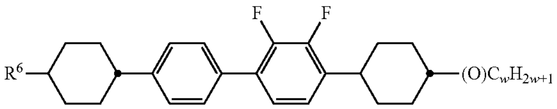

VI-1

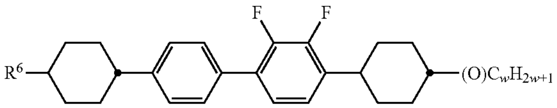

VI-2

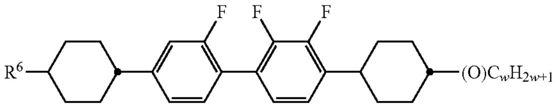

VI-3

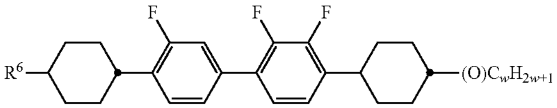

-continued

VI-4

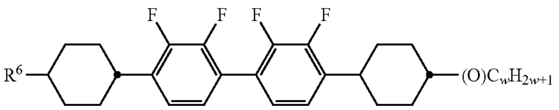

VI-5

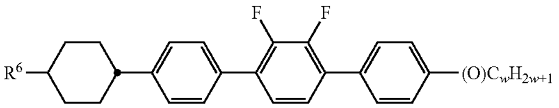

VI-6

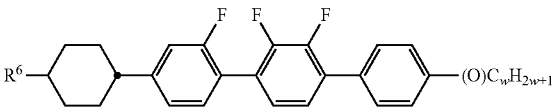

VI-7

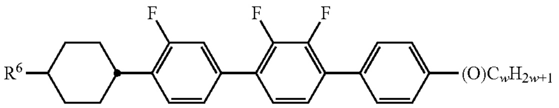

VI-1

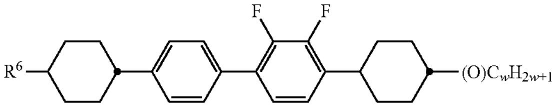

VI-8

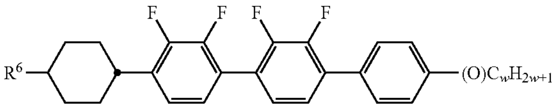

VI-9

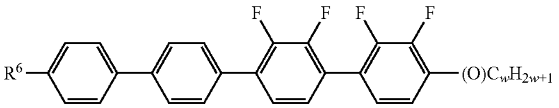

in which $R^6$ each, independently of one another, have one of the meanings indicated for $R^{11}$ in formula I; and w each, independently of one another, denote an integer from 1 to 6.

In a preferred embodiment of the present invention the medium additionally comprises one or more compounds of the formula VII:

VII

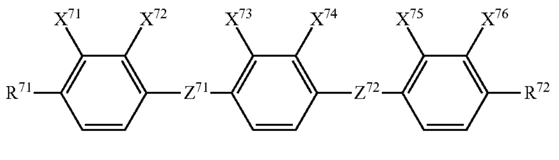

in which $R^{71}$ and $R^{72}$ denote H, F, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group each having 3 to 15 C atoms, where one or more $CH_2$ groups in these radicals may each be replaced, independently of one another, by

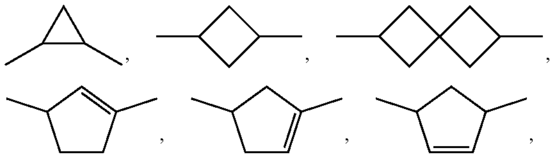

—C≡C—, —$CF_2O$—, —$OCF_2$—, —CH═CH—, —O—, —CO—O—, or —O—CO— in such a way that O atoms are not linked directly to one another, and in which one or more H atoms may be replaced by halogen;

$X^{71}$ to $X^{76}$ identically or differently, denote H or F, preferably at least one of $X^{71}$ to $X^{76}$ denotes F, more preferably at least two of $X^{71}$ to $X^{76}$ denote F; and $Z^{71}$ and $Z^{72}$ identically or differently, denote $CH_2CH_2$ or a single bond.

The compounds of the formula VII are preferably selected from the formulae VII-1 and VII-2:

VII-1

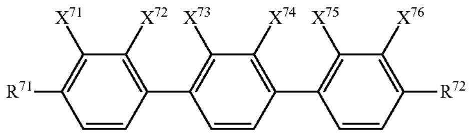

VII-2

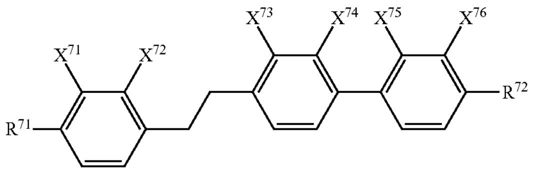

in which the occurring groups have the meanings given for formula VII.

The compounds of the formula VII-1 are preferably selected from the formulae VII-1-1 to VII-1-22, very preferably of the formula VII-1-4:

VII-1-1

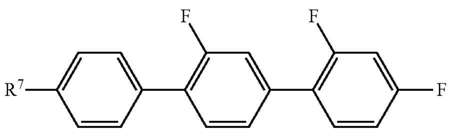

VII-1-2

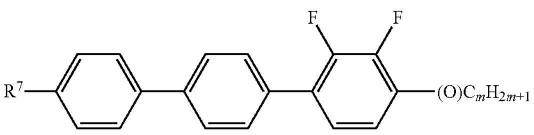

VII-1-3

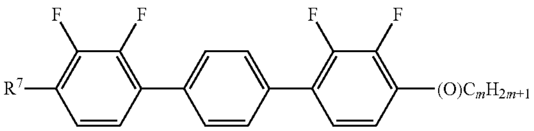

-continued
VII-1-4
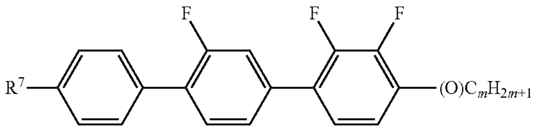
VII-1-5
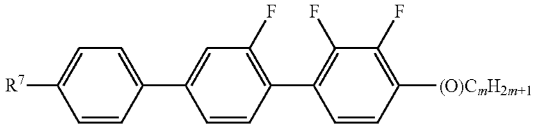
VII-1-6
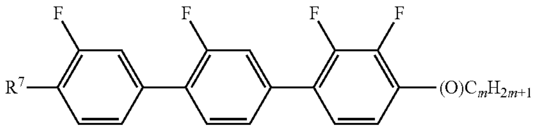
VII-1-7
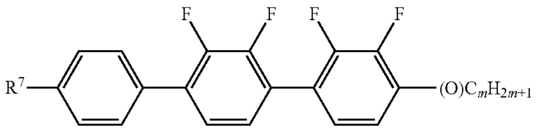
VII-1-8
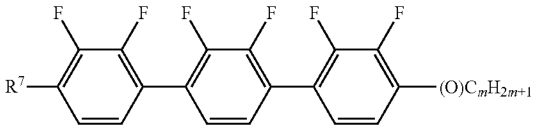
VII-1-9
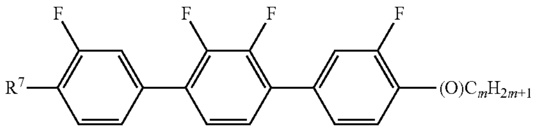
VII-1-10
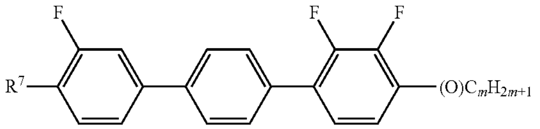
VII-1-11
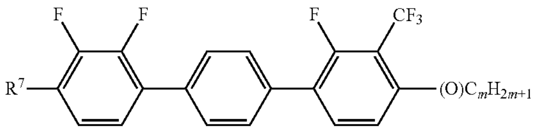
VII-1-12
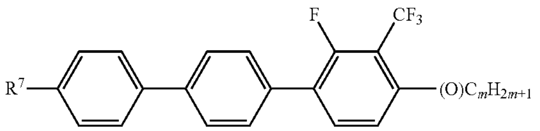
VII-1-13
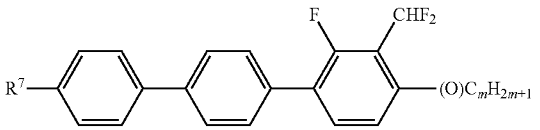
-continued
VII-1-14
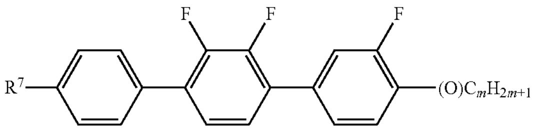
VII-1-15
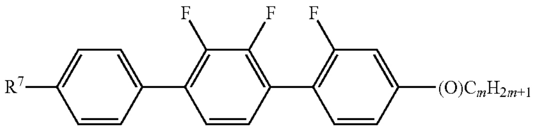
VII-1-16
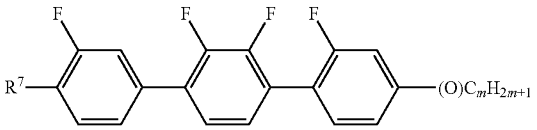
VII-1-17
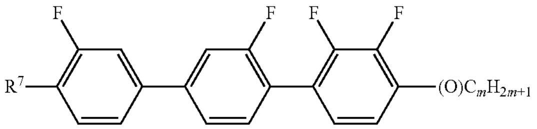
VII-1-18
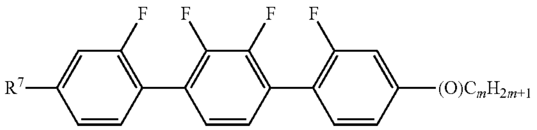
VII-1-19
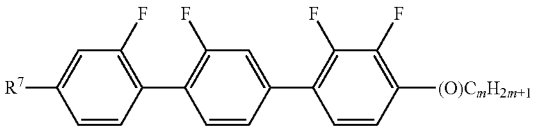
VII-1-20
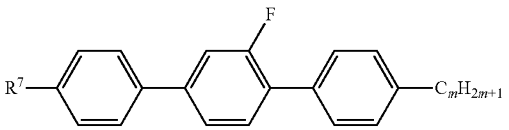
VII-1-21
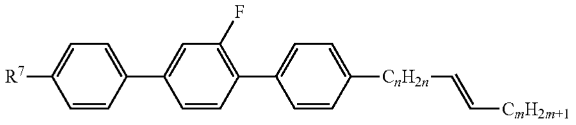
VII-1-22
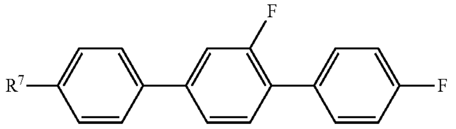
in which
$R^7$ denotes a straight-chain alkyl or alkoxy radical having 1 to 6 C atoms;
(O) denotes —O— or a single bond;
m is 0, 1, 2, 3, 4, 5, or 6; and
n is 0, 1, 2, 3 or 4.
$R^7$ preferably denotes a methyl, ethyl, propyl, butyl, pentyl, hexyl, methoxy, ethoxy, propoxy, butoxy, or pentoxy group.

In the compounds of the formula VII-1-4, (O) preferably denotes —O—.

In the compounds of formula VII-1-22, $R^7$ preferably denotes n-propyl.

The compounds of the formula VII-2 are preferably selected from the formulae VII-2-1 to VII-2-15, very preferably of the formula VII-2-1:

VII-2-1

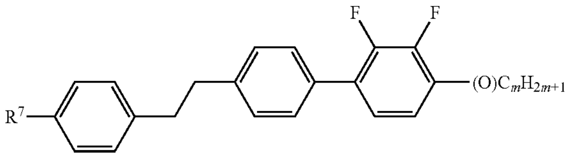

VII-2-2

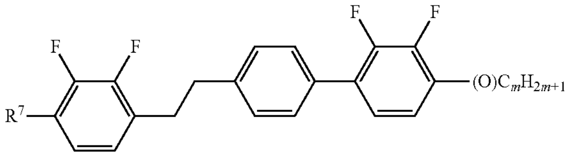

VII-2-3

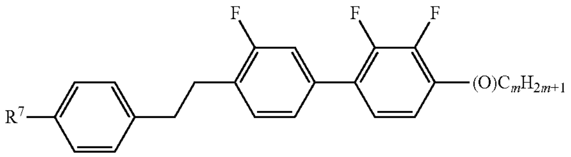

VII-2-4

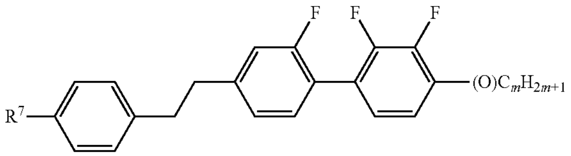

VII-2-5

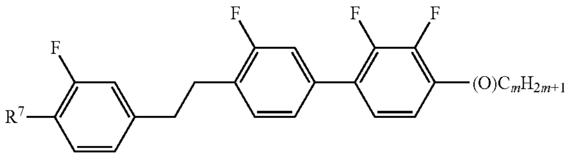

VII-2-6

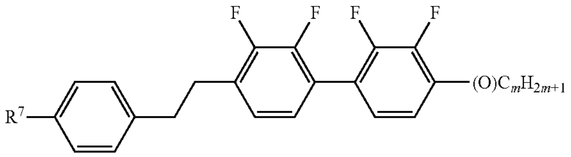

VII-2-7

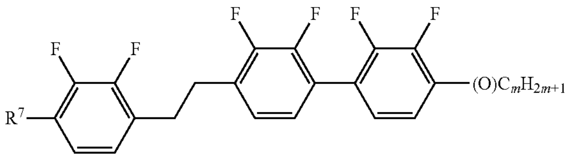

-continued

VII-2-8

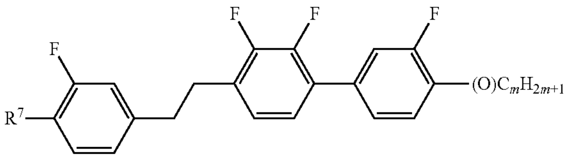

VII-2-9

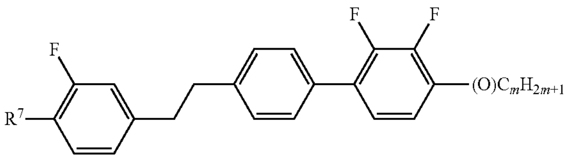

VII-2-10

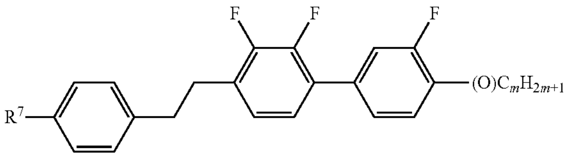

VII-2-11

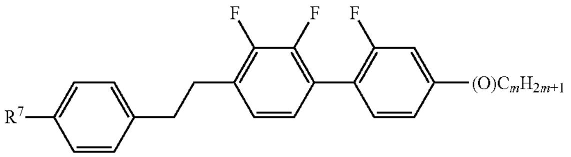

VII-2-12

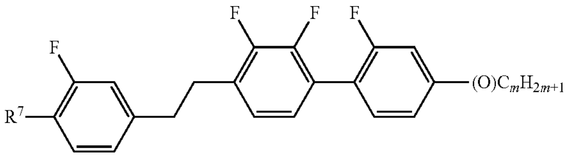

VII-2-13

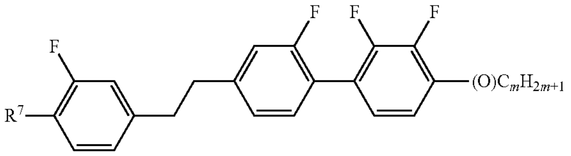

VII-2-14

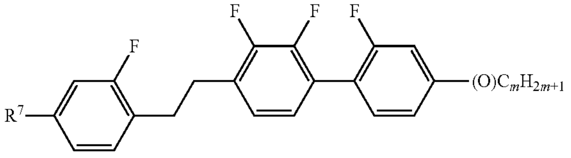

VII-2-15

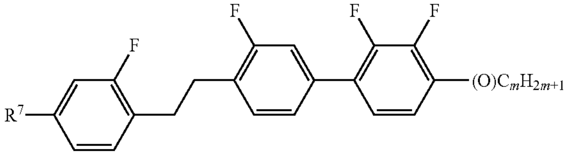

in which $R^7$ denotes a straight-chain alkyl or alkoxy radical having 1 to 6 C atoms;

(O) denotes —O— or a single bond;

m is 0, 1, 2, 3, 4, 5 or 6; and n is 0, 1, 2, 3 or 4.

$R^7$ preferably denotes a methyl, ethyl, propyl, butyl, pentyl, hexyl, methoxy, ethoxy, propoxy, butoxy, or pentoxy group.

Preferably, the medium according to the invention comprises one or more compounds of the formula VIII:

VIII

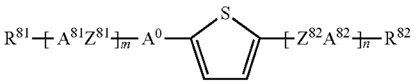

in which $R^{81}$ and $R^{82}$ identically or differently, denote H, halogen, CN, SCN, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group having 3 to 15 C atoms, where one or more $CH_2$ groups in these radicals may each be replaced, independently of one another, by

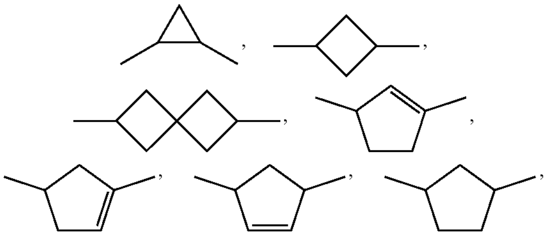

—C≡C—, —$CF_2$O—, —$OCF_2$—, —CH═CH—, by —O—, —CO—O—, or —O—CO— in such a way that O atoms are not linked directly to one another, and in which one or more H atoms may be replaced by halogen;

$A^0$, $A^{81}$, and $A^{82}$ each, independently of one another, denote phenylene-1,4-diyl, in which one or two CH groups may be replaced by N and one or more H atoms may be replaced by halogen, CN, $CH_3$, $CHF_2$, $CH_2F$, $CF_3$, $OCH_3$, $OCHF_2$, or $OCF_3$, cyclohexane-1,4-diyl, in which one or two non-adjacent $CH_2$ groups may be replaced, independently of one another, by O and/or S, and one or more H atoms may be replaced by F, cyclohexene-1,4-diyl, bicyclo[1.1.1]pentane-1,3-diyl, bicyclo[2.2.2]octane-1,4-diyl, spiro[3.3]heptane-2,6-diyl, tetrahydropyran-2,5-diyl, or 1,3-dioxane-2,5-diyl;

$Z^{81}$ and $Z^{82}$ each, independently of one another, denote —$CF_2$O—, —$OCF_2$—, —$CH_2$O—, —$OCH_2$—, —CO—O—, —O—CO—, —$C_2H_4$—, —$C_2F_4$, —$CF_2CH_2$—, —$CH_2CF_2$—, —CFHCFH—, —$CFHCH_2$—, —$CH_2$CFH—, —$CF_2$CFH—, —$CFHCF_2$—, —CH═CH—, —CF═CH—, —CH═CF—, —CF═CF—, —C≡C—, or a single bond;

n denotes 0, 1, 2, or 3, preferably 0, 1, or 2, very preferably 0 or 1, particularly preferably 0; and m denotes 0, 1, 2, or 3, preferably 0, 1, or 2, very preferably 1 or 2, in particular 1, where the compounds of the formula I are excluded from formula VIII.

$A^{81}$ and $A^{82}$ in formula I preferably denote phenylene-1,4-diyl, which may also be mono- or polysubstituted by F, furthermore cyclohexane-1,4-diyl, cyclohexenylene-1,4-diyl, tetrahydropyran-2,5-diyl, or 1,3-dioxane-2,5-diyl, very preferably phenylene-1,4-diyl, which may also be mono- or polysubstituted by F, or cyclohexane-1,4-diyl.

$Z^{81}$ and $Z^{82}$ in formula I preferably denote —$CF_2$O—, —$OCF_2$—, or a single bond, very preferably a single bond.

$A^{81}$ and $A^{82}$ in formula I particularly preferably denote

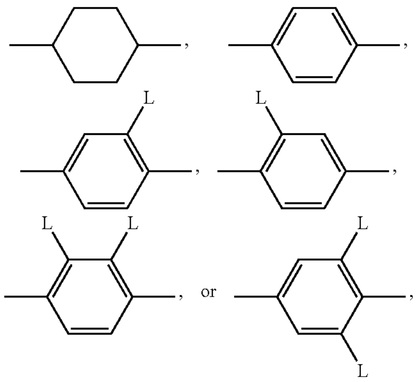

in which L denotes halogen, $CF_3$, or CN, preferably F.

Preference is furthermore given to compounds of the formula VIII in which $R^{81}$ and $R^{82}$ each, independently of one another, denote H, F, or an alkyl, alkoxy, alkenyl, or alkynyl group having 1 to 8, preferably 1 to 5, C atoms, each of which is optionally substituted by halogen, in particular by F.

$R^{81}$ and $R^{82}$ preferably denote H, an optionally fluorinated alkyl or alkoxy group having 1 to 7 C atoms, an optionally fluorinated alkenyl or alkynyl group having 2 to 7 C atoms, or an optionally fluorinated cycloalkyl group having 3 to 12 C atoms.

Preferably, at least one of $R^{81}$ and $R^{82}$ is not H, particularly preferably both of $R^{81}$ and $R^{82}$ are not H. $R^{81}$ is very particularly preferably an alkyl group. $R^{82}$ is furthermore preferably H, an alkyl group, or fluorine. Very particularly preferably, $R^{81}$ is an alkyl group and $R^{82}$ is H or an alkyl group. $R^{81}$, $R^{82}$ each, independently of one another, very particularly preferably denote an unbranched alkyl group having 1 to 5 C atoms. If $R^{81}$ and $R^{82}$ denote a substituted alkyl, alkoxy, alkenyl, or alkynyl group, the total number of C atoms in the two groups $R^{81}$ and $R^{82}$ is preferably fewer than 10.

Preferred compounds of the formula VIII are selected from the following sub-formulae, more preferably from the compounds of the formula VIII-3:

VIII-1

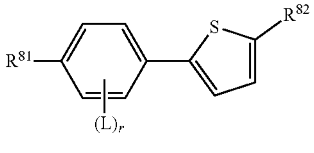

VIII-2

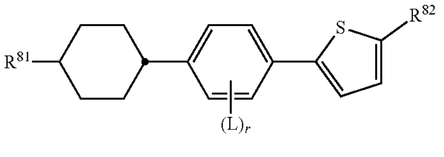

-continued

VIII-3

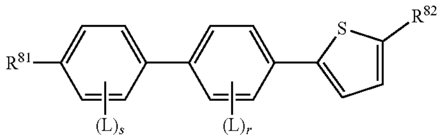

VIII-4

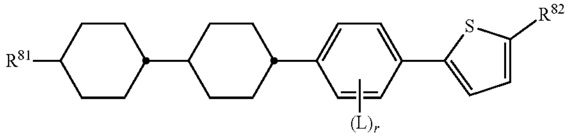

VIII-5

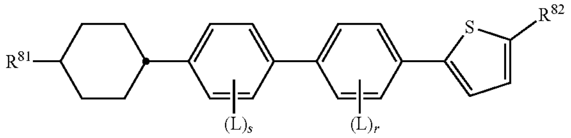

VIII-6

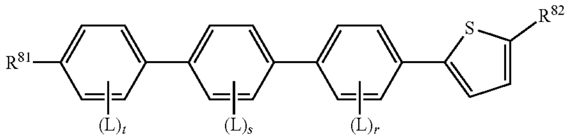

in which $R^{81}$ and $R^{82}$ have the meanings indicated above, L denotes F, and r, s, and t independently are 0, 1, 2, 3, or 4. r preferably is 1 or 2, very preferably 2, and s and t independently are preferably 0 or 1, very preferably 0. $R^{81}$ and $R^{82}$ in particular independently denote n-alkyl having 1 to 5 C atoms.

In a first very preferred embodiment, the compounds of the formulae VIII-1 to VIII-6 are selected from the compounds of the formula VIII-1a to VIII-6a, in particular of the formula VIII-3a:

VIII-1a

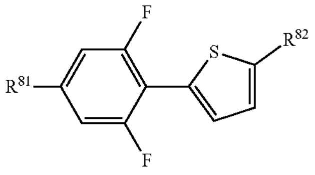

VIII-2a

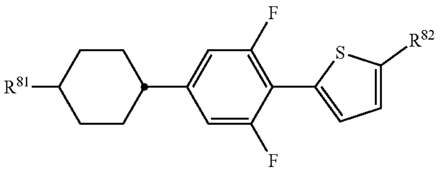

VIII-3a

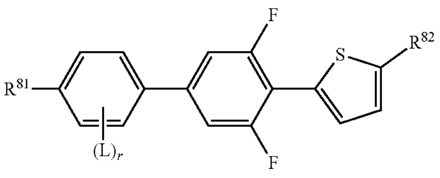

-continued

VIII-4a

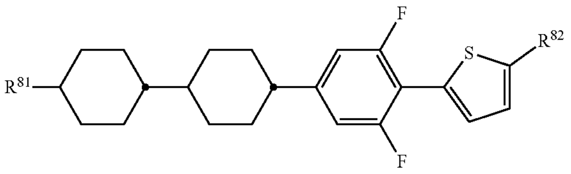

VIII-5a

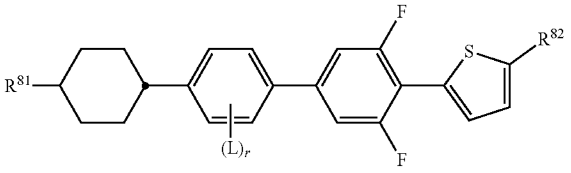

VIII-6a

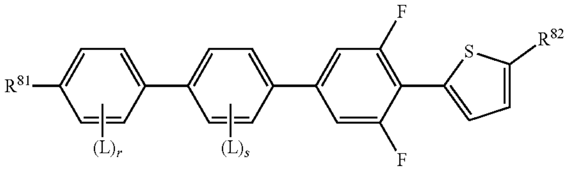

in which $R^{81}$, $R^{82}$, L, r, and s have the meanings defined above.

In a second very preferred embodiment, the compounds of the formulae VIII-1 to VIII-6 are selected from the compounds of the formulae VIII-1b to VIII-5b, in particular of the formula VIII-2b:

VIII-1b

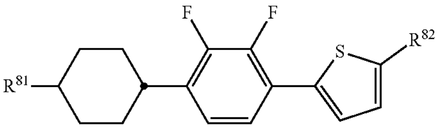

VIII-2b

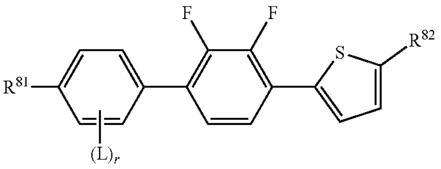

VIII-3b

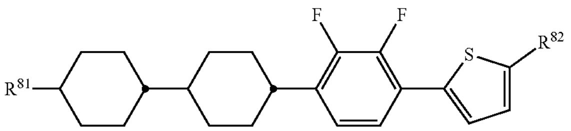

VIII-4b

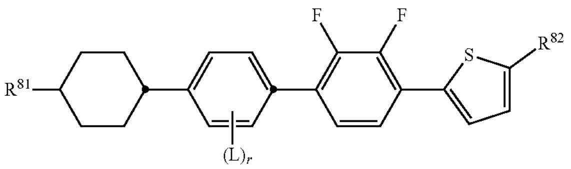

-continued

VIII-5b

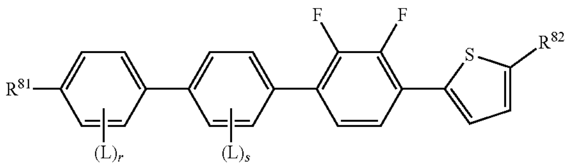

in which $R^{81}$, $R^{82}$, L, r, and s have the meanings defined above.

In a third very preferred embodiment, the compounds of the formulae VIII-1 to VIII-6 are selected from the compounds of the formulae VIII-1c to VIII-6c, in particular of the formula VIII-3c:

VIII-1c

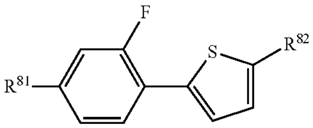

VIII-2c

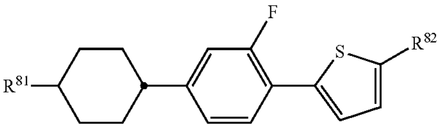

VIII-3c

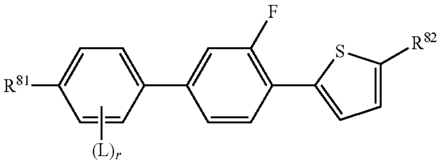

VIII-4c

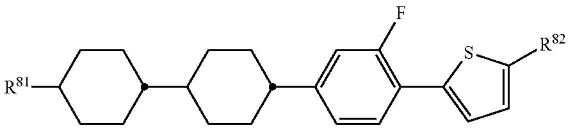

VIII-5c

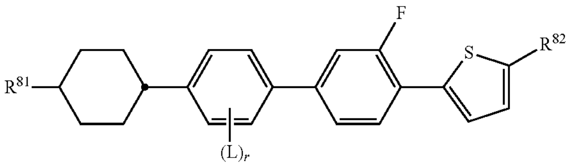

VIII-6c

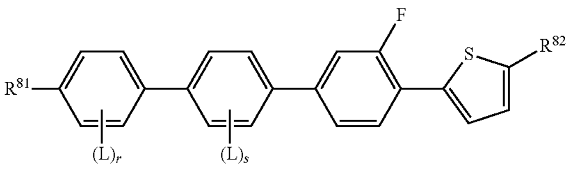

in which $R^{81}$, $R^{82}$, L, r, and s have the meanings defined above.

In a fourth very preferred embodiment, the compounds of the formulae VIII-1 to VIII-6 are selected from the compounds of the formulae VIII-1d to VIII-6d, in particular of the formula VIII-3d: 5

VIII-1d

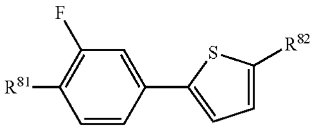

VIII-2d

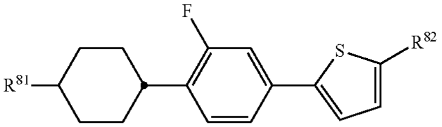

VIII-3d

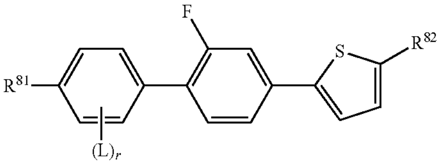

VIII-4d

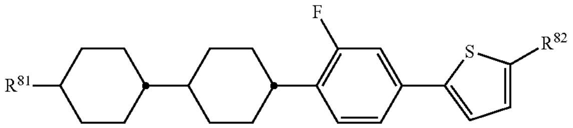

VIII-5d

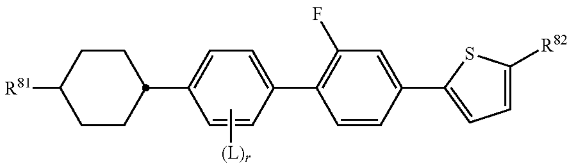

VIII-6d

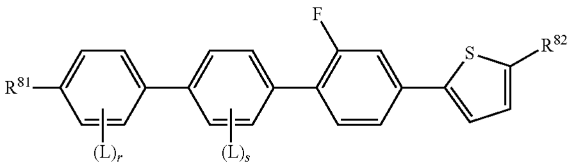

in which $R^{81}$, $R^{82}$, L, r and s have the meanings defined above.

In a particularly preferred embodiment, the medium according to the invention comprises one or more compounds selected from the group of the formulae VIII-1a to VIII-6a and one or more compounds selected from the group of the formulae VIII-1b to VIII-6b.

Very particularly preferably the medium comprises one or more compounds selected from the group of compounds of the formulae VIII-3a, VIII-2b, VIII-3c, and VIII-3d:

VIII-3a

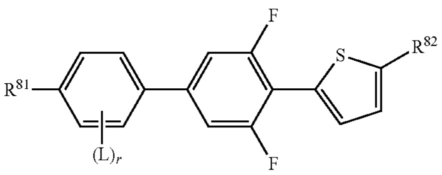

-continued
VIII-2b
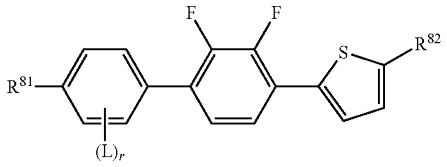
VIII-3c
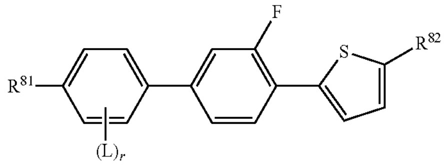
VIII-3d
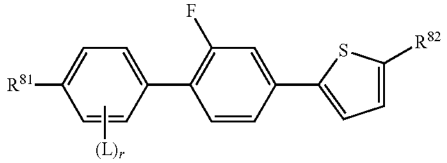
in which $R^{81}$, $R^{82}$, L, and r have the meanings defined above and preferably r is 0.
Most preferred compounds of formula VIII include, in particular, one or more of the following:
VIII-3a-1
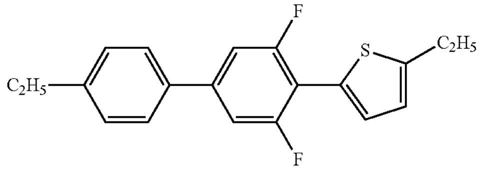
VIII-3a-2
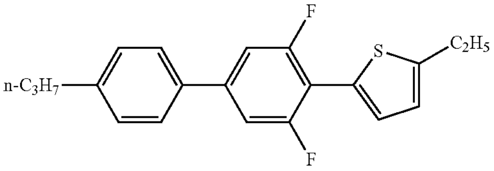
VIII-3a-3
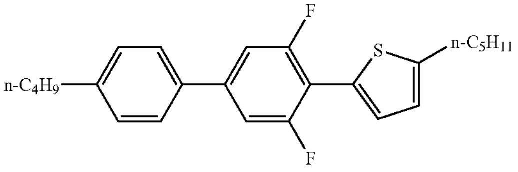
VIII-3a-4
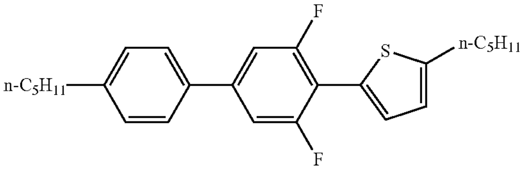
-continued
VIII-3a-5
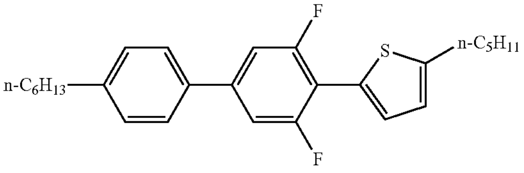
VIII-3a-6
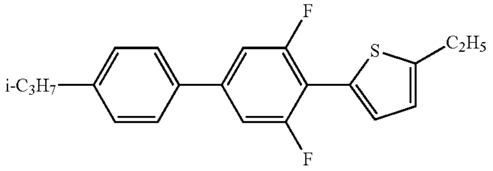
VIII-2b-1
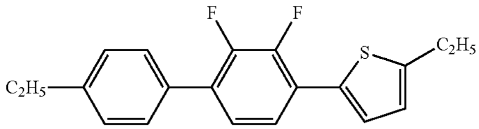
VIII-2b-2
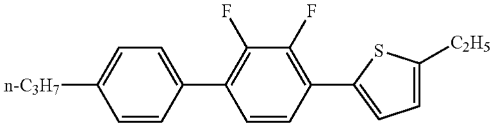
VIII-2b-3
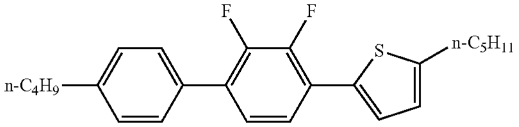
VIII-2b-4
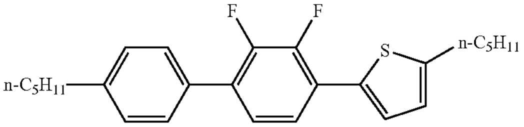
VIII-2b-5
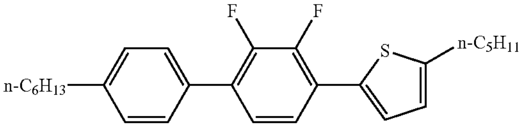
VIII-2b-6
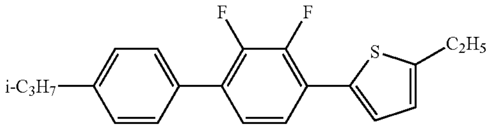
VIII-2c-1
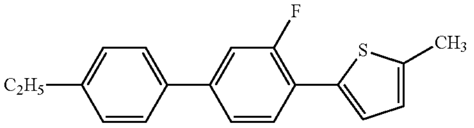

-continued
VIII-2c-2
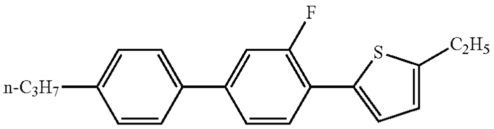
VIII-2c-3
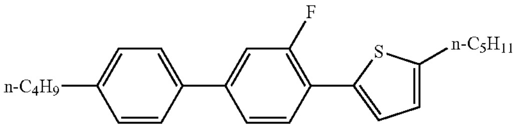
VIII-2c-4
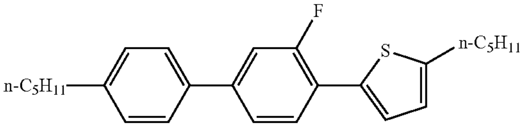
VIII-2c-5
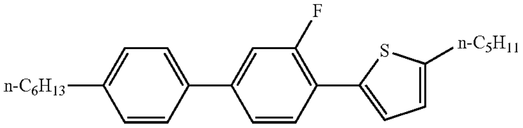
VIII-2c-6
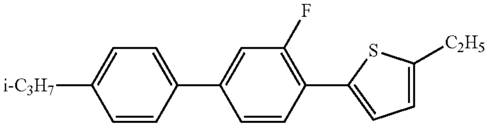
Alternatively, or additionally, the following compounds of formula VIII can be used:
VIII-3a-7
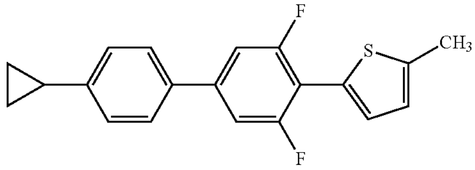
VIII-3a-8
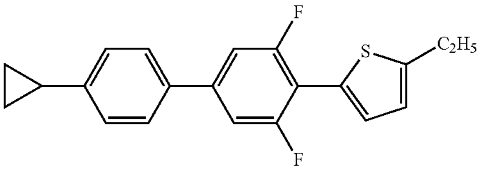
VIII-3a-9
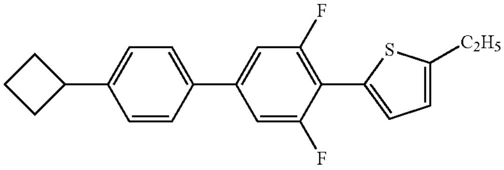
-continued
VIII-3a-10
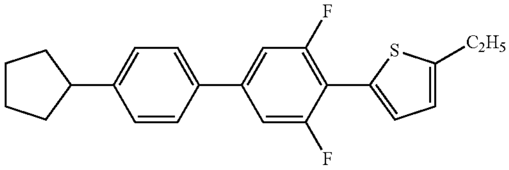
VIII-3a-11
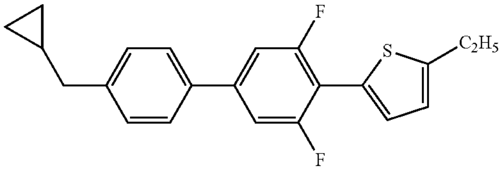
VIII-3a-12
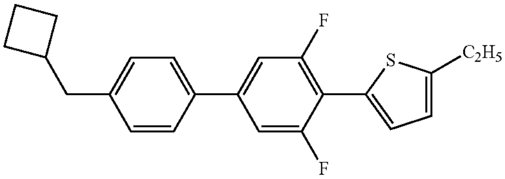
VIII-3a-13
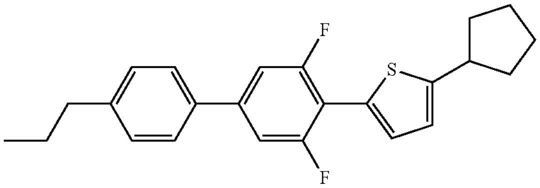
VIII-3a-14
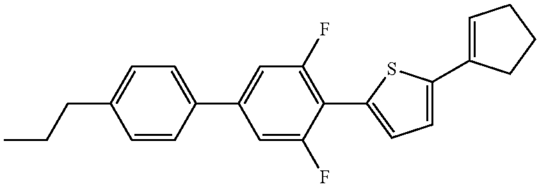
VIII-3a-15
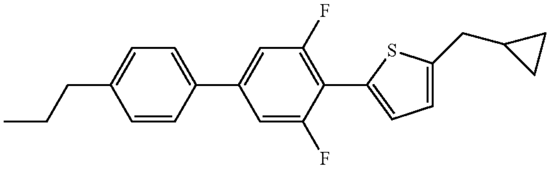
VIII-2b-7
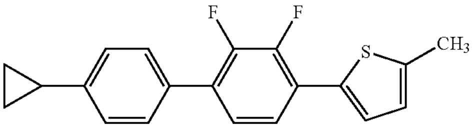
VIII-2b-8
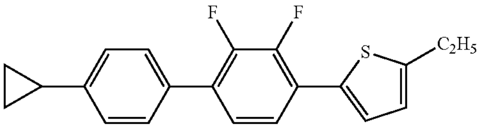

-continued
VIII-2b-9
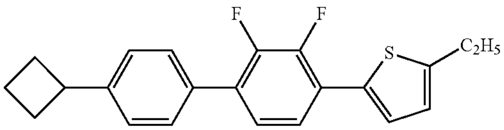
VIII-2b-10
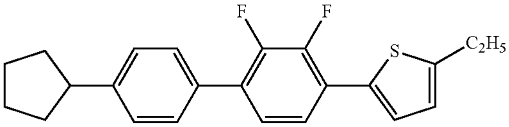
VIII-2b-11
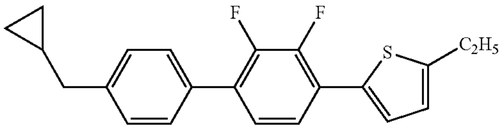
VIII-2b-12
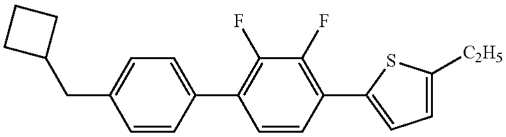
VIII-2b-13
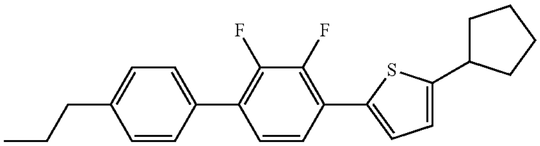
VIII-2b-14
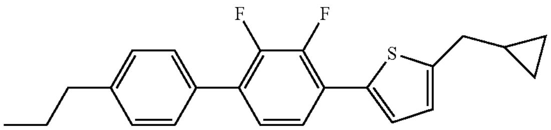
VIII-3c-7
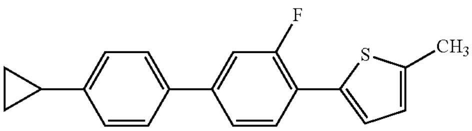
VIII-3c-8
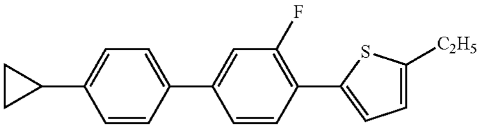
VIII-3c-9
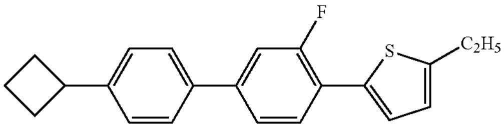
VIII-3c-10
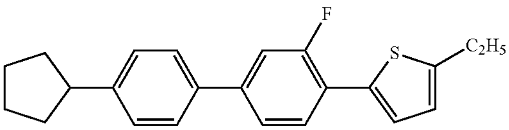
-continued
VIII-3c-11
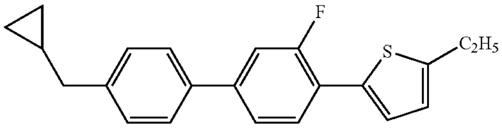
VIII-3c-12
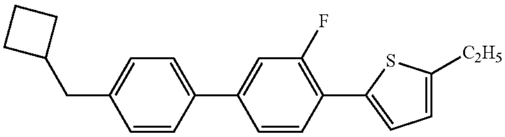
VIII-3c-13
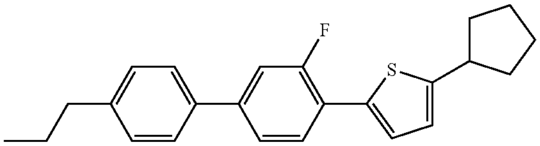
VIII-3c-14
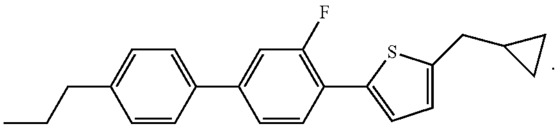
The medium according to the invention optionally comprises one or more compounds with negative dielectric anisotropy, preferably selected from the group consisting of the formulae Y, B, BC, CR, PH-1 and PH-2:
Y
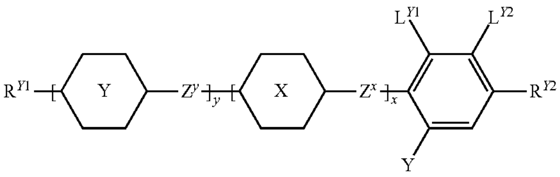
B
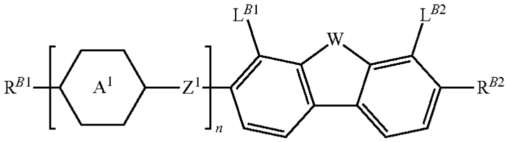
BC
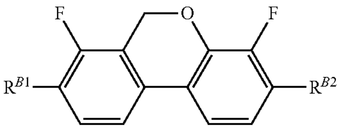
CR
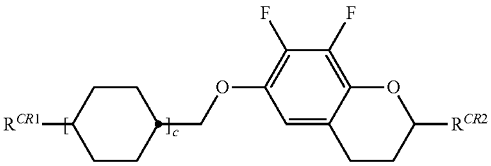

-continued

PH-1

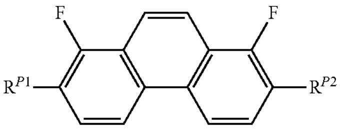

PH-2

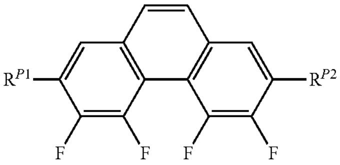

in which $R^{Y1}$, $R^{Y2}$, $R^{B1}$, $R^{B2}$, $R^{CR1}$, $R^{CR2}$, $R^{P1}$, and $R^{P2}$ each, independently of one another, denote H, a straight-chain alkyl or alkoxy group each having 1 to 15 C atoms, a straight-chain alkenyl or alkenyloxy group each having 2 to 15 C atoms, or a branched alkyl, alkoxy, alkenyl, or alkenyloxy group each having 3 to 15 C atoms, where one or more $CH_2$ groups in these radicals may each be replaced, independently of one another, by

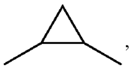, 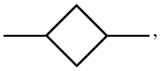, 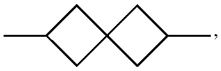, 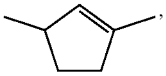, 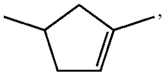, 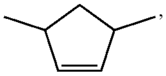,

—CH═CH—, —C≡C—, $—CF_2O—$, $—OCF_2—$, —O—, —CO—O—, or —O—CO— in such a way that O atoms are not linked directly to one another, and in which one or more H atoms may be replaced by halogen;

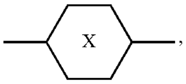, 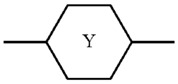 and 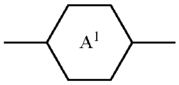

on each occurrence, independently of one another, denote a) 1,4-cyclohexenylene or 1,4-cyclohexylene radical, in which one or two non-adjacent $CH_2$ groups may be replaced by —O— or —S—, b) a 1,4-phenylene radical, in which one or two CH groups may be replaced by N, or c) a radical from the group spiro[3.3]heptane-2,6-diyl, 1,4-bicyclo[2.2.2]octylene, naphthalene-2,6-diyl, decahydronaphthalene-2,6-diyl, 1,2,3,4-tetrahydronaphthalene-2,6-diyl, phenanthrene-2,7-diyl and fluorene-2,7-diyl, where the radicals a), b), and c) may be mono- or polysubstituted by halogen atoms, preferably

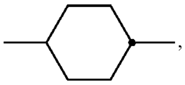, 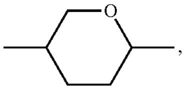, 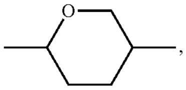,

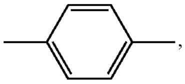, 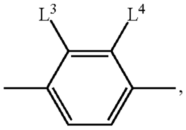, 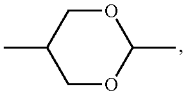,

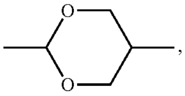, 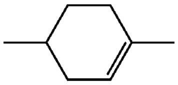 or

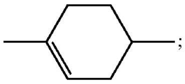;

$Z^x$, $Z^y$ identically or differently denote $—CH_2CH_2—$, —CH═CH—, $—CF_2O—$, $—OCF_2—$, $—CH_2O—$, $—OCH_2—$, —CO—O—, —O—CO—, $—C_2F_4—$, —CF═CF—, $—CH═CH—CH_2O—$, or a single bond, preferably a single bond;

$Z^1$ on each occurrence independently of one another denotes —CO—O—, —O—CO—, $—CF_2O—$, $—OCF_2—$, $—CH_2O—$, $—OCH_2—$, $—CH_2—$, $—CH_2CH_2—$, $—(CH_2)_4—$, $—CH═CH—CH_2O—$, $—C_2F_4—$, $—CH_2CF_2—$, $—CF_2CH_2—$, —CF═CF—, —CH═CF—, —CF═CH—, —CH═CH—, —C≡C—, or a single bond, preferably $CH_2O$ or a single bond;

$L^{Y1}$, $L^{Y2}$, $L^{B1}$, $L^{B2}$, $L^3$, and $L^4$ each, independently of one another, denote F, Cl, $CF_3$ or $CHF_2$, preferably F;

W denotes O or S;

n is 0, 1, or 2, preferably 0 or 1;

c is 0, 1, or 2, preferably 1 or 2; and x and y independently are 0, 1, or 2, where $x+y \leq 3$.

The compounds of the formula Y are preferably selected from the group of compounds of the formulae YA, YB, YC, and YD:

YA

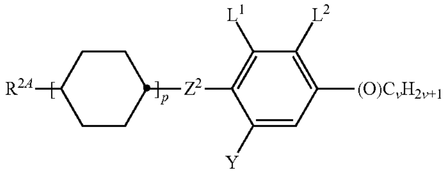

YB

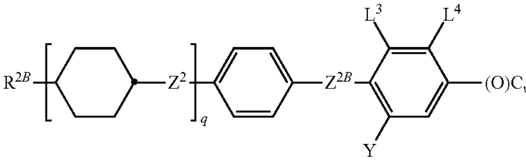

YC

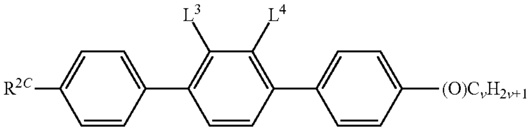

-continued

YD

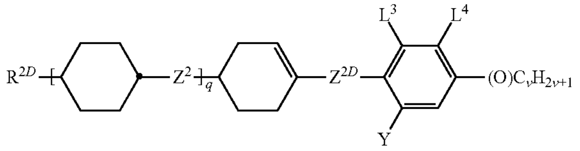

in which $R^{2A}$, $R^{2B}$, $R^{2C}$ and $R^{2D}$ each, independently of one another, denote H, an alkyl or alkenyl radical having up to 15 C atoms which is unsubstituted, monosubstituted by CN or $CF_3$, or at least monosubstituted by halogen, where, in addition, one or more $CH_2$ groups in these radicals may be replaced by —O—, —S—,

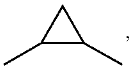, 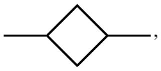, 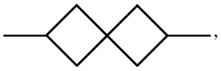, 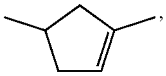, 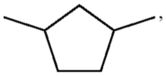,

—C≡C—, —$CF_2$O—, —O$CF_2$—, —OC—O—, or —O—CO— in such a way that O atoms are not linked directly to one another;

$L^1$ to $L^4$ each, independently of one another, denote F, Cl, $CF_3$, or $CHF_2$;

Y denotes H, F, Cl, $CF_3$, $CHF_2$, or $CH_3$, preferably H or $CH_3$, very preferably H;

$Z^2$, $Z^{2B}$ and $Z^{2D}$ each, independently of one another, denote a single bond, —$CH_2CH_2$—, —CH═CH—, —$CF_2$O—, —O$CF_2$—, —$CH_2$O—, —O$CH_2$—, —COO—, —OCO—, —$C_2F_4$—, —CF═CF—, or —CH═CHC$H_2$O—;

(O) denotes O or a single bond;

p denotes 0, 1, or 2;

q denotes 0 or 1; and v denotes 1, 2, 3, 4, 5, or 6.

Preferred compounds of the formulae YA, YB, YC, and YD are indicated below:

YA-1

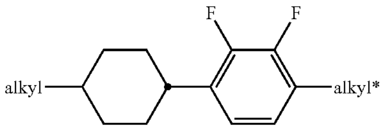

YA-2

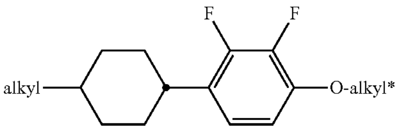

YA-3

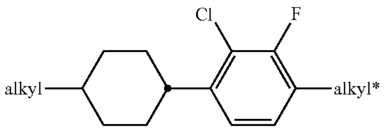

-continued

YA-4

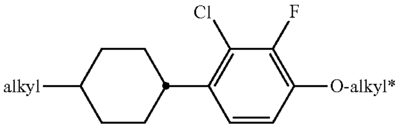

YA-5

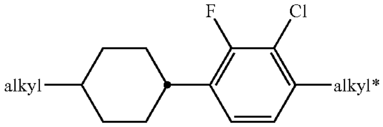

YA-6

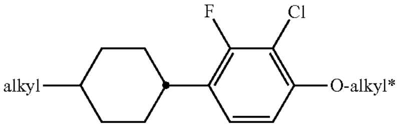

YA-7

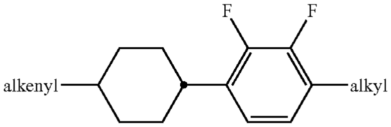

YA-8

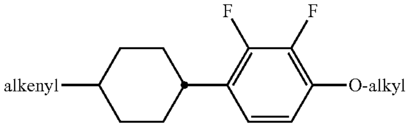

YA-9

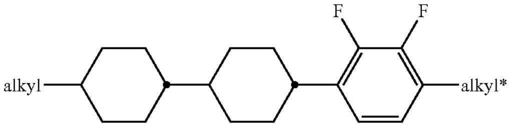

YA-10

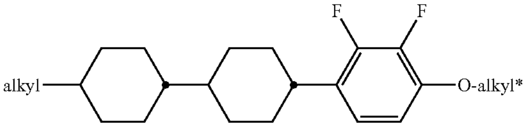

YA-11

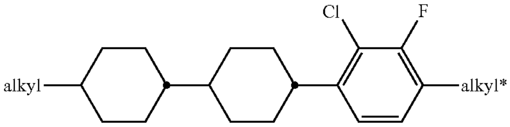

YA-12

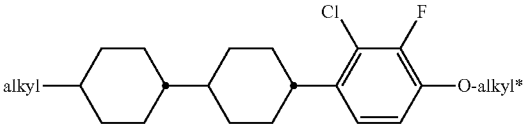

YA-13

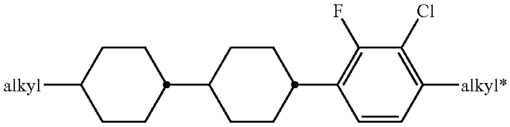

-continued
YA-14
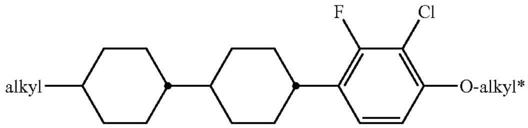
YA-15
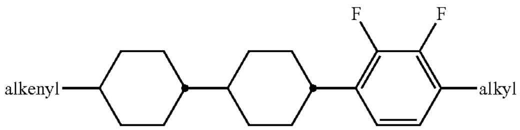
YA-16
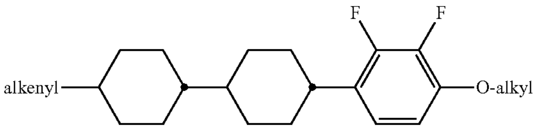
YA-17
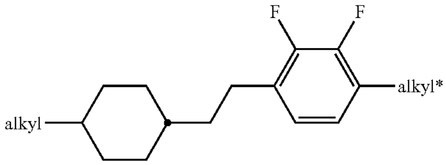
YA-18
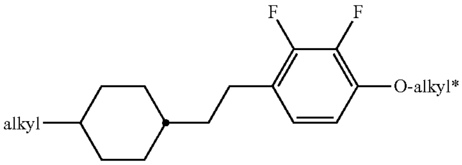
YA-19
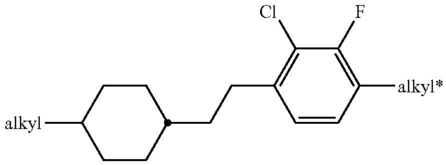
YA-20
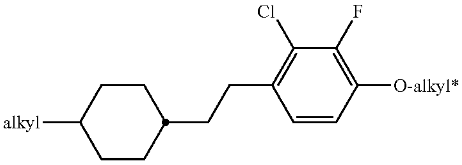
YA-21
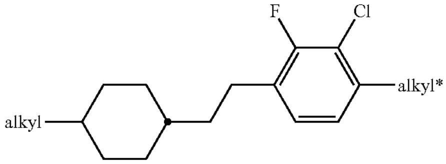
YA-22
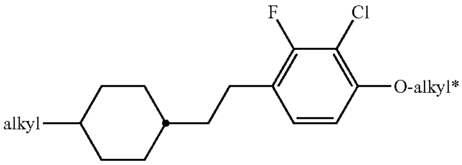
-continued
YA-23
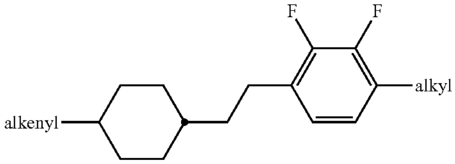
YA24
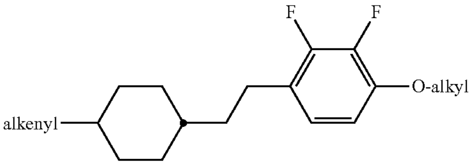
YA-25
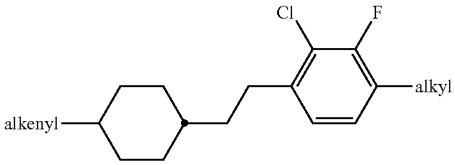
YA-26
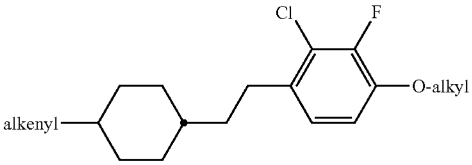
YA-27
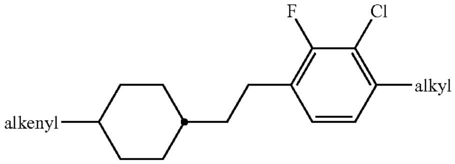
YA-28
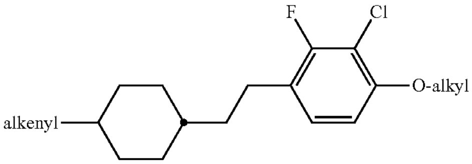
YA-29
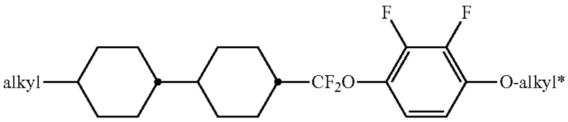
YA-30
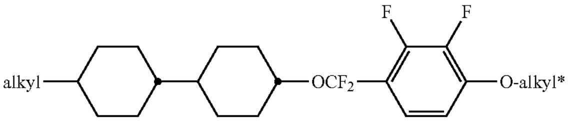
YA-31
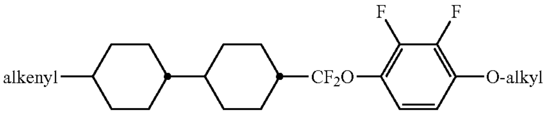

-continued
YA-32
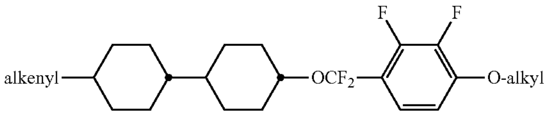
YA-33
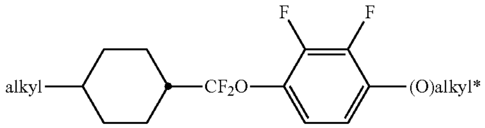
YA-34
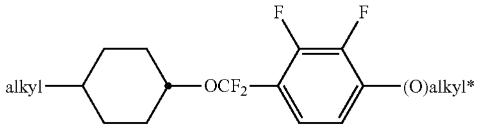
YA-35
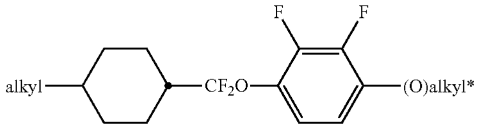
YA-36
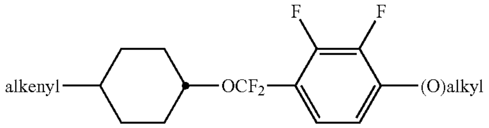
YA-37
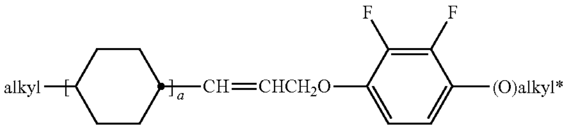
YA-38
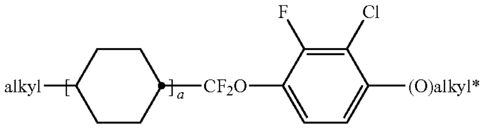
YA-39
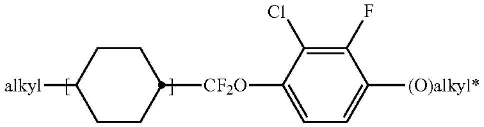
YA-40
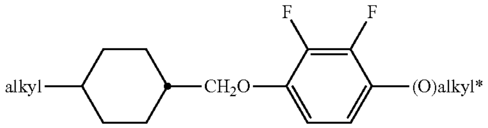
YA-41
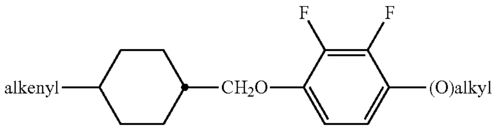
YA-42
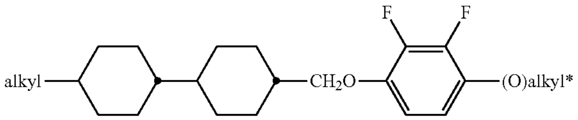
YA-43
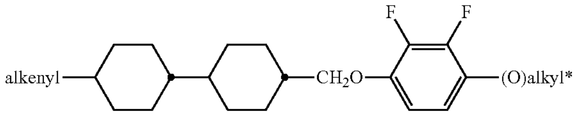
YA-44
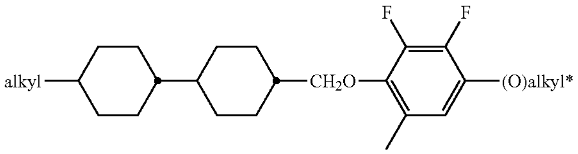
YA-45
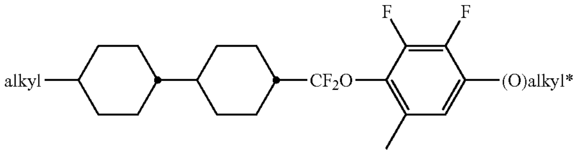
YB-1
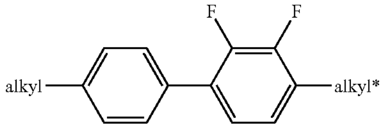
YB-2
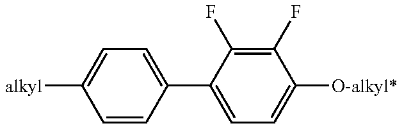
YB-3
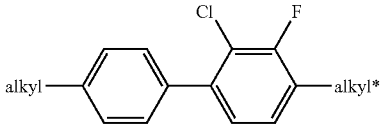
YB-4
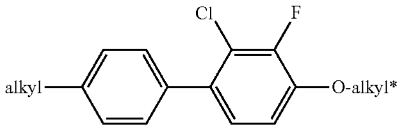
YB-5
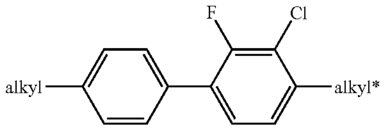
YB-6
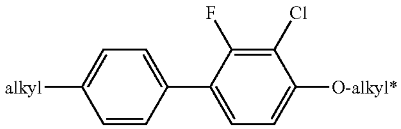

-continued
YB-7
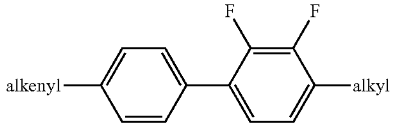
YB-8
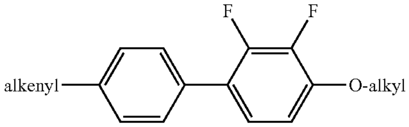
YB-9
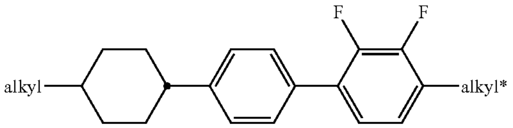
YB-10
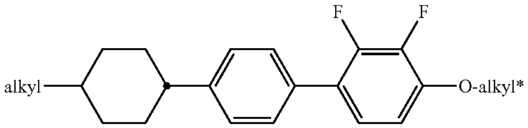
YB-11
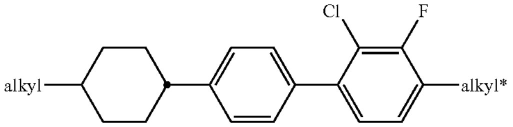
YB-12
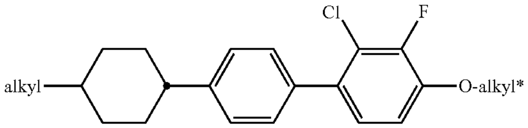
YB-13
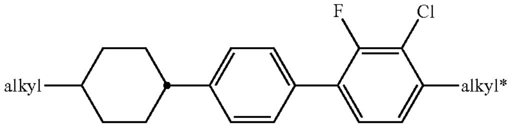
YB-14
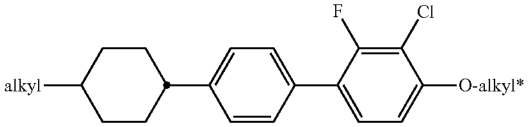
YB-15
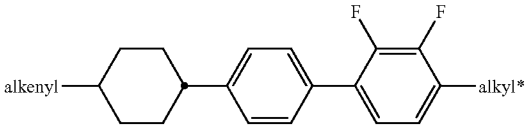
YB-16
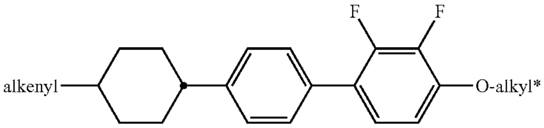
-continued
YB-17
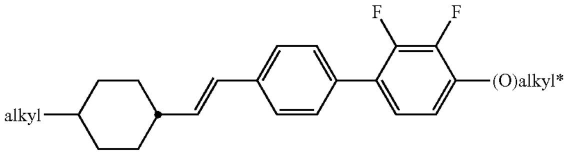
YB-18
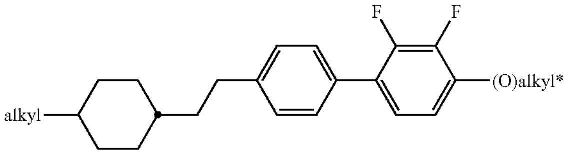
YB-19
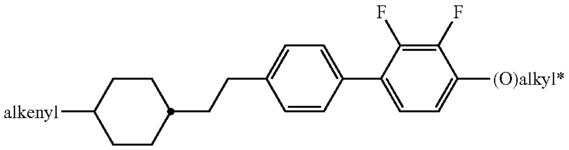
YB-20
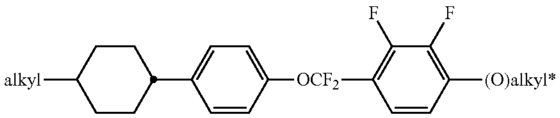
YB-21
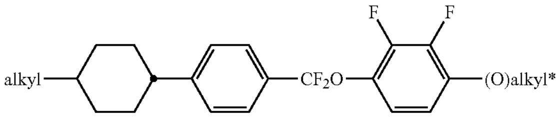
YB-22
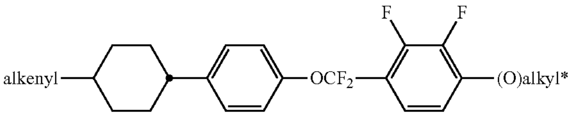
YB-23
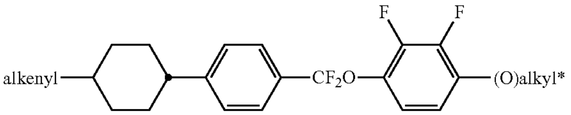
YB-24
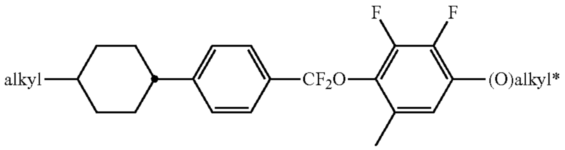
YC-1
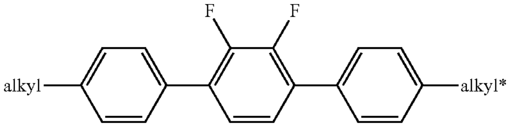
YC-1
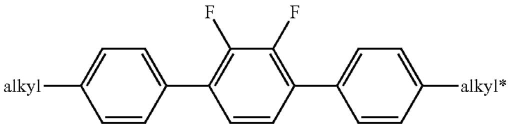

-continued

YD-1

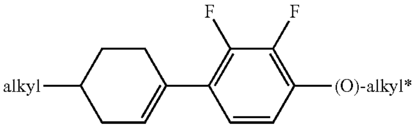

YD-2

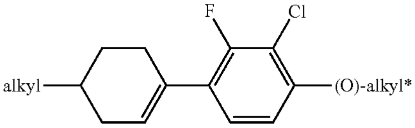

YD-3

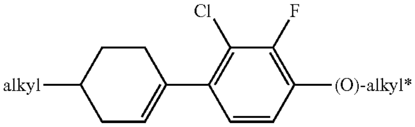

YD-4

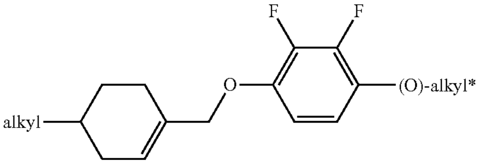

YD-5

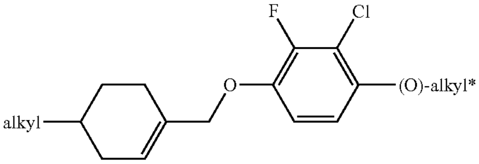

YD-6

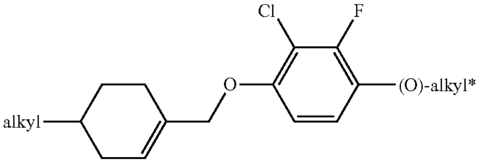

YC-1

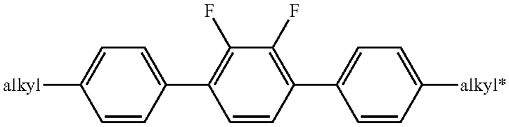

YD-7

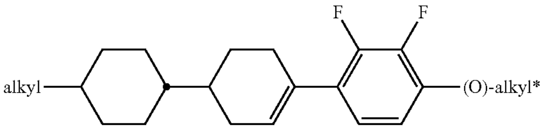

YD-8

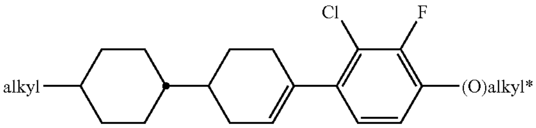

YD-9

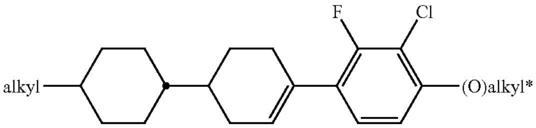

-continued

YD-10

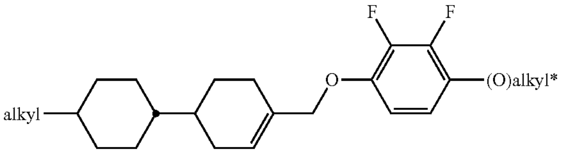

YD-11

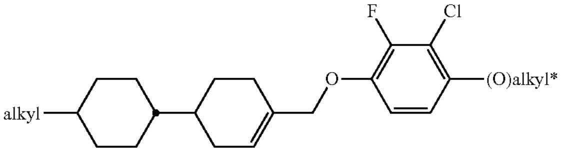

YD-12

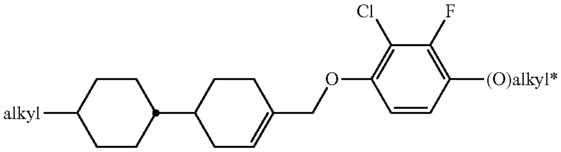

YC-1

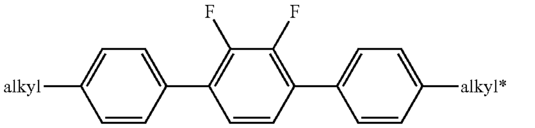

YD-13

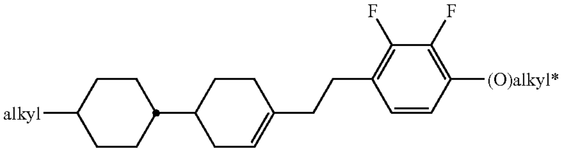

YD-14

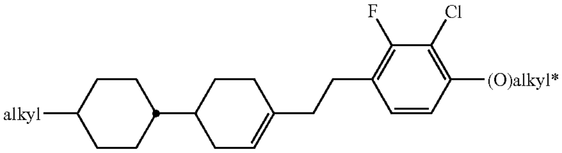

YD-15

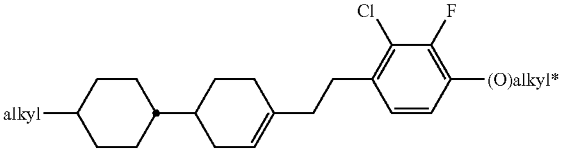

in which a denotes 1 or 2;

alkyl and alkyl* each, independently of one another, denote a straight-chain alkyl radical having 1-6 C atoms;

alkenyl denotes a straight-chain alkenyl radical having 2-6 C atoms; and (O) denotes an oxygen atom or a single bond.

Alkenyl preferably denotes $CH_2{=}CH{-}$, $CH_2{=}CHCH_2CH_2{-}$, $CH_3{-}CH{=}CH{-}$, $CH_3{-}CH_2{-}$ $CH=CH-$, $CH_3-(CH_2)_2-CH=CH-$, $CH_3-(CH_2)_3-CH=CH-$, or $CH_3-CH=CH-(CH_2)_2-$.

Particularly preferred mixtures according to the invention comprise one or more compounds of the formulae YA-2, YA-8, YA-10, YA-16, YA-18, YA-40, YA-41, YA-42, YA-43, YB-2, YB-10, YB-16, YC-1, YD-4, and YD-10.

The proportion of compounds of the formulae YA and/or YB in the mixture as a whole is preferably at least 20% by weight.

Preferred media according to the invention comprise at least one compound of the formula YC-1:

YC-1

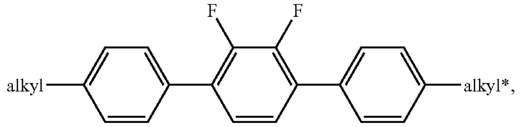

in which alkyl and alkyl* have the meanings indicated above, preferably in amounts of <5% by weight, in particular >3% by weight.

The compounds of formula B are preferably selected from the compounds of the formula B-1 and/or B-2:

B-1

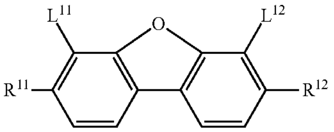

B-2

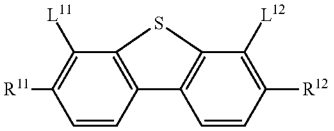

in which $R^{11}$ and $R^{12}$ each, independently of one another, denotes an alkyl, alkenyl, or alkoxy radical having up to 15 C atoms, more preferably one or both of them denote an alkoxy radical; and $L^{11}$ and $L^{12}$ each denote F.

Preferably, the compounds of the formula B-1 are selected from the group of compounds of formulae B-1-1 to B-1-10, preferably of formula B-1-6:

B-1-1

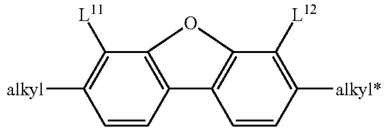

B-1-2

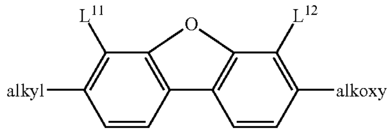

-continued

B-1-3

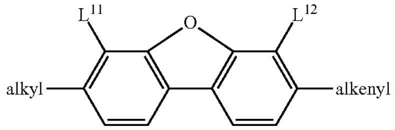

B-1-4

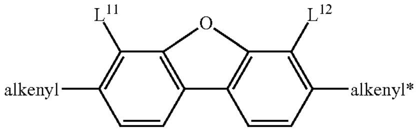

B-1-5

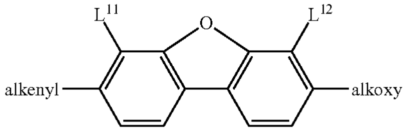

B-1-6

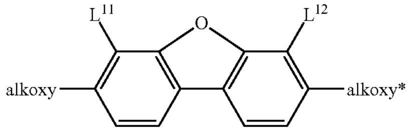

B-1-7

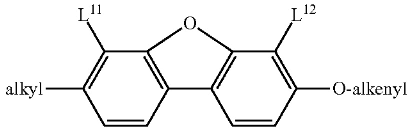

B-1-1

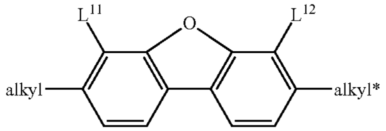

B-1-8

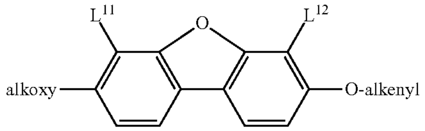

B-1-9

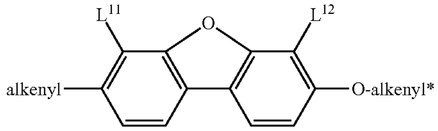

B-1-10

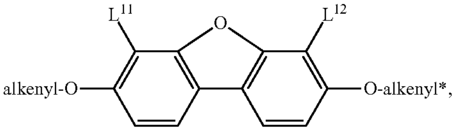

in which alkyl and alkyl* each, independently of one another, denote a straight-chain alkyl radical having 1-6 C atoms;

alkenyl and alkenyl* each, independently of one another, denote a straight-chain alkenyl radical having 2-6 C atoms;

alkoxy and alkoxy* each, independently of one another, denote a straight-chain alkoxy radical having 1-6 C atoms; and $L^{11}$ and $L^{12}$ each, independently of one another, denote F or Cl, preferably both F.

Preferably, the compounds of the formula B-2 are selected from the group of compounds of formulae B-2-1 to B-2-10, preferably of formula B-2-6:

B-2-1

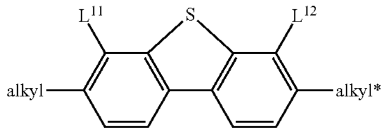

B-2-1

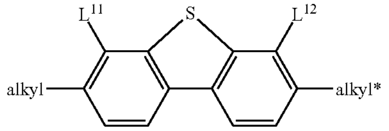

B-2-2

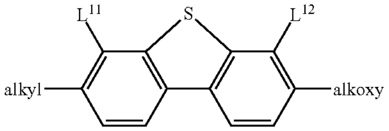

B-2-3

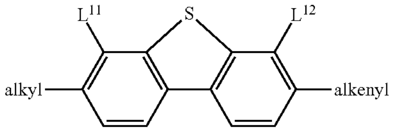

B-2-4

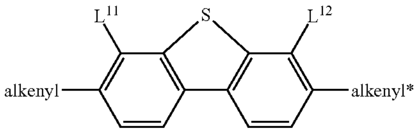

B-2-5

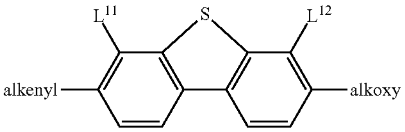

B-2-6

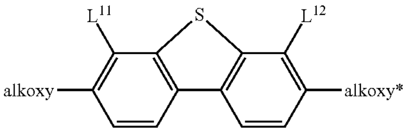

B-2-7

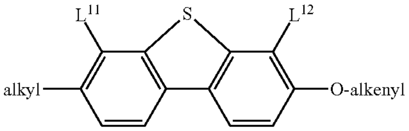

B-2-8

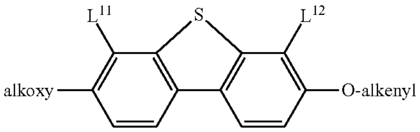

B-2-1

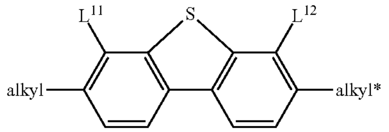

-continued

B-2-9

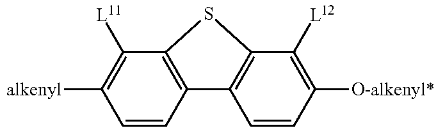

B-2-10

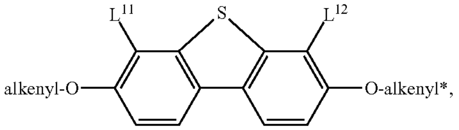

in which alkyl and alkyl* each, independently of one another, denote a straight-chain alkyl radical having 1-6 C atoms;

alkenyl and alkenyl* each, independently of one another, denote a straight-chain alkenyl radical having 2-6 C atoms;

alkoxy and alkoxy* each, independently of one another, denote a straight-chain alkoxy radical having 1-6 C atoms; and $L^{11}$ and $L^{12}$ each, independently of one another, denote F or Cl, preferably both F.

Optionally the medium comprises one or more compounds of the formula BA-1 and/or BA-2:

BA-1

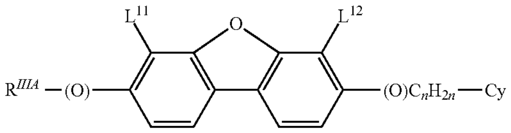

BA-2

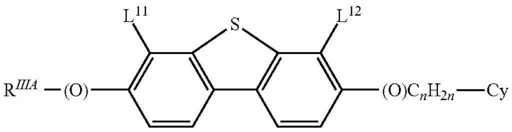

in which $L^{11}$ and $L^{12}$ have the same meanings of $L^{B1}$ and $L^{B2}$ as given under formula B;

(O) denotes O or a single bond;

$R^{IIIA}$ denotes alkyl or alkenyl having up to 7 C atoms or a group Cy-$C_mH_{2m}$—;

m and n are, identically or differently, 0, 1, 2, 3, 4, 5, or 6, preferably 1, 2, or 3, very preferably 1; and Cy denotes a cycloaliphatic group having 3, 4, or 5 ring atoms, which is optionally substituted with alkyl or alkenyl group each having up to 3 C atoms, or with halogen or CN, and preferably denotes cyclopropyl, cyclobutyl, or cyclopentyl.

The compounds of formula BA-1 and/or BA-2 are contained in the medium either alternatively or in addition to the compounds of formula B, preferably additionally.

Very preferred compounds of the formulae BA-1 and BA-2 are the following:

BA-1-1

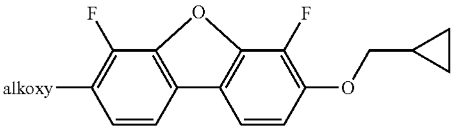

BA-1-2

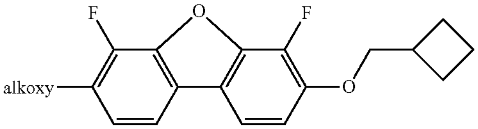

BA-1-3

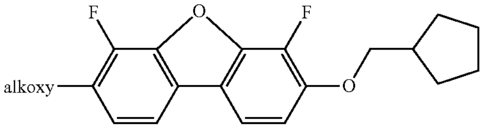

BA-1-1

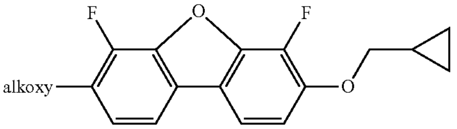

BA-2-1

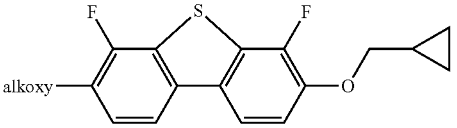

BA-2-2

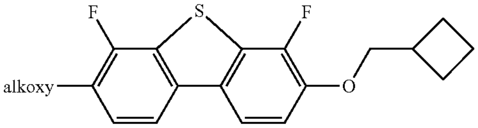

BA-2-3

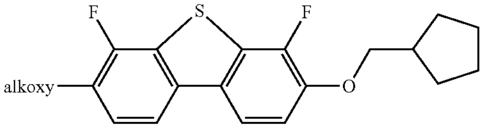

in which alkoxy denotes a straight-chain alkoxy radical having 1-6 C atoms or alternatively $-(CH_2)_nF$ in which n is 2, 3, 4, or 5, preferably $C_2H_4F$.

Alternatively, the medium comprises one or more compounds of the formula BAa-1-3:

BAa-1-3

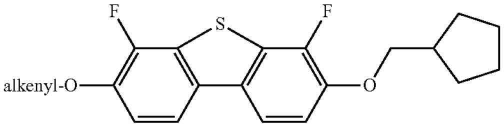

in which alkenyl denotes straight-chain alkenyl group having 2 to 6 C atoms, preferably 4 C atoms, very preferably $CH_3-CH=CH-CH_2-$.

In a preferred embodiment of the present invention, the medium comprises one or more compounds of formula B-3:

B-3

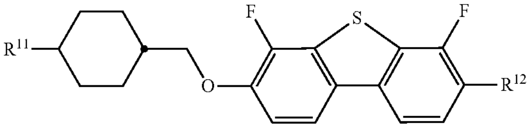

in which $R^{11}$, $R^{12}$ identically or differently, denote H or an alkyl or alkoxy radical having 1 to 15 C atoms, in which one or more $CH_2$ groups in these radicals are optionally replaced, independently of one another, by $-C\equiv C-$, $-CF_2O-$, $-OCF_2-$, $-CH=CH-$,

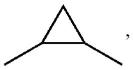 , 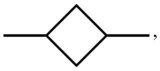 , 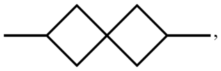 , 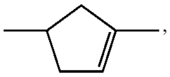 , 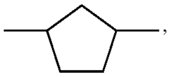 , $-O-$, $-CO-O-$, or $-O-CO-$ in such a way that O atoms are not linked directly to one another, and in which, in addition, one or more H atoms may be replaced by halogen.

The compounds of formula B-3 are preferably selected from the group of compounds of the formulae B-3-1 to B-3-10:

B-3-1

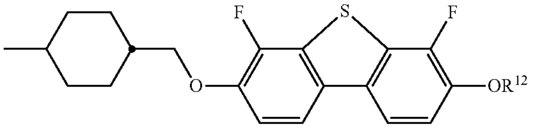

B-3-2

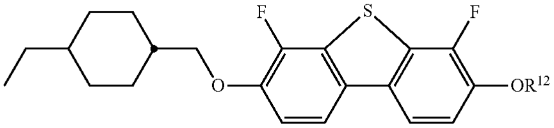

B-3-3

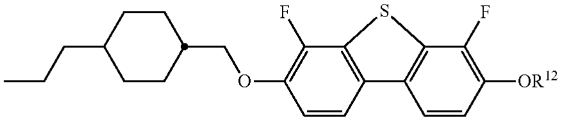

B-3-4

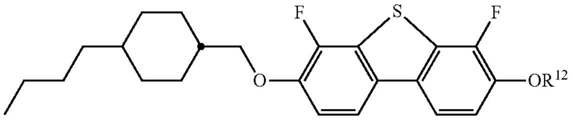

B-3-1

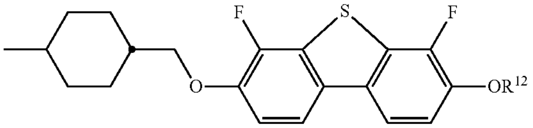

-continued

B-3-5

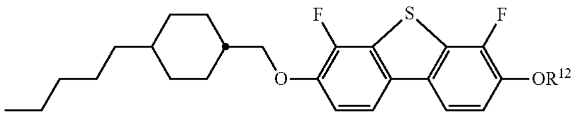

B-3-6

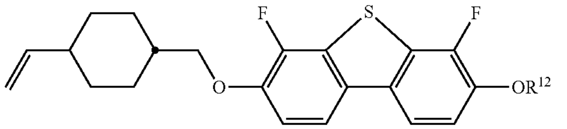

B-3-7

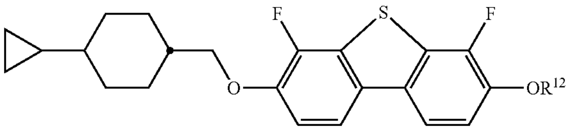

B-3-8

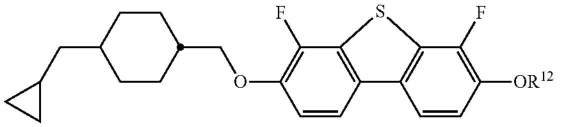

B-3-9

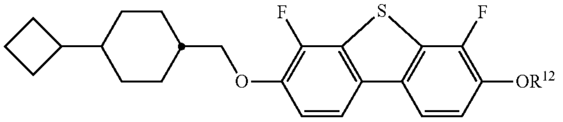

B-3-10

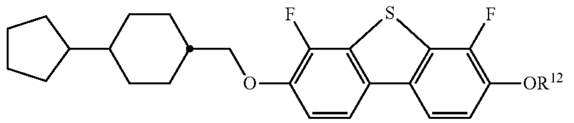

in which $R^{12}$ denotes alkyl having 1 to 7 C-atoms, preferably ethyl, n-propyl, or n-butyl, or alternatively cyclopropylmethyl, cyclobutylmethyl, or cyclopentylmethyl, or alternatively —$(CH_2)_nF$ in which n is 2, 3, 4, or 5, preferably $C_2H_4F$.

In a preferred embodiment of the present invention, the medium comprises one or more compounds of the formulae B-4 to B-6, preferably of formula B-5:

B-4

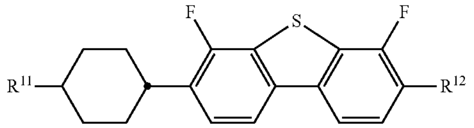

B-5

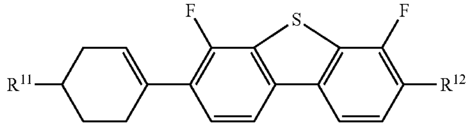

-continued

B-6

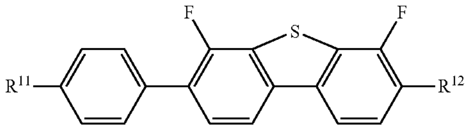

in which the occurring groups have the meanings given above, $R^{11}$ preferably denotes a straight-chain alkyl group having 1 to 7 C atoms, and $R^{12}$ preferably denotes an optionally fluorinated alkoxy group having 1 to 7 C atoms.

In a very preferred embodiment, the medium comprises one or more compounds of the formula B-5-1

B-5-1

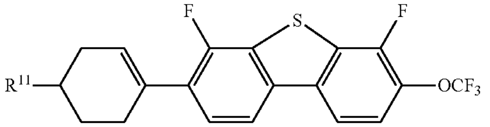

in which $R^{11}$ denotes a straight-chain alkyl group having 1 to 7 C atoms.

In a preferred embodiment the media comprise one or more compounds of the formula I selected from the group of compounds of formulae B-7 to B-9, preferably of formula B-8:

B-7

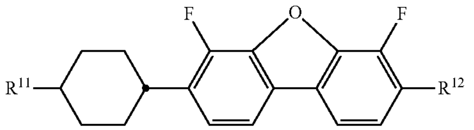

B-7

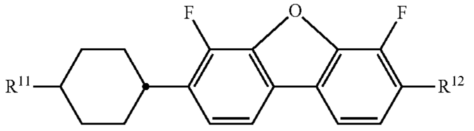

B-8

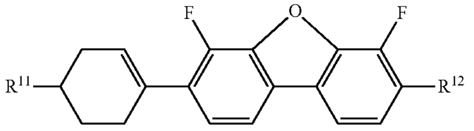

B-9

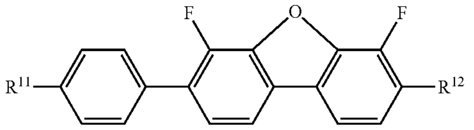

in which the parameters have the meanings given above, $R^{11}$ preferably denotes straight-chain alkyl and $R^{12}$ preferably denotes F or optionally fluorinated alkoxy each having 1 to 7 C atoms.

Particularly preferred compounds of the formulae BC, CR and PH-1 are the compounds BC-1 to BC-7, CR-1 to CR-5, and BP-1 to BP-7:

BC-1

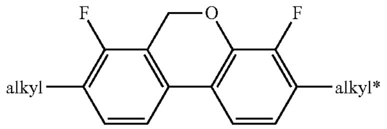

BC-2

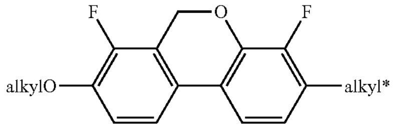

BC-3

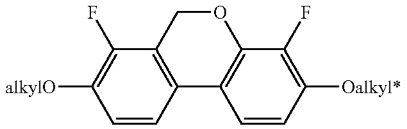

BC-4

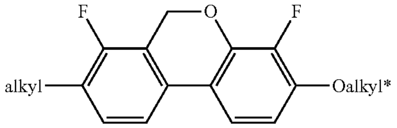

BC-5

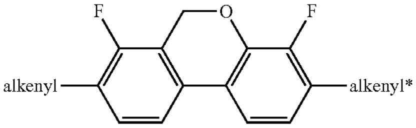

BC-6

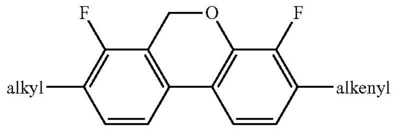

BC-7

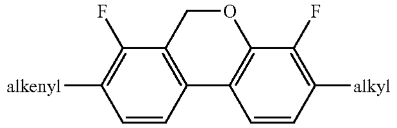

CR-1

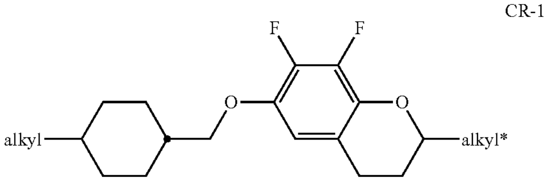

CR-2

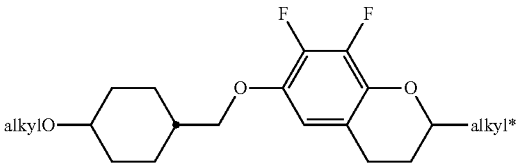

CR-3

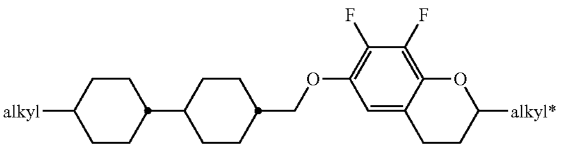

-continued

CR-4

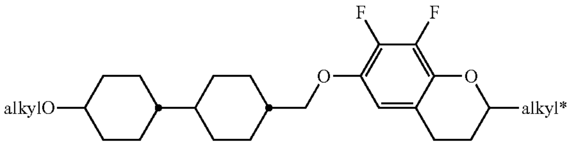

CR-5

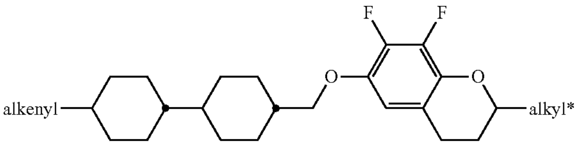

BP-1

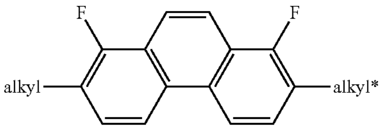

BP-2

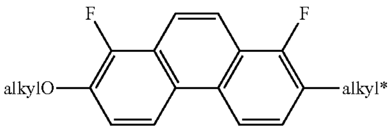

BP-3

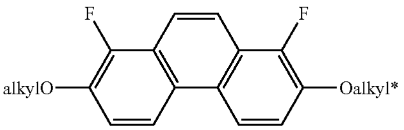

BP-4

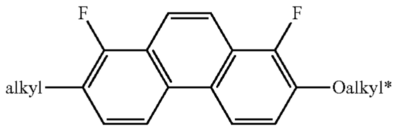

BP-5

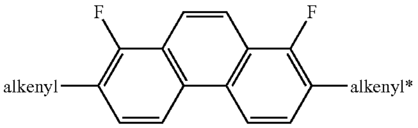

BP-6

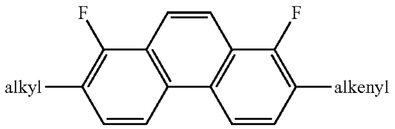

BP-7

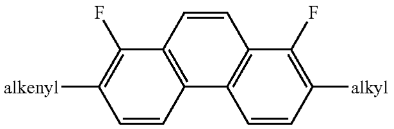

in which alkyl and alkyl* each, independently of one another, denote a straight-chain alkyl radical having 1 to 6 C atoms; and alkenyl and alkenyl* each, independently of one another, denote a straight-chain alkenyl radical having 2 to 6 C atoms.

More preference is given to mixtures comprising one, two or three compounds of the formula BC-2, BC-3, BP-2, and/or BP-3, very preferably BP-2 and/or BP-3, in particular BP-3.

In a preferred embodiment, the medium according to the invention comprises one or more HALS-stabilizers of the formula H:

H

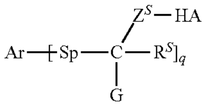

in which

Ar denotes a methylene group or an aromatic hydrocarbon group having 6 to 40 C atoms or a heteroaromatic hydrocarbon group having 4 to 40 C atoms; preferably an aromatic hydrocarbon group having 6 to 40 C atoms;

Sp denotes a spacer group;

$R^S$ denotes H, an alkyl group having 1 to 12 C atoms, or an alkenyl group having 2 to 12 C atoms;

$Z^S$ denotes —O—, —C(O)O—, —$(CH_2)_z$— or —$(CH_2)_z$O—, or a single bond;

HA denotes

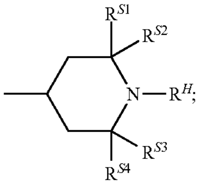

$R^H$ denotes H, O*, $CH_3$, OH, or $OR^S$;

$R^{S1}$, $R^{S2}$, $R^{S3}$ and $R^{S4}$ identically or differently, denote an alkyl having 1 to 6 C atoms, preferably having 1 to 3 C atoms, very preferably $CH_3$;

G denotes H, $R^S$ or a group $Z^S$-HA;

z is an integer from 1 to 6; and q is 2, 3, or 4, preferably 3 or 4;

The compounds of formula I are preferably selected from the compounds of the formulae H-1, H-2 and H-3:

H-1

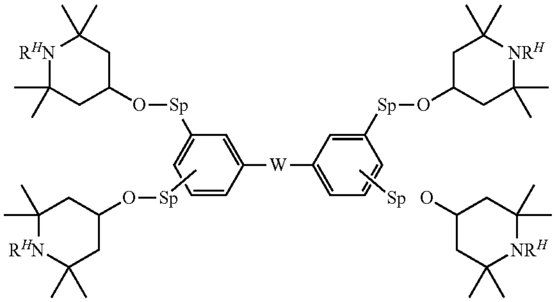

H-2

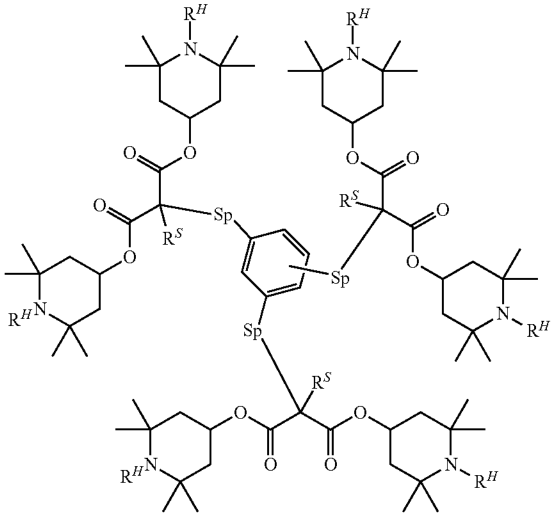

H-3

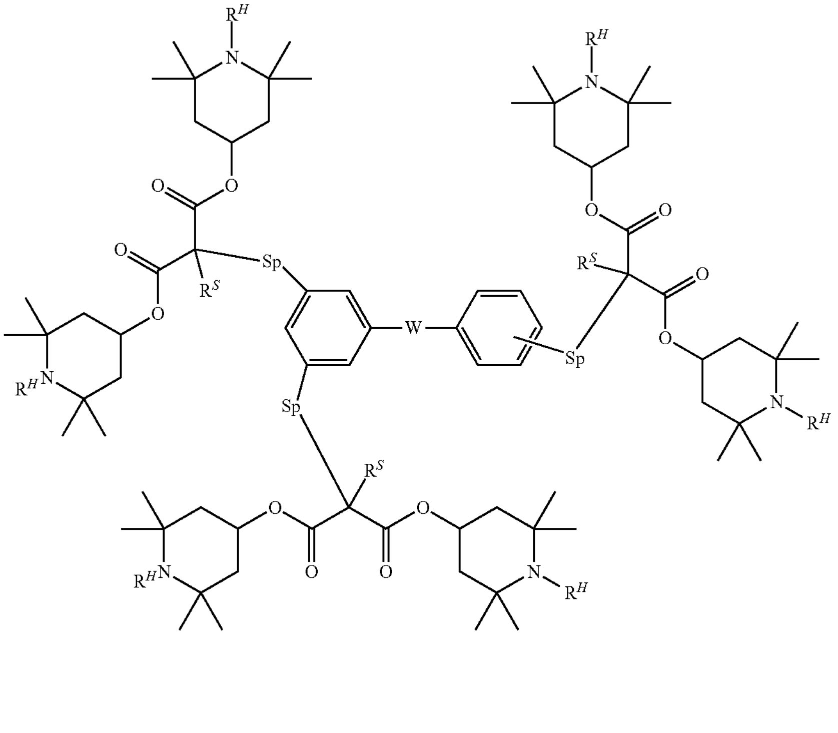

in which $R^H$ has the meanings given above and preferably denotes H or O·;

Sp on each occurrence, identically or differently, denotes a spacer group; and

W denotes a linear or branched, optionally unsaturated alkylene group having 1 to 12 C atoms, in which one or more non-adjacent —$CH_2$— groups may be replaced with —O—.

Preferred compounds of formula H-1 are selected from the compounds of the formula H-1-1:

H-1-1

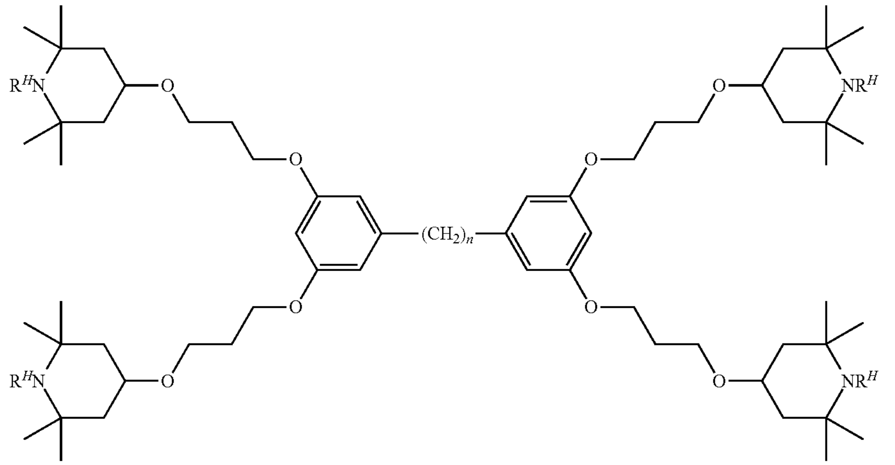

in which $R^H$ has the meanings given above and preferably denotes H or O·, and n is an integer from 0 to 12, preferably 5, 6, 7, 8, or 9, very preferably 7.

Preferred compounds of formula H-2 are selected from the compounds of the formula H-2-1:

H-2-1

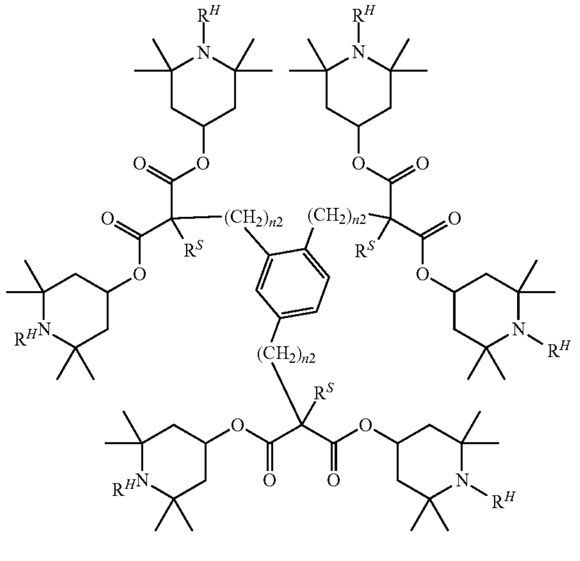

in which $R^H$ has the meanings given above and preferably denotes H or O·, and n2, on each occurrence identically or differently, preferably identically, is an integer from 1 to 12, preferably 2, 3, 4, 5, or 6, very preferably 3, and $R^S$ on each occurrence identically or differently, preferably identically, denotes an alkyl group having 1 to 6 C atoms, preferably n-butyl.

Preferred compounds of formula H-3 are selected from the compounds of the formula H-3-1:
H-3-1
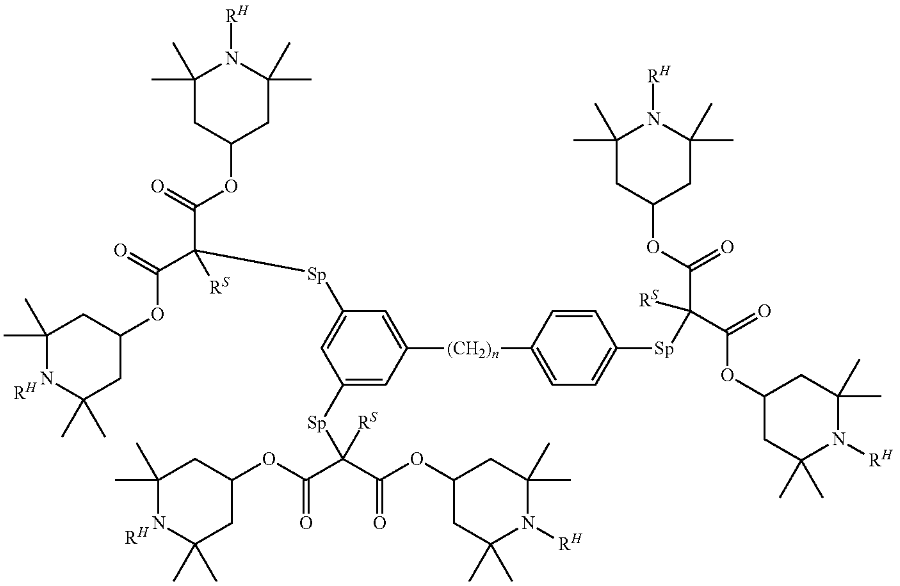
in which
$R^H$ has the meanings given above and preferably denotes H or O·; and
n is an integer from 0 to 12, preferably 5, 6, 7, 8, or 9, very preferably 7.
Preferably, the media according to the invention, comprise a stabilizer selected from the group of compounds of the formulae ST-1 to ST-23:
ST-1
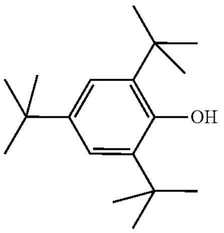
ST-2
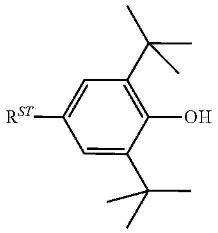
ST-3
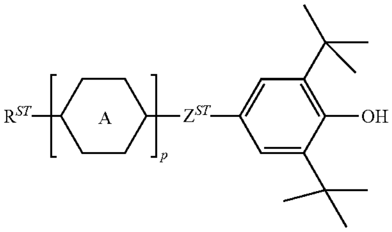
ST-4
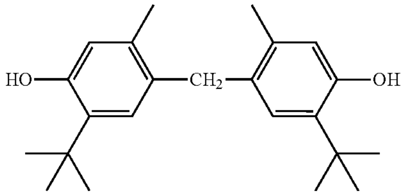
ST-5
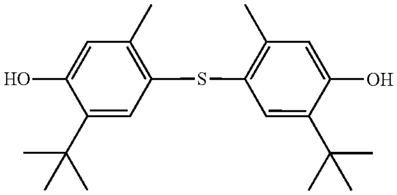
ST-6
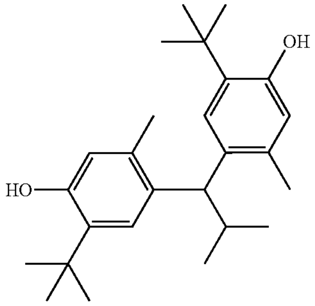

-continued
ST-7
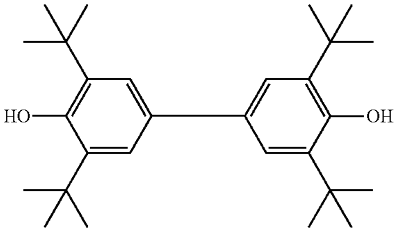
ST-8
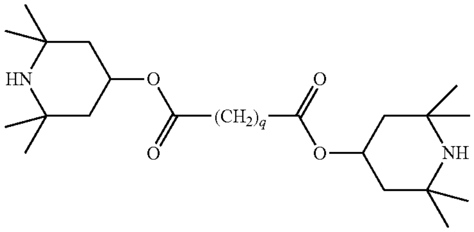
ST-9
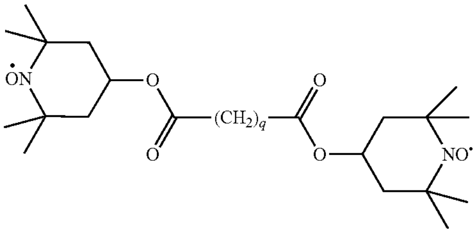
ST-10
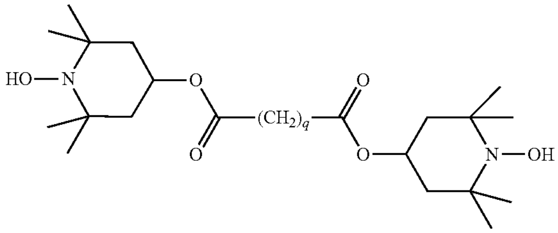
ST-11
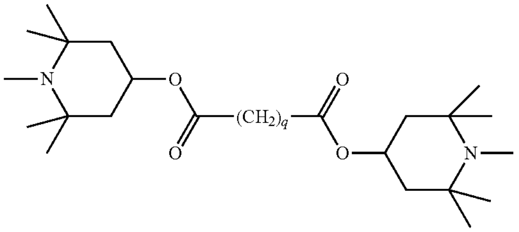
ST-12
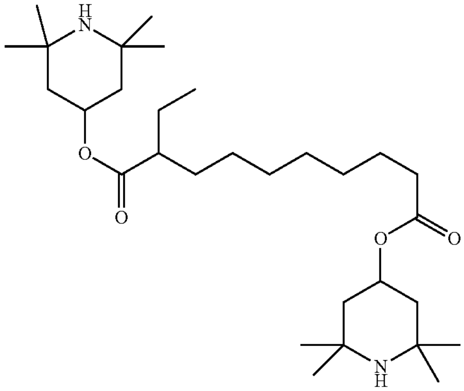
ST-13
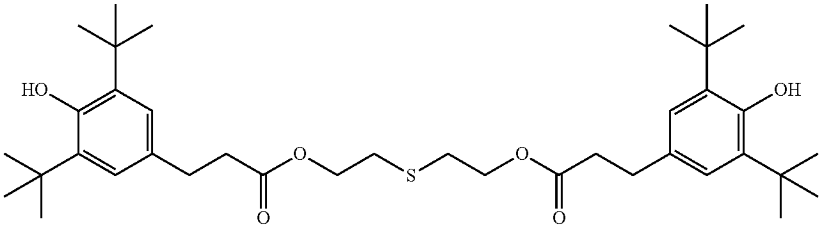
ST-14
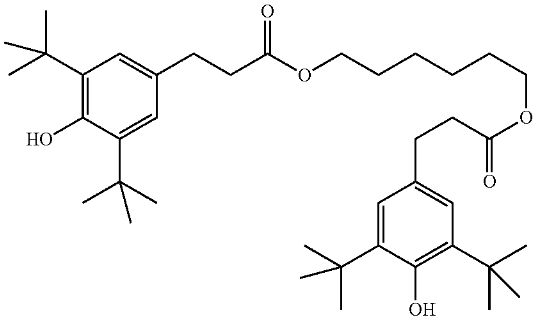
ST-15
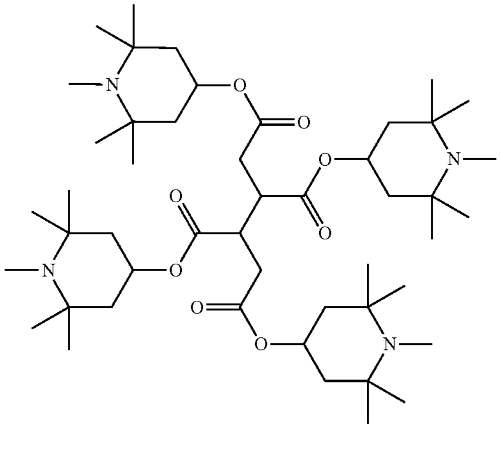

-continued
ST-16
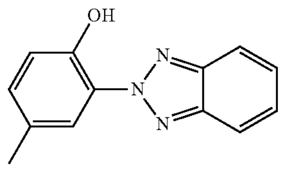
ST-17
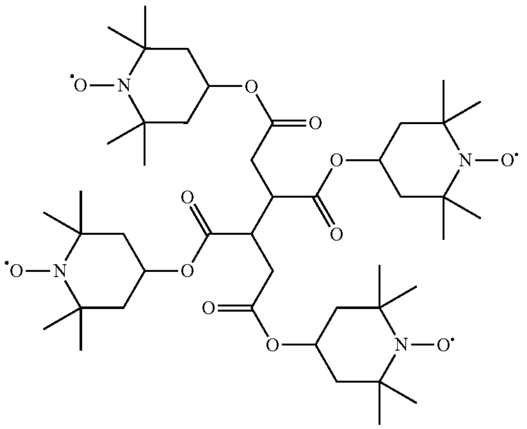
ST-18
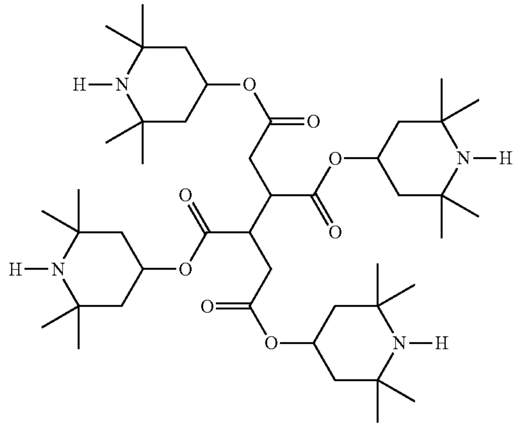
ST-19
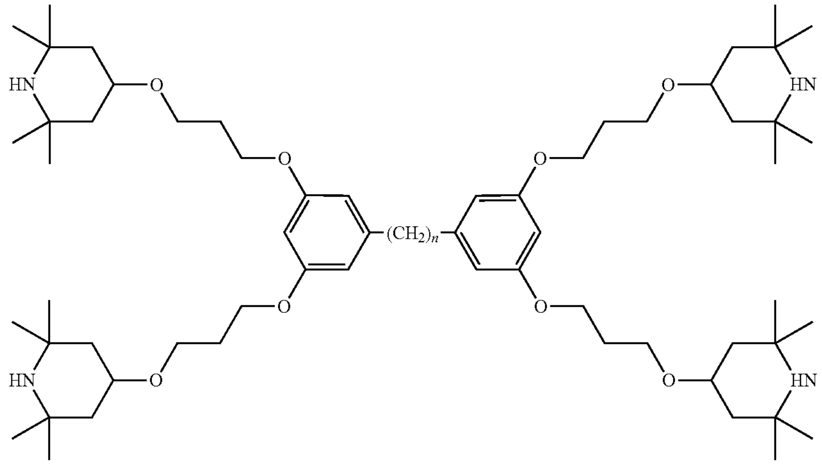

-continued
ST-20
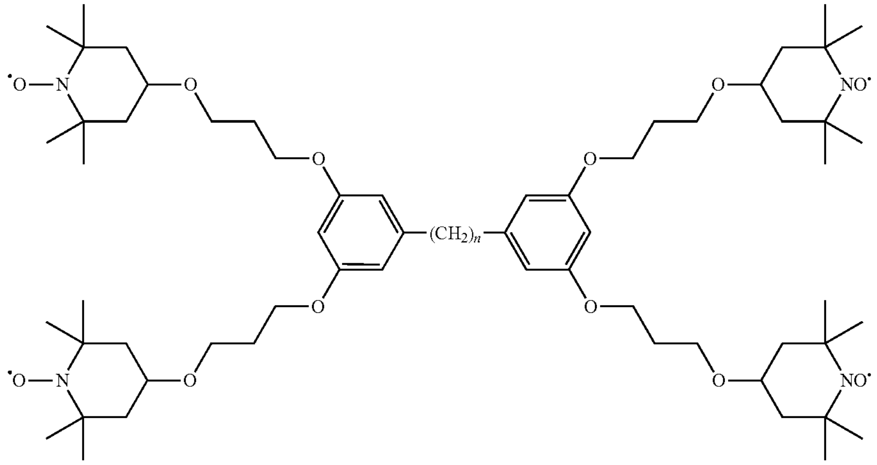
ST-21
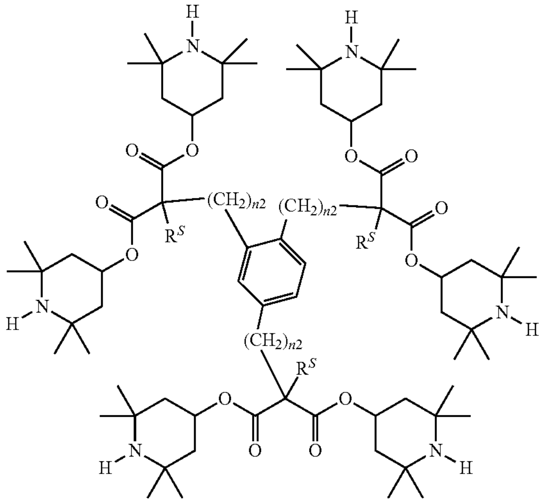
ST-22
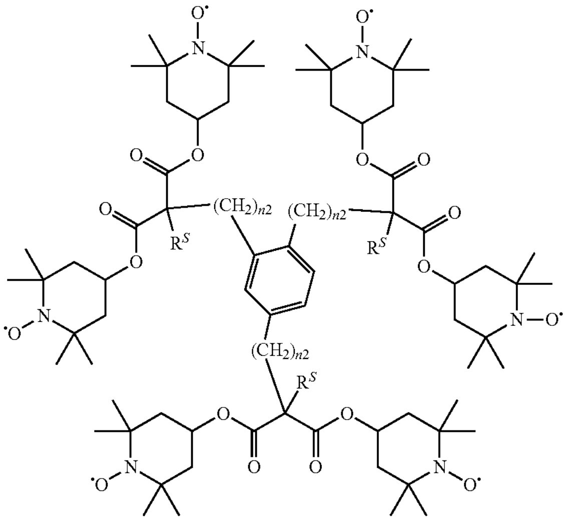
ST-23
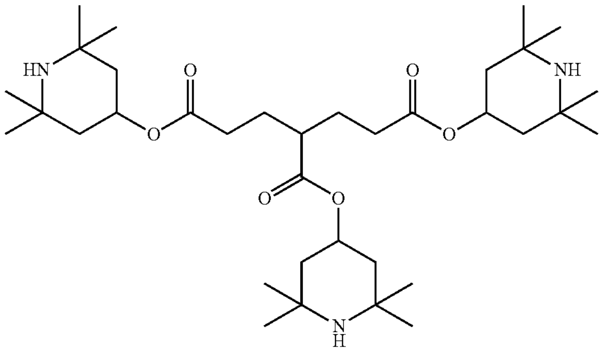
in which
$R^{ST}$ denotes H or an alkyl or alkoxy radical having 1 to 15 C atoms, where, in addition, one or more $CH_2$ groups in these radicals may each be replaced, independently of one another, by —C≡C—, —$CF_2O$—, —$OCF_2$—, —CH═CH—,
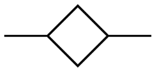, 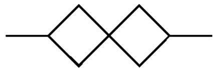, —O—,
—CO—O—, or —O—CO— in such a way that O atoms are not linked directly to one another, and in which, in addition, one or more H atoms may be replaced by halogen;
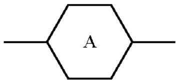
denotes
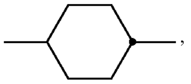
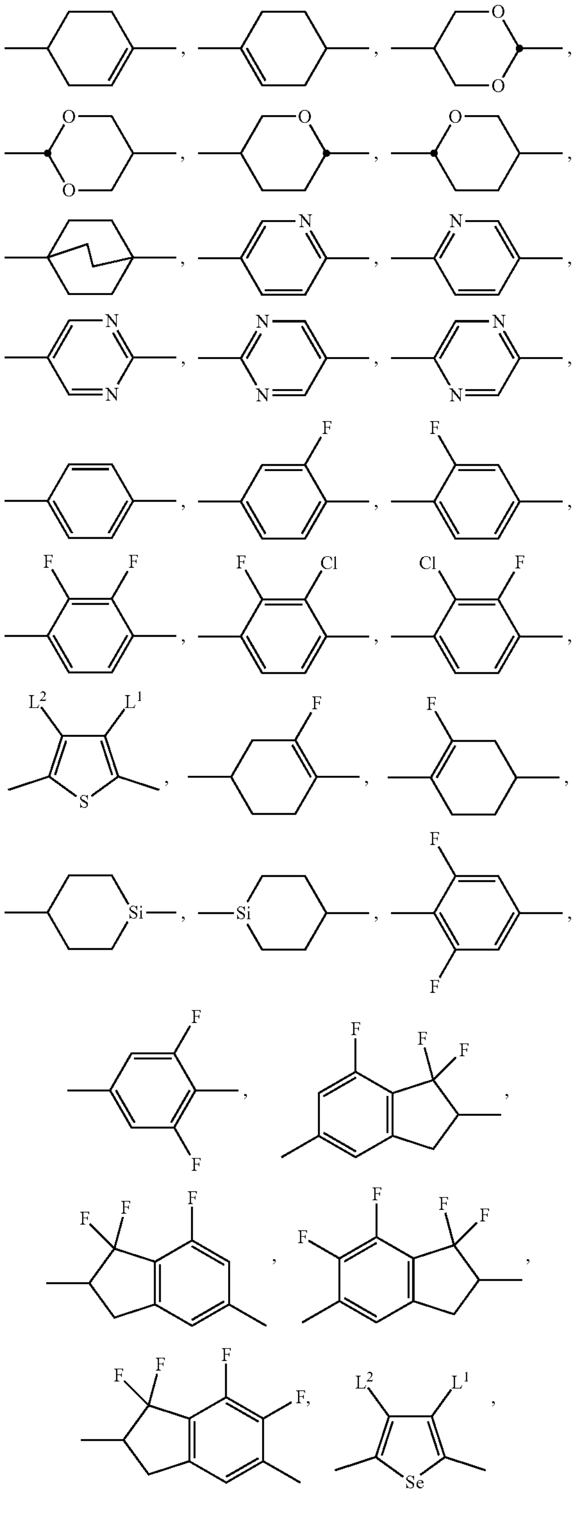
-continued
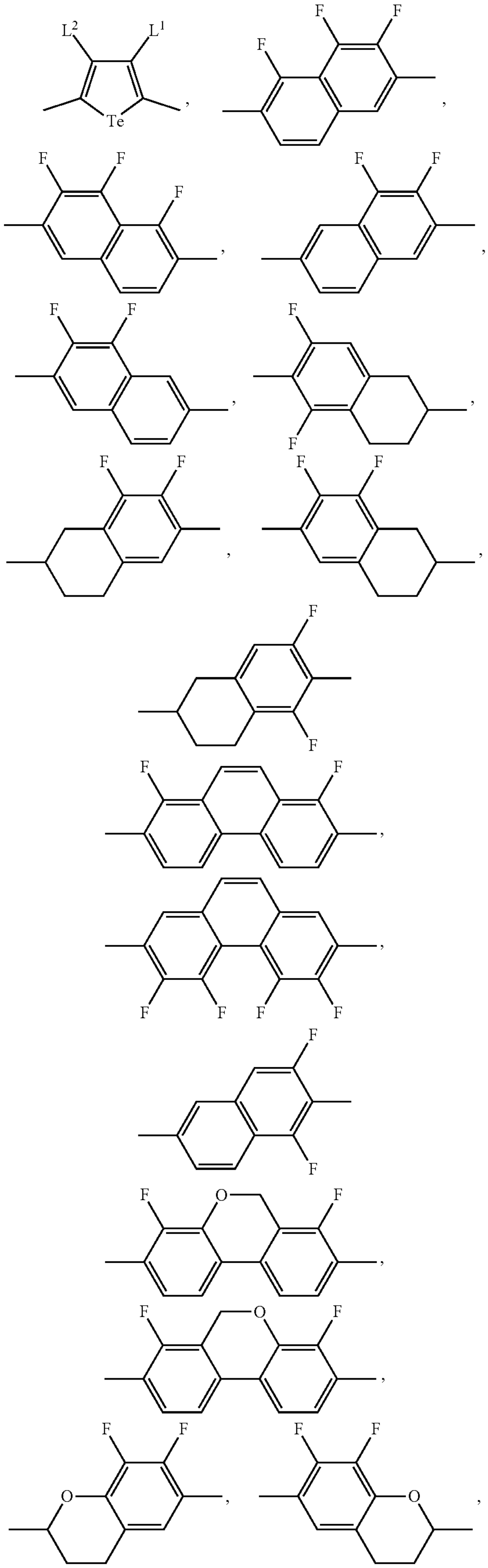

-continued

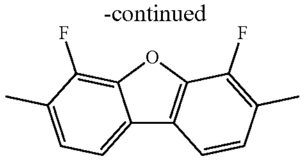

$Z^{ST}$ each, independently of one another, denote —CO—O—, —O—CO—, —$CF_2O$—, —$OCF_2$—, —$CH_2O$—, —$OCH_2$—, —$CH_2$—, —$CH_2CH_2$—, —$(CH_2)_4$—, —CH═CH—, —$CH_2O$—, —$C_2F_4$—, —$CH_2CF_2$—, —$CF_2CH_2$—, —CF═CF—, —CH═CF—, —CF═CH—, —CH═CH—, —C≡C—, or a single bond;

$L^1$ and $L^2$ each, independently of one another, denote F, Cl, $CF_3$, or $CHF_2$;

n is an integer from 0 to 12, preferably 5, 6, 7, 8, or 9, very preferably 7;

n2 on each occurrence identically or differently, preferably identically, is an integer from 1 to 12, preferably 2, 3, 4, 5, or 6, very preferably 3, and $R^S$ on each occurrence, identically or differently, preferably identically, denotes alkyl having 1 to 6 C atoms, preferably n-butyl;

p denotes 1 or 2; and q denotes 1, 2, 3, 4, 5, 6, 7, 8, 9, or 10.

Of the compounds of the formula ST, special preference is given to the compounds of the formulae:

ST-1

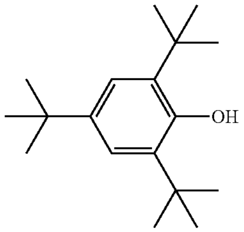

-continued

ST-2a

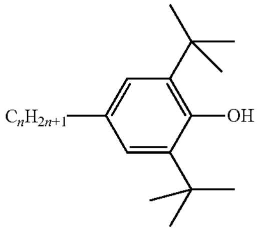

in which n=1, 2, 3, 4, 5, 6 or 7, preferably n=1 or 7

ST-3a

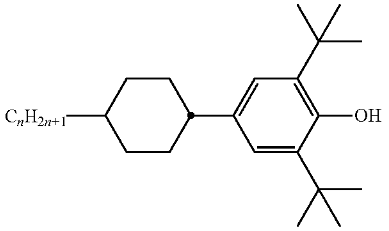

in which n=1, 2, 3, 4, 5, 6 or 7, preferably n=3

ST-3b

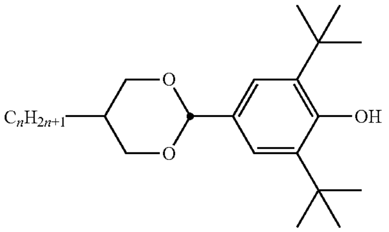

in which n=1, 2, 3, 4, 5, 6 or 7, preferably n=3

ST-3c

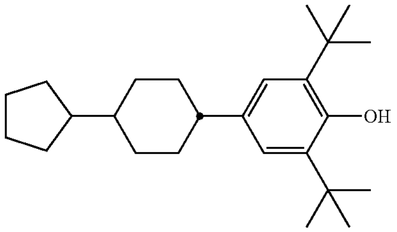

ST-3d

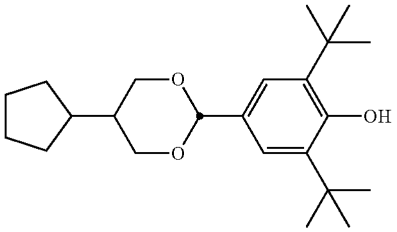

-continued
ST-8-1
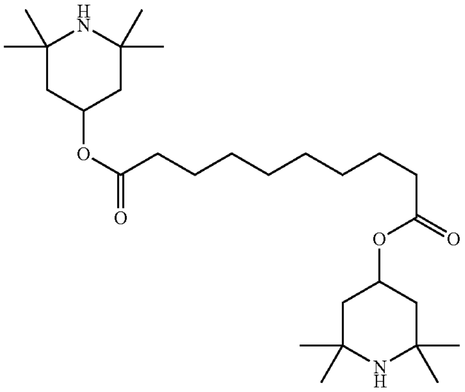
ST-9-1
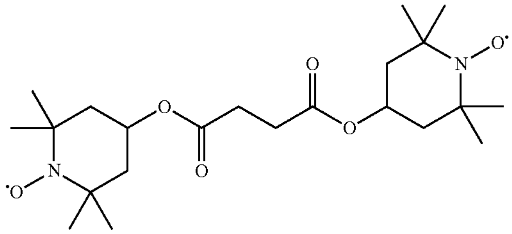
ST-12
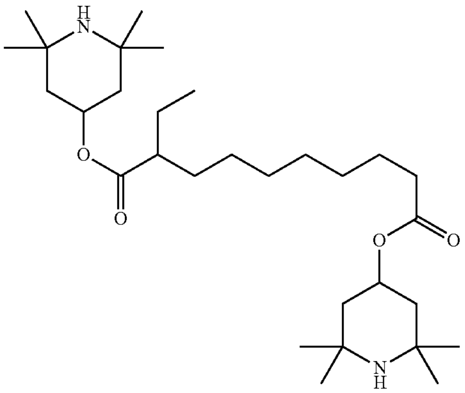
ST-16
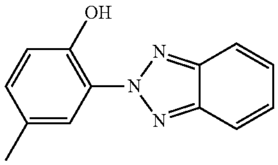
ST-17
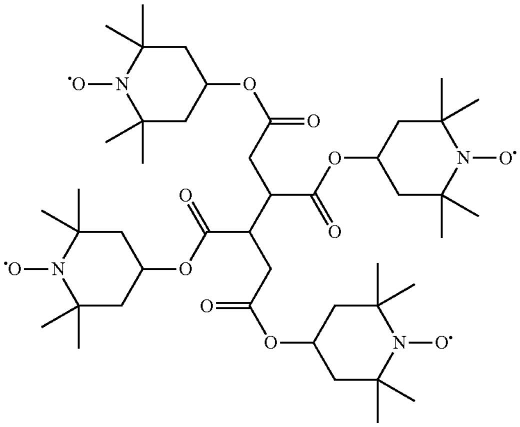
ST-18
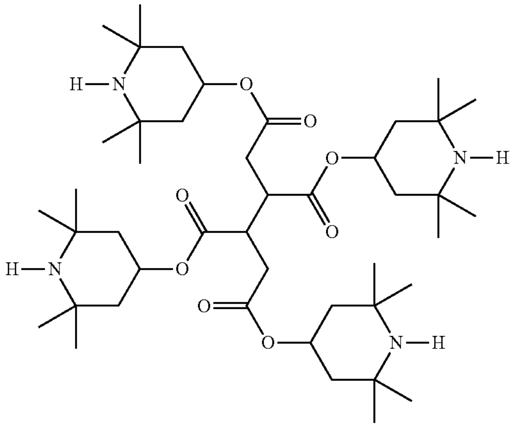
ST-19a
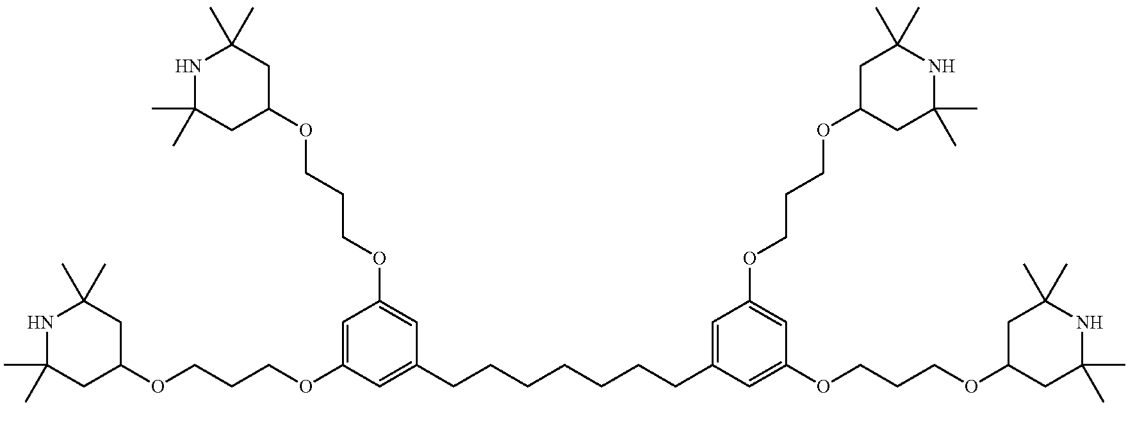

In the compounds of the formulae ST-3a and ST-3b, n preferably denotes 3. In the compounds of the formula ST-2a, n preferably denotes 7.

Very particularly preferred mixtures according to the invention comprise one or more stabilizers from the group of the compounds of the formulae ST-2a-1, ST-3a-1, ST-3b-1, ST-8-1, ST-9-1, and ST-12:

ST-2a-1

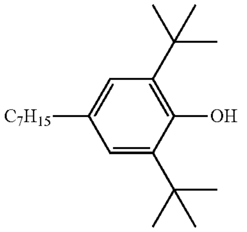

ST-3a-1

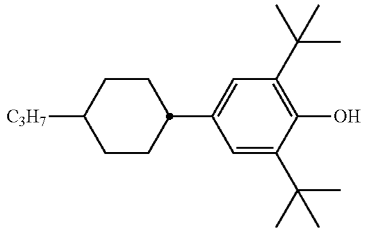

ST-3b-1

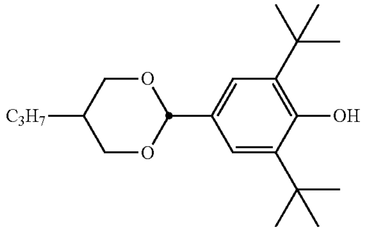

ST-8-1

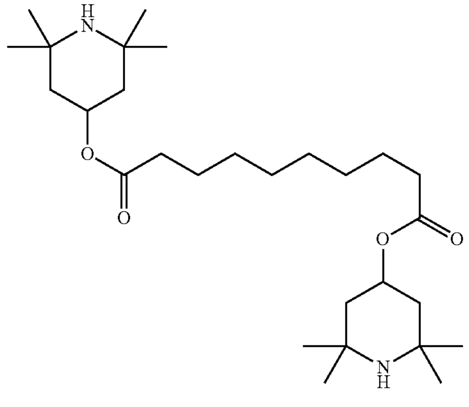

ST-9-1

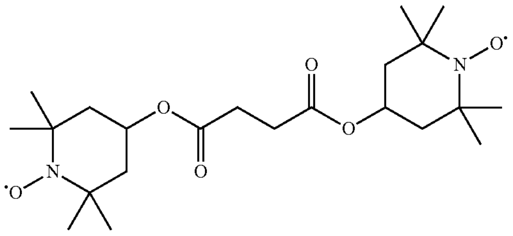

-continued

ST-12

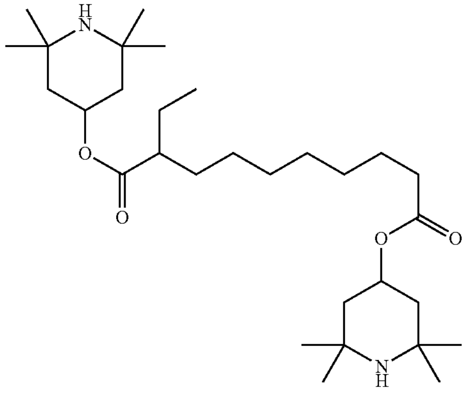

The compounds of the formulae ST-1 to ST-19 are preferably each present in the liquid-crystal mixtures according to the invention in amounts of 0.005-0.5%, based on the mixture.

If the mixtures according to the invention comprise two or more compounds from the group of the compounds of the formulae ST-1 to ST-19, the concentration correspondingly increases to 0.01-1% in the case of two compounds, based on the mixtures.

However, the total proportion of the compounds of the formulae ST-1 to ST-19, based on the mixture according to the invention, should not exceed 2%.

In another preferred embodiment of the present invention the liquid-crystalline medium additionally comprises one or more polymerizable compounds. The polymerizable compounds are preferably selected from formula M $$R^a—B^1—(Z^b—B^2)_m—R^b \quad \text{M}$$

in which the individual radicals, on each occurrence identically or differently, and each, independently of one another, have the following meanings:

$R^a$ and $R^b$ denote P, P-Sp-, H, F, Cl, Br, I, —CN, —$NO_2$, —NCO, —NCS, —OCN, —SCN, $SF_5$ or straight-chain or branched alkyl having 1 to 25 C atoms, in which, in addition, one or more non-adjacent $CH_2$ groups may each be replaced, independently of one another, by —C($R^0$)═C($R^{00}$)—, —C≡C—, —N($R^{00}$)—, —O—, —S—, —CO—, —CO—O—, —O—CO—, —O—CO—O— in such a way that O and/or S atoms are not linked directly to one another, and in which, in addition, one or more H atoms may be replaced by F, Cl, Br, I, CN, P, or P-Sp-, where, if $B^1$ and/or $B^2$ contain a saturated C atom, $R^a$ and/or $R^b$ may also denote a radical which is spiro-linked to this saturated C atom, wherein at least one of the radicals $R^a$ and $R^b$ denotes or contains a group P or P-Sp-;

P denotes a polymerizable group;

Sp denotes a spacer group or a single bond;

$B^1$ and $B^2$ denote an aromatic, heteroaromatic, alicyclic or heterocyclic group, preferably having 4 to 25 ring atoms, which may also contain fused rings, and which is unsubstituted, or mono- or polysubstituted by L;

$Z^b$ denotes —O—, —S—, —CO—, —CO—O—, —OCO—, —O—CO—O—, —$OCH_2$—, —$CH_2O$—, —$SCH_2$—, —$CH_2S$—, —$CF_2O$—, —$OCF_2$—, —$CF_2S$—, —$SCF_2$—, —$(CH_2)_{n1}$—, —$CF_2CH_2$—, —$CH_2CF_2$—, —$(CF_2)_{n1}$—, —CH═CH—, —CF═CF—, —C≡C—, —CH═CH—COO—, —OCO—CH═CH—, $CR^0R^{00}$, or a single bond;

$R^0$ and $R^{00}$ each, independently of one another, denote H or alkyl having 1 to 12 C atoms;

m denotes 0, 1, 2, 3, or 4;

n1 denotes 1, 2, 3, or 4;

L denotes P, P-Sp-, OH, $CH_2OH$, F, Cl, Br, I, —CN, —$NO_2$, —NCO, —NCS, —OCN, —SCN, —C(═O)$N(R^x)_2$, —C(═O)$Y^1$, —C(═O)$R^x$, —$N(R^x)_2$, an optionally substituted silyl group, an optionally substituted aryl group having 6 to 20 C atoms, or a straight-chain or branched alkyl, alkoxy, alkylcarbonyl, alkoxycarbonyl, alkylcarbonyloxy, or alkoxycarbonyloxy group having 1 to 25 C atoms, in which, in addition, one or more H atoms may be replaced by F, Cl, P, or P-Sp-;

P and Sp have the meanings indicated above;

$Y^1$ denotes halogen; and $R^x$ denotes P, P-Sp-, H, halogen, a straight-chain, branched, or cyclic alkyl group having 1 to 25 C atoms, in which, in addition, one or more non-adjacent $CH_2$ groups may be replaced by —O—, —S—, —CO—, —CO—O—, —O—CO—, or —O—CO—O— in such a way that O and/or S atoms are not linked directly to one another, and in which, in addition, one or more H atoms may be replaced by F, Cl, P, or P-Sp-, an optionally substituted aryl or aryloxy group having 6 to 40 C atoms, or an optionally substituted heteroaryl or heteroaryloxy group having 2 to 40 C atoms.

Particularly preferred compounds of the formula I are those in which $B^1$ and $B^2$ each, independently of one another, denote 1,4-phenylene, 1,3-phenylene, naphthalene-1,4-diyl, naphthalene-2,6-diyl, phenanthrene-2,7-diyl, 9,10-dihydro-phenanthrene-2,7-diyl, anthracene-2,7-diyl, fluorene-2,7-diyl, coumarin, or flavone, where, in addition, one or more CH groups in these groups may be replaced by N, cyclohexane-1,4-diyl, in which, in addition, one or more non-adjacent $CH_2$ groups may be replaced by O and/or S, 1,4-cyclohexenylene, bicycle[1.1.1]pentane-1,3-diyl, bicyclo[2.2.2]octane-1,4-diyl, spiro[3.3]heptane-2,6-diyl, piperidine-1,4-diyl, decahydronaphthalene-2,6-diyl, 1,2,3,4-tetrahydronaphthalene-2,6-diyl, indane-2,5-diyl, or octahydro-4,7-methanoindane-2,5-diyl, where all these groups may be unsubstituted, monosubstituted, or polysubstituted by L as defined above.

Particularly preferred compounds of the formula M are those in which $B^1$ and $B^2$ each, independently of one another, denote 1,4-phenylene, 1,3-phenylene, naphthalene-1,4-diyl, or naphthalene-2,6-diyl.

Very preferred compounds of formula M are selected from the following formulae:

M1

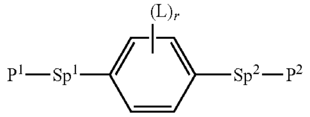

M2

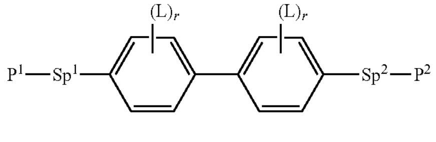

-continued

M3

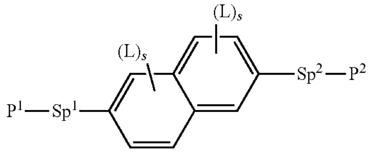

M4

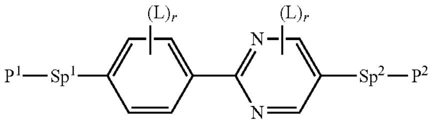

M5

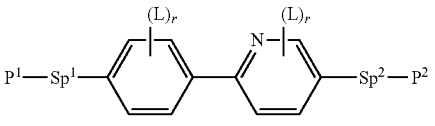

M6

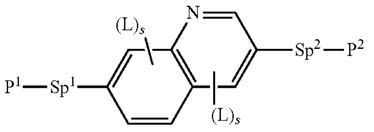

M7

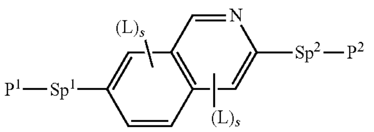

M8

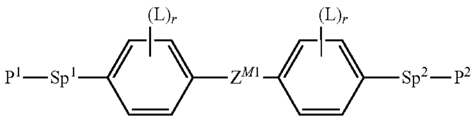

M9

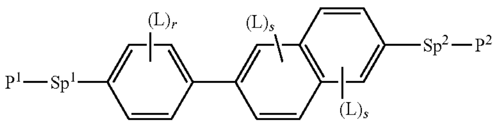

M10

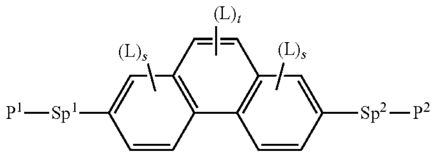

M11

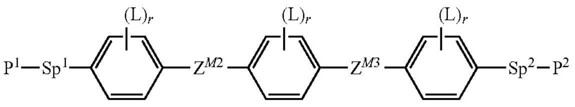

M12

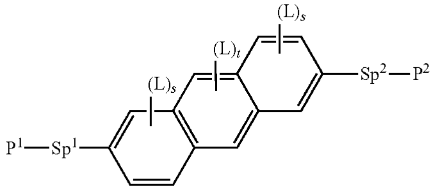

M13

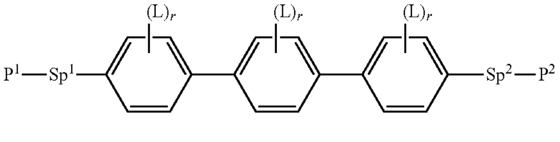

-continued
M14
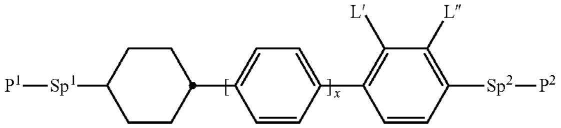
M15
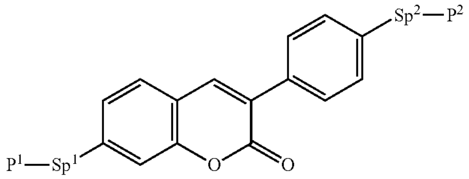
M16
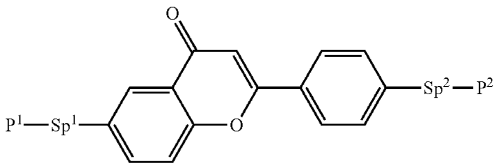
M17
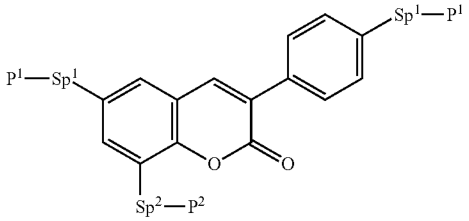
M18
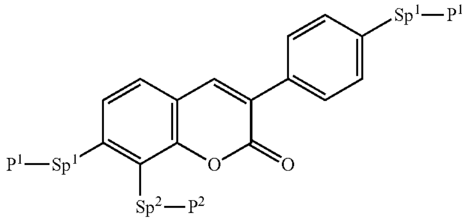
M19
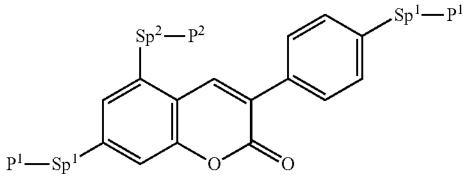
M20
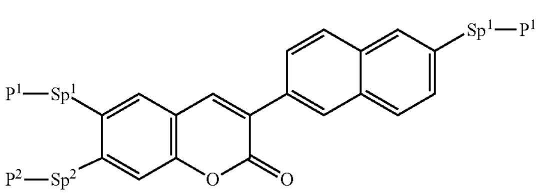
-continued
M21
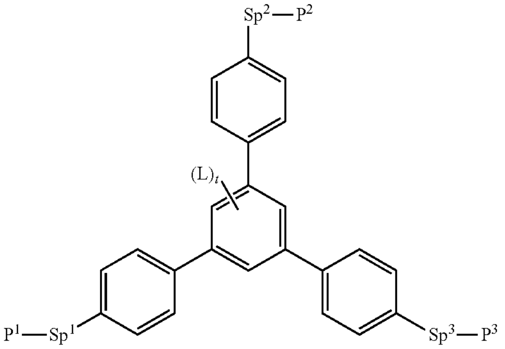
M22
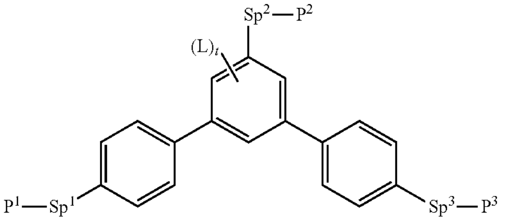
M23
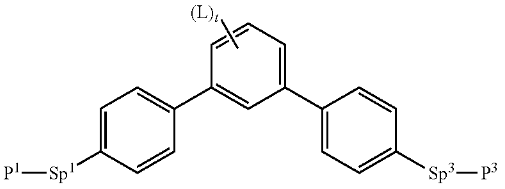
M24
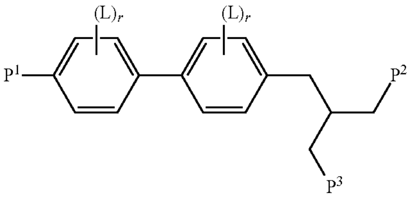
M25
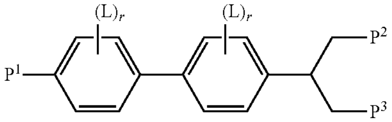
M26
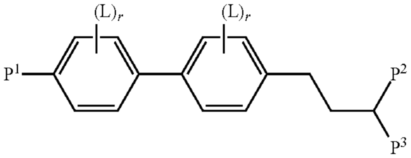
M27
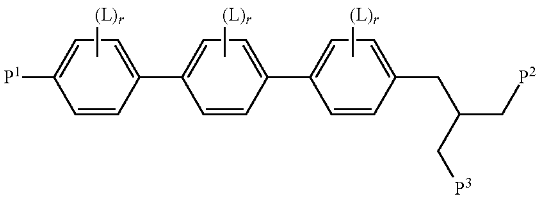

-continued

M28

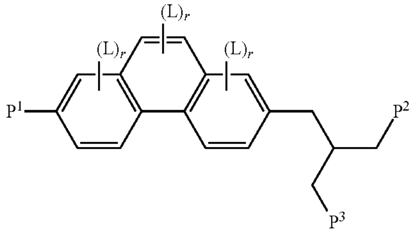

M29

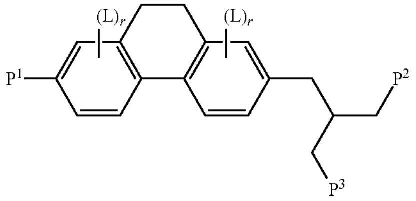

M30

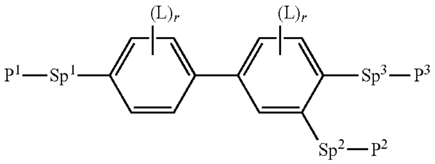

M31

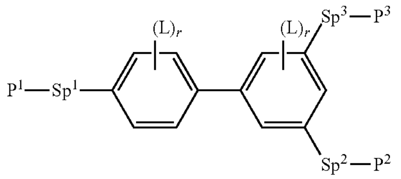

in which the individual radicals, on each occurrence identically or differently, and each, independently of one another, have the following meanings:

$P^1$, $P^2$, and $P^3$ each denote a polymerizable group, preferably selected from vinyloxy, acrylate, methacrylate, fluoroacrylate, chloroacrylate, oxetane, and epoxy;

$Sp^1$, $Sp^2$, and $Sp^3$ each denote a single bond or a spacer group where, in addition, one or more of the radicals $P^1$-$Sp^1$-, $P^1$-$Sp^2$- and $P^3$-$Sp^3$- may denote $R^{aa}$, with the proviso that at least one of the radicals $P^1$-$Sp^1$-, $P^2$-$Sp^2$ and $P^3$-$Sp^3$- present is different from $R^{aa}$, preferably denote $-(CH_2)_{p1}-$, $-(CH_2)_{p1}-O-$, $-(CH_2)_{p1}-CO-O-$, or $-(CH_2)_{p1}-O-CO-O-$, wherein p1 is an integer from 1 to 12;

$R^{aa}$ denotes H, F, Cl, CN, or a straight-chain or branched alkyl group having 1 to 25 C atoms, in which, in addition, one or more non-adjacent $CH_2$ groups may each be replaced, independently of one another, by $-C(R^0)=C(R^{00})-$, $-C\equiv C-$, $-N(R^0)-$, $-O-$, $-S-$, $-CO-$, $-CO-O-$, $-O-CO-$, or $-O-CO-O-$ in such a way that O and/or S atoms are not linked directly to one another, and in which, in addition, one or more H atoms may be replaced by F, Cl, CN, or $P^1$-$Sp^1$-, particularly preferably a straight-chain or branched, optionally mono- or polyfluorinated alkyl, alkoxy, alkenyl, alkynyl, alkylcarbonyl, alkoxycarbonyl, alkylcarbonyloxy, or alkoxycarbonyloxy radical having 1 to 12 C atoms (where the alkenyl and alkynyl radicals have at least two C atoms and the branched radicals have at least three C atoms);

$R^0$, and $R^{00}$ each denote H or an alkyl group having 1 to 12 C atoms;

$R^y$ and $R^z$ each denote H, F, $CH_3$, or $CF_3$;

$X^1$, $X^2$, and $X^3$ each denote $-CO-O-$, $-O-CO-$, or a single bond, $Z^{M1}$ denotes $-O-$, $-CO-$, $-C(R^yR^z)-$, or $-CF_2CF_2-$;

$Z^{M2}$, $Z^{M3}$ each denote $-CO-O-$, $-O-CO-$, $-CH_2O-$, $-OCH_2-$, $-CF_2O-$, $-OCF_2-$ or $-(CH_2)_n-$, where n is 2, 3, or 4;

L denotes F, Cl, CN, a straight-chain, optionally mono- or polyfluorinated alkyl, alkoxy, alkenyl, alkynyl, alkylcarbonyl, alkoxycarbonyl, alkylcarbonyloxy, or alkoxycarbonyloxy group having 1 to 12 C atoms, or a branched, optionally mono- or polyfluorinated alkyl, alkoxy, alkenyl, alkynyl, alkylcarbonyl, alkoxycarbonyl, alkylcarbonyloxy, or alkoxycarbonyloxy group having 3 to 12 C atoms;

L', L" each denote H, F or Cl;

r is 0, 1, 2, 3, or 4;

S is 0, 1, 2, or 3;

t is 0, 1, or 2; and

X is 0 or 1.

Especially preferred are compounds of formulae M2 and M13.

Further preferred are tri-reactive compounds M15 to M31, in particular M17, M18, M19, M22, M23, M24, M25, M30, and M31.

In the compounds of formulae M1 to M31 the group

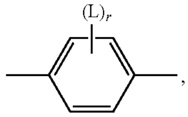, in which L has one of the meanings indicated above and r denotes 0, 1, 2, 3, or 4, in particular denotes:

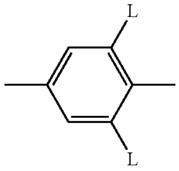, 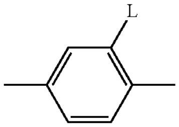,

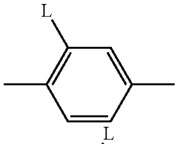, 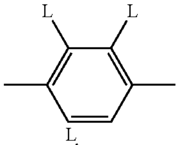,

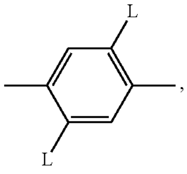 or 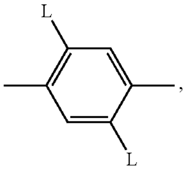, in which L on each occurrence, identically or differently, has one of the meanings given above or below, and is preferably F, Cl, CN, $NO_2$, $CH_3$, $C_2H_5$, $C(CH_3)_3$, $CH(CH_3)_2$, $CH_2CH(CH_3)$ $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, or P-Sp-, very preferably F, Cl, CN, $CH_3$, $C_2H_5$, $OCH_3$, $COCH_3$, $OCF_3$, or P-Sp-, more preferably F, Cl, $CH_3$, $OCH_3$, $COCH_3$, or $OCF_3$, especially F or $CH_3$.

Preferred compounds of formulae M1 to M31 are those in which $P^1$, $P^2$, and $P^3$ denote an acrylate, methacrylate, oxetane, or epoxy group, very preferably an acrylate or methacrylate group.

Further preferred compounds of formulae M1 to M31 are those in which $Sp^1$, $Sp^2$, and $Sp^3$ are a single bond.

Further preferred compounds of formulae M1 to M31 are those in which one of $Sp^1$, $Sp^2$, and $Sp^3$ is a single bond and another one of $Sp^1$, $Sp^2$, and $Sp^3$ is different from a single bond.

Further preferred compounds of formulae M1 to M31 are those in which those groups $Sp^1$, $Sp^2$, and $Sp^3$ that are different from a single bond denote —$(CH_2)_{s1}$—X"—, wherein s1 is an integer from 1 to 6, preferably 2, 3, 4, or 5, and X" is X" is the linkage to the benzene ring and is-O—, —O—CO—, —CO—O—, —O—CO—O—, or a single bond.

Particular preference is given to liquid-crystalline media comprising one, two, or three polymerizable compounds of formula M, preferably selected from formulae M1 to M31.

Further preferably the liquid-crystalline media according to the present invention comprise one or more polymerizable compounds selected from Table E below.

Preferably the proportion of polymerizable compounds in the liquid-crystalline medium, preferably selected from formula M and Table E, is from 0.01 to 5%, very preferably from 0.05 to 1%, most preferably from 0.1 to 0.5%.

It was observed that the addition of one or more polymerizable compounds to the liquid-crystalline medium, like those selected from formula M and Table E, leads to advantageous properties like fast response times. Such a liquid-crystalline medium is especially suitable for use in PSA displays where it shows low image sticking, a quick and complete polymerization, the quick generation of a low pretilt angle which is stable after UV exposure, a high reliability, high VHR value after UV exposure, and a high birefringence. By appropriate selection of the polymerizable compounds, it is possible to increase the absorption of the liquid-crystalline medium at longer UV wavelengths, so that it is possible to use such longer UV wavelengths for polymerization, which is advantageous for the display manufacturing process.

The polymerizable group P is a group which is suitable for a polymerization reaction, such as, for example, free-radical or ionic chain polymerization, polyaddition or polycondensation, or for a polymer-analogous reaction, for example addition or condensation onto a main polymer chain. Particular preference is given to groups for chain polymerization, in particular those containing a C═C double bond or —C≡C-triple bond, and groups which are suitable for polymerization with ring opening, such as, for example, oxetane or epoxide groups.

Preferred groups P are selected from the group consisting of $CH_2$═$CW^1$—CO—O—, $CH_2$═$CW^1$—CO—,

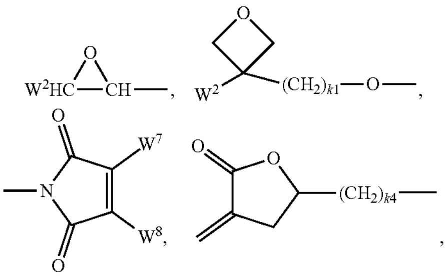

, $CH_2$═$CW^2$—$(O)_{k3}$—, $CW^1$═CH—CO—$(O)_{k3}$—, $CW^1$═CH—CO—NH—, $CH_2$═$CW^1$—CO—NH—, $CH_3$—CH═CH—O—, $(CH_2$═$CH)_2$CH—OCO—, $(CH_2$═CH—$CH_2)_2$CH—OCO—, $(CH_2$═$CH)_2$CH—O—, $(CH_2$═CH—$CH_2)_2$N—, $(CH_2$═CH—$CH_2)_2$N—CO—, HO—$CW^2W^3$—, HS—$CW^2W^3$—, $HW^2$N—, HO—$CW^2W^3$—NH—, $CH_2$═$CW^1$—CO—NH—, $CH_2$═CH—$(COO)_{k1}$-Phe-$(O)_{k2}$—, $CH_2$═CH—$(CO)_{k1}$-Phe-$(O)_{k2}$—, Phe-CH═CH—, HOOC—, OCN—, and $W^4W^5W^6$Si—, in which

- $W^1$ denotes H, F, Cl, CN, $CF_3$, a phenyl or alkyl group having 1 to 5 C atoms, in particular H, F, Cl, or $CH_3$;
- $W^2$ and $W^3$ each, independently of one another, denote H or an alkyl group having 1 to 5 C atoms, in particular H, methyl, ethyl, or n-propyl;
- $W^4$, $W^5$, and $W^6$ each, independently of one another, denote Cl, an oxaalkyl group having 1 to 5 C atoms, or an oxacarbonylalkyl group having 1 to 5 C atoms;
- $W^7$ and $W^8$ each, independently of one another, denote H, Cl or alkyl having 1 to 5 C atoms;
- Phe denotes 1,4-phenylene, which is optionally substituted by one or more radicals L as defined above which are other than P-Sp-; and
- $k_1$, $k_2$, and $k_3$ each, independently of one another, denote 0 or 1, $k_3$ preferably denotes 1, and $k_4$ denotes an integer from 1 to 10.

Very preferred groups P are selected from the group consisting of $CH_2$═$CW^1$—CO—O—, $CH_2$═$CW^1$—CO—,

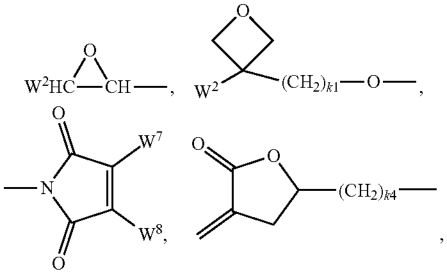

, $CH_2$═$CW^2$—O—, $CH_2$═$CW^2$—, $CW^1$═CH—CO—$(O)_{k3}$—, $CW^1$═CH—CO—NH—, $CH_2$═$CW^1$—CO—NH—, $(CH_2$═$CH)_2$CH—OCO—, $(CH_2$═CH—$CH_2)_2$CH—OCO—, $(CH_2$═$CH)_2$CH—O—, $(CH_2$═CH—$CH_2)_2$N—, $(CH_2$═CH—$CH_2)_2$N—CO—, $CH_2$═$CW^1$—CO—NH—, $CH_2$═CH—$(COO)_{k1}$-Phe-$(O)_{k2}$—, $CH_2$═CH—$(CO)_{k1}$-Phe-$(O)_{k2}$—, Phe-CH═CH—, and $W^4W^5W^6$Si—, in which

- $W^1$ denotes H, F, Cl, CN, $CF_3$, a phenyl or alkyl group having 1 to 5 C atoms, in particular H, F, Cl, or $CH_3$;
- $W^2$ and $W^3$ each, independently of one another, denote H or an alkyl group having 1 to 5 C atoms, in particular H, methyl, ethyl, or n-propyl;
- $W^4$, $W^5$, and $W^6$ each, independently of one another, denote Cl, an oxaalkyl group having 1 to 5 C atoms, or an oxacarbonylalkyl group having 1 to 5 C atoms;
- $W^7$ and $W^8$ each, independently of one another, denote H, Cl, or an alkyl having 1 to 5 C atoms;
- Phe denotes 1,4-phenylene;
- $k_1$, $k_2$, and $k_3$ each, independently of one another, denote 0 or 1, $k_3$ preferably denotes 1; and
- $k_4$ denotes an integer from 1 to 10.

Very particularly preferred groups P are selected from the group consisting of $CH_2$═$CW^1$—CO—O—, in particular $CH_2$═CH—CO—O—, $CH_2$═$C(CH_3)$—CO—O—, and $CH_2$═CF—CO—O—, furthermore $CH_2$═CH—O—, ($CH_2$═CH) 2CH—O—CO—, ($CH_2$═CH) 2CH—O—,

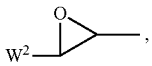, and 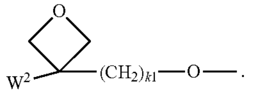

Further preferred polymerizable groups P are selected from the group consisting of vinyloxy, acrylate, methacrylate, fluoroacrylate, chloroacrylate, oxetane, and epoxide, most preferably from acrylate and methacrylate.

If Sp is different from a single bond, it is preferably of the formula Sp"-X", so that the respective radical P-Sp- conforms to the formula P-Sp"-X"—, wherein Sp" denotes an alkylene group having 1 to 20, preferably 1 to 12, C atoms, which is optionally mono- or polysubstituted by F, Cl, Br, I, or CN and in which, in addition, one or more non-adjacent $CH_2$ groups may each be replaced, independently of one another, by —O—, —S—, —NH—, —N($R^0$)—, —Si($R^0R^{00}$)—, —CO—, —CO—O—, —O—CO—, —O—CO—O—, —S—O—, —CO—S—, —N($R^{00}$)—CO—O—, —O—CO—N($R^0$)—, —N($R^0$)—CO—N($R^{00}$)—, —CH═CH—, or —C≡C— in such a way that O and/or S atoms are not linked directly to one another;

X" denotes —O—, —S—, —CO—, —CO—O—, —O—CO—, —O—CO—O—, —CO—N($R^0$)—, —N($R^0$)—CO—, —N($R^0$)—CO—N($R^{00}$)—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH═N—, —N═CH—, —N═N—, —CH═$CR^0$—, —$CY^2$═$CY^3$—, —C≡C—, —CH═CH—CO—O—, —O—CO—CH═CH—, or a single bond;

$R^0$ and $R^{00}$ each, independently of one another, denote H or an alkyl group having 1 to 20 C atoms; and $Y^2$ and $Y^3$ each, independently of one another, denote H, F, Cl, or CN.

X" is preferably —O—, —S—, —CO—, —COO—, —OCO—, —O—COO—, —CO—$NR^0$—, —$NR^0$—CO—, —$NR^0$—CO—$NR^{00}$—, or a single bond.

Typical spacer groups Sp and -Sp"-X"— are, for example, —$(CH_2)_{p1}$—, —$(CH_2CH_2O)_{q1}$—$CH_2CH_2$—, —$CH_2CH_2$—S—$H_2CH_2$—, —$CH_2CH_2$—NH—$CH_2CH_2$—, or —($SiR^0R^{00}$—O$)_{p1}$—, in which p1 is an integer from 1 to 12, q1 is an integer from 1 to 3, and $R^0$ and $R^{00}$ have the meanings indicated above.

Particularly preferred groups Sp and -Sp"-X"— are —$(CH_2)_{p1}$—, —$(CH_2)_{p1}$—O—, $(CH_2)_{p1}$—O—CO—, —$(CH_2)_{p1}$—CO—O—, or —$(CH_2)_{p1}$—O—CO—O—, in which p1 and q1 have the meanings indicated above.

Particularly preferred groups Sp" are, in each case a straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene, or butenylene group.

For the production of PSA displays, the polymerizable compounds contained in the liquid-crystalline medium are polymerized or crosslinked (if one compound contains two or more polymerizable groups) by in-situ polymerization in the liquid-crystalline medium between the substrates of the LC display, optionally while a voltage is applied to the electrodes.

The structure of the PSA displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PS-VA displays are described, for example, in US 2006/0066793 A1.

The combination of compounds of the preferred embodiments mentioned above with the polymerized compounds described above causes low threshold voltages, low rotational viscosities and very good low-temperature stabilities in the liquid-crystalline media according to the invention at the same time as constantly high clearing points and high VHR values.

The use of liquid-crystalline media containing polymerizable compounds allows the rapid establishment of a particularly low pretilt angle in PSA displays. In particular, the liquid-crystalline media exhibit significantly shortened response times, in particular also the grey-shade response times, in PSA displays compared with the media from the prior art.

In further preferred embodiments, taken alone or in combination with one another, the medium according to the invention comprises the following compounds, where the acronyms are explained in Table D below:

one, two or more compounds of formula I in a total concentration in the range of from 0.5% to 10%, preferably 1% to 8%, particularly preferably 2% to 7%;

and/or one or more compounds of formula II, preferably of formula II-1 and optionally II-3, more preferably of the sub-formulae II-1a, II-1f, II-1g, II-1h, II-3a, and/or II-3d, in a total concentration in the range of from 5% to 35%, preferably from 6% to 32%, particularly preferably from 8% to 28%;

and/or one or more compounds of formula II-1, more preferably of the sub-formulae II-1a, II-1f, II-1g, and/or II-1h, in particular of formula II-1a-1 and II-1f-1, or of formula II-1a-1 and II-1f-1 and II-1h-1, or of formula II-1f-1, II-1g-1, and II-1h-1, preferably in a total concentration in the range of from 2% to 22%, preferably from 3% to 19%, particularly preferably from 4% to 17%;

and/or one or more compounds of formula of II-1f-1, in a total concentration in the range of from 0.3% to 8%, preferably 0.5% to 6%, particularly preferably 1% to 5%;

and/or one or more compounds of formula of II-1g-1, in a total concentration in the range of from 1% to 15%, preferably 2% to 12%, particularly preferably 3% to 10%;

and/or one or more compounds of formula of II-1a-1, in a total concentration in the range of from 0.5% to 15%, preferably 1% to 10%;

and/or one or more compounds of formula III in a total concentration in the range of from 0.1% to 30%, preferably from 0.2% to 28%, more preferably from 0.3% to 25%, preferably selected from the group of compounds of formula III-2, more preferably of the formulae III-2c, III-2d, III-2g, III-2i, III-2l, and/or III-2m, very preferably of the formulae III-2c-3, III-2d-1, III-2g-2, III-2l-3, and/or III-2m-1, where the concentration of the compound(s) of the formula III-2m-1 is very preferably 0.1% to 1%;

and/or one or more compounds of the formula YA, preferably of the formula YA-2 and/or YA-10 in a total concentration in the range of from 1% to 10%, preferably 2% to 8%, particularly preferably 3% to 7%;

and/or one or more compounds of the formula YD, preferably of the formula YD-7 and/or YD-10 in a total concentration in the range of from 1% to 10%, preferably 2% to 8%, particularly preferably 3% to 7%;

and/or one or more compounds of the formula YB, preferably of the formulae YB-2 and/or YB-10 in a total concentration in the range of from 0.5% to 10%, preferably 1% to 7%, particularly preferably 2% to 5%;

and/or one or more compounds of the formula I and YD and optionally YA, preferably selected from the compounds of the formulae YA-2, YA-10, YD-7, and YD-10 in a total concentration in the range of from 1% to 20%, preferably 3% to 17%, particularly preferably 4% to 14%;

and/or one or more compounds of the formula B, preferably B-2, very preferably of the formula B-2-6 in a total concentration in the range of from 0.1% to 10%, preferably 0.5% to 8%, particularly preferably 1% to 6%;

and/or one or more compounds of the formula B, preferably B-5, very preferably of the formula B-5-1 or LB(S)-n-OT, in particular LB(S)-3-OT, in a total concentration in the range of from 0.1% to 10%, preferably 0.5% to 8%, particularly preferably 1% to 6%;

and/or one or more compounds of the formula B-2 and one or more compounds of the formula B-5, in a total concentration in the range of from 1% to 20%, preferably 2% to 15%, particularly preferably 5% to 11%;

and/or less than 5% of one or more compounds of the formula IV-1, preferably less than 3%, very preferably less than 1%;

and/or one or more compounds of formula IV, preferably of the formula IV-3, in a total concentration in the range of from 15% to 60%, more preferably 18% to 50%, very preferably 20% to 45%, preferably selected from the compounds of the formulae IV-3-1 to IV-3-6, in particular selected from the compounds of formula IV-3-1, IV-3-2, IV-3-4, and IV-3-6;

and/or 0.5% to 8%, preferably 1% to 6% of the compound IV-3-6 (CC-3-2V1) or IV-3-4 (CC-4-V1);

and/or one or more compounds of formula IVa, preferably of formula IVa-2, preferably in a total concentration in the range of from 0.1% to 3%, more preferably from 0.2% to 2%;

and/or one or more compounds of formula IVb, preferably of formula IVb-2, very preferably of formula IVb-2-3, preferably in a total concentration in the range of from 0.2% to 8%, more preferably from 0.5% to 7%, in particular from 1% to 6%;

and/or one or more compounds of formula V, preferably selected from the group consisting of the compounds V-1-1, V-1-6, V-2-1, V-2-2, V-2-3, V-2-4, V-3-5, and V-4-1, preferably in a total concentration in the range of from 5% to 50%, preferably from 10% to 40%, in particular from 15% to 33%;

and/or one or more compounds of formula CL, preferably selected from the formula CL-3, preferably in a total concentration in the range of from 1% to 15%, preferably from 2% to 12%, in particular from 3% to 10%;

and/or one or more compounds of formula V-1-1 or V-1-6, preferably selected from the compounds CCC-n-V, CCC-V-V, and CVCC-n-m, preferably in a total concentration in the range of from 0.5% to 15%, preferably from 1% to 12%, in particular from 2% to 10%;

and/or one or more compounds of formula V-2-1 and/or V-2-2, preferably CCP-n-m, CCP-Vn-m, and/or CPP-n-m, very particularly selected from the group consisting of CCP-3-1, CCP-V-1, and CCP-V2-1, preferably in a total concentration in the range of from 8% to 35%, more preferably from 10% to 30%, very preferably from 12% to 28%;

and/or one or more compounds of formula VII, preferably of the formula VII-1-20 and/or VII-1-21, preferably in a total concentration in the range of from 1% to 15%, preferably from 2% to 13%, in particular from 3% to 11%;

and/or one or more compounds of formula VIII, preferably selected from the compounds of the formula VIII-3, more preferably VIII-3a, preferably in a total concentration in the range of from 1% to 25%, preferably 2% to 20%, in particular 3% to 18%, 5% to 18%, or 10% to 18%;

and/or one or more compounds of the formula I and V-3-4, preferably in a total concentration in the range of from 1% to 15%, preferably from 2% to 13%, in particular from 3% to 12%;

and/or the compound CC-3-V preferably in a concentration of ≥20%, more preferably ≥30%, very preferably ≥40%, preferably in combination with ≥2%, more preferably ≥5% of CC-3-V1, CC-4-V1, and/or CC-3-2V1.

The liquid-crystalline media according to the invention, while retaining the nematic phase down to −20° C. and preferably down to −30° C., particularly preferably down to −40° C., and the clearing point≥90° C., preferably ≥100° C., at the same time allow rotational viscosities $\gamma_1$ of ≤200 mPa·s, particularly preferably ≤150 mPa·s, to be achieved, enabling excellent MLC displays having fast response times. The rotational viscosities are determined at 20° C.

The dielectric anisotropy Δε of the liquid-crystalline media according to the invention at 20° C. and 1 KHz is positive, preferably ≥+1.5, preferably in the range of from 1.5 to 12, more preferably from 2.0 to 10.0, very preferably from 2.5 to 9.0, and particularly preferably from 3.0 to 8.5.

In a preferred embodiment, the dielectric anisotropy Δε of the liquid-crystalline media according to the invention at 20° C. and 1 kHz is preferably in the range of from 3.8 to 4.8.

The birefringence Δn of the liquid-crystalline media according to the invention is preferably from 0.080 to 0.140, very preferably from 0.090 to 0.135, in particular from 0.091 to 0.132.

In a preferred embodiment of the present invention the medium has a birefringence of from 0.090 to 0.115, very preferably from 0.095 to 0.110, in particular from 0.100 to 0.113.

In a preferred embodiment of the present invention the medium has a birefringence of from 0.110 to 0.130, very preferably from 0.119 to 0.128, in particular from 0.120 to 0.123.

In a preferred embodiment of the present invention the medium has a birefringence of from 0.120 to 0.140, very preferably from 0.125 to 0.135, in particular from 0.129 to 0.132.

The rotational viscosity $\gamma_1$ of the liquid-crystalline media according to the invention is preferably ≤180 mPa·s, more preferably ≤160 mPa·s, very preferably ≤150 mPa·s.

The ratio $\gamma_1/K_1$ of the liquid-crystalline media according to the invention is preferably ≤5.5 mPa·s/pN, more preferably ≤5.3 mPa·s/pN, very preferably ≤5.0 mPa·s/pN.

Herein, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$, $C_lH_{2l+1}$, $C_nH_{2n-1}$, $C_mH_{2m}$, and $C_lH_{2l}$ denote straight-chain alkyl or alkylene, respectively, in each case having n, m, or l C atoms, wherein n and m, independently are 0, 1, 2, 3, 4, 5, 6, or 7 and l is 1, 2 or 3. Table A lists the codes used for the ring elements of the core structures of the compounds, while Table B and Table C show the linking groups and end groups. Table D shows illustrative structures of compounds with their respective abbreviations.

TABLE A

| Ring elements | | | |
|---|---|---|---|
| C | 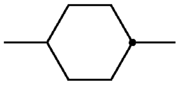 | | |
| D | 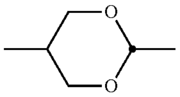 | DI | 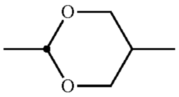 |
| A | 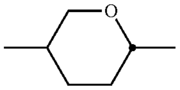 | AI | 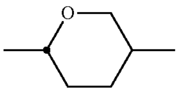 |
| G | 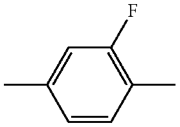 | GI | 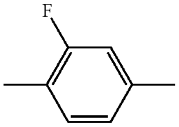 |
| U | 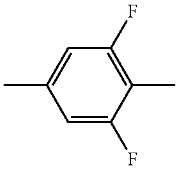 | UI | 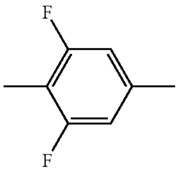 |
| U(1) | 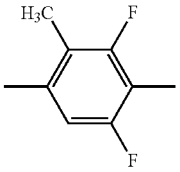 | U(1)I | 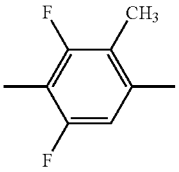 |
| Y | 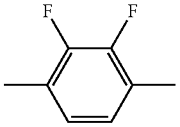 | Y(1) | 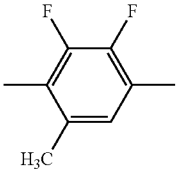 |
| M | 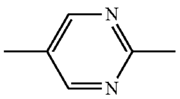 | MI | 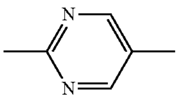 |

TABLE A-continued
| Ring elements | | | |
| --- | --- | --- | --- |
| N | 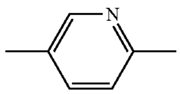 | NI | 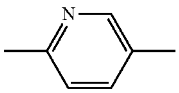 |
| K | 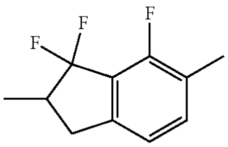 | KI | 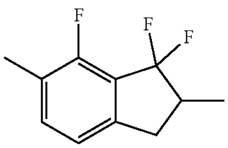 |
| Np | 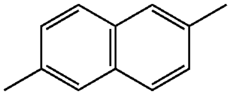 | | |
| L | 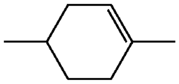 | LI | 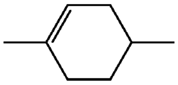 |
| F | 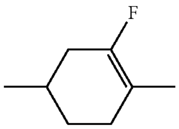 | FI | 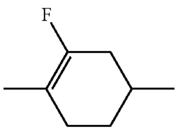 |
| P | 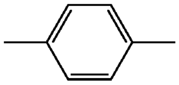 | P(o) | 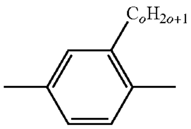 |
| P(i3) | 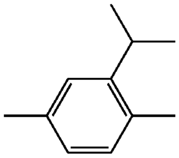 | PI(o) | 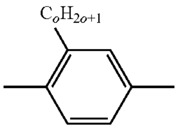 |
| O | 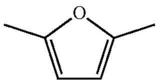 | S | 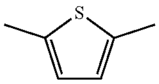 |
| | | cpS | 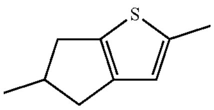 |
| B | 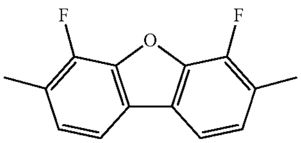 | B(S) | 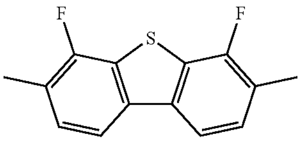 |
| B(P) | 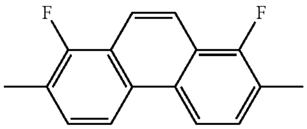 | B(A) | 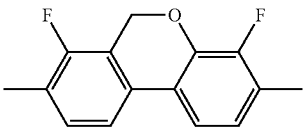 |

TABLE B

| Linking groups | | | |
|---|---|---|---|
| E | —$CH_2CH_2$— | Z | —CO—O— |
| V | —CH═CH— | ZI | —O—CO— |
| X | —CF═CH— | O | —$CH_2$—O— |
| XI | —CH═CF— | OI | —O—$CH_2$— |

TABLE B-continued

| Linking groups | | | |
|---|---|---|---|
| B | —CF═CF— | Q | —$CF_2$—O— |
| T | —C≡C— | QI | —O—$CF_2$— |
| W | —$CF_2CF_2$— | | |

TABLE C

| End groups | | | |
|---|---|---|---|
| | | Right-hand side | |
| Left-hand side | | Used alone | |
| -n- | $C_nH_{2+1}$— | -n | —$C_nH_{2n+1}$ |
| -nO— | $C_nH_{2n+1}$—O— | —On | —O—$C_nH_{2n+1}$ |
| -V- | $CH_2$═CH— | -V | —CH═$CH_2$ |
| -nV- | $C_nH_{2n+1}$—CH═CH— | -nV | —$C_nH_{2n}$—CH═$CH_2$ |
| -Vn- | $CH_2$═CH—$C_nH_{2n+1}$— | -Vn | —CH═CH—$C_nH_{2n+1}$ |
| -nVm- | $C_nH_{2n+1}$—CH═CH—$C_mH_{2m}$— | -nVm | —$C_nH_{2n}$—CH═CH—$C_mH_{2m+1}$ |
| —N— | N≡C— | —N | —C≡N |
| —S— | S═C═N— | —S | —N═C═S |
| —F— | F— | —F | —F |
| —Cl— | Cl— | —Cl | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO— | $CFH_2O$— | —OM | —$OCFH_2$ |
| -DO— | $CF_2HO$— | —OD | —$OCF_2H$ |
| -TO— | $CF_3O$— | —OT | —$OCF_3$ |
| -FXO— | $CF_2$═CH—O— | —OXF | —O—CH═$CF_2$ |
| -A- | H—C≡C— | -A | —C≡C—H |
| -nA- | $C_nH_{2n+1}$—C≡C— | -An | —C≡C—$C_nH_{2n+1}$ |
| —NA- | N≡C—C≡C— | -AN | —C≡C—C≡N |
| -(cn)- | 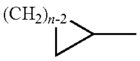 | -(cn) | 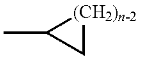 |
| -(cn)m- | 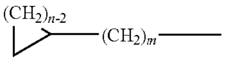 | -m(cn) | 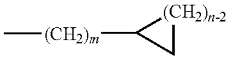 |
| -(c5-1en)m- | 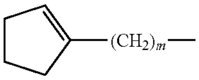 | -m(c5-1en) | 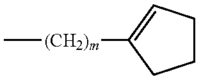 |
| -(c5-2en)m- | 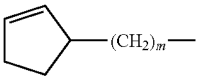 | -m(c5-2en) | 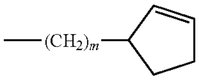 |
| -(c5-3en)m- | 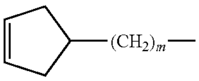 | -m(c5-3en) | 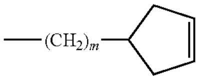 |
| Used in combination with others | | | |
| -...A...- | —C≡C— | -...A... | —C≡C— |
| -...V...- | —CH═CH— | -...V... | —CH═CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF═CF— | -...W... | —CF═CF— |

in which n and m each denote integers, and the three dots "..." are placeholders for other abbreviations from this table.

TABLE D
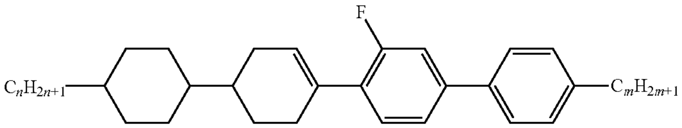
CLGIP-n-m
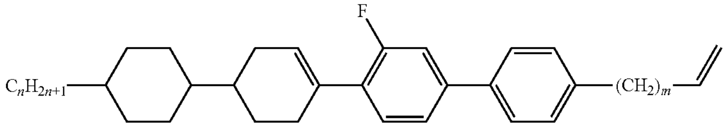
CLGIP-n-mV
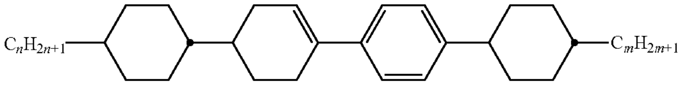
CLPC-n-m
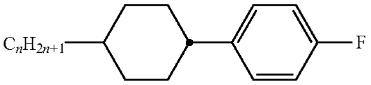
CP-n-F
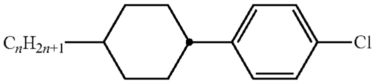
CP-n-Cl
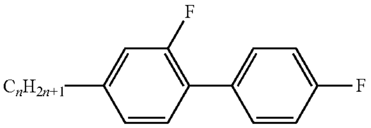
GP-n-F
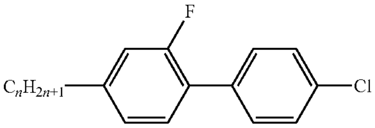
GP-n-Cl
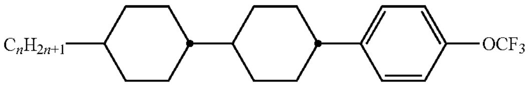
CCP-n-OT
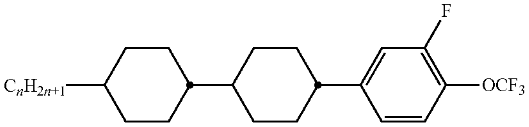
CCG-n-OT
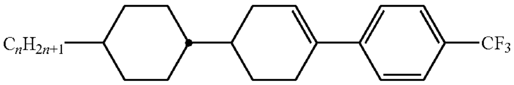
CLP-n-T TABLE D-continued
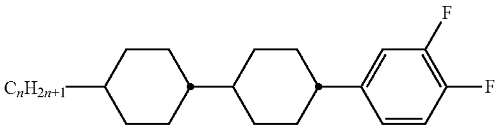
CCG-n-F
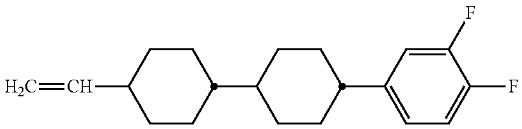
CCG-V-F
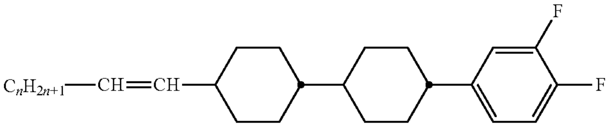
CCG-nV-F
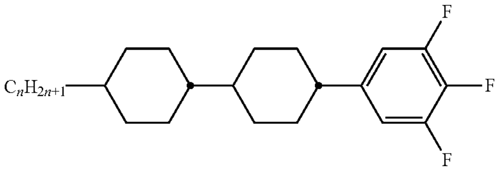
CCU-n-F
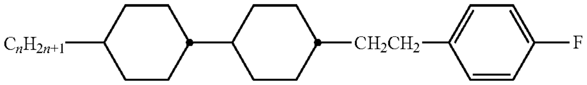
CCEP-n-F
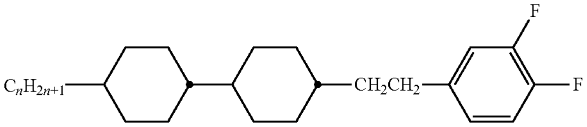
CCEU-n-F
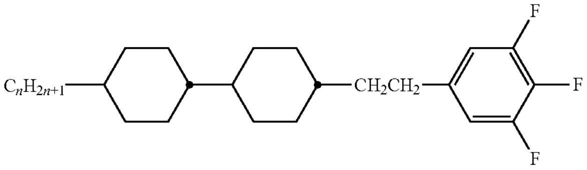
CCEU-n-F
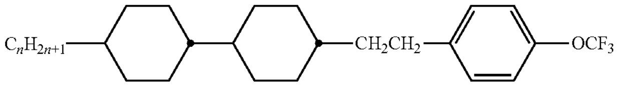
CCEP-n-OT TABLE D-continued
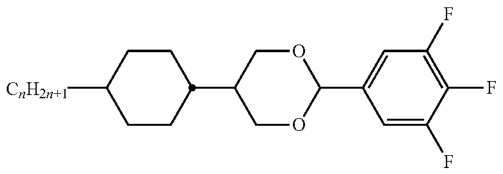
CDU-n-F
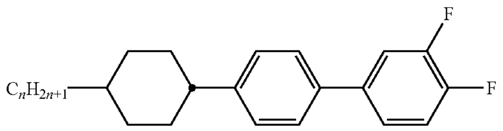
CPG-n-F
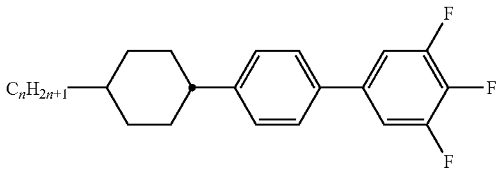
CPU-n-F
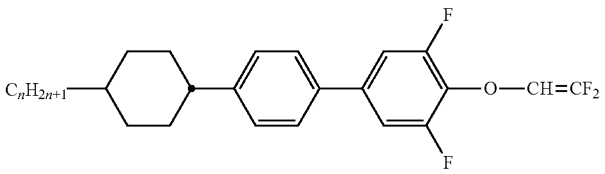
CPU-n-OXF
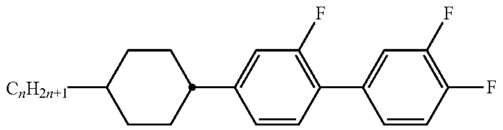
CGG-n-F
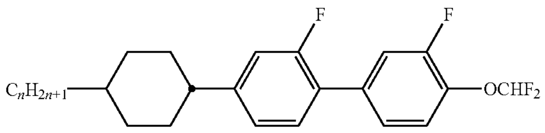
CGG-n-OD
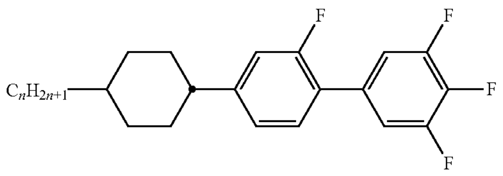
CGU-n-F TABLE D-continued
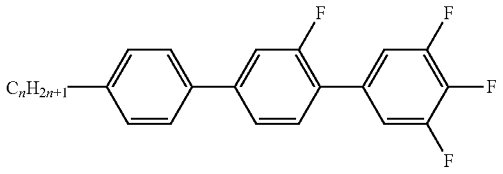
PGU-n-F
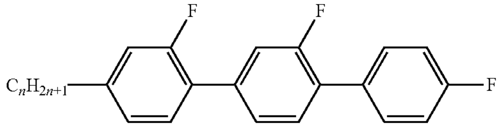
GGP-n-F
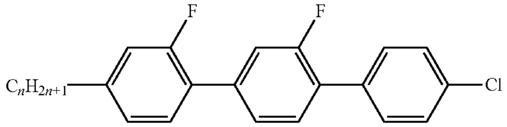
GGP-n-Cl
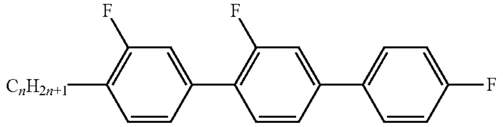
GIGIP-n-F
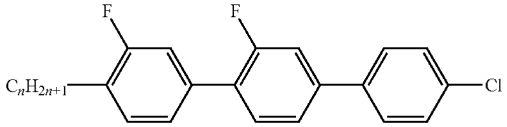
GIGIP-n-Cl
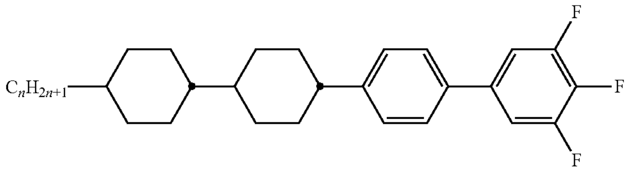
CCPU-n-F
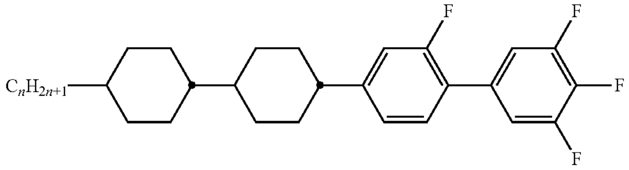
CCGU-n-F
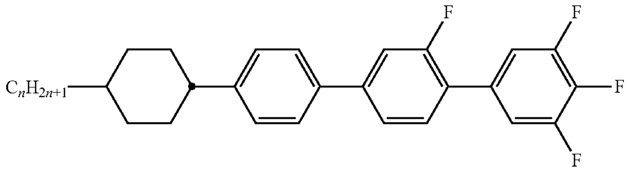
CPGU-n-F TABLE D-continued
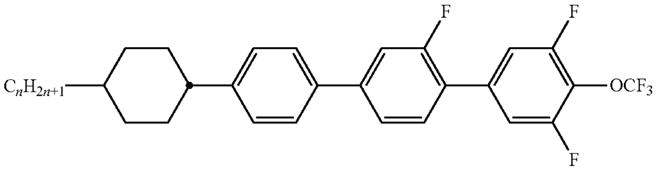
CPGU-n-OT
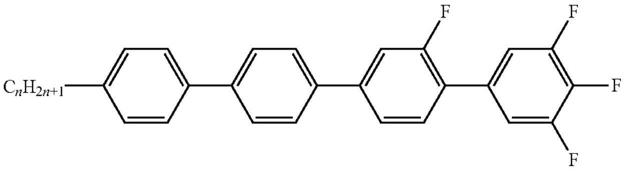
PPGU-n-F
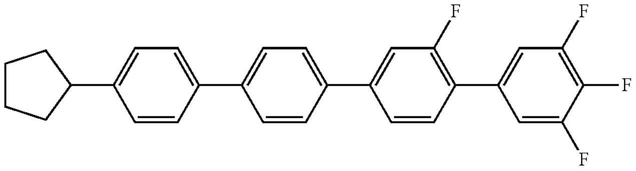 [SMILES: Fc1cc(-c2ccc(-c3ccc(C4CCCC4)cc3)cc2)ccc1-c1cc(F)c(F)c(F)c1]
PPGU-(c5)-F
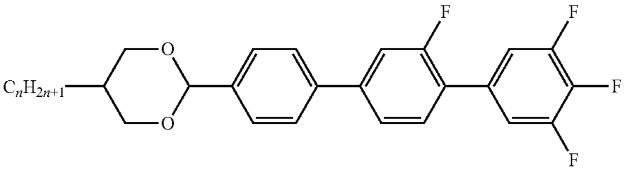
DPGU-n-F
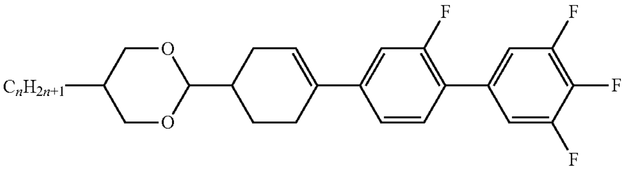
DLGU-n-F
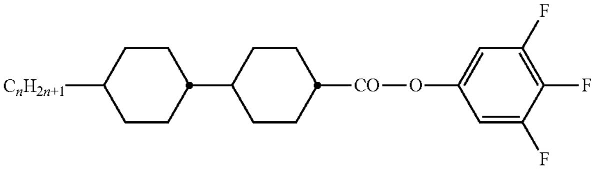
CCZU-n-F
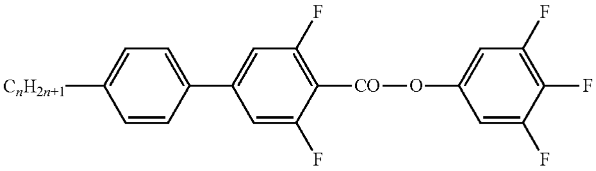
PUZU-n-F TABLE D-continued
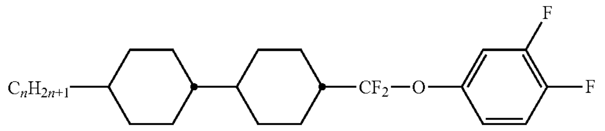
CCQG-n-F
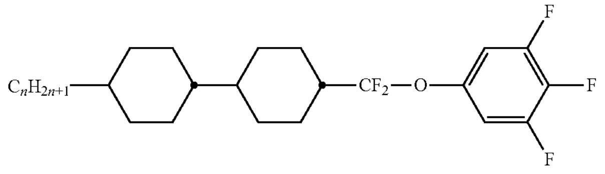
CCQU-n-F
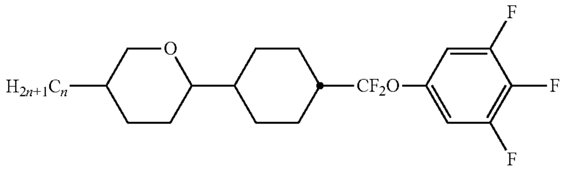
ACQU-n-F
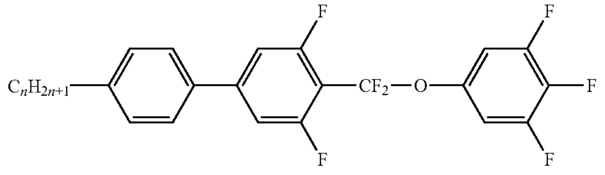
PUQU-n-F
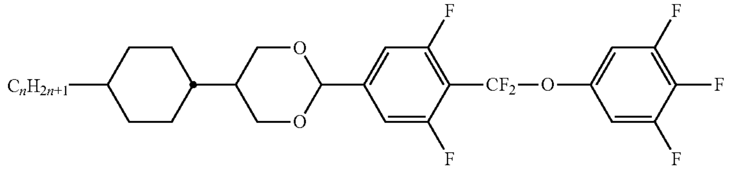
CDUQU-n-F
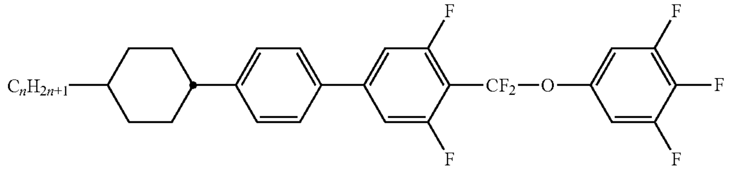
CPUQU-n-F
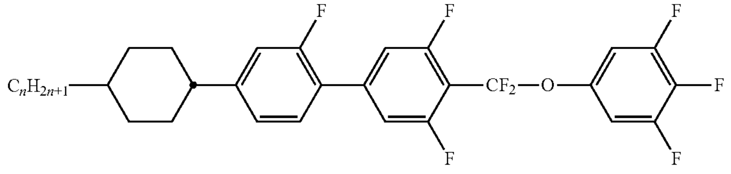
CGUQU-n-F TABLE D-continued
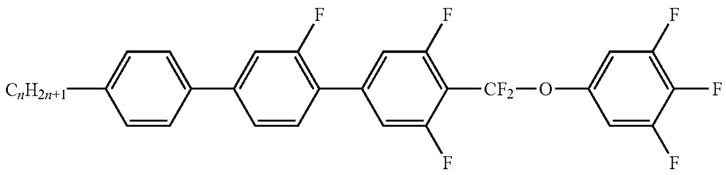
PGUQU-n-F
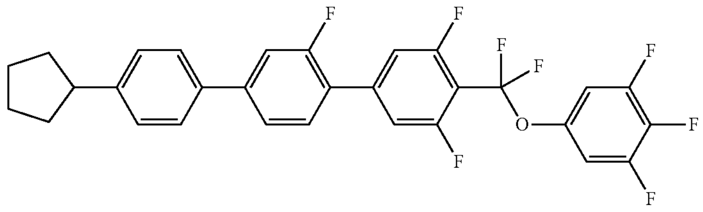 [SMILES: Fc1cc(-c2ccc(C3CCCC3)cc2)ccc1-c1cc(F)c(C(F)(F)Oc2cc(F)c(F)c(F)c2)c(F)c1]
PGUQU(c5)-F
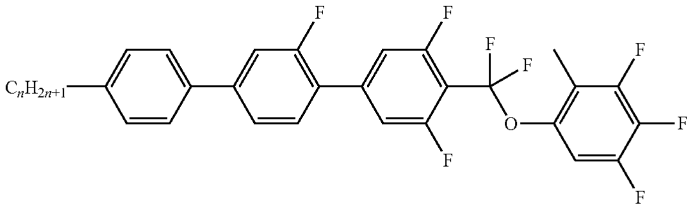
PGUQU(1)-n-F
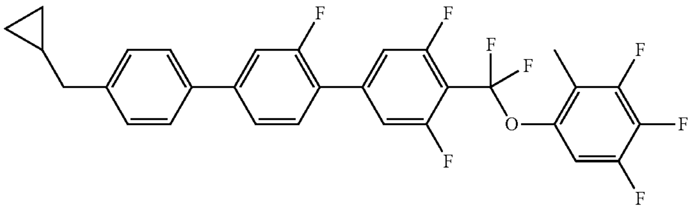 [SMILES: Cc1c(OC(F)(F)c2c(F)cc(-c3ccc(-c4ccc(CC5CC5)cc4)cc3F)cc2F)cc(F)c(F)c1F]
PGUQU(1)-(c3)1-F
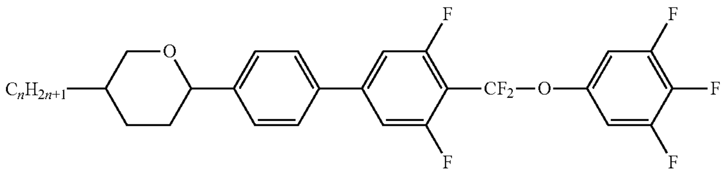
APUQU-n-F
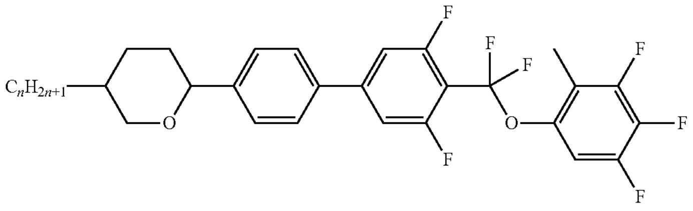
APUQU(1)-n-F TABLE D-continued
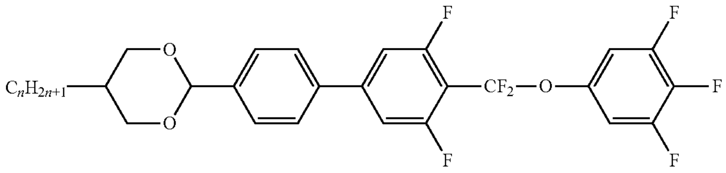
DPUQU-n-F
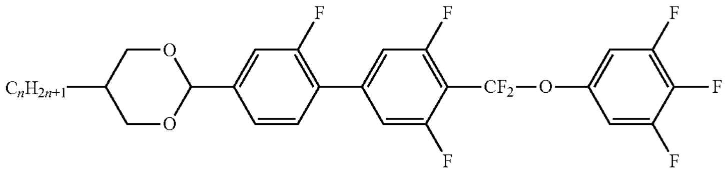
DGUQU-n-F
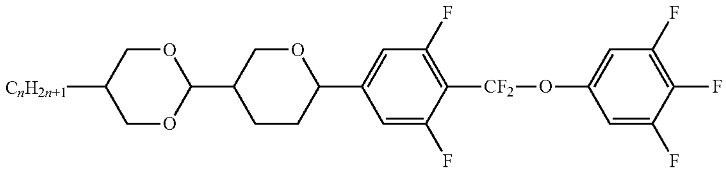
DAUQU-n-F
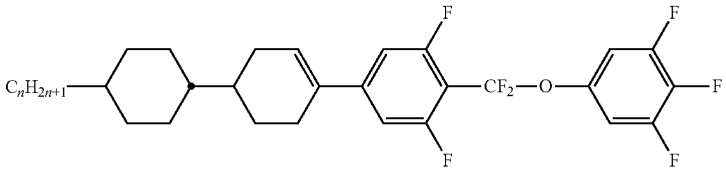
CLUQU-n-F
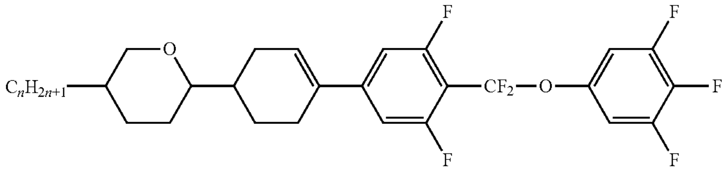
ALUQU-n-F
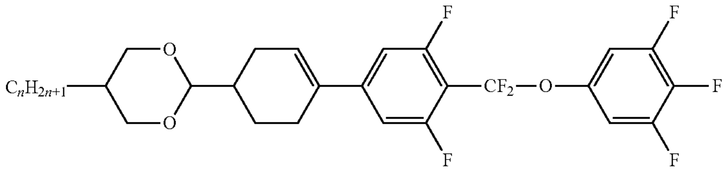
DLUQU-n-F
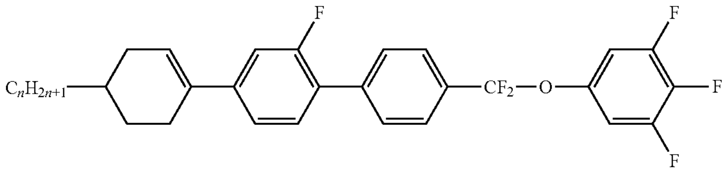
LGPQU-n-F TABLE D-continued
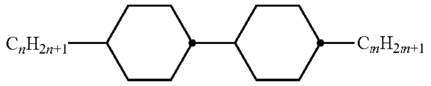
CC-n-m
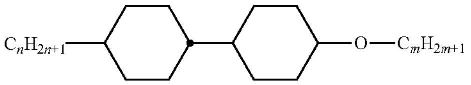
CC-n-Om
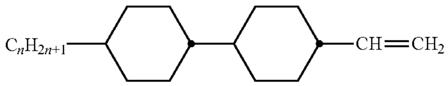
CC-n-V
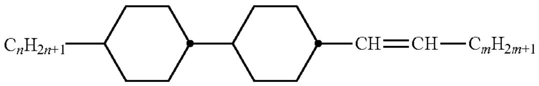
CC-n-Vm
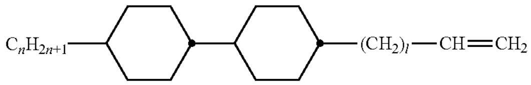
CC-n-IV
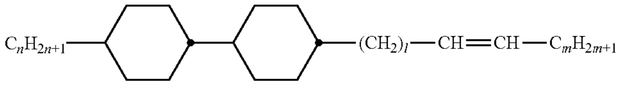
CC-n-IVm
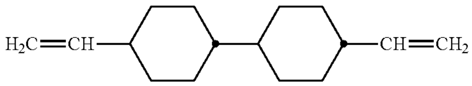
CC-V-V
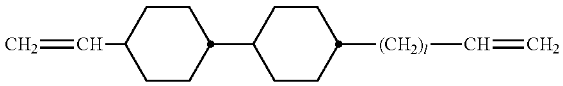
CC-V-IV
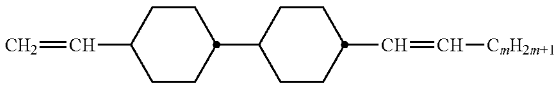
CC-V-Vm
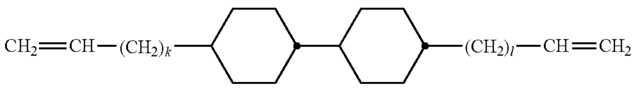
CC-Vk-IV
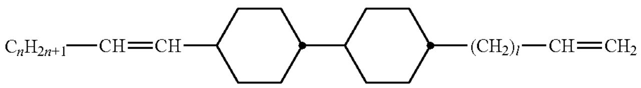
CC-nV-IV TABLE D-continued
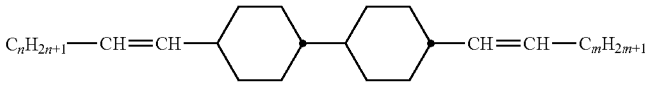
CC-nV-Vm
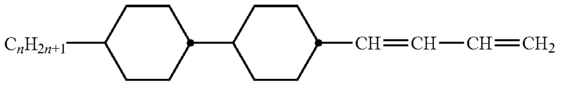
CC-n-VV
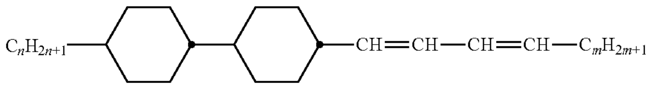
CC-n-VVm
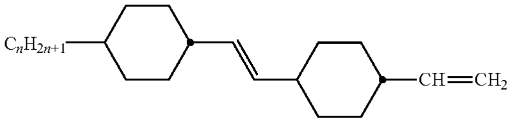
CVC-n-V
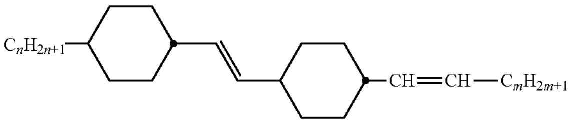
CVC-n-Vm
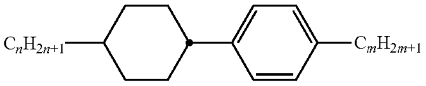
CP-n-m
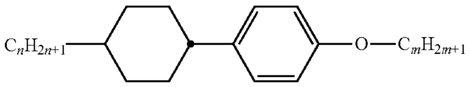
CP-n-Om
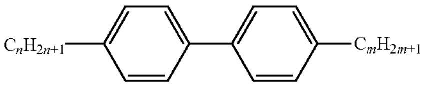
PP-n-m
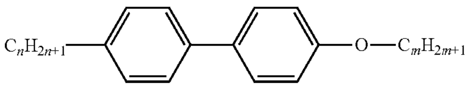
PP-n-Om
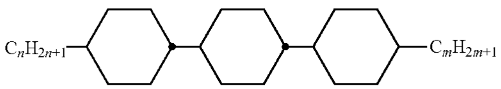
CCC-n-m
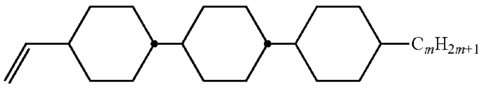
CCC-V-m TABLE D-continued
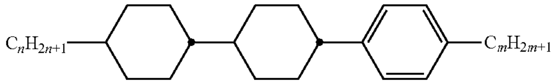
CCP-n-m
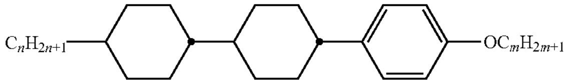
CCP-n-Om
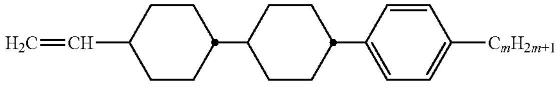
CCP-V-m
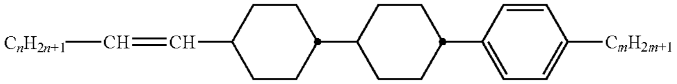
CCP-nV-m
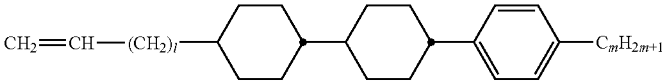
CCP-Vl-m
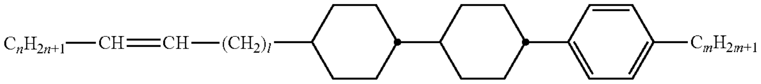
CCP-nVl-m
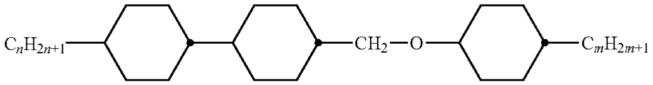
CCOC-n-m
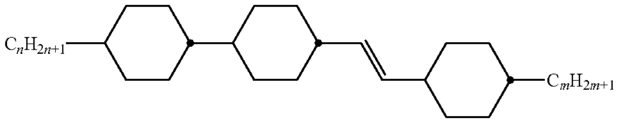
CCVC-n-m
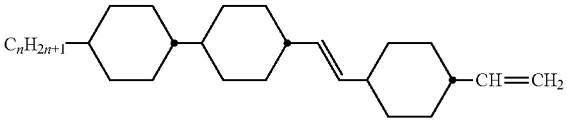
CCVC-n-V
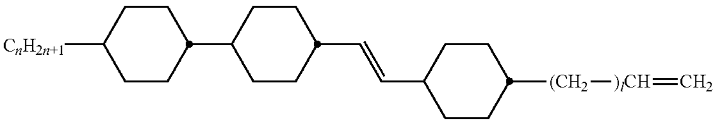
CCVC-n-lV TABLE D-continued
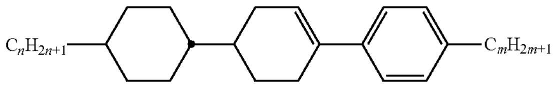
CLP-n-m
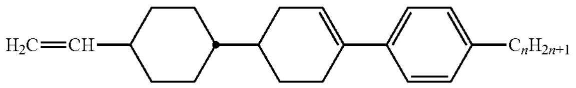
CLP-V-n
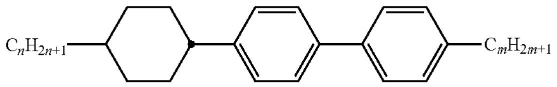
CPP-n-m
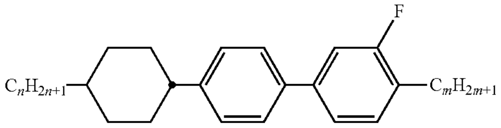
CPG-n-m
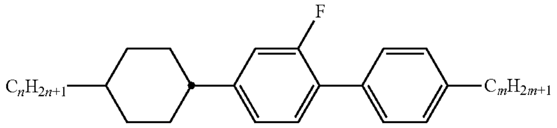
CGP-n-m
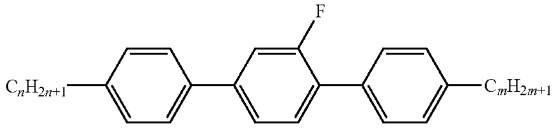
PGP-n-m
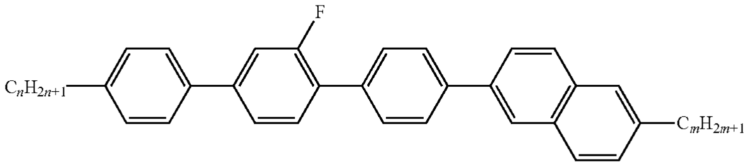
PGPNp-n-m
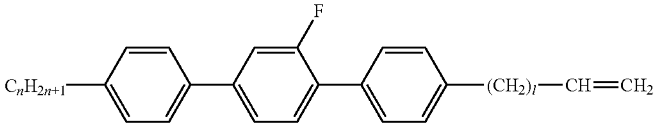
PGP-n-IV
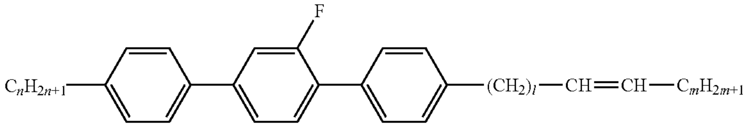
PGP-n-IVm TABLE D-continued
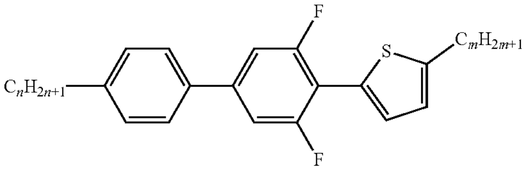
PUS-n-m
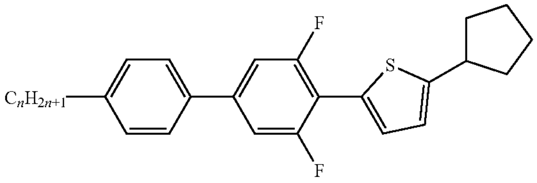
PUS-n-(c5)
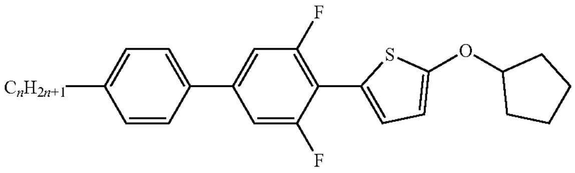
PUS-n-O(c5)
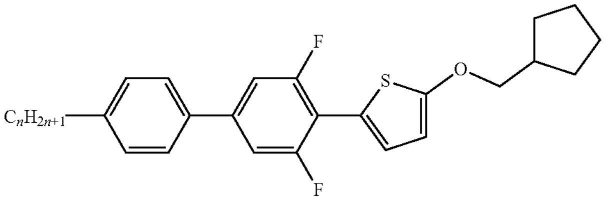
PUS-n-O1(c5)
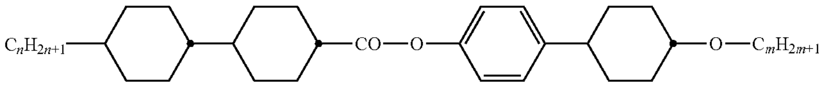
CCZPC-n-m
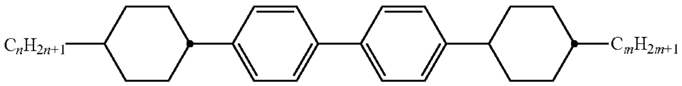
CPPC-n-m
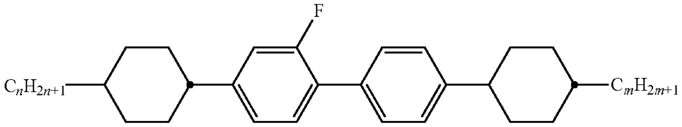
CGPC-n-m
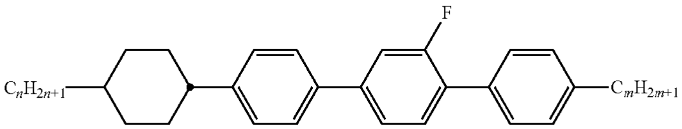
CPGP-n-m TABLE D-continued
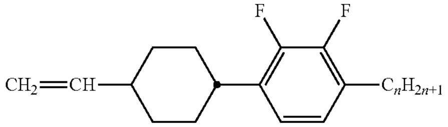
CY-V-n
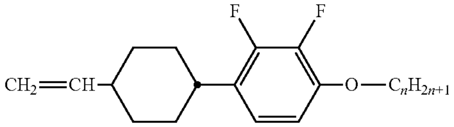
CY-V-On
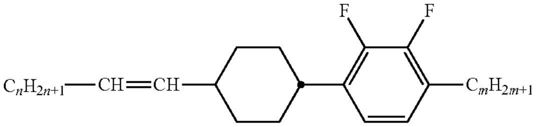
CY-nV-m
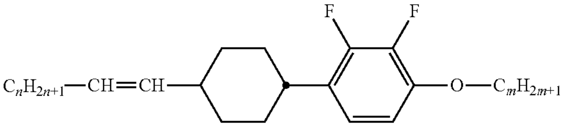
CY-nV-Om
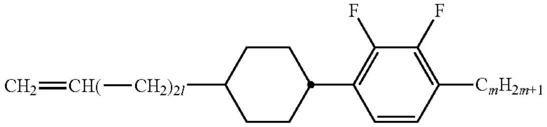
CY-VI-m
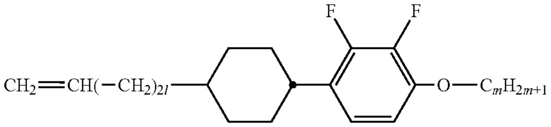
CY-VI-Om
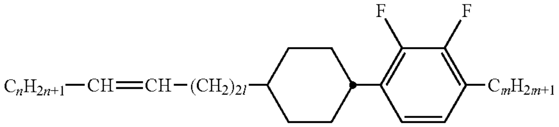
CY-nVI-m
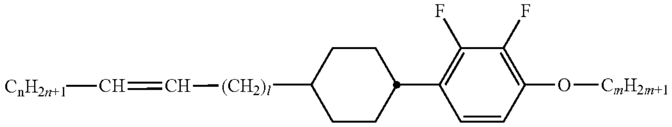
CY-nVI-Om
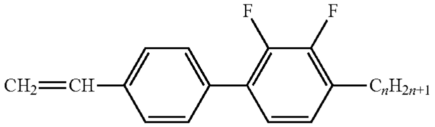
PY-V-n TABLE D-continued
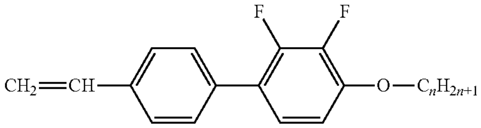
PY-V-On
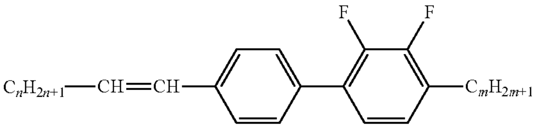
PY-nV-m
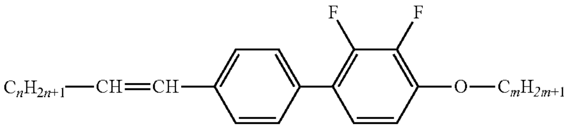
PY-nV-Om
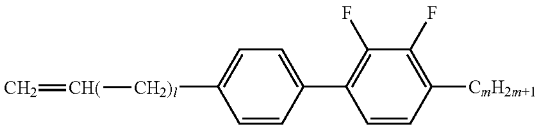
PY-VI-m
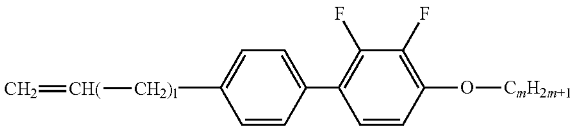
PY-VI-Om
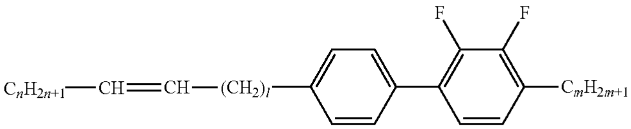
PY-nVI-m
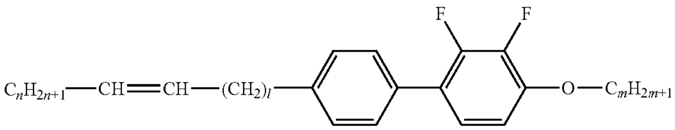
PY-nVI-Om
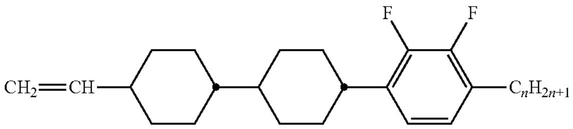
CCY-V-n TABLE D-continued
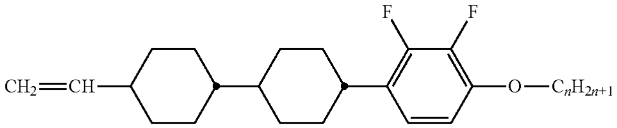
CCY-V-On
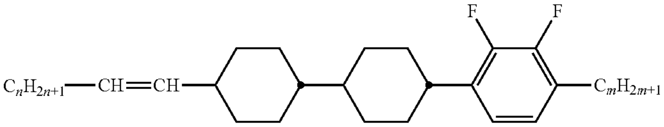
CCY-nV-m
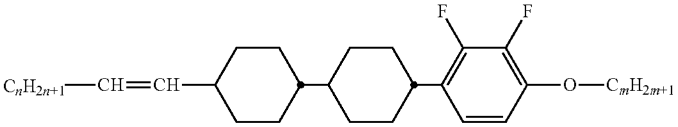
CCY-nV-Om
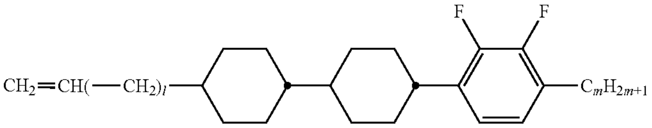
CCY-VI-m
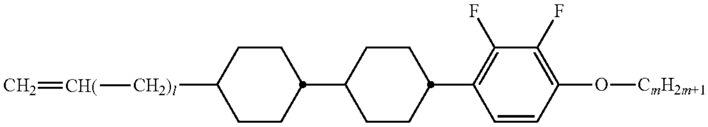
CCY-VI-Om
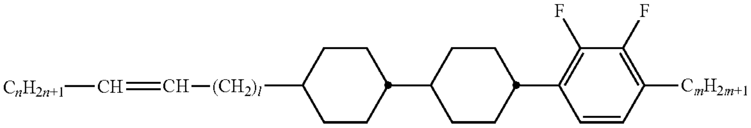
CCY-nVI-m
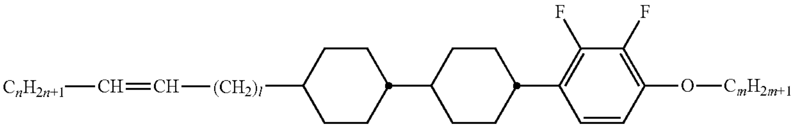
CCY-nVI-Om
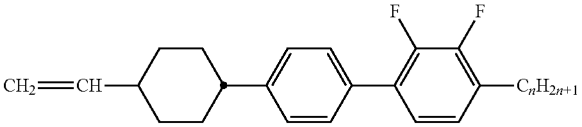
CPY-V-n TABLE D-continued
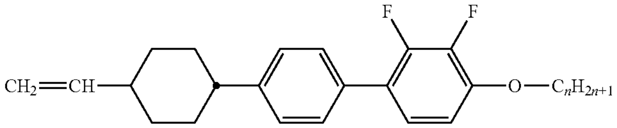
CPY-V-On
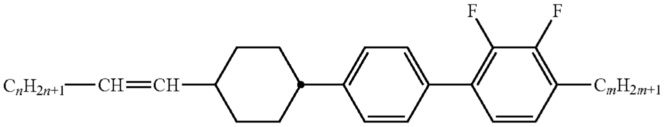
CPY-nV-m
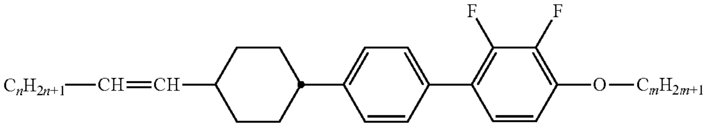
CPY-nV-Om
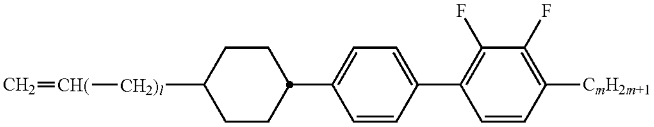
CPY-Vl-m
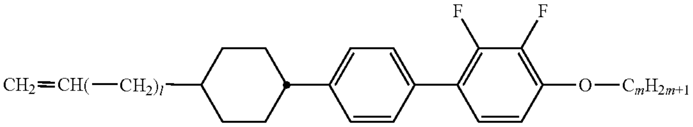
CPY-Vl-Om
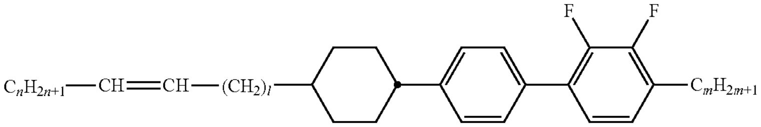
CPY-nVl-k
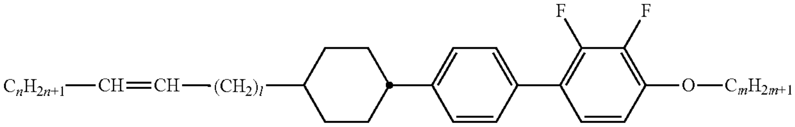
CPY-nVl-Om
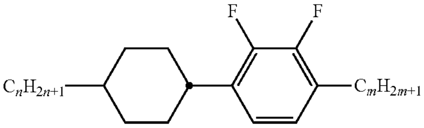
CY-n-m TABLE D-continued
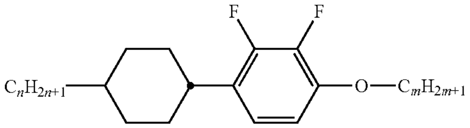
CY-n-Om
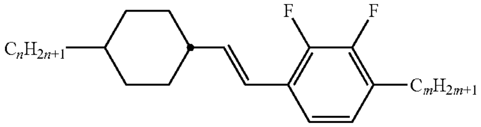
CVY-n-m
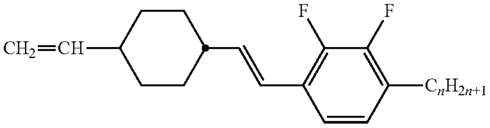
CVY-V-n
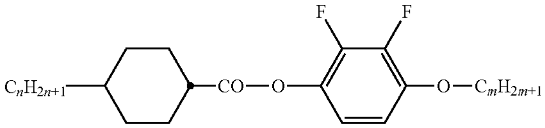
CZY-n-Om
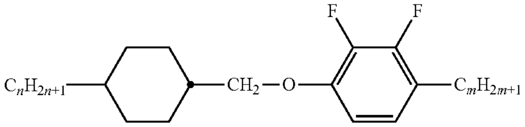
COY-n-m
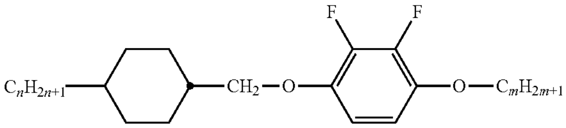
COY-n-Om
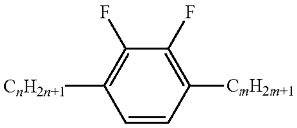
Y-n-m
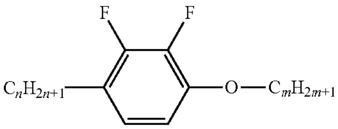
Y-n-Om TABLE D-continued
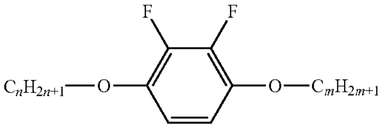
Y-nO—Om
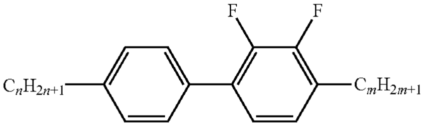
PY-n-m
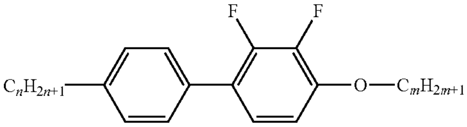
PY-n-Om
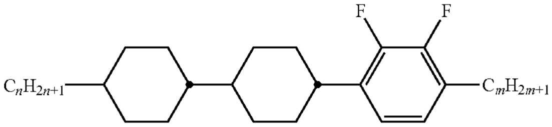
CCY-n-m
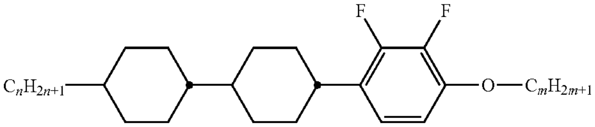
CCY-n-Om
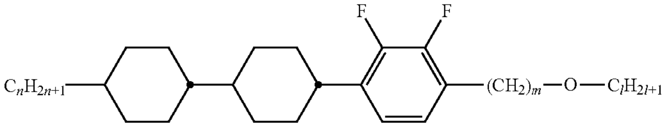
CCY-n-mOI
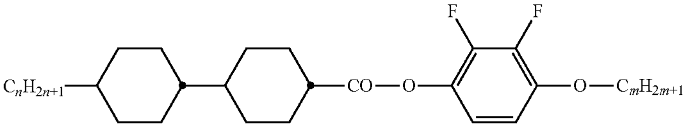
CCZY-n-Om
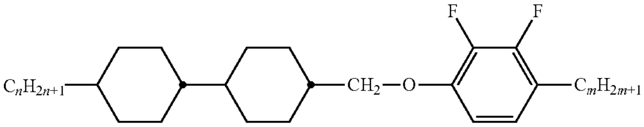
CCOY-n-m TABLE D-continued
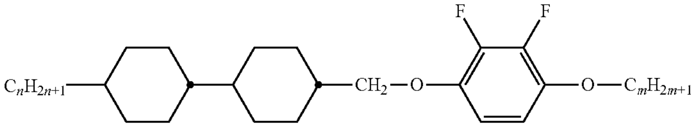
CCOY-n-Om
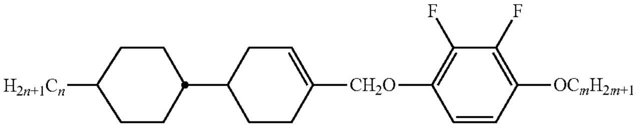
CLOY-n-Om
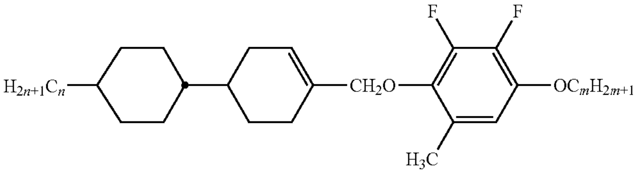
CLOY(1)-n-Om
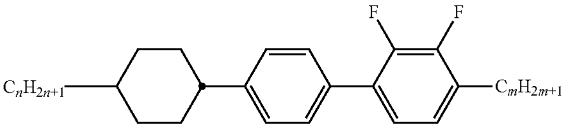
CPY-n-m
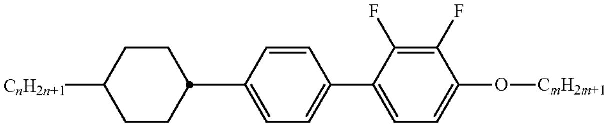
CPY-n-Om
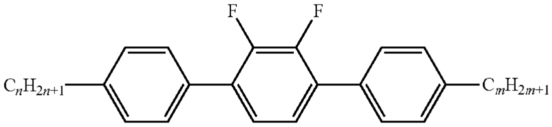
PYP-n-m
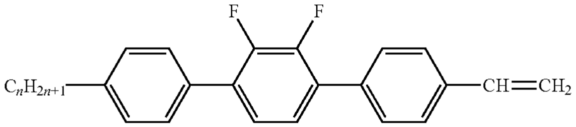
PYP-n-V
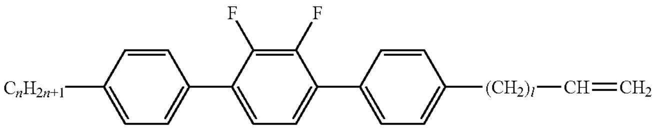
PYP-n-IV TABLE D-continued
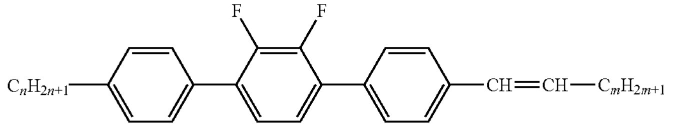
PYP-n-Vm
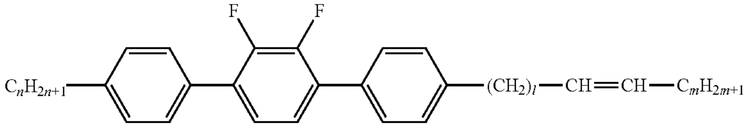
PYP-n-IVm
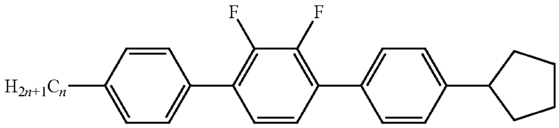
PYP-n-(c5)
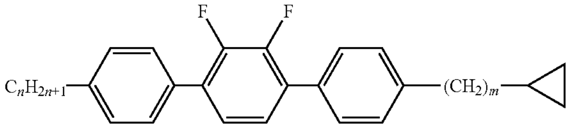
PYP-n-m(c3)
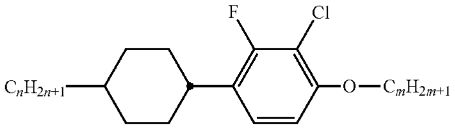
CP(F,Cl)-n-Om
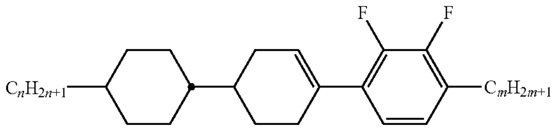
CLY-n-m
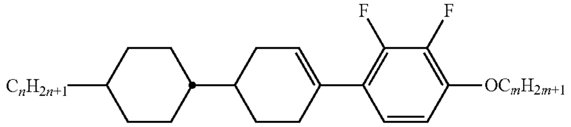
CLY-n-Om
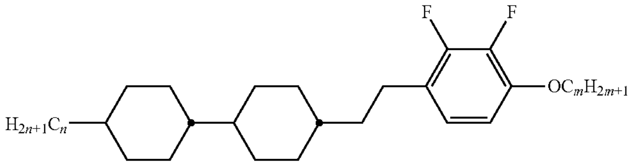
CCEY-n-Om TABLE D-continued
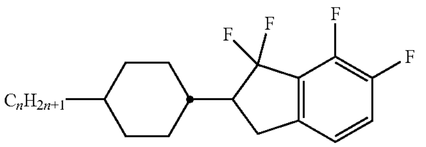
CK-n-F
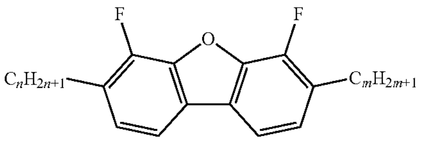
B-n-m
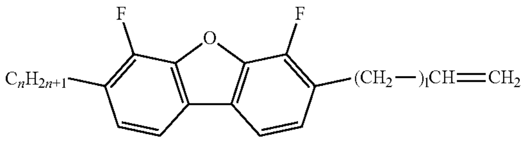
B-n-IV
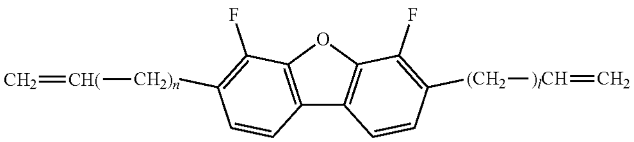
B-Vn-IV
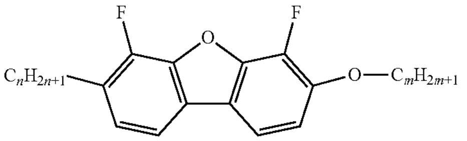
B-n-Om
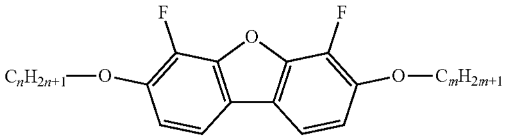
B-nO—Om
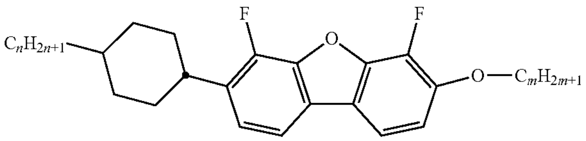
CB-n-Om
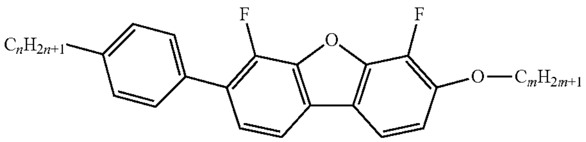
PB-n-Om TABLE D-continued
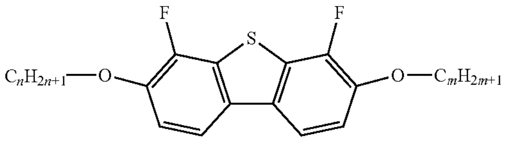
B(S)-nO—Om
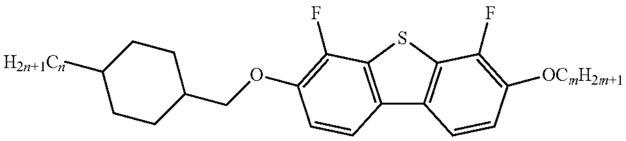
COB(S)-n-Om
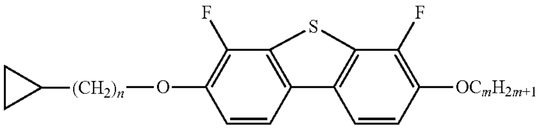
B(S)-(c3)nO—Om
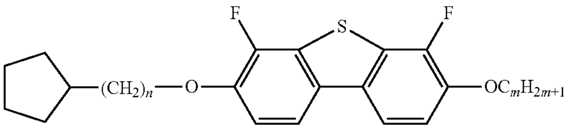
B(S)-(c5)nO—Om
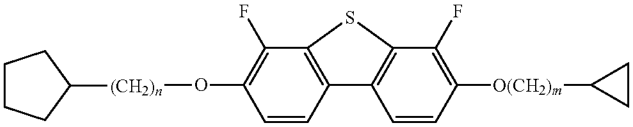
B(S)-(c5)nO—Om(c3)
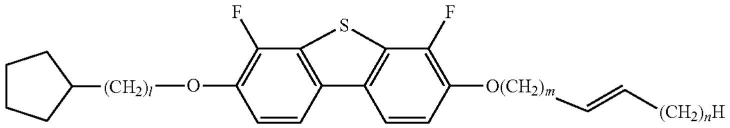
B(S)-(c5)IO—OmVn
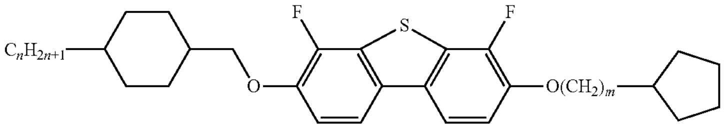
COB(S)-n-Om(c5)
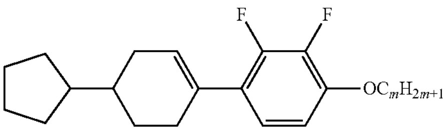
LY-(c5)-Om TABLE D-continued
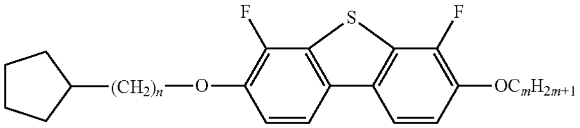
B(S)-(c5-3en)nO—Om
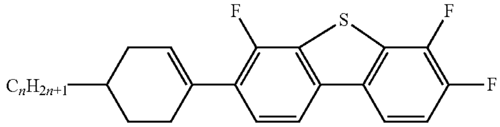
LB(S)-n-F
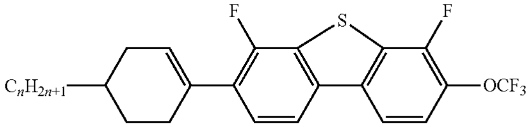
LB(S)-n-OT
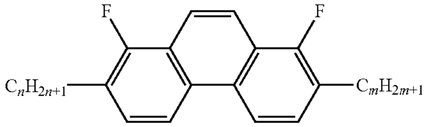
B(P)-n-m
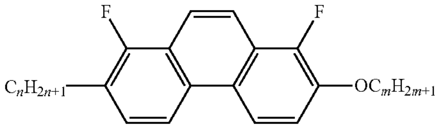
B(P)-n-Om
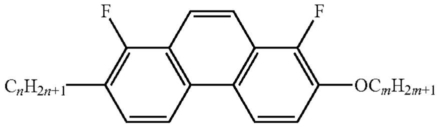
B(P)-n-Om
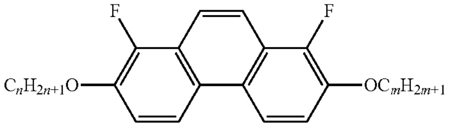
B(P)-nO—Om
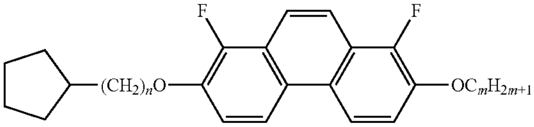
B(P)-(c5)nO—Om TABLE D-continued
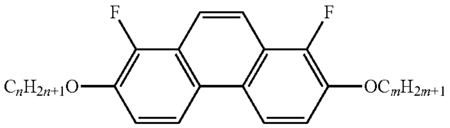
B(A)-nO—Om
In a preferred embodiment of the present invention, the media comprise one or more compounds selected from the group of the compounds of Table D.
Table E shows chiral dopants which are preferably employed in the mixtures according to the invention.
TABLE E
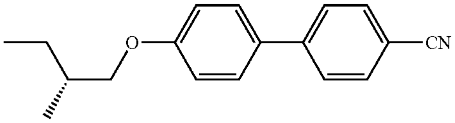 [SMILES: CC[C@@H](C)COc1ccc(-c2ccc(C#N)cc2)cc1]
C 15
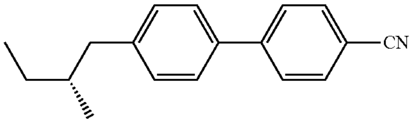 [SMILES: CC[C@@H](C)Cc1ccc(-c2ccc(C#N)cc2)cc1]
CB 15
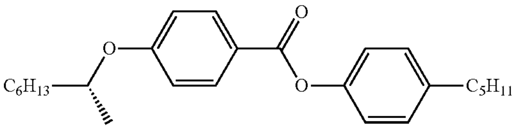
CM 21
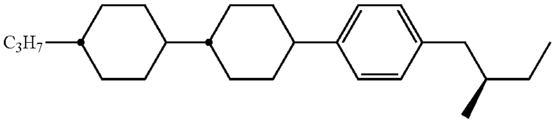
CM 44
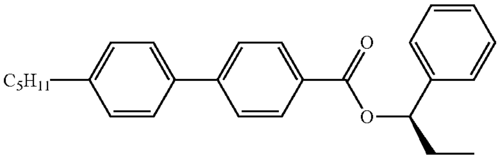
CM 45
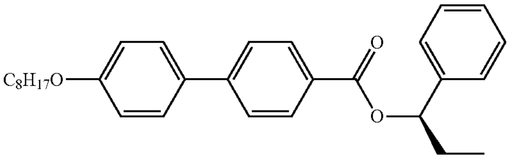
CM 47

TABLE E-continued
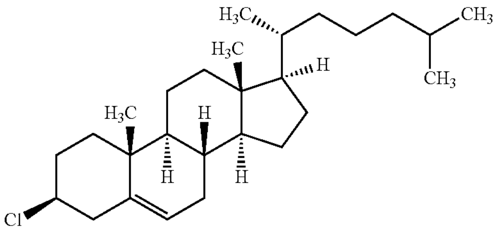
CC
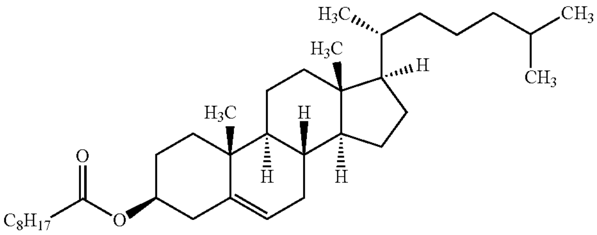
CN
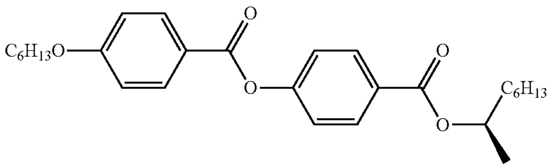
R/S-811
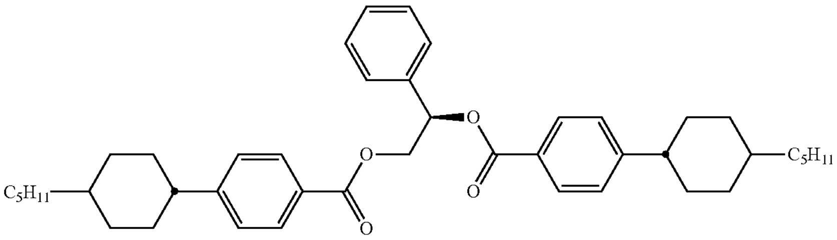
R/S-1011
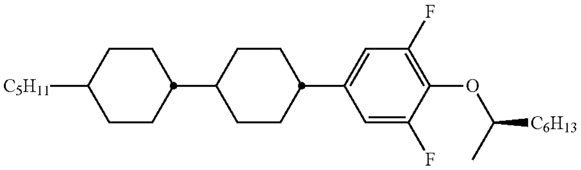
R/S-2011
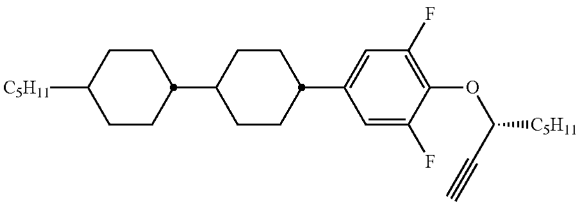
R/S-3011

TABLE E-continued
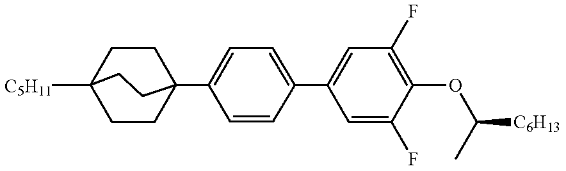
R/S-4011
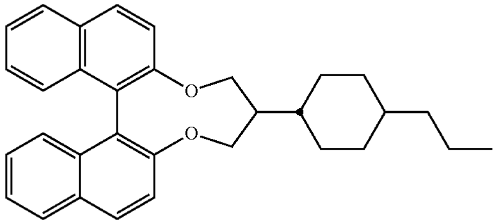
R/S-5011
Preferably, the media according to the invention comprise one or more compounds selected from the group of the compounds from Table E.
TABLE F
Table F shows illustrative reactive mesogenic compounds (RM) which can be used in the LC media in accordance with the present invention.
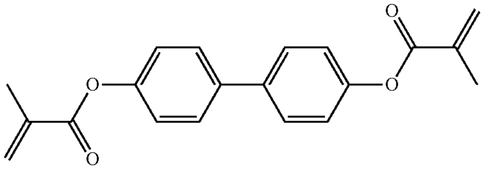
RM-1
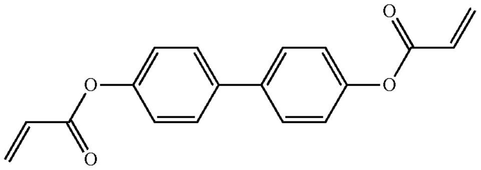 [SMILES: C=CC(=O)Oc1ccc(-c2ccc(OC(=O)C=C)cc2)cc1]
RM-2
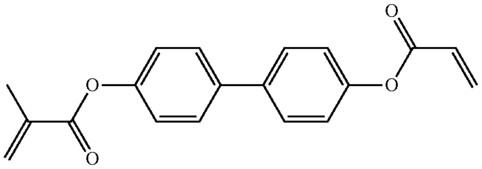 [SMILES: C=CC(=O)Oc1ccc(-c2ccc(OC(=O)C(=C)C)cc2)cc1]
RM-3
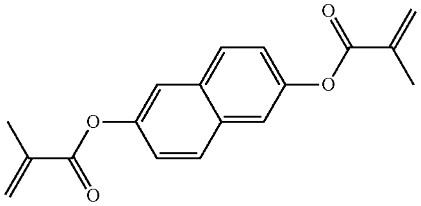 [SMILES: C=C(C)C(=O)Oc1ccc2cc(OC(=O)C(=C)C)ccc2c1]
RM-4

TABLE F-continued
Table F shows illustrative reactive mesogenic compounds (RM) which can be used in the LC media in accordance with the present invention.
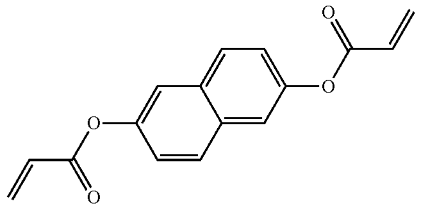 [SMILES: C=CC(=O)Oc1ccc2cc(OC(=O)C=C)ccc2c1]
RM-5
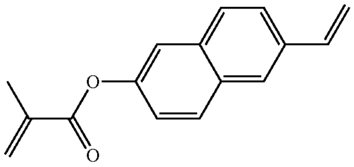 [SMILES: C=Cc1ccc2cc(OC(=O)C(=C)C)ccc2c1]
RM-6
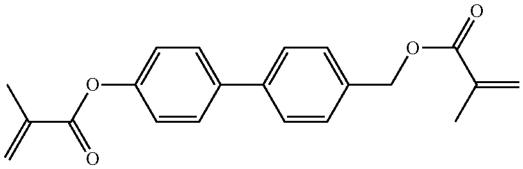 [SMILES: C=C(C)C(=O)OCc1ccc(-c2ccc(OC(=O)C(=C)C)cc2)cc1]
RM-7
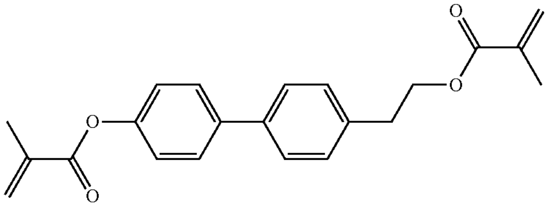 [SMILES: C=C(C)C(=O)OCCc1ccc(-c2ccc(OC(=O)C(=C)C)cc2)cc1]
RM-8
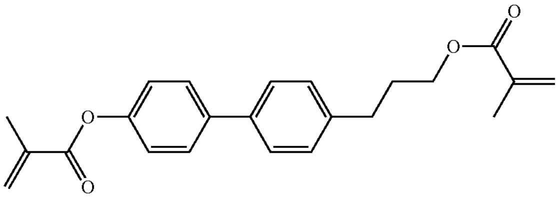 [SMILES: C=C(C)C(=O)OCCCc1ccc(-c2ccc(OC(=O)C(=C)C)cc2)cc1]
RM-9
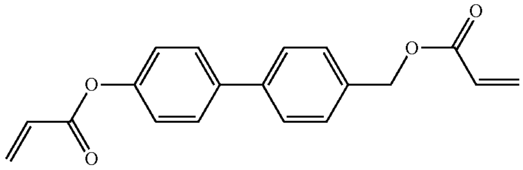 [SMILES: C=CC(=O)OCc1ccc(-c2ccc(OC(=O)C=C)cc2)cc1]
RM-10

TABLE F-continued
Table F shows illustrative reactive mesogenic compounds (RM) which can be used in the LC media in accordance with the present invention.
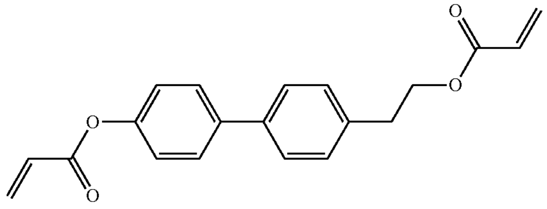 [SMILES: C=CC(=O)OCCc1ccc(-c2ccc(OC(=O)C=C)cc2)cc1]
RM-11
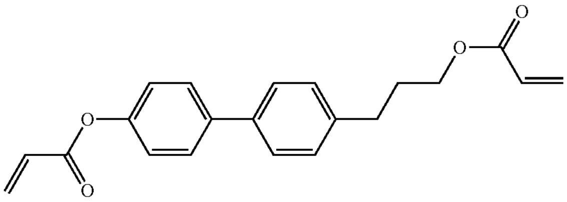 [SMILES: C=CC(=O)OCCCc1ccc(-c2ccc(OC(=O)C=C)cc2)cc1]
RM-12
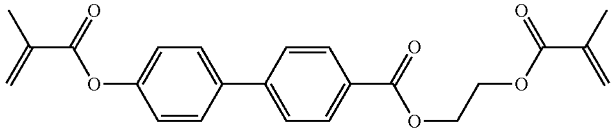 [SMILES: C=C(C)C(=O)OCCOC(=O)c1ccc(-c2ccc(OC(=O)C(=C)C)cc2)cc1]
RM-13
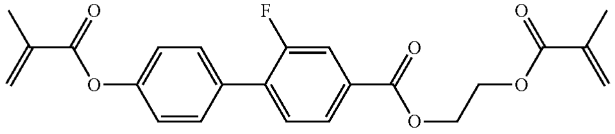 [SMILES: C=C(C)C(=O)OCCOC(=O)c1ccc(-c2ccc(OC(=O)C(=C)C)cc2)c(F)c1]
RM-14
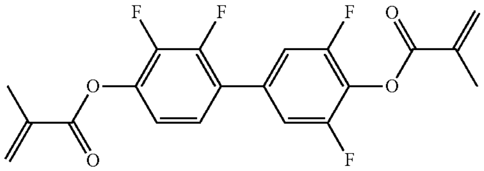 [SMILES: C=C(C)C(=O)Oc1ccc(-c2cc(F)c(OC(=O)C(=C)C)c(F)c2)c(F)c1F]
RM-15
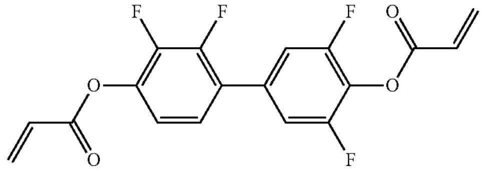 [SMILES: C=CC(=O)Oc1ccc(-c2cc(F)c(OC(=O)C=C)c(F)c2)c(F)c1F]
RM-16
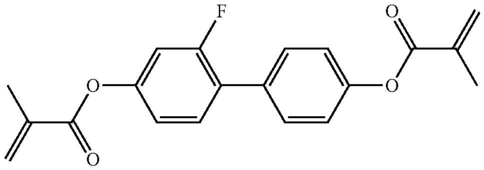
RM-17

TABLE F-continued
Table F shows illustrative reactive mesogenic compounds (RM) which can be used in the LC media in accordance with the present invention.
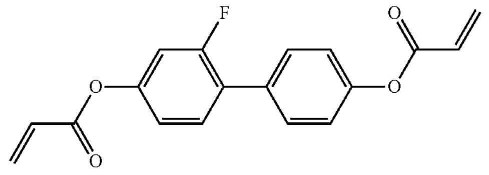 [SMILES: C=CC(=O)Oc1ccc(-c2ccc(OC(=O)C=C)cc2F)cc1]
RM-18
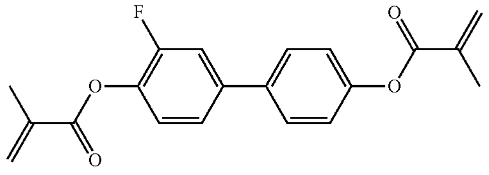
RM-19
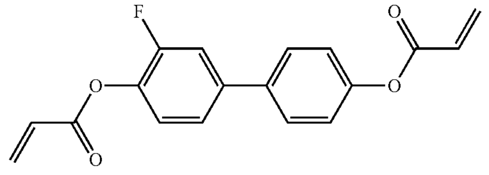 [SMILES: C=CC(=O)Oc1ccc(-c2ccc(OC(=O)C=C)c(F)c2)cc1]
RM-20
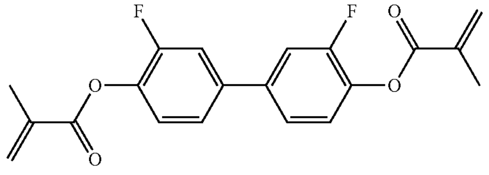
RM-21
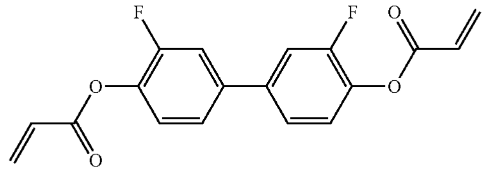 [SMILES: C=CC(=O)Oc1ccc(-c2ccc(OC(=O)C=C)c(F)c2)cc1F]
RM-22
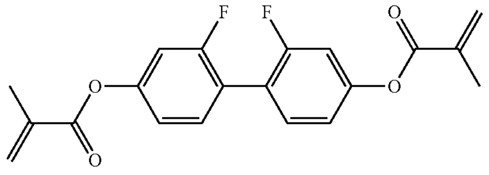 [SMILES: C=C(C)C(=O)Oc1ccc(-c2ccc(OC(=O)C(=C)C)cc2F)c(F)c1]
RM-23
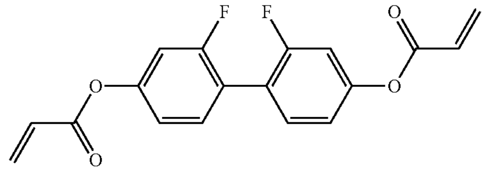 [SMILES: C=CC(=O)Oc1ccc(-c2ccc(OC(=O)C=C)cc2F)c(F)c1]
RM-24

TABLE F-continued
Table F shows illustrative reactive mesogenic compounds (RM) which can be used in the LC media in accordance with the present invention.
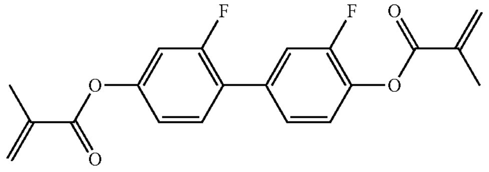
RM-25
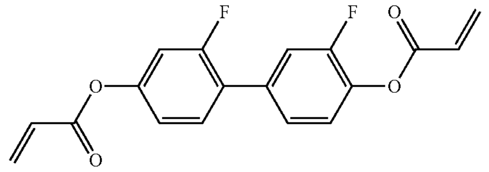 [SMILES: C=CC(=O)Oc1ccc(-c2ccc(OC(=O)C=C)c(F)c2)c(F)c1]
RM-26
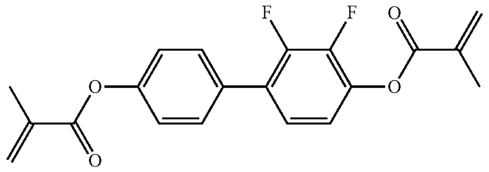
RM-27
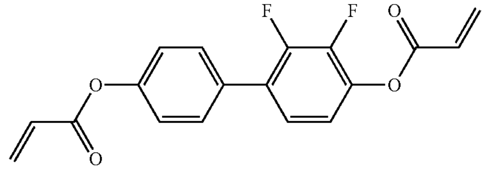 [SMILES: C=CC(=O)Oc1ccc(-c2ccc(OC(=O)C=C)c(F)c2F)cc1]
RM-28
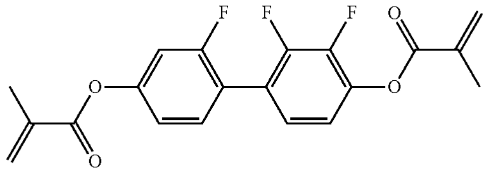 [SMILES: C=C(C)C(=O)Oc1ccc(-c2ccc(OC(=O)C(=C)C)c(F)c2F)c(F)c1]
RM-29
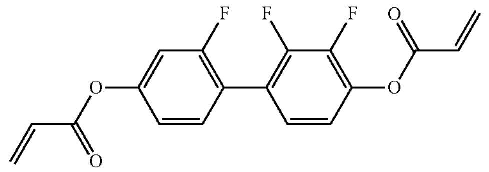
RM-30
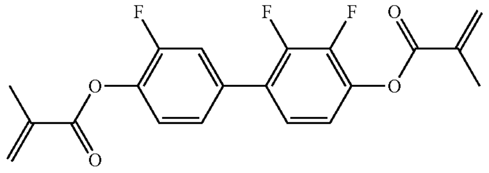 [SMILES: C=C(C)C(=O)Oc1ccc(-c2ccc(OC(=O)C(=C)C)c(F)c2F)cc1F]
RM-31

TABLE F-continued
Table F shows illustrative reactive mesogenic compounds (RM) which can be used in the LC media in accordance with the present invention.
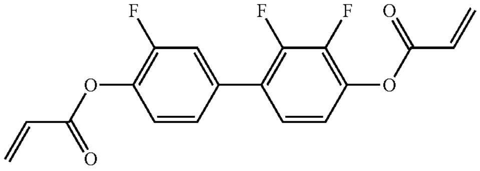
RM-32
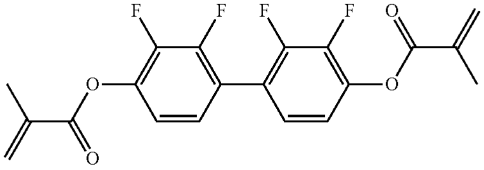
RM-33
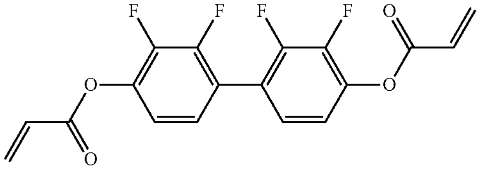 [SMILES: C=CC(=O)Oc1ccc(-c2ccc(OC(=O)C=C)c(F)c2F)c(F)c1F]
RM-34
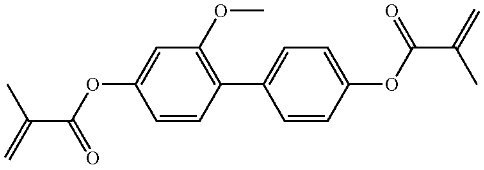 [SMILES: C=C(C)C(=O)Oc1ccc(-c2ccc(OC(=O)C(=C)C)cc2OC)cc1]
RM-35
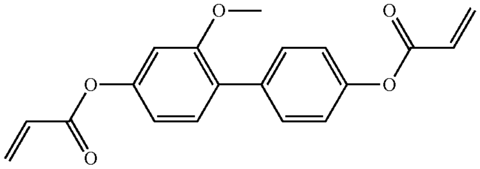 [SMILES: C=CC(=O)Oc1ccc(-c2ccc(OC(=O)C=C)cc2OC)cc1]
RM-36
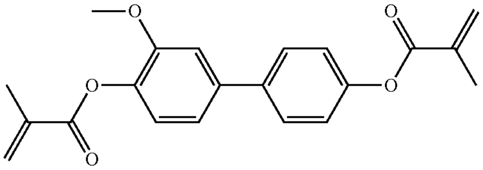
RM-37
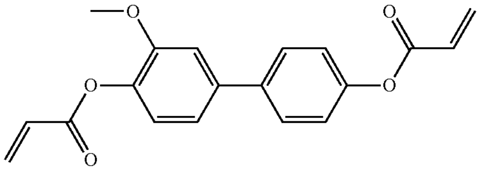 [SMILES: C=CC(=O)Oc1ccc(-c2ccc(OC(=O)C=C)c(OC)c2)cc1]
RM-38

TABLE F-continued
Table F shows illustrative reactive mesogenic compounds (RM) which can be used in the LC media in accordance with the present invention.
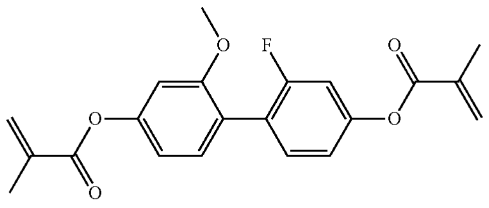 [SMILES: C=C(C)C(=O)Oc1ccc(-c2ccc(OC(=O)C(=C)C)cc2OC)c(F)c1]
RM-39
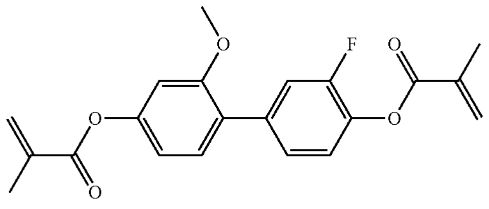 [SMILES: C=C(C)C(=O)Oc1ccc(-c2ccc(OC(=O)C(=C)C)c(F)c2)c(OC)c1]
RM-40
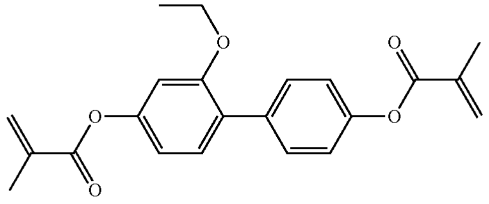 [SMILES: C=C(C)C(=O)Oc1ccc(-c2ccc(OC(=O)C(=C)C)cc2OCC)cc1]
RM-41
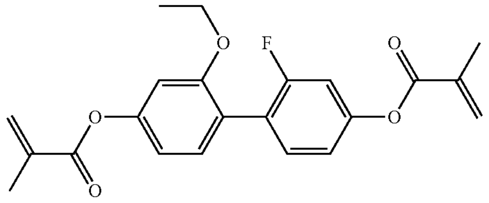 [SMILES: C=C(C)C(=O)Oc1ccc(-c2ccc(OC(=O)C(=C)C)cc2OCC)c(F)c1]
RM-42
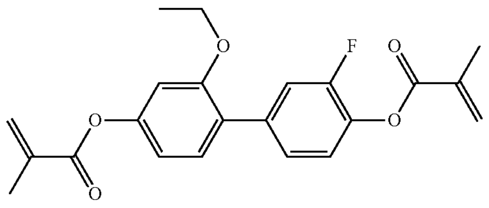 [SMILES: C=C(C)C(=O)Oc1ccc(-c2ccc(OC(=O)C(=C)C)c(F)c2)c(OCC)c1]
RM-43
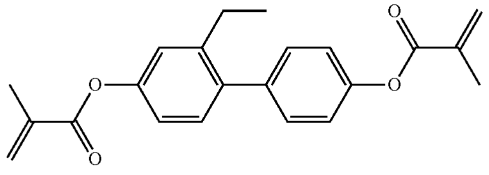 [SMILES: C=C(C)C(=O)Oc1ccc(-c2ccc(OC(=O)C(=C)C)cc2CC)cc1]
RM-44

TABLE F-continued
| Table F shows illustrative reactive mesogenic compounds (RM) which can be used in the LC media in accordance with the present invention. |
|---|
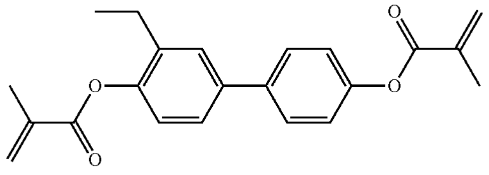 [SMILES: C=C(C)C(=O)Oc1ccc(-c2ccc(OC(=O)C(=C)C)c(CC)c2)cc1]
RM-45
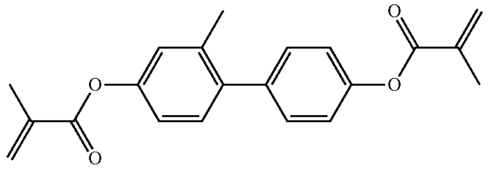 [SMILES: C=C(C)C(=O)Oc1ccc(-c2ccc(OC(=O)C(=C)C)cc2C)cc1]
RM-46
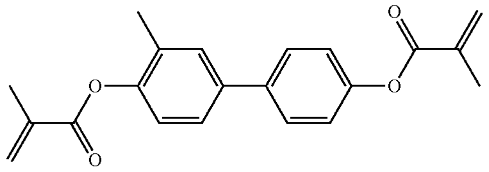
RM-47
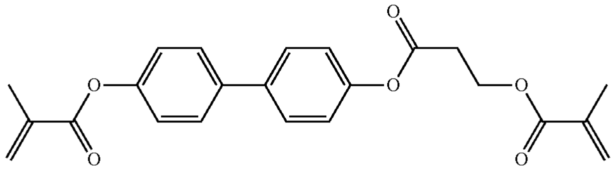 [SMILES: C=C(C)C(=O)OCCC(=O)Oc1ccc(-c2ccc(OC(=O)C(=C)C)cc2)cc1]
RM-48
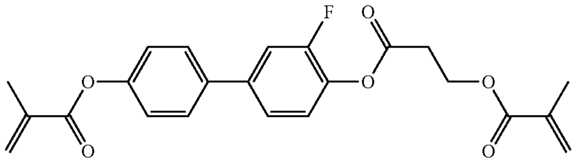 [SMILES: C=C(C)C(=O)OCCC(=O)Oc1ccc(-c2ccc(OC(=O)C(=C)C)cc2)cc1F]
RM-49
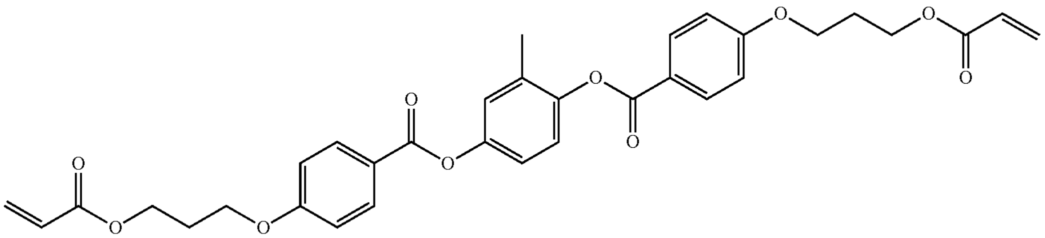 [SMILES: C=CC(=O)OCCCOc1ccc(C(=O)Oc2ccc(OC(=O)c3ccc(OCCCOC(=O)C=C)cc3)c(C)c2)cc1]
RM-50

TABLE F-continued
Table F shows illustrative reactive mesogenic compounds (RM) which can be used in the LC media in accordance with the present invention.
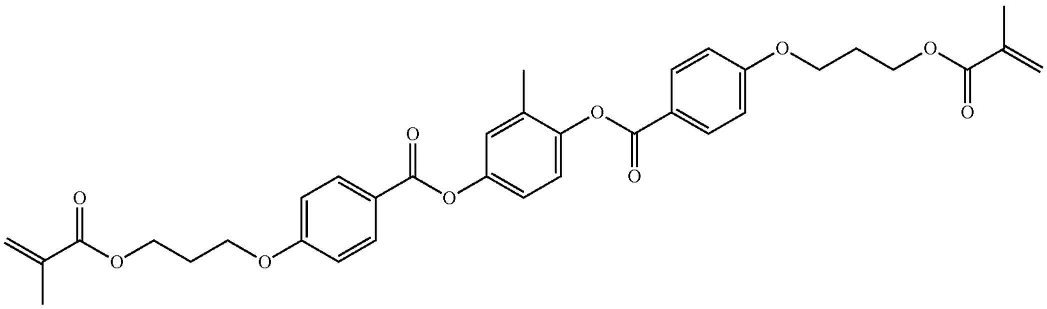 [SMILES: C=C(C)C(=O)OCCCOc1ccc(C(=O)Oc2ccc(OC(=O)c3ccc(OCCCOC(=O)C(=C)C)cc3)c(C)c2)cc1]
RM-51
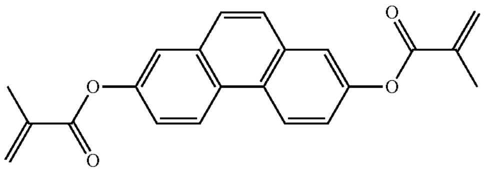 [SMILES: C=C(C)C(=O)Oc1ccc2c(ccc3cc(OC(=O)C(=C)C)ccc32)c1]
RM-52
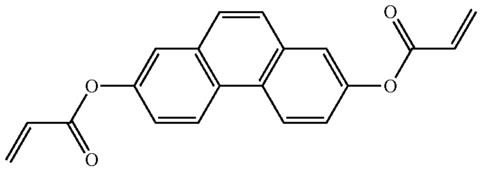 [SMILES: C=CC(=O)Oc1ccc2c(ccc3cc(OC(=O)C=C)ccc32)c1]
RM-53
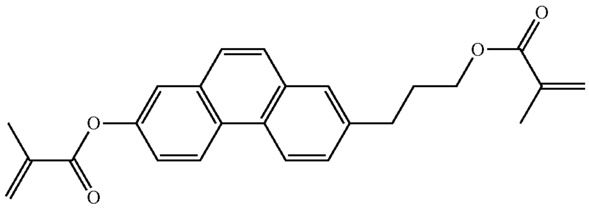 [SMILES: C=C(C)C(=O)OCCCc1ccc2c(ccc3cc(OC(=O)C(=C)C)ccc32)c1]
RM-54
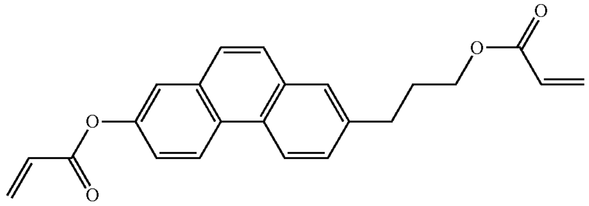 [SMILES: C=CC(=O)OCCCc1ccc2c(ccc3cc(OC(=O)C=C)ccc32)c1]
RM-55

TABLE F-continued
Table F shows illustrative reactive mesogenic compounds (RM) which can be used in the LC media in accordance with the present invention.
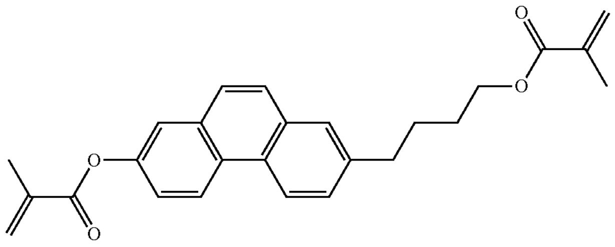 [SMILES: C=C(C)C(=O)OCCCCc1ccc2c(ccc3cc(OC(=O)C(=C)C)ccc32)c1]
RM-56
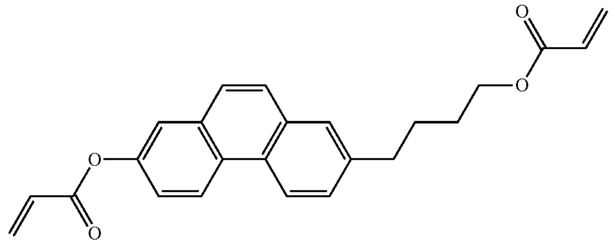 [SMILES: C=CC(=O)OCCCCc1ccc2c(ccc3cc(OC(=O)C=C)ccc32)c1]
RM-57
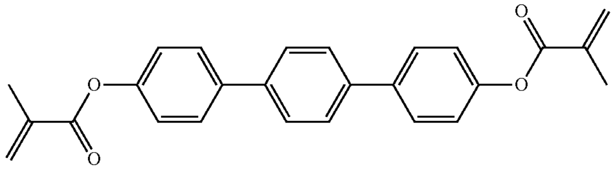 [SMILES: C=C(C)C(=O)Oc1ccc(-c2ccc(-c3ccc(OC(=O)C(=C)C)cc3)cc2)cc1]
RM-58
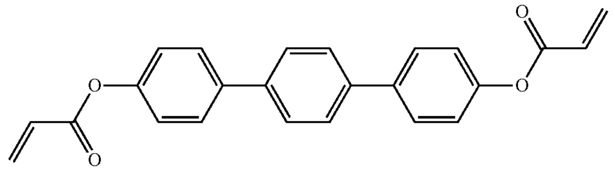 [SMILES: C=CC(=O)Oc1ccc(-c2ccc(-c3ccc(OC(=O)C=C)cc3)cc2)cc1]
RM-59
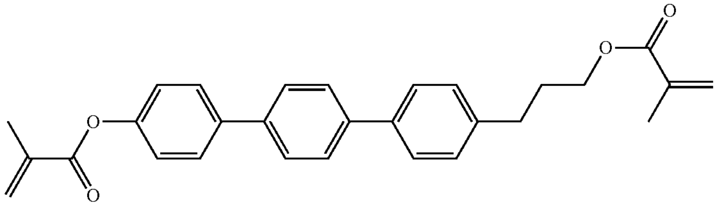 [SMILES: C=C(C)C(=O)OCCCc1ccc(-c2ccc(-c3ccc(OC(=O)C(=C)C)cc3)cc2)cc1]
RM-60
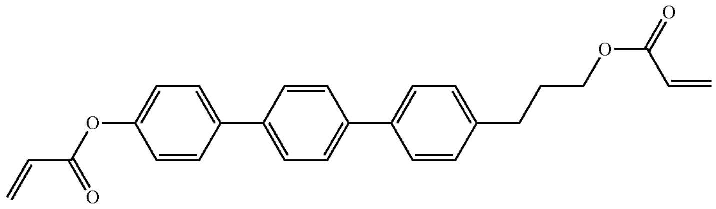 [SMILES: C=CC(=O)OCCCc1ccc(-c2ccc(-c3ccc(OC(=O)C=C)cc3)cc2)cc1]
RM-61

TABLE F-continued
| Table F shows illustrative reactive mesogenic compounds (RM) which can be used in the LC media in accordance with the present invention. |
| --- |
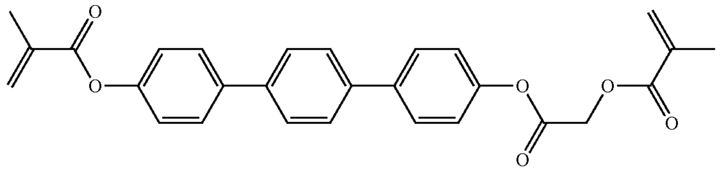
RM-62
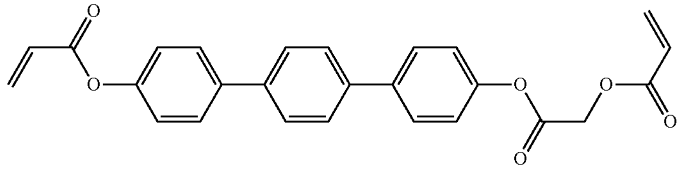 [SMILES: C=CC(=O)OCC(=O)Oc1ccc(-c2ccc(-c3ccc(OC(=O)C=C)cc3)cc2)cc1]
RM-63
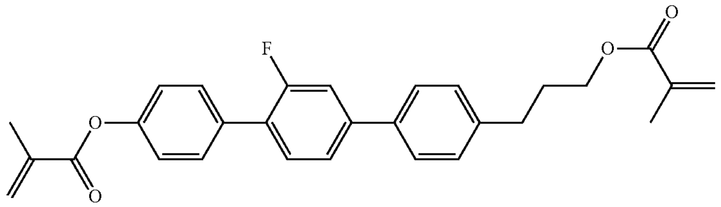 [SMILES: C=C(C)C(=O)OCCCc1ccc(-c2ccc(-c3ccc(OC(=O)C(=C)C)cc3)c(F)c2)cc1]
RM-64
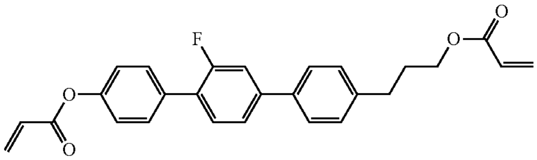 [SMILES: C=CC(=O)OCCCc1ccc(-c2ccc(-c3ccc(OC(=O)C=C)cc3)c(F)c2)cc1]
RM-65
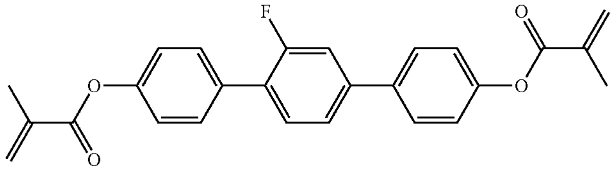 [SMILES: C=C(C)C(=O)Oc1ccc(-c2ccc(-c3ccc(OC(=O)C(=C)C)cc3)c(F)c2)cc1]
RM-66
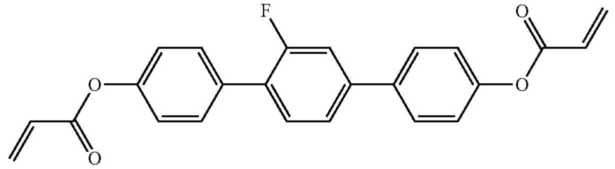 [SMILES: C=CC(=O)Oc1ccc(-c2ccc(-c3ccc(OC(=O)C=C)cc3)c(F)c2)cc1]
RM-67
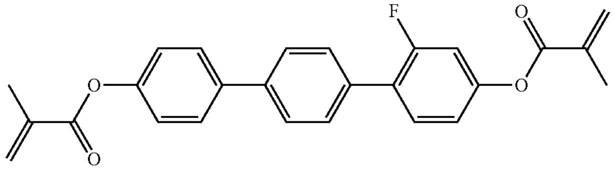 [SMILES: C=C(C)C(=O)Oc1ccc(-c2ccc(-c3ccc(OC(=O)C(=C)C)cc3F)cc2)cc1]
RM-68

TABLE F-continued
| Table F shows illustrative reactive mesogenic compounds (RM) which can be used in the LC media in accordance with the present invention. |
| --- |
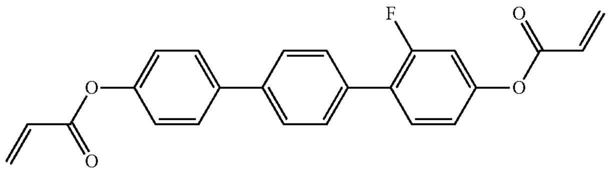 [SMILES: C=CC(=O)Oc1ccc(-c2ccc(-c3ccc(OC(=O)C=C)cc3F)cc2)cc1]
RM-69
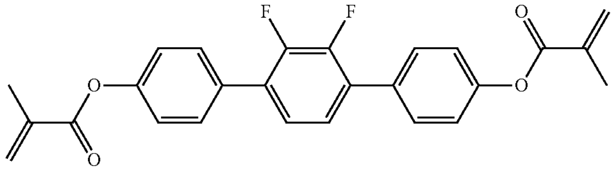 [SMILES: C=C(C)C(=O)Oc1ccc(-c2ccc(-c3ccc(OC(=O)C(=C)C)cc3)c(F)c2F)cc1]
RM-70
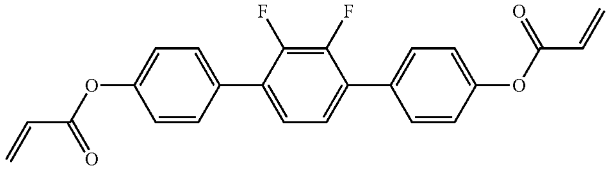 [SMILES: C=CC(=O)Oc1ccc(-c2ccc(-c3ccc(OC(=O)C=C)cc3)c(F)c2F)cc1]
RM-71
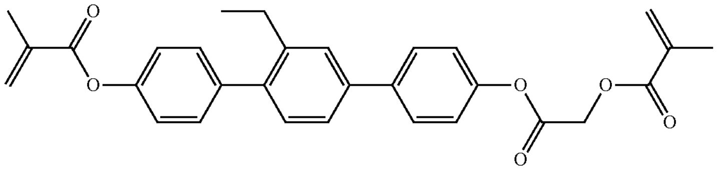 [SMILES: C=C(C)C(=O)OCC(=O)Oc1ccc(-c2ccc(-c3ccc(OC(=O)C(=C)C)cc3)c(CC)c2)cc1]
RM-72
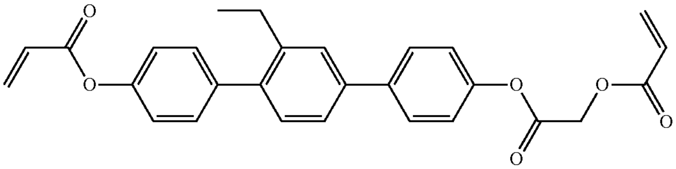 [SMILES: C=CC(=O)OCC(=O)Oc1ccc(-c2ccc(-c3ccc(OC(=O)C=C)cc3)c(CC)c2)cc1]
RM-73
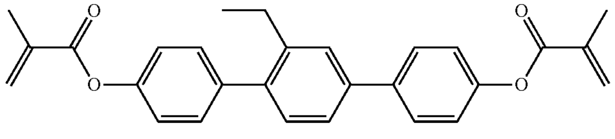 [SMILES: C=C(C)C(=O)Oc1ccc(-c2ccc(-c3ccc(OC(=O)C(=C)C)cc3)c(CC)c2)cc1]
RM-74
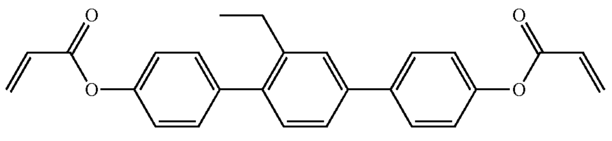 [SMILES: C=CC(=O)Oc1ccc(-c2ccc(-c3ccc(OC(=O)C=C)cc3)c(CC)c2)cc1]
RM-75

TABLE F-continued
Table F shows illustrative reactive mesogenic compounds (RM) which can be used in the LC media in accordance with the present invention.
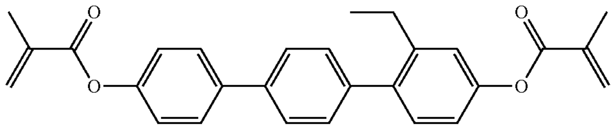 [SMILES: C=C(C)C(=O)Oc1ccc(-c2ccc(-c3ccc(OC(=O)C(=C)C)cc3CC)cc2)cc1]
RM-76
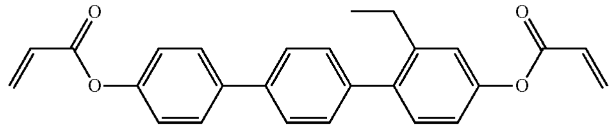 [SMILES: C=CC(=O)Oc1ccc(-c2ccc(-c3ccc(OC(=O)C=C)cc3CC)cc2)cc1]
RM-77
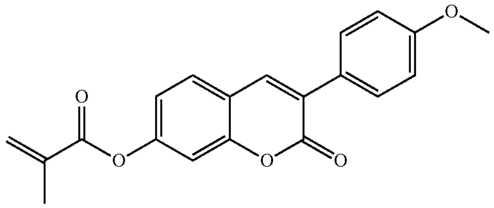 [SMILES: C=C(C)C(=O)Oc1ccc2cc(-c3ccc(OC)cc3)c(=O)oc2c1]
RM-78
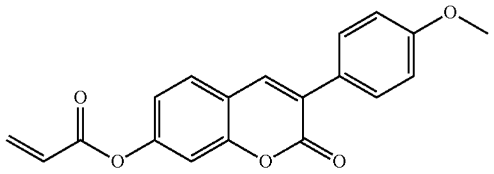 [SMILES: C=CC(=O)Oc1ccc2cc(-c3ccc(OC)cc3)c(=O)oc2c1]
RM-79
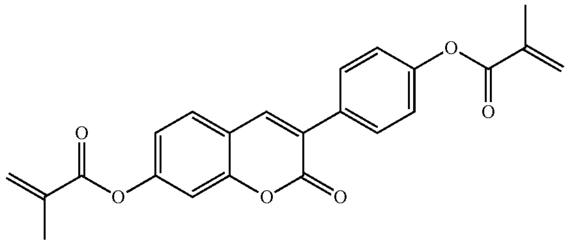 [SMILES: C=C(C)C(=O)Oc1ccc(-c2cc3ccc(OC(=O)C(=C)C)cc3oc2=O)cc1]
RM-80
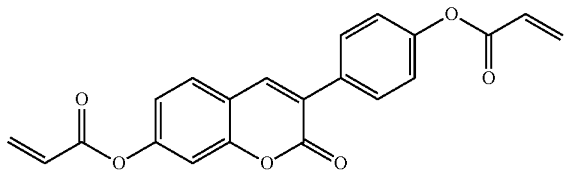 [SMILES: C=CC(=O)Oc1ccc(-c2cc3ccc(OC(=O)C=C)cc3oc2=O)cc1]
RM-81

TABLE F-continued
Table F shows illustrative reactive mesogenic compounds (RM) which can be used in the LC media in accordance with the present invention.
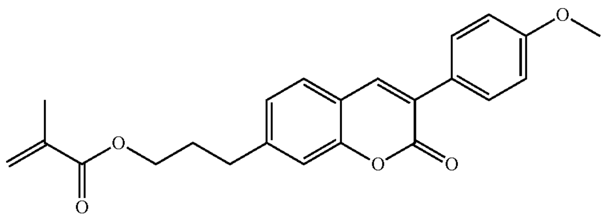 [SMILES: C=C(C)C(=O)OCCCc1ccc2cc(-c3ccc(OC)cc3)c(=O)oc2c1]
RM-82
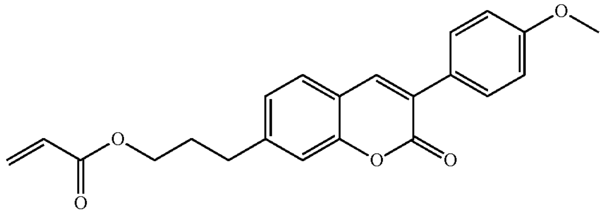 [SMILES: C=CC(=O)OCCCc1ccc2cc(-c3ccc(OC)cc3)c(=O)oc2c1]
RM-83
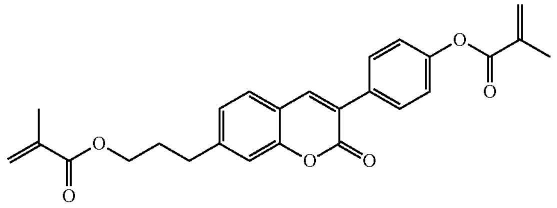 [SMILES: C=C(C)C(=O)OCCCc1ccc2cc(-c3ccc(OC(=O)C(=C)C)cc3)c(=O)oc2c1]
RM-84
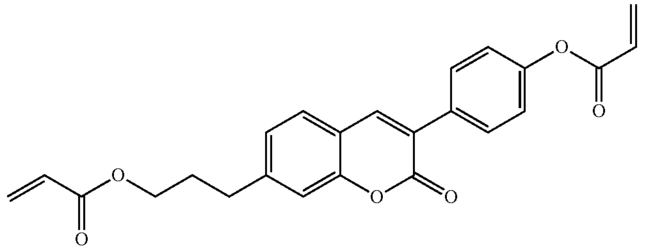 [SMILES: C=CC(=O)OCCCc1ccc2cc(-c3ccc(OC(=O)C=C)cc3)c(=O)oc2c1]
RM-85
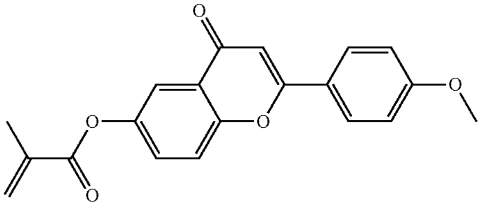 [SMILES: C=C(C)C(=O)Oc1ccc2oc(-c3ccc(OC)cc3)cc(=O)c2c1]
RM-86

TABLE F-continued
Table F shows illustrative reactive mesogenic compounds (RM) which can be used in the LC media in accordance with the present invention.
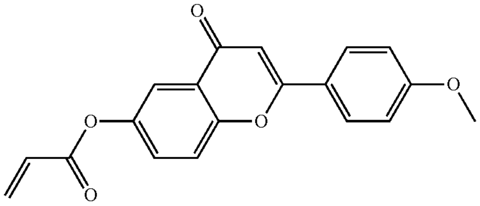 [SMILES: C=CC(=O)Oc1ccc2oc(-c3ccc(OC)cc3)cc(=O)c2c1]
RM-87
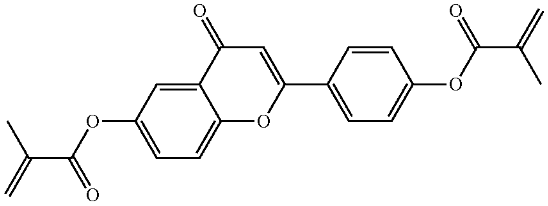 [SMILES: C=C(C)C(=O)Oc1ccc(-c2cc(=O)c3cc(OC(=O)C(=C)C)ccc3o2)cc1]
RM-88
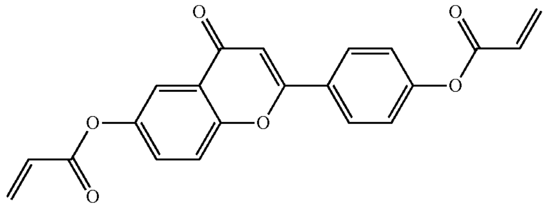 [SMILES: C=CC(=O)Oc1ccc(-c2cc(=O)c3cc(OC(=O)C=C)ccc3o2)cc1]
RM-89
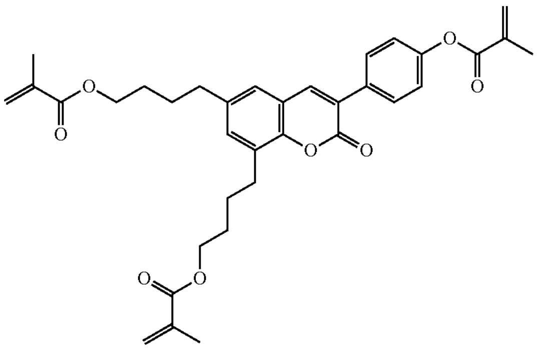 [SMILES: C=C(C)C(=O)OCCCCc1cc(CCCCOC(=O)C(=C)C)c2oc(=O)c(-c3ccc(OC(=O)C(=C)C)cc3)cc2c1]
RM-90
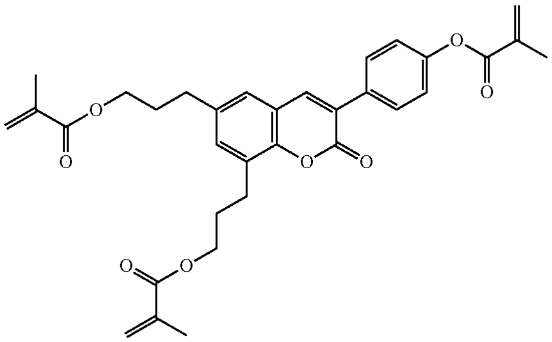 [SMILES: C=C(C)C(=O)OCCCc1cc(CCCOC(=O)C(=C)C)c2oc(=O)c(-c3ccc(OC(=O)C(=C)C)cc3)cc2c1]
RM-91

TABLE F-continued
Table F shows illustrative reactive mesogenic compounds (RM) which can be used in the LC media in accordance with the present invention.
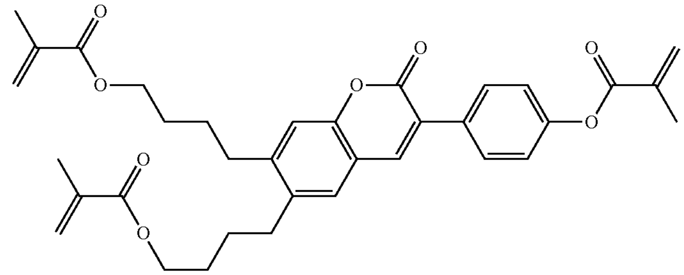 [SMILES: C=C(C)C(=O)OCCCCc1cc2cc(-c3ccc(OC(=O)C(=C)C)cc3)c(=O)oc2cc1CCCCOC(=O)C(=C)C]
RM-92
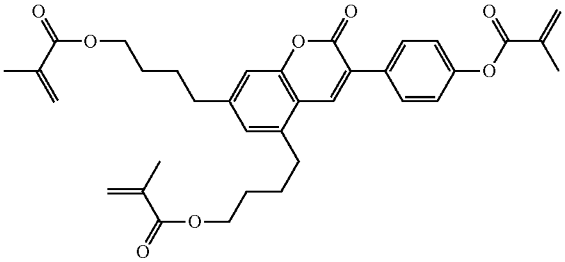 [SMILES: C=C(C)C(=O)OCCCCc1cc(CCCCOC(=O)C(=C)C)c2cc(-c3ccc(OC(=O)C(=C)C)cc3)c(=O)oc2c1]
RM-93
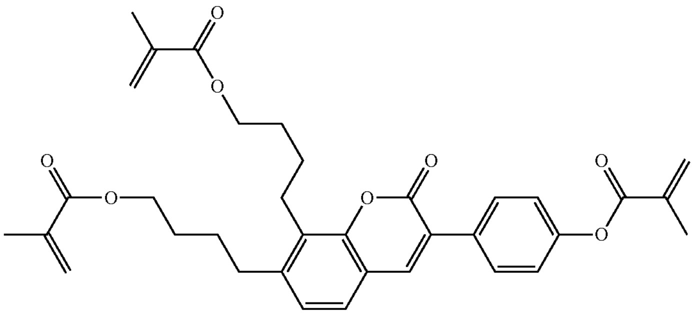 [SMILES: C=C(C)C(=O)OCCCCc1ccc2cc(-c3ccc(OC(=O)C(=C)C)cc3)c(=O)oc2c1CCCCOC(=O)C(=C)C]
RM-94
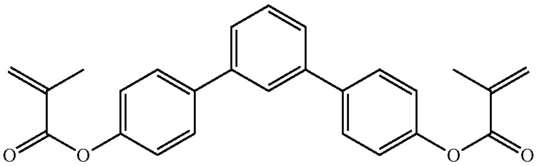 [SMILES: C=C(C)C(=O)Oc1ccc(-c2cccc(-c3ccc(OC(=O)C(=C)C)cc3)c2)cc1]
RM-95
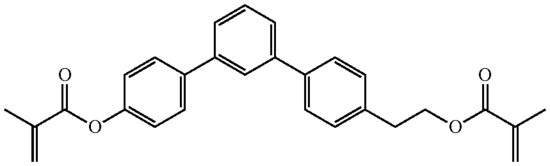 [SMILES: C=C(C)C(=O)OCCc1ccc(-c2cccc(-c3ccc(OC(=O)C(=C)C)cc3)c2)cc1]
RM-96

TABLE F-continued
Table F shows illustrative reactive mesogenic compounds (RM) which can be used in the LC media in accordance with the present invention.
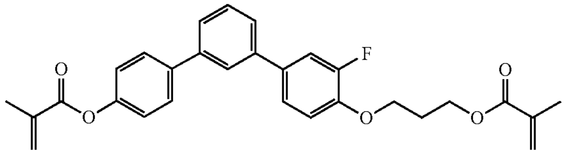 [SMILES: C=C(C)C(=O)OCCCOc1ccc(-c2cccc(-c3ccc(OC(=O)C(=C)C)cc3)c2)cc1F]
RM-97
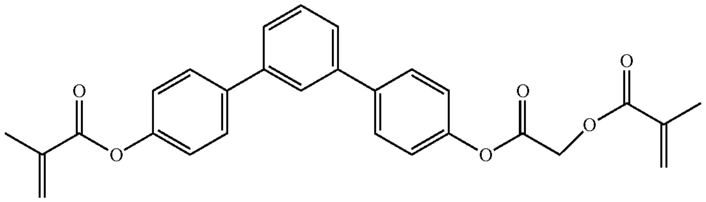 [SMILES: C=C(C)C(=O)OCC(=O)Oc1ccc(-c2cccc(-c3ccc(OC(=O)C(=C)C)cc3)c2)cc1]
RM-98
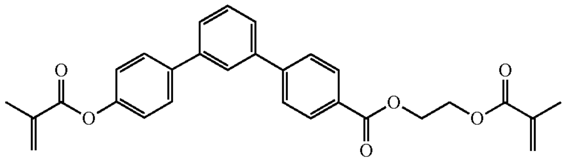 [SMILES: C=C(C)C(=O)OCCOC(=O)c1ccc(-c2cccc(-c3ccc(OC(=O)C(=C)C)cc3)c2)cc1]
RM-99
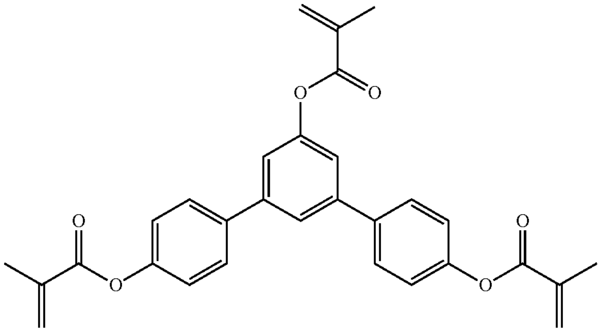 [SMILES: C=C(C)C(=O)Oc1ccc(-c2cc(OC(=O)C(=C)C)cc(-c3ccc(OC(=O)C(=C)C)cc3)c2)cc1]
RM-100
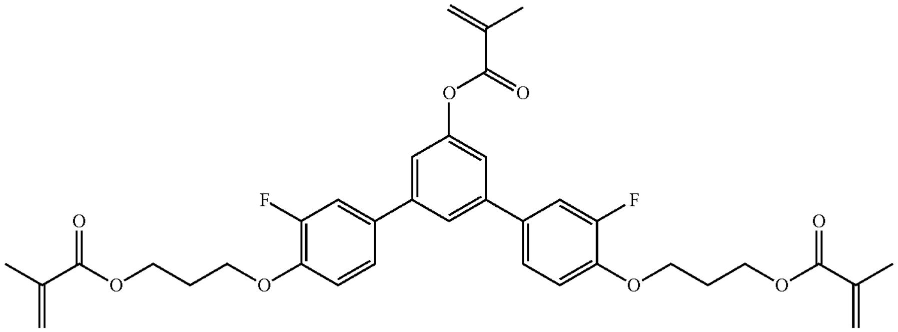 [SMILES: C=C(C)C(=O)OCCCOc1ccc(-c2cc(OC(=O)C(=C)C)cc(-c3ccc(OCCCOC(=O)C(=C)C)c(F)c3)c2)cc1F]
RM-101

TABLE F-continued
| Table F shows illustrative reactive mesogenic compounds (RM) which can be used in the LC media in accordance with the present invention. |
| --- |
| 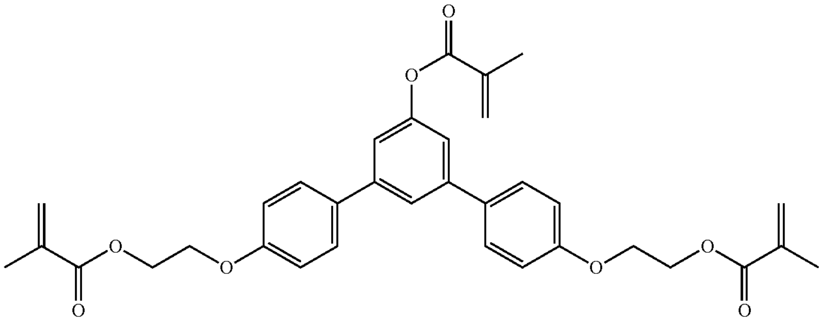 [SMILES: C=C(C)C(=O)OCCOc1ccc(-c2cc(OC(=O)C(=C)C)cc(-c3ccc(OCCOC(=O)C(=C)C)cc3)c2)cc1] |
| RM-102 |
| 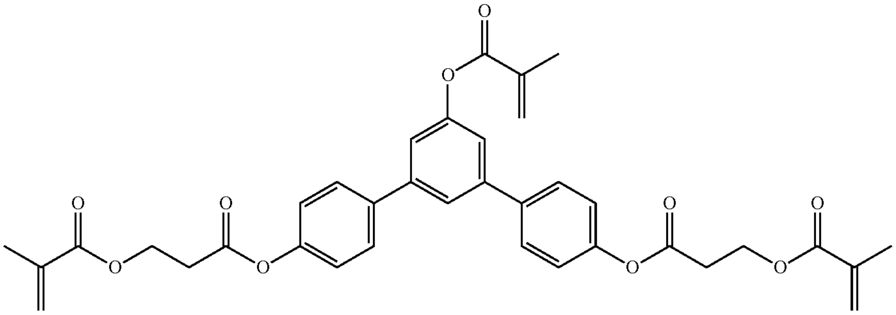 [SMILES: C=C(C)C(=O)OCCC(=O)Oc1ccc(-c2cc(OC(=O)C(=C)C)cc(-c3ccc(OC(=O)CCOC(=O)C(=C)C)cc3)c2)cc1] |
| RM-103 |
| 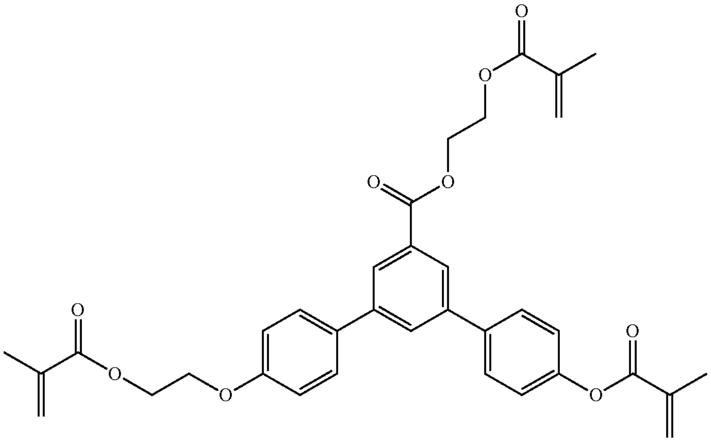 [SMILES: C=C(C)C(=O)OCCOC(=O)c1cc(-c2ccc(OCCOC(=O)C(=C)C)cc2)cc(-c2ccc(OC(=O)C(=C)C)cc2)c1] |
| RM-104 |

TABLE F-continued
Table F shows illustrative reactive mesogenic compounds (RM) which can be used in the LC media in accordance with the present invention.
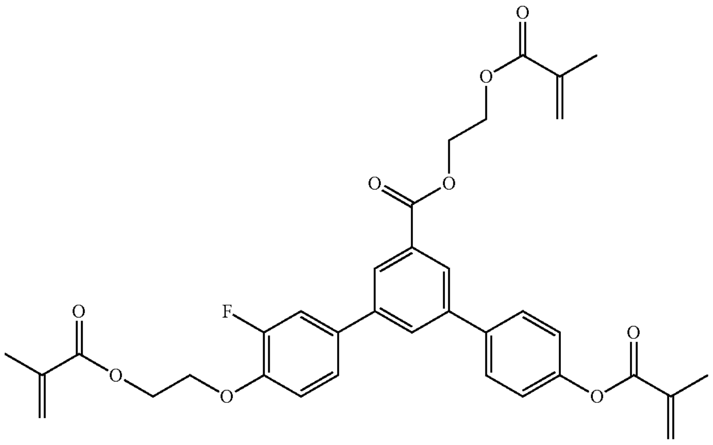 [SMILES: C=C(C)C(=O)OCCOC(=O)c1cc(-c2ccc(OC(=O)C(=C)C)cc2)cc(-c2ccc(OCCOC(=O)C(=C)C)c(F)c2)c1]
RM-105
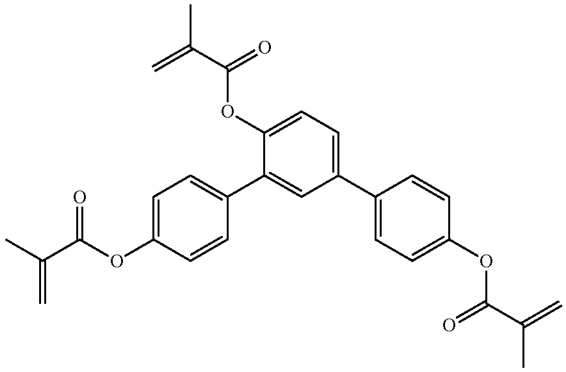 [SMILES: C=C(C)C(=O)Oc1ccc(-c2ccc(OC(=O)C(=C)C)c(-c3ccc(OC(=O)C(=C)C)cc3)c2)cc1]
RM-106
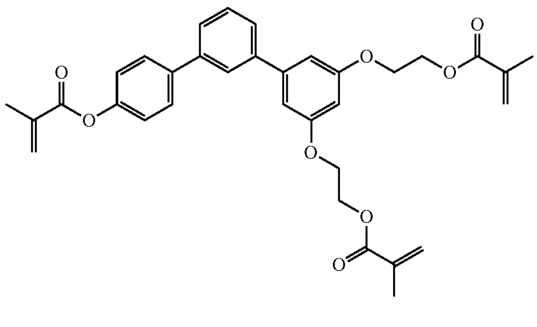 [SMILES: C=C(C)C(=O)OCCOc1cc(OCCOC(=O)C(=C)C)cc(-c2cccc(-c3ccc(OC(=O)C(=C)C)cc3)c2)c1]
RM-107

TABLE F-continued
Table F shows illustrative reactive mesogenic compounds (RM) which can be used in the LC media in accordance with the present invention.
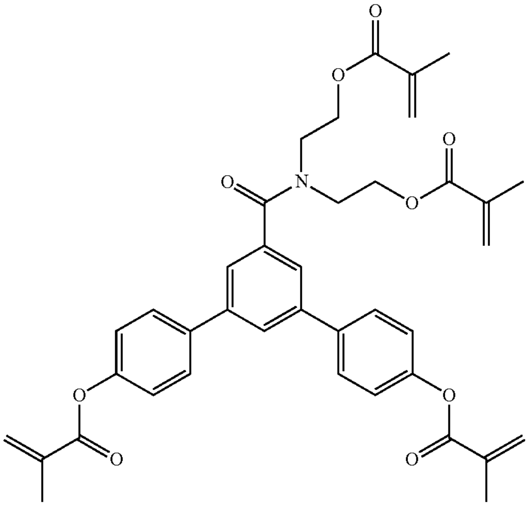 [SMILES: C=C(C)C(=O)OCCN(CCOC(=O)C(=C)C)C(=O)c1cc(-c2ccc(OC(=O)C(=C)C)cc2)cc(-c2ccc(OC(=O)C(=C)C)cc2)c1]
RM-108
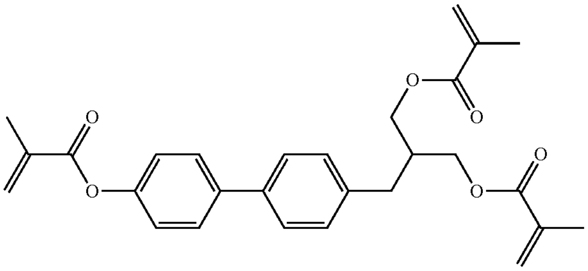 [SMILES: C=C(C)C(=O)OCC(COC(=O)C(=C)C)Cc1ccc(-c2ccc(OC(=O)C(=C)C)cc2)cc1]
RM-109
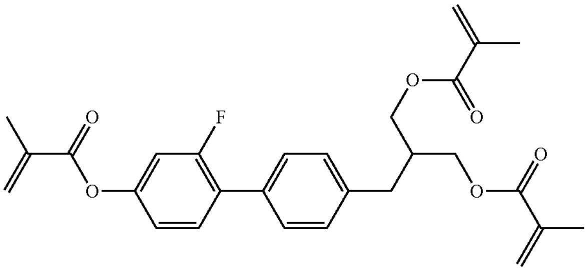 [SMILES: C=C(C)C(=O)OCC(COC(=O)C(=C)C)Cc1ccc(-c2ccc(OC(=O)C(=C)C)cc2F)cc1]
RM-110
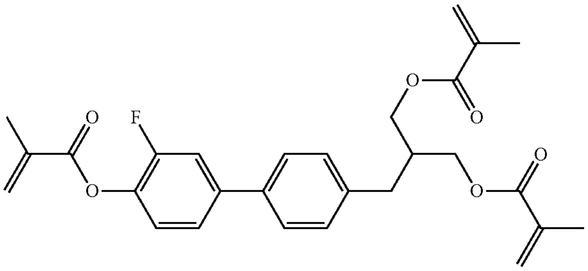 [SMILES: C=C(C)C(=O)OCC(COC(=O)C(=C)C)Cc1ccc(-c2ccc(OC(=O)C(=C)C)c(F)c2)cc1]
RM-111

TABLE F-continued
Table F shows illustrative reactive mesogenic compounds (RM) which can be used in the LC media in accordance with the present invention.
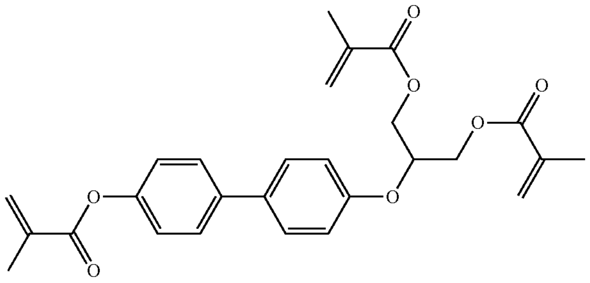 [SMILES: C=C(C)C(=O)OCC(COC(=O)C(=C)C)Oc1ccc(-c2ccc(OC(=O)C(=C)C)cc2)cc1]
RM-112
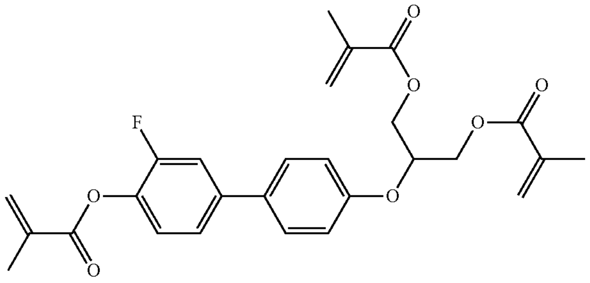 [SMILES: C=C(C)C(=O)OCC(COC(=O)C(=C)C)Oc1ccc(-c2ccc(OC(=O)C(=C)C)c(F)c2)cc1]
RM-113
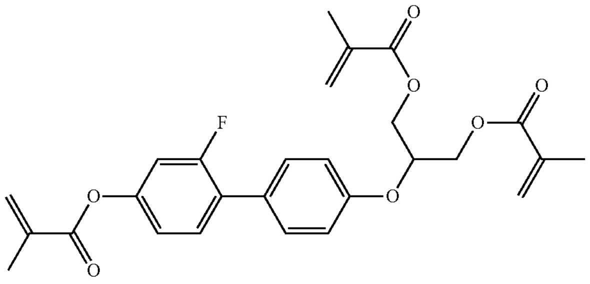 [SMILES: C=C(C)C(=O)OCC(COC(=O)C(=C)C)Oc1ccc(-c2ccc(OC(=O)C(=C)C)cc2F)cc1]
RM-114
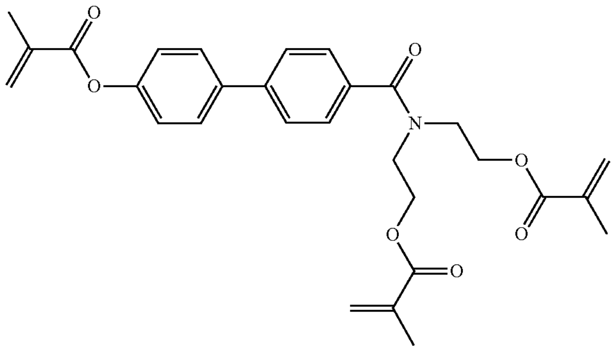 [SMILES: C=C(C)C(=O)OCCN(CCOC(=O)C(=C)C)C(=O)c1ccc(-c2ccc(OC(=O)C(=C)C)cc2)cc1]
RM-115

TABLE F-continued
Table F shows illustrative reactive mesogenic compounds (RM) which can be used in the LC media in accordance with the present invention.
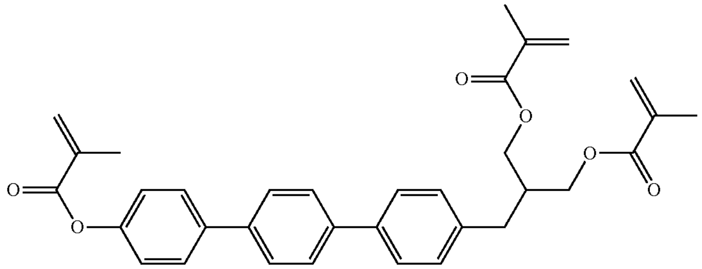 [SMILES: C=C(C)C(=O)OCC(COC(=O)C(=C)C)Cc1ccc(-c2ccc(-c3ccc(OC(=O)C(=C)C)cc3)cc2)cc1]
RM-116
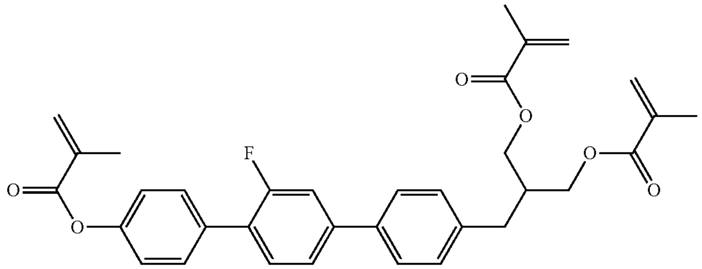
RM-117
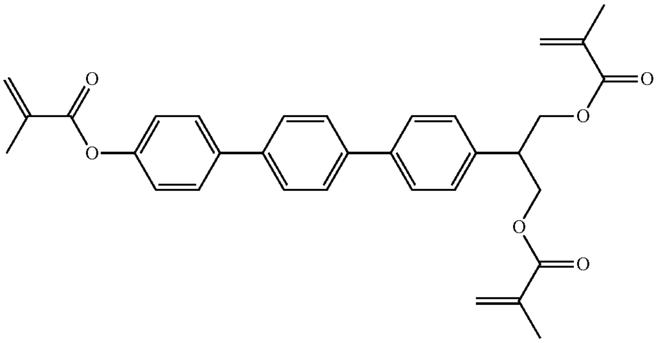 [SMILES: C=C(C)C(=O)OCC(COC(=O)C(=C)C)c1ccc(-c2ccc(-c3ccc(OC(=O)C(=C)C)cc3)cc2)cc1]
RM-118
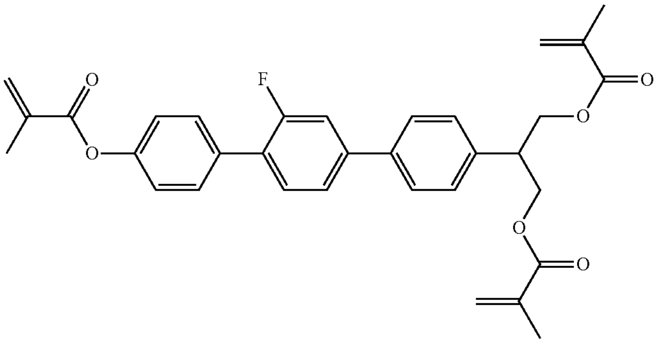 [SMILES: C=C(C)C(=O)OCC(COC(=O)C(=C)C)c1ccc(-c2ccc(-c3ccc(OC(=O)C(=C)C)cc3)c(F)c2)cc1]
RM-119

TABLE F-continued
| Table F shows illustrative reactive mesogenic compounds (RM) which can be used in the LC media in accordance with the present invention. |
|---|
| 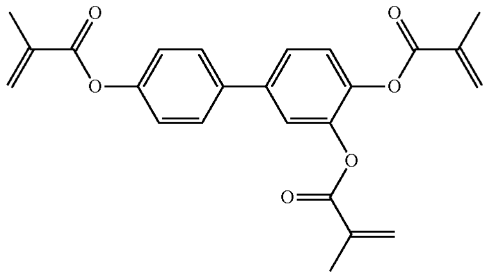 [SMILES: C=C(C)C(=O)Oc1ccc(-c2ccc(OC(=O)C(=C)C)c(OC(=O)C(=C)C)c2)cc1] |
| RM-120 |
| 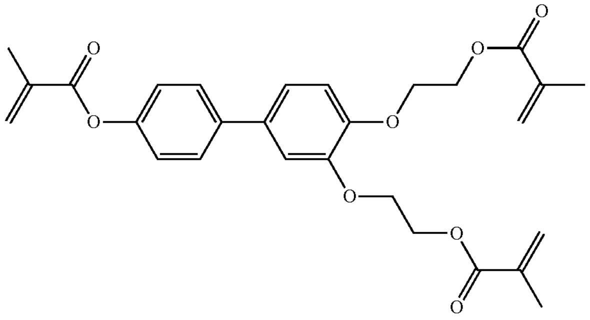 [SMILES: C=C(C)C(=O)OCCOc1ccc(-c2ccc(OC(=O)C(=C)C)cc2)cc1OCCOC(=O)C(=C)C] |
| RM-121 |
| 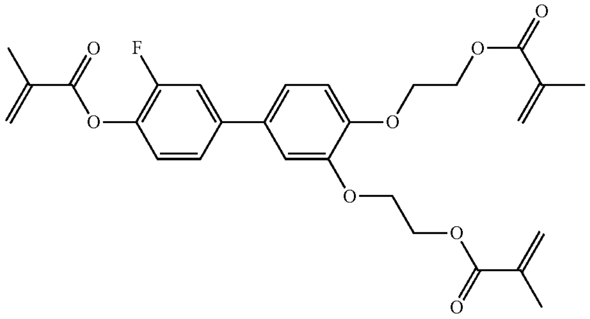 [SMILES: C=C(C)C(=O)OCCOc1ccc(-c2ccc(OC(=O)C(=C)C)c(F)c2)cc1OCCOC(=O)C(=C)C] |
| RM-122 |
| 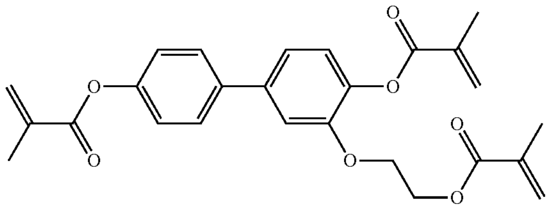 [SMILES: C=C(C)C(=O)OCCOc1cc(-c2ccc(OC(=O)C(=C)C)cc2)ccc1OC(=O)C(=C)C] |
| RM-123 |
| 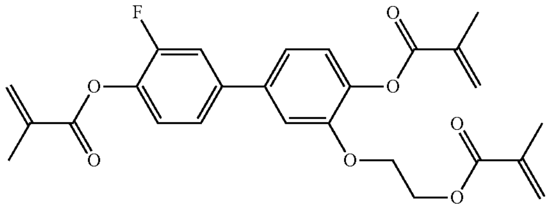 [SMILES: C=C(C)C(=O)OCCOc1cc(-c2ccc(OC(=O)C(=C)C)c(F)c2)ccc1OC(=O)C(=C)C] |
| RM-124 |

TABLE F-continued
Table F shows illustrative reactive mesogenic compounds (RM) which can be used in the LC media in accordance with the present invention.
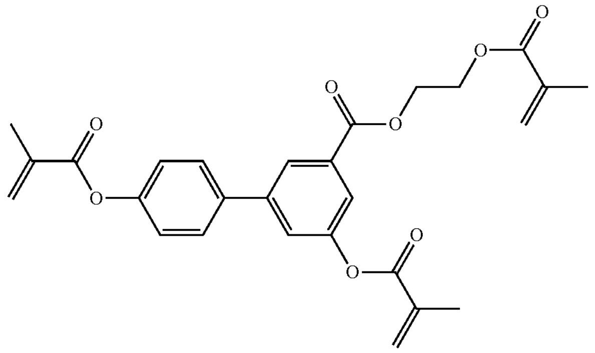 [SMILES: C=C(C)C(=O)OCCOC(=O)c1cc(OC(=O)C(=C)C)cc(-c2ccc(OC(=O)C(=C)C)cc2)c1]
RM-125
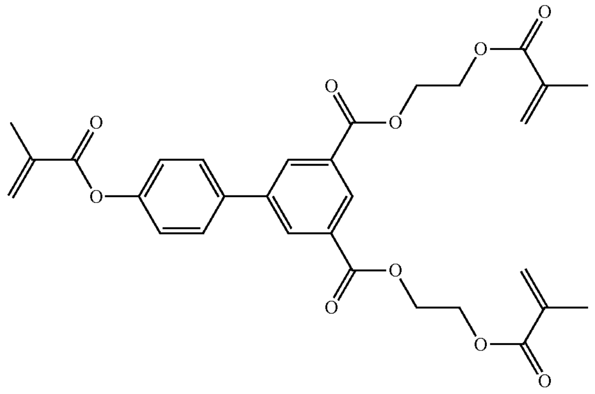 [SMILES: C=C(C)C(=O)OCCOC(=O)c1cc(C(=O)OCCOC(=O)C(=C)C)cc(-c2ccc(OC(=O)C(=C)C)cc2)c1]
RM-126
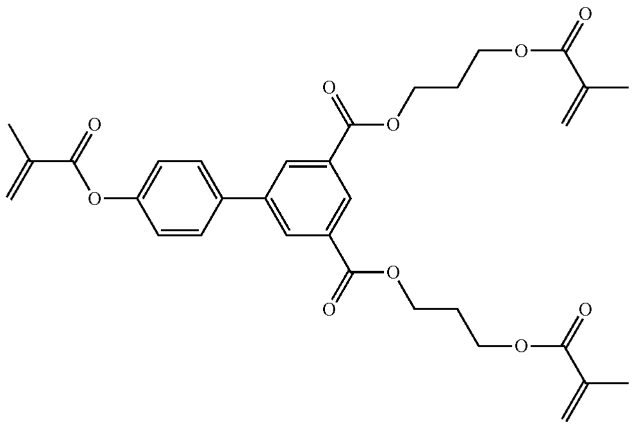 [SMILES: C=C(C)C(=O)OCCCOC(=O)c1cc(C(=O)OCCCOC(=O)C(=C)C)cc(-c2ccc(OC(=O)C(=C)C)cc2)c1]
RM-127

TABLE F-continued
| Table F shows illustrative reactive mesogenic compounds (RM) which can be used in the LC media in accordance with the present invention. |
| --- |
| 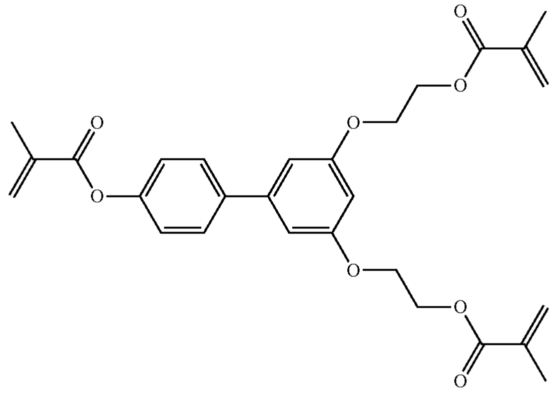 [SMILES: C=C(C)C(=O)OCCOc1cc(OCCOC(=O)C(=C)C)cc(-c2ccc(OC(=O)C(=C)C)cc2)c1] |
| RM-128 |
| 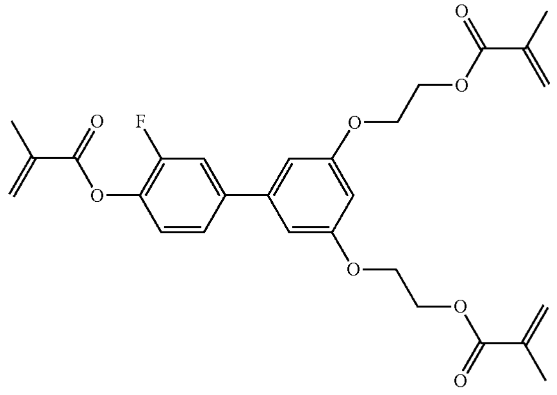 [SMILES: C=C(C)C(=O)OCCOc1cc(OCCOC(=O)C(=C)C)cc(-c2ccc(OC(=O)C(=C)C)c(F)c2)c1] |
| RM-129 |
| 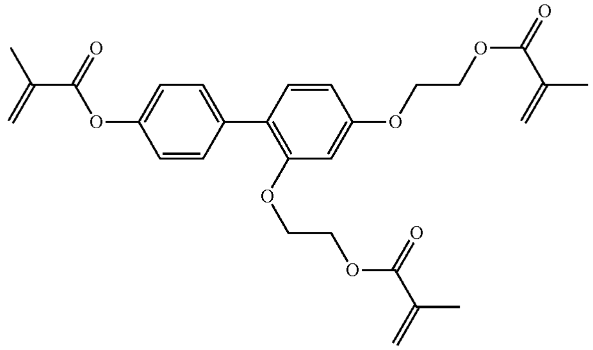 [SMILES: C=C(C)C(=O)OCCOc1ccc(-c2ccc(OC(=O)C(=C)C)cc2)c(OCCOC(=O)C(=C)C)c1] |
| RM-130 |

TABLE F-continued
| Table F shows illustrative reactive mesogenic compounds (RM) which can be used in the LC media in accordance with the present invention. |
|---|
| 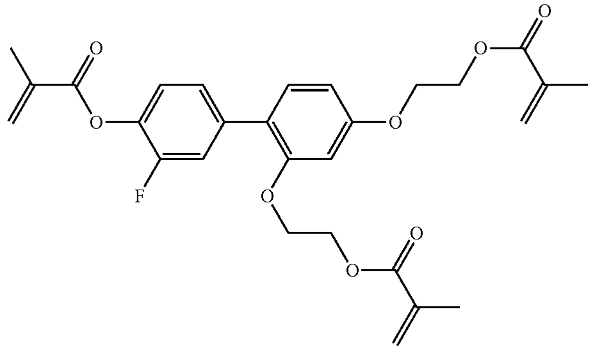 [SMILES: C=C(C)C(=O)OCCOc1ccc(-c2ccc(OC(=O)C(=C)C)c(F)c2)c(OCCOC(=O)C(=C)C)c1] |
| RM-131 |
| 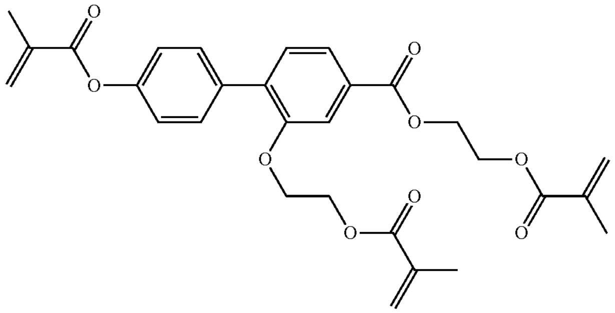 [SMILES: C=C(C)C(=O)OCCOC(=O)c1ccc(-c2ccc(OC(=O)C(=C)C)cc2)c(OCCOC(=O)C(=C)C)c1] |
| RM-132 |
| 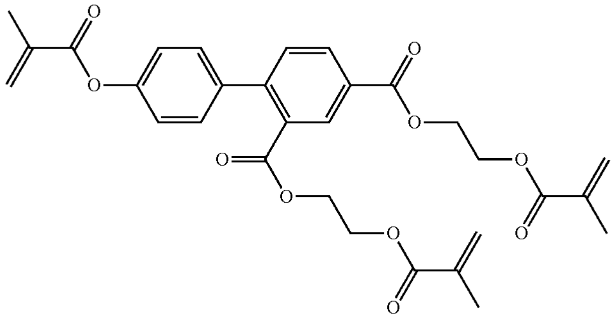 [SMILES: C=C(C)C(=O)OCCOC(=O)c1ccc(-c2ccc(OC(=O)C(=C)C)cc2)c(C(=O)OCCOC(=O)C(=C)C)c1] |
| RM-133 |
| 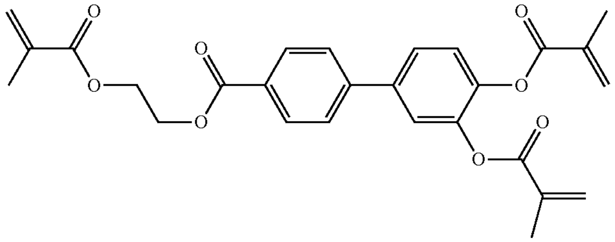 [SMILES: C=C(C)C(=O)OCCOC(=O)c1ccc(-c2ccc(OC(=O)C(=C)C)c(OC(=O)C(=C)C)c2)cc1] |
| RM-134 |

TABLE F-continued
| Table F shows illustrative reactive mesogenic compounds (RM) which can be used in the LC media in accordance with the present invention. |
|---|
| 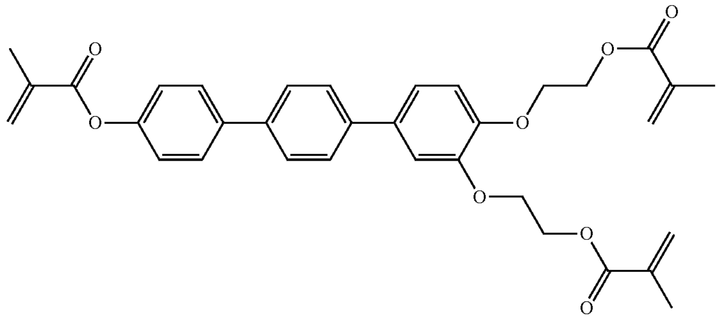 [SMILES: C=C(C)C(=O)OCCOc1ccc(-c2ccc(-c3ccc(OC(=O)C(=C)C)cc3)cc2)cc1OCCOC(=O)C(=C)C] |
| RM-135 |
| 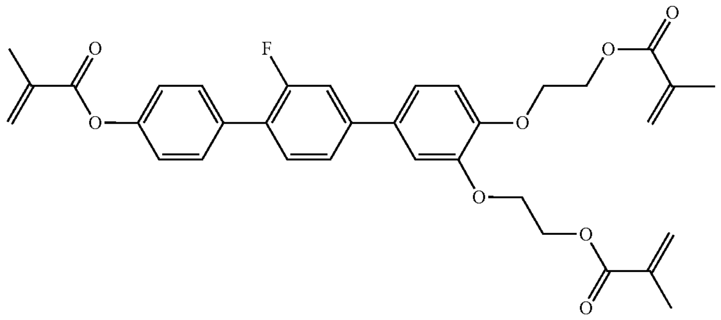 [SMILES: C=C(C)C(=O)OCCOc1ccc(-c2ccc(-c3ccc(OC(=O)C(=C)C)cc3)c(F)c2)cc1OCCOC(=O)C(=C)C] |
| RM-136 |
| 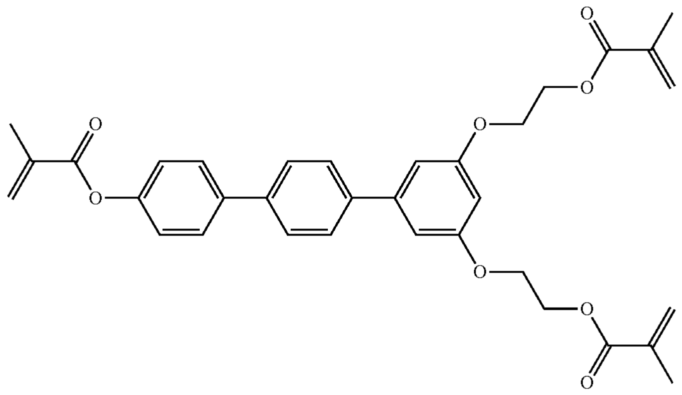 [SMILES: C=C(C)C(=O)OCCOc1cc(OCCOC(=O)C(=C)C)cc(-c2ccc(-c3ccc(OC(=O)C(=C)C)cc3)cc2)c1] |
| RM-137 |

TABLE F-continued
| Table F shows illustrative reactive mesogenic compounds (RM) which can be used in the LC media in accordance with the present invention. |
|---|
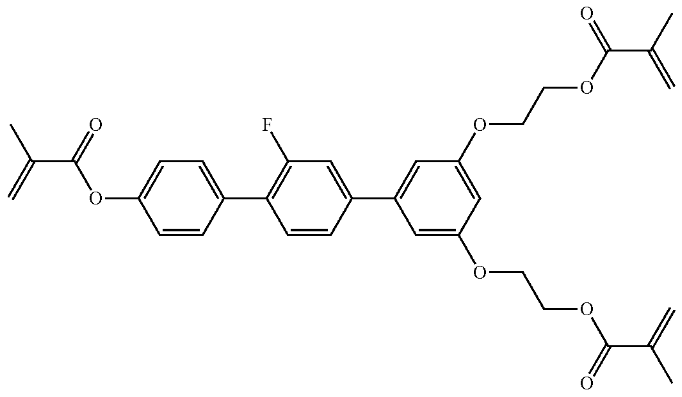 [SMILES: C=C(C)C(=O)OCCOc1cc(OCCOC(=O)C(=C)C)cc(-c2ccc(-c3ccc(OC(=O)C(=C)C)cc3)c(F)c2)c1]
RM-138
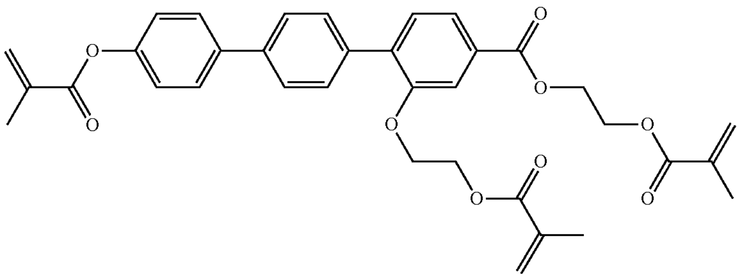 [SMILES: C=C(C)C(=O)OCCOC(=O)c1ccc(-c2ccc(-c3ccc(OC(=O)C(=C)C)cc3)cc2)c(OCCOC(=O)C(=C)C)c1]
RM-139
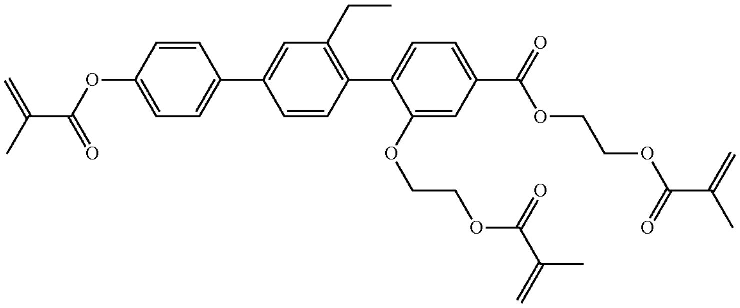 [SMILES: C=C(C)C(=O)OCCOC(=O)c1ccc(-c2ccc(-c3ccc(OC(=O)C(=C)C)cc3)cc2CC)c(OCCOC(=O)C(=C)C)c1]
RM-140
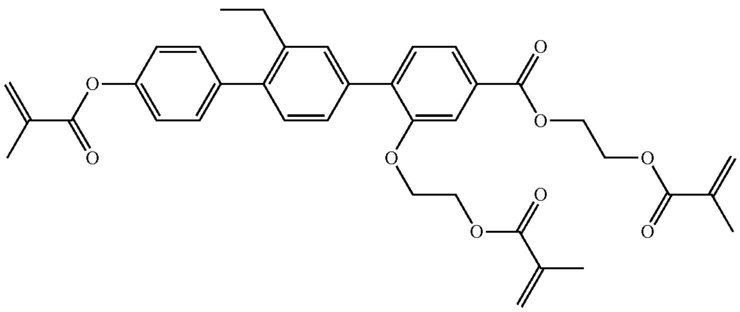 [SMILES: C=C(C)C(=O)OCCOC(=O)c1ccc(-c2ccc(-c3ccc(OC(=O)C(=C)C)cc3)c(CC)c2)c(OCCOC(=O)C(=C)C)c1]
RM-141

TABLE F-continued
Table F shows illustrative reactive mesogenic compounds (RM) which can be used in the LC media in accordance with the present invention.
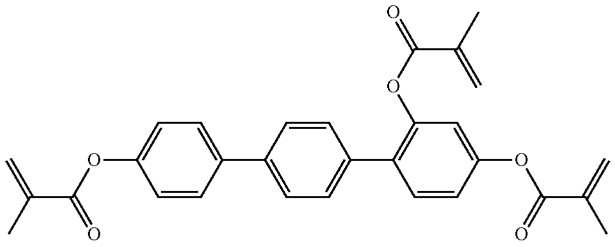 [SMILES: C=C(C)C(=O)Oc1ccc(-c2ccc(-c3ccc(OC(=O)C(=C)C)cc3OC(=O)C(=C)C)cc2)cc1]
RM-142
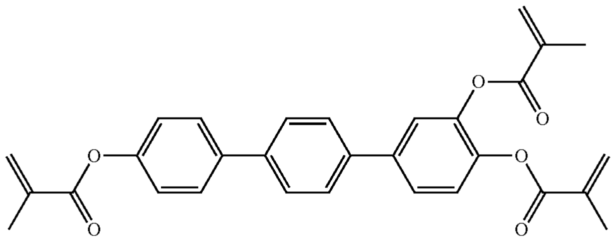 [SMILES: C=C(C)C(=O)Oc1ccc(-c2ccc(-c3ccc(OC(=O)C(=C)C)c(OC(=O)C(=C)C)c3)cc2)cc1]
RM-143
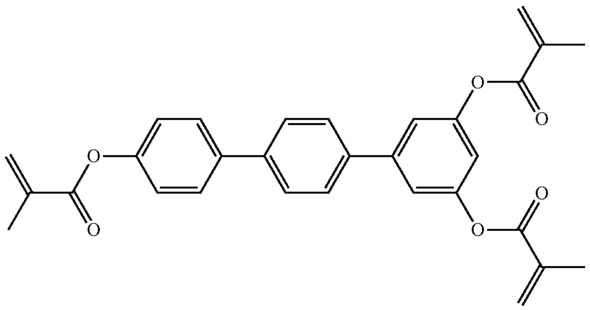 [SMILES: C=C(C)C(=O)Oc1ccc(-c2ccc(-c3cc(OC(=O)C(=C)C)cc(OC(=O)C(=C)C)c3)cc2)cc1]
RM-144
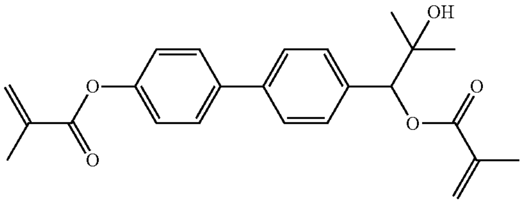 [SMILES: C=C(C)C(=O)Oc1ccc(-c2ccc(C(OC(=O)C(=C)C)C(C)(C)O)cc2)cc1]
RM-145
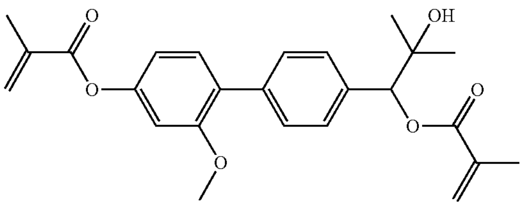 [SMILES: C=C(C)C(=O)Oc1ccc(-c2ccc(C(OC(=O)C(=C)C)C(C)(C)O)cc2)c(OC)c1]
RM-146

TABLE F-continued
Table F shows illustrative reactive mesogenic compounds (RM) which can be used in the LC media in accordance with the present invention.
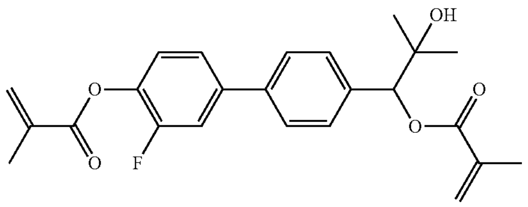 [SMILES: C=C(C)C(=O)Oc1ccc(-c2ccc(C(OC(=O)C(=C)C)C(C)(C)O)cc2)cc1F]
RM-147
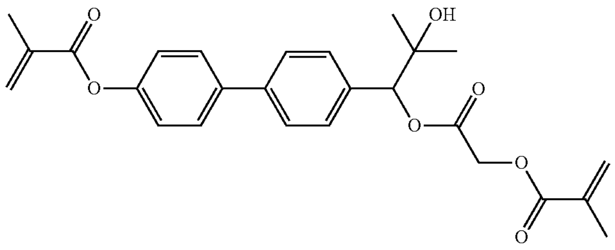 [SMILES: C=C(C)C(=O)OCC(=O)OC(c1ccc(-c2ccc(OC(=O)C(=C)C)cc2)cc1)C(C)(C)O]
RM-148
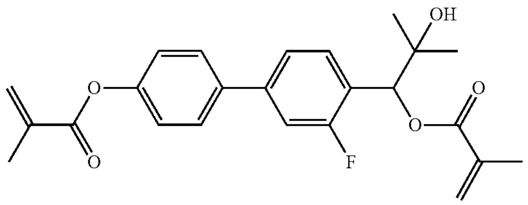 [SMILES: C=C(C)C(=O)Oc1ccc(-c2ccc(C(OC(=O)C(=C)C)C(C)(C)O)c(F)c2)cc1]
RM-149
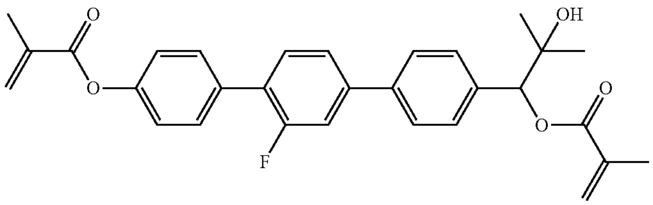 [SMILES: C=C(C)C(=O)Oc1ccc(-c2ccc(-c3ccc(C(OC(=O)C(=C)C)C(C)(C)O)cc3)cc2F)cc1]
RM-150
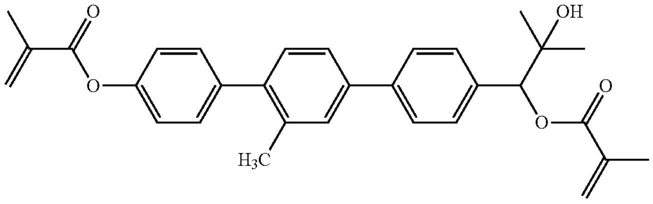 [SMILES: C=C(C)C(=O)Oc1ccc(-c2ccc(-c3ccc(C(OC(=O)C(=C)C)C(C)(C)O)cc3)cc2C)cc1]
RM-151

TABLE F-continued
Table F shows illustrative reactive mesogenic compounds (RM) which can be used in the LC media in accordance with the present invention.
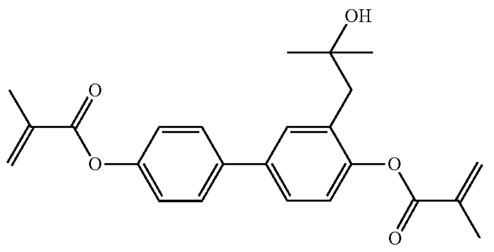 [SMILES: C=C(C)C(=O)Oc1ccc(-c2ccc(OC(=O)C(=C)C)c(CC(C)(C)O)c2)cc1]
RM-152
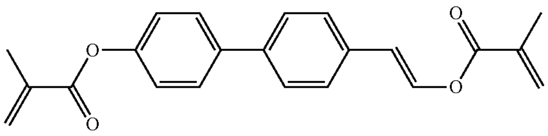 [SMILES: C=C(C)C(=O)O/C=C/c1ccc(-c2ccc(OC(=O)C(=C)C)cc2)cc1]
RM-153
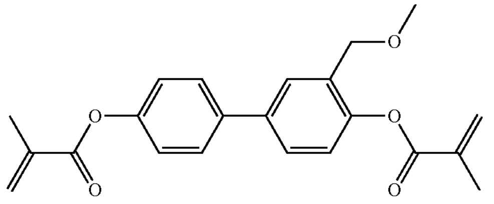 [SMILES: C=C(C)C(=O)Oc1ccc(-c2ccc(OC(=O)C(=C)C)c(COC)c2)cc1]
RM-154
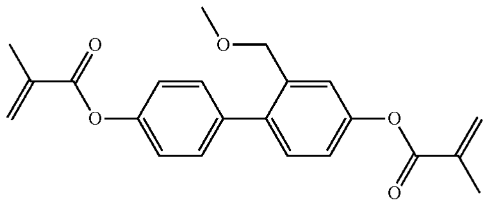 [SMILES: C=C(C)C(=O)Oc1ccc(-c2ccc(OC(=O)C(=C)C)cc2COC)cc1]
RM-155
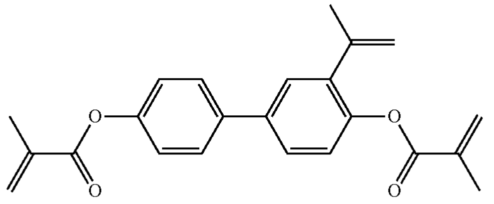 [SMILES: C=C(C)C(=O)Oc1ccc(-c2ccc(OC(=O)C(=C)C)c(C(=C)C)c2)cc1]
RM-156
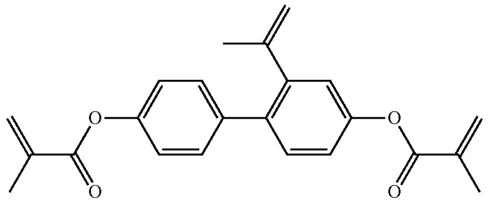 [SMILES: C=C(C)C(=O)Oc1ccc(-c2ccc(OC(=O)C(=C)C)cc2C(=C)C)cc1]
RM-157

TABLE F-continued
Table F shows illustrative reactive mesogenic compounds (RM) which can be used in the LC media in accordance with the present invention.
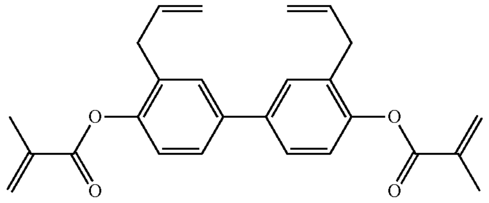 [SMILES: C=CCc1cc(-c2ccc(OC(=O)C(=C)C)c(CC=C)c2)ccc1OC(=O)C(=C)C]
RM-158
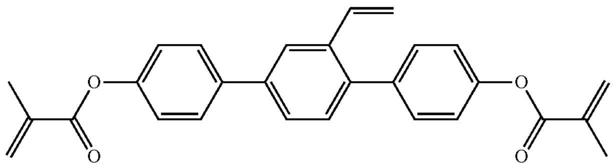 [SMILES: C=Cc1cc(-c2ccc(OC(=O)C(=C)C)cc2)ccc1-c1ccc(OC(=O)C(=C)C)cc1]
RM-159
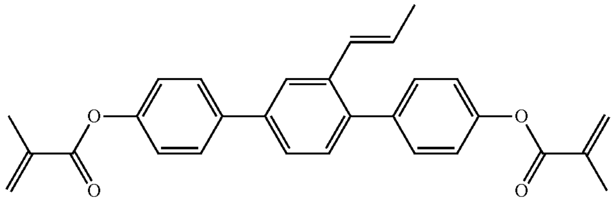 [SMILES: C=C(C)C(=O)Oc1ccc(-c2ccc(-c3ccc(OC(=O)C(=C)C)cc3)c(/C=C/C)c2)cc1]
RM-160
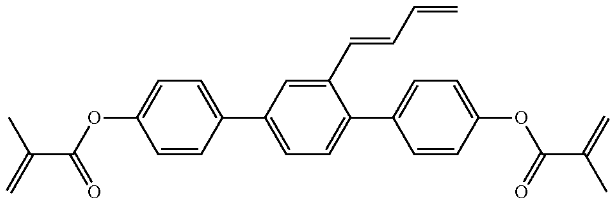 [SMILES: C=C/C=C/c1cc(-c2ccc(OC(=O)C(=C)C)cc2)ccc1-c1ccc(OC(=O)C(=C)C)cc1]
RM-161
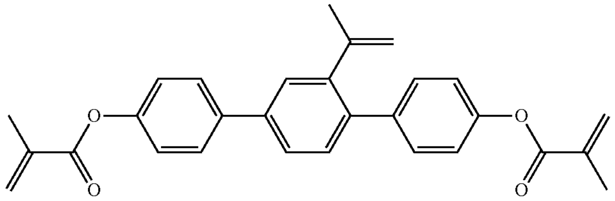 [SMILES: C=C(C)C(=O)Oc1ccc(-c2ccc(-c3ccc(OC(=O)C(=C)C)cc3)c(C(=C)C)c2)cc1]
RM-162
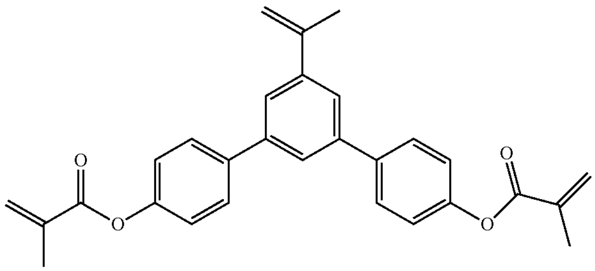 [SMILES: C=C(C)C(=O)Oc1ccc(-c2cc(C(=C)C)cc(-c3ccc(OC(=O)C(=C)C)cc3)c2)cc1]
RM-163

TABLE F-continued
Table F shows illustrative reactive mesogenic compounds (RM) which can be used in the LC media in accordance with the present invention.
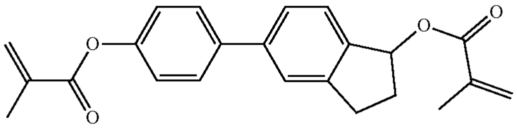 [SMILES: C=C(C)C(=O)Oc1ccc(-c2ccc3c(c2)CCC3OC(=O)C(=C)C)cc1]
RM-164
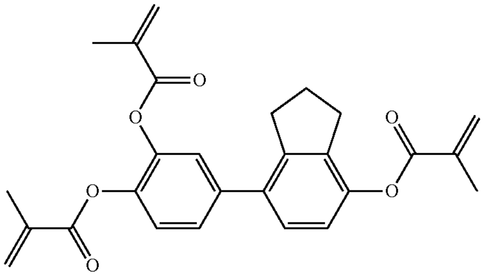 [SMILES: C=C(C)C(=O)Oc1ccc(-c2ccc(OC(=O)C(=C)C)c3c2CCC3)cc1OC(=O)C(=C)C]
RM-165
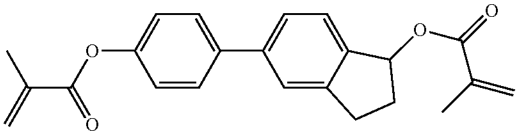 [SMILES: C=C(C)C(=O)Oc1ccc(-c2ccc3c(c2)CCC3OC(=O)C(=C)C)cc1]
RM-166
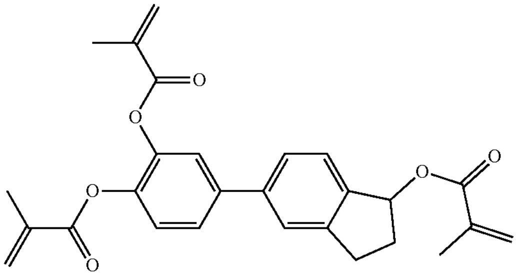 [SMILES: C=C(C)C(=O)Oc1ccc(-c2ccc3c(c2)CCC3OC(=O)C(=C)C)cc1OC(=O)C(=C)C]
RM-167
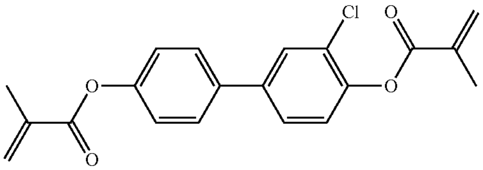 [SMILES: C=C(C)C(=O)Oc1ccc(-c2ccc(OC(=O)C(=C)C)c(Cl)c2)cc1]
RM-168
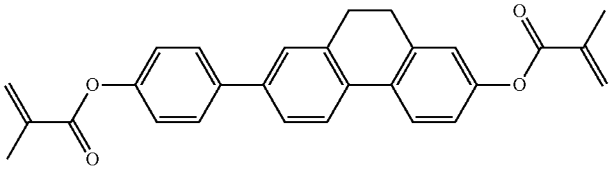 [SMILES: C=C(C)C(=O)Oc1ccc(-c2ccc3c(c2)CCc2cc(OC(=O)C(=C)C)ccc2-3)cc1]
RM-169

TABLE F-continued
Table F shows illustrative reactive mesogenic compounds (RM) which can be used in the LC media in accordance with the present invention.
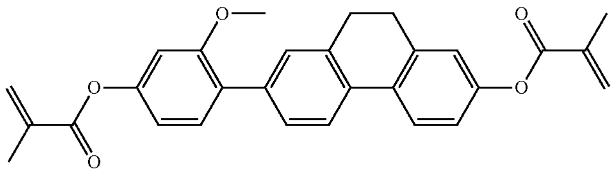
RM-170
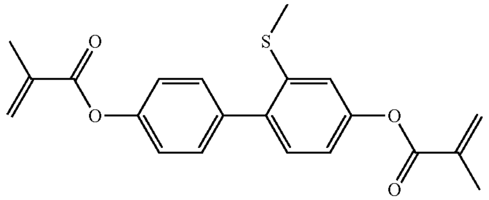 [SMILES: C=C(C)C(=O)Oc1ccc(-c2ccc(OC(=O)C(=C)C)cc2SC)cc1]
RM-171
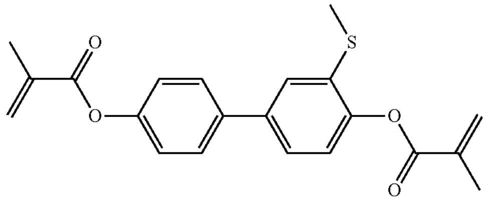 [SMILES: C=C(C)C(=O)Oc1ccc(-c2ccc(OC(=O)C(=C)C)c(SC)c2)cc1]
RM-172
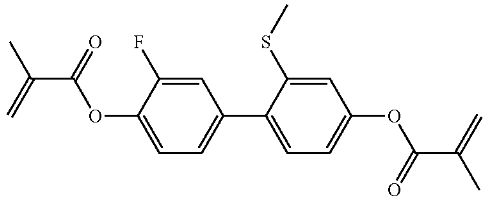 [SMILES: C=C(C)C(=O)Oc1ccc(-c2ccc(OC(=O)C(=C)C)c(F)c2)c(SC)c1]
RM-173
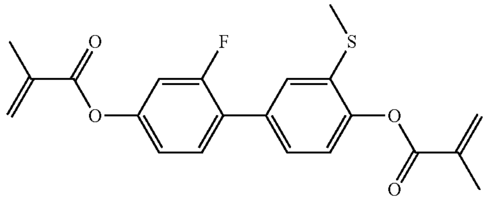 [SMILES: C=C(C)C(=O)Oc1ccc(-c2ccc(OC(=O)C(=C)C)c(SC)c2)c(F)c1]
RM-174
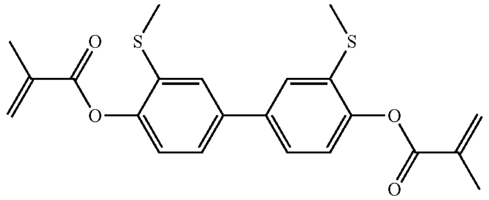 [SMILES: C=C(C)C(=O)Oc1ccc(-c2ccc(OC(=O)C(=C)C)c(SC)c2)cc1SC]
RM-175

TABLE F-continued
Table F shows illustrative reactive mesogenic compounds (RM) which can be used in the LC media in accordance with the present invention.
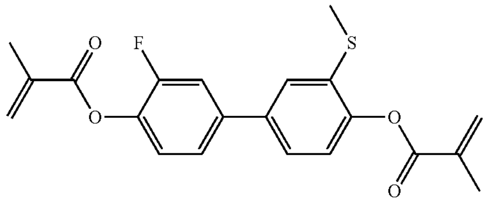 [SMILES: C=C(C)C(=O)Oc1ccc(-c2ccc(OC(=O)C(=C)C)c(SC)c2)cc1F]
RM-176
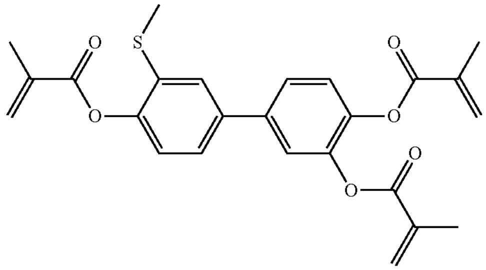 [SMILES: C=C(C)C(=O)Oc1ccc(-c2ccc(OC(=O)C(=C)C)c(SC)c2)cc1OC(=O)C(=C)C]
RM-177
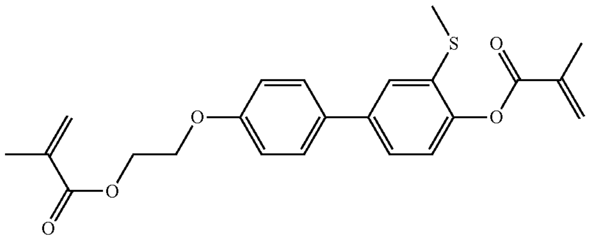
RM-178
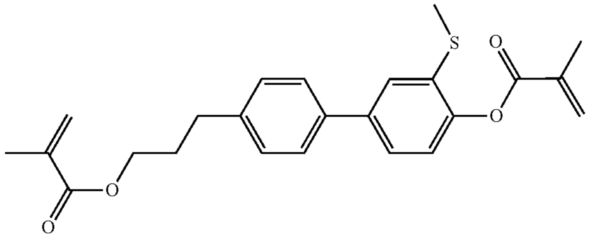 [SMILES: C=C(C)C(=O)OCCCc1ccc(-c2ccc(OC(=O)C(=C)C)c(SC)c2)cc1]
RM-179
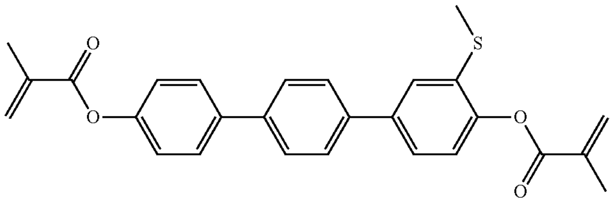 [SMILES: C=C(C)C(=O)Oc1ccc(-c2ccc(-c3ccc(OC(=O)C(=C)C)c(SC)c3)cc2)cc1]
RM-180

TABLE F-continued

Table F shows illustrative reactive mesogenic compounds (RM) which can be used in the LC media in accordance with the present invention.

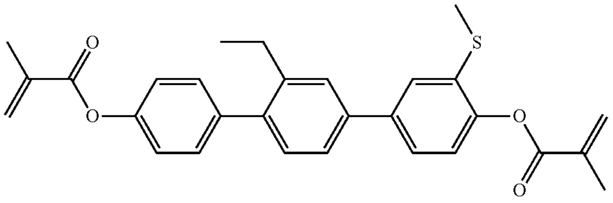 [SMILES: C=C(C)C(=O)Oc1ccc(-c2ccc(-c3ccc(OC(=O)C(=C)C)c(SC)c3)cc2CC)cc1]

RM-181

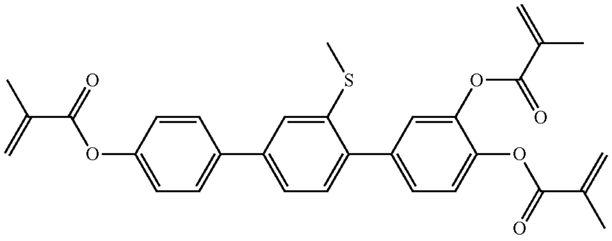 [SMILES: C=C(C)C(=O)Oc1ccc(-c2ccc(-c3ccc(OC(=O)C(=C)C)c(OC(=O)C(=C)C)c3)c(SC)c2)cc1]

RM-182

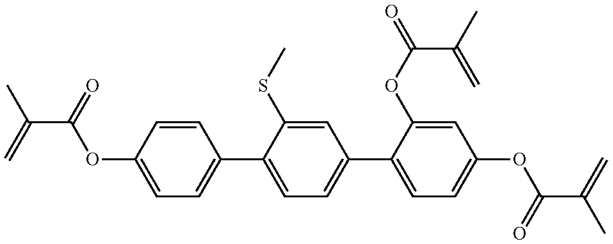 [SMILES: C=C(C)C(=O)Oc1ccc(-c2ccc(-c3ccc(OC(=O)C(=C)C)cc3OC(=O)C(=C)C)cc2SC)cc1]

RM-183

In a preferred embodiment, the mixtures according to the invention comprise one or more polymerizable compounds, preferably selected from the polymerizable compounds of the formulae RM-1 to RM-182. Of these, compounds RM-1, RM-4, RM-8, RM-17, RM-19, RM-35, RM-37, RM-39, RM-40, RM-41, RM-48, RM-52, RM-54, RM-57, RM-58, RM-64, RM-74, RM-76, RM-88, RM-91, RM-102, RM-103, RM-109, RM-116, RM-117, RM-120, RM-121, RM-122, RM-139, RM-140, RM-142, RM-143, RM-145, RM-146, RM-147, RM-149, RM-156 to RM-163, RM-169, RM-170, and RM-171 to RM-183 are particularly preferred.

WORKING EXAMPLES

The following examples are intended to explain the invention without limiting it. In the examples, m.p. denotes the melting point and $T_{(N,I)}$ denotes the clearing point of a liquid-crystalline substance in degrees Celsius; Furthermore: C denotes crystalline solid state, S denotes smectic phase (the index denotes the phase type), N denotes nematic state, Ch denotes cholesteric phase, I denotes isotropic phase, $T_g$ denotes glass-transition temperature. The number between two symbols indicates the conversion temperature in degrees Celsius.

The host mixture used for determination of the optical anisotropy Δn of single compounds is the commercial mixture ZLI-4792 (Merck KGaA). The dielectric anisotropy Δε is determined using commercial mixture ZLI-2857. The physical data of the compound to be investigated are obtained from the change in the dielectric constants of the host mixture after addition of the compound to be investigated and extrapolation to 100% of the compound employed. In general, 10% of the compound to be investigated are dissolved in the host mixture, depending on the solubility.

Unless indicated otherwise, parts or percent data denote parts by weight or percent by weight.

Above and Below:

| | |
|---|---|
| $V_o$ | denotes threshold voltage, capacitive [V] at 20° C., |
| $n_e$ | denotes extraordinary refractive index at 20° C. and 589 nm, |
| $n_o$ | denotes ordinary refractive index at 20° C. and 589 nm, |
| Δn | denotes optical anisotropy (birefringence) at 20° C. and 589 nm, |
| ε⊥ | denotes dielectric permittivity perpendicular to the director at 20° C. and 1 kHz, |
| ε∥ | denotes dielectric permittivity parallel to the director at 20° C. and 1 kHz, |
| Δε | denotes dielectric anisotropy at 20° C. and 1 kHz, |
| cl.p., T(N, I) | denotes clearing point [° C.], |
| $\gamma_1$ | denotes rotational viscosity measured at 20° C. [mPa · s], |
| $K_1$ | denotes elastic constant, "splay" deformation at 20° C. [pN], |
| $K_2$ | denotes elastic constant, "twist" deformation at 20° C. [pN], |
| $K_3$ | denotes elastic constant, "bend" deformation at 20° C. [pN], |
| $K_{av}$ | denotes average elastic constant defined as $K_{av} = (1.5 \cdot K_1 + K_3)$ [pN] at 20° C. |
| LTS | denotes low-temperature stability (nematic phase), determined in test cells or in the bulk, as specified. |

Unless explicitly noted otherwise, all values indicated in the present application for temperatures, such as, for example, the melting point T(C,N), the transition from the smectic(S) to the nematic (N) phase T(S,N) and the clearing point T(N,I) or cl.p., are indicated in degrees Celsius (C).

The term "threshold voltage" for the present invention relates to the capacitive threshold ($V_0$), also called the Freedericksz threshold, unless explicitly indicated otherwise. In the examples, as is generally usual, the optical threshold can also be indicated for 10% relative contrast ($V_{10}$).

The display used for measurement of the capacitive threshold voltage consists of two plane-parallel glass outer plates at a separation of 20 μm, which each have on the insides an electrode layer and an unrubbed polyimide alignment layer on top, which cause a homeotropic edge alignment of the liquid-crystal molecules.

The display or test cell used for measurement of the tilt angle consists of two plane-parallel glass outer plates at a separation of 4 μm, which each have on the insides an electrode layer and a polyimide alignment layer on top, where the two polyimide layers are rubbed antiparallel to one another and cause a homeotropic edge alignment of the liquid-crystal molecules.

The polymerizable compounds are polymerized in the display or test cell by irradiation with UV light of defined intensity for a prespecified time, with a voltage simultaneously being applied to the display (usually 10 V to 30 V alternating current, 1 kHz). In the examples, unless indicated otherwise, a metal halide lamp and an intensity of 100 $mW/cm^2$ is used for polymerization. The intensity is measured using a standard meter (Hoenle UV-meter high end with UV sensor).

The tilt angle is determined using the Mueller Matrix Polarimeter "AxoScan" from Axometrics. A low value (i.e. a large deviation from the 90° angle) corresponds to a large tilt here.

Unless stated otherwise, the term "tilt angle" means the angle between the LC director and the substrate, and "LC director" means in a layer of LC molecules with uniform orientation the preferred orientation direction of the optical main axis of the LC molecules, which corresponds, in case of calamitic, uniaxially positive birefringent LC molecules, to their molecular long axis.

Unless indicated otherwise, the VHR is determined at 20° C. ($VHR_{20}$) and after 5 minutes in an oven at 100° C. ($VHR_{100}$) in a commercially available instrument Model LCM-1 (O0004) from TOYO Corporation, Japan. The voltage used has a frequency of in a range from 1 Hz to 60 Hz, unless indicated more precisely.

The stability to UV irradiation is investigated in a "Suntest CPS+", a commercial instrument from Heraeus, Germany, using a Xenon lamp NXE1500B. The sealed test cells are irradiated for 2.0 h, unless explicitly indicated, without additional heating. The irradiation power in the wavelength range from 300 nm to 800 nm is 765 $W/m^2$ V. A UV "cut-off" filter having an edge wavelength of 310 nm is used in order to simulate the so-called window glass mode. In each series of experiments, at least four test cells are investigated for each condition, and the respective results are indicated as averages of the corresponding individual measurements.

In order to investigate the low-temperature stability, also known as "LTS", i.e. the stability of the LC mixture in the bulk against spontaneous crystallisation of individual components at low temperatures or the occurrence of smectic phases, as the case may be, several sealed bottles, each containing about 1 g of the material, are stored at one or more given temperatures, typically of −10° C., −20° C., −30° C., and/or −40° C., and it is inspected at regular intervals visually, whether a phase transition is observed or not. As soon as the first one of the samples at a given temperature shows a change, the test is discontinued, and the time until the last inspection, at which no change has been observed, is noted as the respective LTS. The test is run for 1000 h. If after 1000 h no change has occurred, the result is "LTS>1000 h".

The ion density from which the resistivity is calculated is measured using the commercially available LC Material Characteristics Measurement System Model 6254 from Toyo Corporation, Japan, using VHR test cells with AL16301 Polyimide (JSR Corp., Japan) having a 3.2-μm cell gap. The measurement is performed after 5 min of storage in an oven at 60° C. or 100° C.

The so-called "HTP" denotes the helical twisting power of an optically active or chiral substance in an LC medium (in μm). Unless indicated otherwise, the HTP is measured in the commercially available nematic LC host mixture MLD-6260 (Merck KGaA) at a temperature of 20° C.

The Clearing point is measured using the Mettler Thermosystem FP900. The optical anisotropy (Δn) is measured using an Abbe-Refraktometer H005 (Natrium-spectral lamp Na10 at 589 nm, 20° C.). The dielectric anisotropy (Δε) is measured using an LCR-Meter E4980A/Agilent (G005) at 20° C. (ε-parallel-cells with JALS 2096-R1). The turn on voltage ($V_0$) is measured using an LCR-Meter E4980A/Agilent (G005) at 20° C. (ε-parallel-cells with JALS 2096-R1). The rotational viscosity ($\gamma_1$) is measured using a TOYO LCM-2 (0002) at 20° C. (gamma 1 negative cells with JALS-2096-R 1). The elastic constant ($K_1$, splay) is measured using an LCR-Meter E4980A/Agilent (G005) at 20° C. (ε parallel-cells with JALS 2096-$R^1$). $K_3$: The elastic constant ($K_3$, bend) is measured using an LCR-Meter E4980A/Agilent (G005) at 20° C. (&-parallel-cells with JALS 2096-$R^1$).

Unless explicitly noted otherwise, all concentrations in the present application are indicated in percent by weight and relate to the corresponding mixture as a whole, comprising all solid or liquid-crystalline components, without solvents. All physical properties are determined in accordance with "Merck Liquid Crystals, Physical Properties of Liquid Crystals", Status November 1997, Merck KGaA, Germany, and apply for a temperature of 20° C., unless explicitly indicated otherwise.

The following mixture examples having positive dielectric anisotropy are suitable, in particular, for liquid-crystal displays which have at least one planar alignment layer, such as, for example, IPS and FFS displays, in particular UB-FFS (=ultra-bright FFS), and for VA displays.

The dielectric anisotropy Δε, birefringence Δn and rotational viscosity $\gamma_1$ of single compounds are extrapolated from a 10% solution in the liquid crystal host mixture ZLI-4792 (Merck KGaA, Darmstadt).

SYNTHESIS EXAMPLES

Synthesis Example 1: 4'-Ethyl-3-fluoro-4-[4-(4-propylcyclohexyl)cyclohex-1-en-1-yl]-1,1'-biphenyl

Step 1:4-{4'-ethyl-3-fluoro-[1,1'-biphenyl]-4-yl}-4'-propyl-[1,1'-bi(cyclohexane)]-4-ol

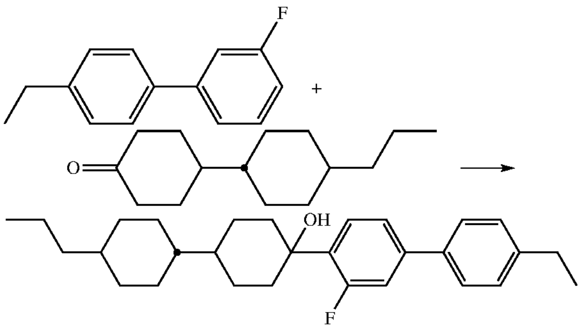

50 g (250 mmol) of 4'-ethyl-3-fluoro-1,1'-biphenyl are dissolved in 350 mL of THF and cooled to −70° C. 200 mL (1.1 eq) of sec-BuLi (1.4 M in cyclohexane) is added dropwise. The solution is stirred for 1.5 h at −70° C. before a solution of 60 g (270 mmol) of trans-4'-propyl[1,1'-bicyclohexyl]-4-one in 250 ml of THF is added dropwise at −70° C. The reaction mixture is stirred for 2 h and then allowed to warm to room temperature. The reaction is quenched with water and 100 mL of 2N HCl. The organic phase is extracted with MTBE and evaporated. The crude product is crystallized by cooling from 400 mL of warm heptane to give 4-{4'-ethyl-3-fluoro-[1,1'-biphenyl]-4-yl}-4'-propyl-[1,1'-bi(cyclohexane)]-4-ol as colorless crystals, which is used in the next step without further purification. GC-MS (+EI): two isomers with 422 g/mol.

Step 2

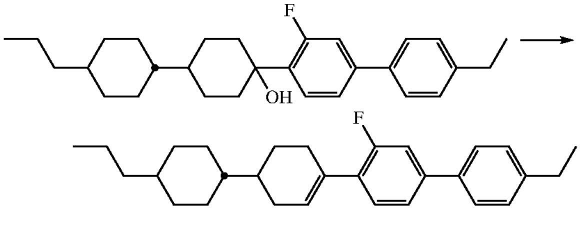

77 g (182 mmol) of 4-{4'-ethyl-3-fluoro-[1,1'-biphenyl]-4-yl}-4'-propyl-[1,1'-bi(cyclohexane)]-4-ol is dissolved in 1 L of toluene. 3.5 g (18 mmol) of 4-toluene-sulfonic acid monohydrate is added and the reaction mixture is refluxed in a Dean Stark apparatus for 2 h. The solution is cooled to room temperature and is extracted with MTBE. The crude product is dissolved in 200 mL of methylene chloride, filtered through silica, and evaporated to dryness. Crystallization from 1-chlorbutane yields 4'-ethyl-3-fluoro-4-[4-(4-propylcyclohexyl)cyclohex-1-en-1-yl]-1,1'-biphenyl as a colorless solid. Phase sequence: K 64 SmB 165 SmA 176 N 290.3 I.

GC-MS (+EI): 404.3 g/mol $^1$H NMR (500 MHZ, Chloroform-d) δ 7.52 (d, J=8.2 Hz, 2H), 7.36-7.23 (m, 5H), 6.03 (dt, J=5.2, 2.5 Hz, 1H), 2.72 (q, J=7.6 Hz, 2H), 2.56-2.40 (m, 2H), 2.29 (ddt, J=17.8, 5.6, 2.9 Hz, 1H), 2.06-1.91 (m, 2H), 1.90-1.76 (m, 4H), 1.51-1.27 (m, 7H), 1.24-1.14 (m, 4H), 1.13-0.98 (m, 2H), 0.91 (t, J=7.3 Hz, 5H).

$\Delta\varepsilon = 2.9$ $\Delta n = 0.2229$

Synthesis Example 2

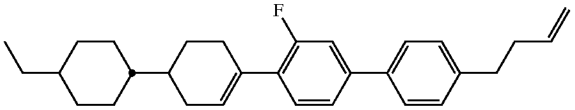

In analogy to Synthesis Example 1, 4'-(but-3-en-1-yl)-4-[4-(4-ethylcyclohexyl)cyclohex-1-en-1-yl]-3-fluoro-1,1'-biphenyl is obtained as colorless crystals, phase sequence: K 134 SmA 178 N 275.8 I.

$\Delta\varepsilon = 2.5$

MIXTURE EXAMPLES

The composition and physical properties of the nematic mixtures M1 to M41 are given in the following tables. The composition is given in percent by weight.

| Mixture Example M1 | | | |
|---|---|---|---|
| CGPC-5-3 | 1.0 | cl.p. [° C.]: | 120.6 |
| CC-3-V | 26.5 | Δn [589 nm, 20° C.]: | 0.1291 |
| CC-3-V1 | 6.0 | Δε [1 kHz, 20° C.]: | 4.1 |
| CCP-V-1 | 15.0 | $\gamma_1$ [mPa · s, 20° C.]: | 103 |
| CCP-V2-1 | 10.0 | $K_1$ [pN, 20° C.]: | 19.4 |
| CCVC-3-V | 8.5 | $K_3$ [pN, 20° C.]: | 20.4 |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-3-F | 0.5 | | |
| PUS-3-2 | 13.0 | | |
| Σ | 100.0 | | |

| Mixture Example M2 | | | |
|---|---|---|---|
| CGPC-5-3 | 0.5 | cl.p. [° C.]: | 123.8 |
| CC-3-V | 26.0 | Δn [589 nm, 20° C.]: | 0.1297 |
| CC-3-V1 | 6.0 | Δε [1 kHz, 20° C.]: | 4.3 |
| CCP-V-1 | 15.0 | $\gamma_1$ [mPa · s, 20° C.]: | 107 |
| CCP-V2-1 | 10.0 | $K_1$ [pN, 20° C.]: | 19.9 |
| CCVC-3-V | 8.5 | $K_3$ [pN, 20° C.]: | 20.6 |
| CDUQU-3-F | 2.0 | | |

-continued

| Mixture Example M2 | |
|---|---|
| CLGIP-3-2 | 5.0 |
| DGUQU-4-F | 4.0 |
| CP-3-O2 | 0.5 |
| PGUQU-3-F | 5.0 |
| PGUQU-4-F | 2.0 |
| PPGU-3-F | 0.5 |
| PUS-3-2 | 15.0 |
| Σ | 100.0 |

| Mixture Example M3 | | | |
|---|---|---|---|
| PUQU-3-F | 12.0 | cl.p. [° C.]: | 101.9 |
| APUQU-3-F | 2.0 | Δn [589 nm, 20° C.]: | 0.1032 |
| CDUQU-3-F | 4.0 | Δε [1 kHz, 20° C.]: | 8.2 |
| CDU-3-F | 4.0 | $\gamma_1$ [mPa · s, 20° C.]: | 111 |
| CPG-3-F | 6.0 | $K_1$ [pN, 20° C.]: | 13.8 |
| CPG-5-F | 4.0 | $K_3$ [pN, 20° C.]: | 18.6 |
| CCQU-3-F | 8.0 | | |
| CCG-V-F | 10.0 | | |
| CC-3-V | 21.5 | | |
| CCP-V-1 | 12.0 | | |
| CCP-V2-1 | 8.0 | | |
| CCP-3-1 | 4.0 | | |
| CLGIP-3-2 | 4.0 | | |
| PPGU-3-F | 0.5 | | |
| Σ | 100.0 | | |

| Mixture Example M4 | | | |
|---|---|---|---|
| APUQU-2-F | 4.0 | cl.p. [° C.]: | 122.6 |
| APUQU-3-F | 4.0 | Δn [589 nm, 20° C.]: | 0.1206 |
| CC-3-V | 34.5 | Δε [1 kHz, 20° C.]: | 6.6 |
| CCP-V-1 | 12.0 | $\gamma_1$ [mPa · s, 20° C.]: | 121 |
| CCP-V2-1 | 7.0 | $K_1$ [pN, 20° C.]: | 17.8 |
| CCZPC-3-3 | 3.0 | $K_3$ [pN, 20° C.]: | 20.1 |
| CCZPC-3-5 | 3.0 | | |
| CCVC-3-V | 3.5 | | |
| CDUQU-3-F | 2.0 | | |
| CLGIP-3-2 | 5.0 | | |
| DPGU-4-F | 2.0 | | |
| PGP-2-2V | 9.0 | | |
| PGUQU-3-F | 5.5 | | |
| PPGU-3-F | 0.5 | | |
| PUQU-3-F | 5.0 | | |
| Σ | 100.0 | | |

| Mixture Example M5 | | | |
|---|---|---|---|
| APUQU-2-F | 3.0 | cl.p. [° C.]: | 101.2 |
| APUQU-3-F | 2.5 | Δn [589 nm, 20° C.]: | 0.1046 |
| CC-3-2V1 | 3.0 | Δε [1 kHz, 20° C.]: | 4.1 |
| CC-3-V | 37.0 | $\gamma_1$ [mPa · s, 20° C.]: | 78 |
| CC-3-V1 | 5.0 | $K_1$ [pN, 20° C.]: | 16.1 |
| CCP-V-1 | 13.0 | $K_3$ [pN, 20° C.]: | 18.5 |
| CCP-V2-1 | 7.5 | | . |
| CCVC-3-V | 5.0 | | |
| CDUQU-3-F | 2.0 | | |
| CLGIP-3-2 | 4.0 | | |
| DGUQU-4-F | 2.0 | | |
| PGP-2-3 | 5.0 | | |
| PGP-2-4 | 4.5 | | |
| PPGU-3-F | 0.5 | | |
| PUQU-3-F | 6.0 | | |
| Σ | 100.0 | | |

| Mixture Example M6 | | | |
|---|---|---|---|
| B(S)—2O—O4 | 2.5 | cl.p. [° C.]: | 109.5 |
| B(S)—2O—O5 | 2.5 | Δn [589 nm, 20° C.]: | 0.1181 |
| CPP-3-2 | 5.0 | Δε [1 kHz, 20° C.]: | 4.20 |
| CC-3-V | 32.5 | $\gamma_1$ [mPa · s, 20° C.]: | 98.7 |
| CC-3-V1 | 5.0 | | |
| CCGU-3-F | 3.5 | | |
| CCP-3-1 | 2.0 | | |
| CCP-V-1 | 14.0 | | |
| CCP-V2-1 | 5.0 | | |
| CCVC-3-V | 4.0 | | |
| CLGIP-3-2 | 2.0 | | |
| DGUQU-4-F | 2.5 | | |
| PGP-2-2V | 5.0 | | |
| PGUQU-3-F | 3.0 | | |
| PGUQU-4-F | 5.0 | | |
| PPGU-3-F | 0.5 | | |
| PUQU-3-F | 3.0 | | |
| LB(S)-3-OT | 3.0 | | |
| Σ | 100.0 | | |

| Mixture Example M7 | | | |
|---|---|---|---|
| B(S)—2O—O5 | 4.0 | cl.p. [° C.]: | 110 |
| CPP-3-2 | 4.0 | Δn [589 nm, 20° C.]: | 0.1299 |
| CC-3-V | 35.0 | Δε [1 kHz, 20° C.]: | 3.79 |
| CCP-V-1 | 13.5 | $\gamma_1$ [mPa · s, 20° C.]: | 105.2 |
| CCP-V2-1 | 2.0 | | |
| CCVC-3-V | 5.0 | | |
| CDUQU-3-F | 1.5 | | |
| DGUQU-4-F | 4.0 | | |
| DLGU-3-F | 3.0 | | |
| LB(S)-3-OT | 4.0 | | |
| PGP-1-2V | 3.0 | | |
| PGP-2-2V | 7.0 | | |
| PPGU-3-F | 0.5 | | |
| PUQU-3-F | 4.5 | | |
| PUS-3-2 | 4.0 | | |
| CLGIP-3-2 | 5.0 | | |
| Σ | 100.0 | | |

| Mixture Example M8 | | | |
|---|---|---|---|
| PUQU-3-F | 6.0 | cl.p. [° C.]: | 120.0 |
| PGUQU-3-F | 4.0 | Δn [589 nm, 20° C.]: | 0.1191 |
| APUQU-2-F | 4.0 | Δε [1 kHz, 20° C.]: | 6.13 |
| APUQU-3-F | 4.0 | $\gamma_1$ [mPa · s, 20° C.]: | 127.3 |
| CDUQU-3-F | 2.0 | | |
| DPGU-4-F | 2.0 | | |
| CC-3-V | 33.0 | | |
| CCP-V-1 | 12.0 | | |
| CCP-V2-1 | 9.5 | | |
| PGP-2-2V | 6.0 | | |
| CCVC-3-V | 3.0 | | |
| CCZPC-3-3 | 2.5 | | |
| CCZPC-3-5 | 2.5 | | |
| CLGIP-3-2 | 5.0 | | |
| PPGU-3-F | 0.5 | | |
| B(S)—2O—O4 | 2.0 | | |
| B(S)—2O—O5 | 2.0 | | |
| Σ | 100.0 | | |

Mixture Example M9

| | | | |
|---|---|---|---|
| B(P)—2O—O3 | 4.0 | cl.p. [° C.]: | 115.5 |
| CPP-3-2 | 4.0 | Δn [589 nm, 20° C.]: | 0.1302 |
| CC-3-V | 35.0 | Δε [1 kHz, 20° C.]: | 4.09 |
| CCP-V-1 | 13.5 | $\gamma_1$ [mPa · s, 20° C.]: | 101 |
| CCP-V2-1 | 2.0 | | |
| CCVC-3-V | 5.0 | | |
| CDUQU-3-F | 1.5 | | |
| DGUQU-4-F | 4.0 | | |
| DLGU-3-F | 3.0 | | |
| LB(S)-3-OT | 4.0 | | |
| PGP-1-2V | 3.0 | | |
| PGP-2-2V | 7.0 | | |
| PPGU-3-F | 0.5 | | |
| PUQU-3-F | 4.5 | | |
| PUS-3-2 | 4.0 | | |
| CLGIP-3-2 | 5.0 | | |
| Σ | 100.0 | | |

Mixture Example M10

| | | | |
|---|---|---|---|
| B(S)—4O—O1(c5-3en) | 4.0 | cl.p. [° C.]: | 109 |
| CPP-3-2 | 4.0 | Δn [589 nm, 20° C.]: | 0.1293 |
| CC-3-V | 35.0 | Δε [1 kHz, 20° C.]: | 3.68 |
| CCP-V-1 | 13.5 | $\gamma_1$ [mPa · s, 20° C.]: | 111 |
| CCP-V2-1 | 2.0 | | |
| CCVC-3-V | 5.0 | | |
| CDUQU-3-F | 1.5 | | |
| DGUQU-4-F | 4.0 | | |
| DLGU-3-F | 3.0 | | |
| LB(S)-3-OT | 4.0 | | |
| PGP-1-2V | 3.0 | | |
| PGP-2-2V | 7.0 | | |
| PPGU-3-F | 0.5 | | |
| PUQU-3-F | 4.5 | | |
| PUS-3-2 | 4.0 | | |
| CLGIP-3-2 | 5.0 | | |
| Σ | 100.0 | | |

Mixture Example M11

| | | | |
|---|---|---|---|
| PUQU-3-F | 4.0 | cl.p. [° C.]: | 100.0 |
| APUQU-2-F | 6.0 | Δn [589 nm, 20° C.]: | 0.1093 |
| APUQU-3-F | 6.0 | Δε [1 kHz, 20° C.]: | 6.70 |
| CDUQU-3-F | 8.0 | $\gamma_1$ [mPa · s, 20° C.]: | 106 |
| CCGU-3-F | 4.0 | | |
| CC-3-V | 40.0 | | |
| CCP-V-1 | 12.0 | | |
| CLGIP-3-2 | 2.5 | | |
| PGP-2-2V | 7.0 | | |
| PPGU-3-F | 0.5 | | |
| CCOY-3-O2 | 5.0 | | |
| CPY-3-O2 | 5.0 | | |
| Σ | 100.0 | | |

Mixture Example M12

| | | | |
|---|---|---|---|
| PUQU-3-F | 4.0 | cl.p. [° C.]: | 101.0 |
| APUQU-2-F | 6.0 | Δn [589 nm, 20° C.]: | 0.1092 |
| APUQU-3-F | 6.0 | Δε [1 kHz, 20° C.]: | 6.90 |
| CDUQU-3-F | 8.0 | $\gamma_1$ [mPa · s, 20° C.]: | 103 |
| CCGU-3-F | 4.0 | | |
| CC-3-V | 40.0 | | |
| CCP-V-1 | 12.0 | | |
| CLGIP-3-2 | 2.5 | | |
| PGP-2-2V | 7.0 | | |
| PPGU-3-F | 0.5 | | |

-continued

Mixture Example M12

| | |
|---|---|
| CCEY-3-O2 | 5.0 |
| CPY-3-O2 | 5.0 |
| Σ | 100.0 |

Mixture Example M13

| | | | |
|---|---|---|---|
| B(S)—2O—O4 | 2.5 | cl.p. [° C.]: | 112 |
| B(S)—2O—O5 | 2.5 | | |
| CPP-1V-2 | 5.0 | | |
| CC-3-V | 32.5 | | |
| CC-3-V1 | 5.0 | | |
| CCGU-3-F | 3.5 | | |
| CCP-3-1 | 2.0 | | |
| CCP-V-1 | 14.0 | | |
| CCP-V2-1 | 5.0 | | |
| CCVC-3-V | 4.0 | | |
| CLGIP-3-2 | 2.0 | | |
| DGUQU-4-F | 2.5 | | |
| PGP-2-2V | 5.0 | | |
| PGUQU-3-F | 3.0 | | |
| PGUQU-4-F | 5.0 | | |
| PPGU-3-F | 0.5 | | |
| PUQU-3-F | 3.0 | | |
| LB(S)-3-OT | 3.0 | | |
| Σ | 100.0 | | |

Mixture Example M14

| | | | |
|---|---|---|---|
| CGPC-5-3 | 1.0 | cl.p. [° C.]: | 120 |
| CC-3-V | 26.5 | Δn [589 nm, 20° C.]: | 0.1285 |
| CC-3-V1 | 6.0 | Δε [1 kHz, 20° C.]: | 4.2 |
| CCP-V-1 | 15.0 | $\gamma_1$ [mPa · s, 20° C.]: | 104 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU(1)-3-F | 4.5 | | |
| PGUQU-4-F | 2.0 | | |
| PPGU-3-F | 0.5 | | |
| PUS-3-2 | 13.0 | | |
| Σ | 100.0 | | |

Mixture Example M15

| | | | |
|---|---|---|---|
| CGPC-5-3 | 1.0 | cl.p. [° C.]: | 124 |
| CC-3-V | 26.5 | Δn [589 nm, 20° C.]: | 0.1258 |
| CC-3-V1 | 6.0 | Δε [1 kHz, 20° C.]: | 4.0 |
| CCP-V-1 | 15.0 | $\gamma_1$ [mPa · s, 20° C.]: | 108 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-3-F | 0.5 | | |
| PUS-3-(c5) | 13.0 | | |
| Σ | 100.0 | | |

Mixture Example M16

| | | | |
|---|---|---|---|
| CGPC-5-3 | 1.0 | cl.p. [° C.]: | 125 |
| CC-3-V | 26.5 | Δn [589 nm, 20° C.]: | 0.1249 |
| CC-3-V1 | 6.0 | Δε [1 kHz, 20° C.]: | 4.2 |
| CCP-V-1 | 15.0 | $\gamma_1$ [mPa · s, 20° C.]: | 116 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-3-F | 0.5 | | |
| PUS-3-O1(c5) | 13.0 | | |
| Σ | 100.0 | | |

Mixture Example M17

| | | | |
|---|---|---|---|
| CGPC-5-3 | 1.0 | cl.p. [° C.]: | 124 |
| CC-3-V | 26.5 | Δn [589 nm, 20° C.]: | 0.1276 |
| CC-3-V1 | 6.0 | Δε [1 kHz, 20° C.]: | 4.2 |
| CCP-V-1 | 15.0 | $\gamma_1$ [mPa · s, 20° C.]: | 113 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-3-F | 0.5 | | |
| PUS-3-O(c5) | 13.0 | | |
| Σ | 100.0 | | |

Mixture Example M18

| | | | |
|---|---|---|---|
| CGPC-5-3 | 1.0 | cl.p. [° C.]: | 127 |
| CC-3-V | 26.5 | Δn [589 nm, 20° C.]: | 0.1289 |
| CC-3-V1 | 6.0 | Δε [1 kHz, 20° C.]: | 4.2 |
| CCP-V-1 | 15.0 | $\gamma_1$ [mPa · s, 20° C.]: | 108 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-3-F | 0.5 | | |
| PUS-(c5)-2 | 13.0 | | |
| Σ | 100.0 | | |

Mixture Example M19

| | | | |
|---|---|---|---|
| APUQU-2-F | 4.0 | cl.p. [° C.]: | 121 |
| APUQU(1)-3-F | 4.0 | Δn [589 nm, 20° C.]: | 0.1211 |
| CC-3-V | 34.5 | Δε [1 kHz, 20° C.]: | 6.9 |
| CCP-V-1 | 12.0 | $\gamma_1$ [mPa · s, 20° C.]: | 122 |
| CCP-V2-1 | 7.0 | | |
| CCZPC-3-3 | 3.0 | | |
| CCZPC-3-5 | 3.0 | | |
| CCVC-3-V | 3.5 | | |
| CDUQU-3-F | 2.0 | | |

-continued

Mixture Example M19

| | |
|---|---|
| CLGIP-3-2 | 5.0 |
| DPGU-4-F | 2.0 |
| PGP-2-2V | 9.0 |
| PGUQU-3-F | 5.5 |
| PPGU-3-F | 0.5 |
| PUQU(1)-3-F | 5.0 |
| Σ | 100.0 |

Mixture Example M20

| | | | |
|---|---|---|---|
| APUQU-2-F | 4.0 | cl.p. [° C.]: | 121 |
| APUQU-3-F | 4.0 | Δn [589 nm, 20° C.]: | 0.1200 |
| CC-3-V | 34.5 | Δε [1 kHz, 20° C.]: | 6.5 |
| CCP-V-1 | 12.0 | $\gamma_1$ [mPa · s, 20° C.]: | 120 |
| CCP-V2-1 | 7.0 | | |
| CCZPC-3-3 | 3.0 | | |
| CCZPC-3-5 | 3.0 | | |
| CCVC-3-V | 3.5 | | |
| CDUQU-3-F | 2.0 | | |
| CLGIP-3-2 | 5.0 | | |
| DPGU-4-F | 2.0 | | |
| PGP-2-2V | 9.0 | | |
| PGUQU-(c3)1-F | 5.5 | | |
| PPGU-3-F | 0.5 | | |
| PUQU-3-F | 5.0 | | |
| Σ | 100.0 | | |

Mixture Example M21

| | | |
|---|---|---|
| CGPC-5-3 | 1.0 | cl.p. [° C.]: |
| CC-3-V | 26.5 | Δn [589 nm, 20° C.]: |
| CC-3-V1 | 6.0 | Δε [1 kHz, 20° C.]: |
| CCP-V-1 | 15.0 | $\gamma_1$ [mPa · s, 20° C.]: |
| CCP-V2-1 | 10.0 | $K_1$ [pN, 20° C.]: |
| CCVC-3-V | 5.5 | $K_3$ [pN, 20° C.]: |
| CCC-3-V | 3.0 | |
| CDUQU-3-F | 2.0 | |
| CLGIP-3-2 | 2.5 | |
| DGUQU-4-F | 4.0 | |
| CP-3-O2 | 0.5 | |
| PGP-2-2V | 4.0 | |
| PGUQU-3-F | 4.5 | |
| PGUQU-4-F | 2.0 | |
| PPGU-3-F | 0.5 | |
| PUS-3-2 | 13.0 | |
| Σ | 100.0 | |

Mixture Example M22

| | | | |
|---|---|---|---|
| CC-3-2V1 | 5.0 | cl.p. [° C.]: | 112.6 |
| CC-3-V | 23.25 | Δn [589 nm, 20° C.]: | 0.1068 |
| CC-3-V1 | 11.5 | Δε [1 kHz, 20° C.]: | 6.0 |
| CCP-3-1 | 6.0 | $\gamma_1$ [mPa · s, 20° C.]: | 104 |
| CCP-3-3 | 3.0 | $K_1$ [pN, 20° C.]: | 21.0 |
| CCP-3-OT | 8.0 | $K_3$ [pN, 20° C.]: | 21.0 |
| CCP-5-OT | 5.0 | | |
| CCP-V2-1 | 4.5 | | |
| CDUQU-3-F | 5.0 | | |
| CLGIP-3-2 | 4.0 | | |
| CLP-V-1 | 5.0 | | |
| DGUQU-4-F | 7.0 | | |
| CP-3-O2 | 3.0 | | |
| PGS-2-1 | 5.25 | | |
| PGUQU-3-F | 4.5 | | |
| Σ | 100.0 | | |

Mixture Example M23

| | | | |
|---|---|---|---|
| CC-3-2V1 | 6.0 | cl.p. [° C.]: | 112.4 |
| CC-3-V | 22.5 | Δn [589 nm, 20° C.]: | 0.1020 |
| CC-3-V1 | 12.0 | Δε [1 kHz, 20° C.]: | 5.9 |
| CCP-3-1 | 6.0 | $\gamma_1$ [mPa · s, 20° C.]: | 103 |
| CCP-3-3 | 3.0 | $K_1$ [pN, 20° C.]: | 20.8 |
| CCP-3-OT | 8.0 | $K_3$ [pN, 20° C.]: | 21.3 |
| CCP-5-OT | 5.0 | | |
| CCP-V2-1 | 6.0 | | |
| CDUQU-3-F | 5.0 | | |
| CLGIP-3-2 | 3.5 | | |
| CLP-V-1 | 5.0 | | |
| DGUQU-4-F | 7.0 | | |
| CP-3-O2 | 3.0 | | |
| PGS-2-1 | 3.5 | | |
| PGUQU-3-F | 4.5 | | |
| Σ | 100.0 | | |

Mixture Example M24

| | | | |
|---|---|---|---|
| CC-3-2V1 | 6.0 | cl.p. [° C.]: | 114.8 |
| CC-3-V | 21.5 | Δn [589 nm, 20° C.]: | 0.1032 |
| CC-3-V1 | 10.0 | Δε [1 kHz, 20° C.]: | 5.9 |
| CCP-3-1 | 5.0 | $\gamma_1$ [mPa · s, 20° C.]: | 107 |
| CCP-3-3 | 3.0 | $K_1$ [pN, 20° C.]: | 21.5 |
| CCP-3-OT | 8.0 | $K_3$ [pN, 20° C.]: | 21.9 |
| CCP-5-OT | 5.0 | | |
| CCP-V-1 | 2.0 | | |
| CCP-V2-1 | 6.0 | | |
| CDUQU-3-F | 7.0 | | |
| CLP-V-1 | 7.0 | | |
| CLGIP-3-2 | 3.0 | | |
| DGUQU-4-F | 7.0 | | |
| CP-3-O2 | 3.0 | | |
| PGS-2-1 | 4.0 | | |
| PGUQU-3-F | 2.5 | | |
| Σ | 100.0 | | |

Mixture Example M25

| | | | |
|---|---|---|---|
| CC-3-2V1 | 6.0 | cl.p. [° C.]: | 114.5 |
| CC-3-V | 23.0 | Δn [589 nm, 20° C.]: | 0.1034 |
| CC-3-V1 | 10.0 | Δε [1 kHz, 20° C.]: | 5.8 |
| CCP-3-1 | 6.0 | $\gamma_1$ [mPa · s, 20° C.]: | 106 |
| CCP-3-3 | 3.0 | $K_1$ [pN, 20° C.]: | 21.2 |
| CCP-3-OT | 8.0 | $K_3$ [pN, 20° C.]: | 21.2 |
| CCP-5-OT | 5.0 | | |
| CCP-V2-1 | 6.0 | | |
| CDUQU-3-F | 4.25 | | |
| CLGIP-3-2 | 4.0 | | |
| CLP-V-1 | 7.0 | | |
| DGUQU-4-F | 7.0 | | |
| CP-3-O2 | 3.0 | | |
| PGS-2-1 | 3.0 | | |
| PGUQU-3-F | 4.75 | | |
| Σ | 100.0 | | |

Mixture Example M26

| | | | |
|---|---|---|---|
| CGPC-5-3 | 0.5 | cl.p. [° C.]: | 122.3 |
| CC-3-V | 26.0 | Δn [589 nm, 20° C.]: | 0.1297 |
| CC-3-V1 | 6.0 | Δε [1 kHz, 20° C.]: | 4.25 |
| CCP-V-1 | 15.0 | $\gamma_1$ [mPa · s, 20° C.]: | 105.2 |
| CCP-V2-1 | 10.0 | $K_1$ [pN, 20° C.]: | 19.5 |
| CCVC-3-V | 8.5 | $K_3$ [pN, 20° C.]: | 20.4 |
| CDUQU-3-F | 2.0 | | |
| CLGIP-2-2V | 5.0 | | |
| DGUQU-4-F | 4.0 | | |
| CP-3-O2 | 0.5 | | |
| PGUQU-3-F | 5.0 | | |
| PGUQU-4-F | 2.0 | | |
| PPGU-3-F | 0.5 | | |
| PUS-3-2 | 15.0 | | |
| Σ | 100.0 | | |

Mixture Example M27

| | | | |
|---|---|---|---|
| CGPC-5-3 | 0.5 | cl.p. [° C.]: | 124.5 |
| CC-3-V | 26.0 | Δn [589 nm, 20° C.]: | 0.1303 |
| CC-3-V1 | 6.0 | Δε [1 kHz, 20° C.]: | 5.23 |
| CCP-V-1 | 15.0 | $\gamma_1$ [mPa · s, 20° C.]: | 101.1 |
| CCP-V2-1 | 10.0 | $K_1$ [pN, 20° C.]: | 17.9 |
| CCVC-3-V | 8.5 | $K_3$ [pN, 20° C.]: | 19.3 |
| CLUQU-3-F | 2.0 | | |
| CLGIP-3-2 | 5.0 | | |
| DGUQU-4-F | 4.0 | | |
| CP-3-O2 | 0.5 | | |
| PGUQU-3-F | 5.0 | | |
| PGUQU-4-F | 2.0 | | |
| PPGU-3-F | 0.5 | | |
| PUS-3-2 | 15.0 | | |
| Σ | 100.0 | | |

Mixture Example M28

| | | | |
|---|---|---|---|
| CGPC-5-3 | 1.75 | cl.p. [° C.]: | 119.5 |
| CC-3-V | 28.25 | Δn [589 nm, 20° C.]: | 0.1298 |
| CC-3-V1 | 6.0 | Δε [1 kHz, 20° C.]: | 4.1 |
| CCP-V-1 | 15.0 | $\gamma_1$ [mPa · s, 20° C.]: | 103 |
| CCP-V2-1 | 10.0 | $K_1$ [pN, 20° C.]: | 19.1 |
| CCVC-3-V | 3.5 | $K_3$ [pN, 20° C.]: | 19.9 |
| CDUQU-3-F | 2.0 | | |
| CLGIP-3-2 | 2.5 | | |
| CLPC-3-2 | 3.0 | | |
| DGUQU-4-F | 4.0 | | |
| CP-3-O2 | 0.5 | | |
| PGP-2-2V | 3.5 | | |
| PGUQU-3-F | 4.5 | | |
| PGUQU-4-F | 2.0 | | |
| PPGU-3-F | 0.5 | | |
| PUS-3-2 | 13.0 | | |
| Σ | 100.0 | | |

Mixture Example M29

| | | | |
|---|---|---|---|
| APUQU-2-F | 4.0 | cl.p. [° C.]: | 122.0 |
| APUQU-3-F | 4.0 | Δn [589 nm, 20° C.]: | 0.1220 |
| CC-3-V | 37.5 | Δε [1 kHz, 20° C.]: | 6.5 |
| CCP-V-1 | 12.0 | $\gamma_1$ [mPa · s, 20° C.]: | 125 |
| CCP-V2-1 | 2.5 | $K_1$ [pN, 20° C.]: | 17.9 |
| CCPC-33 | 3.0 | $K_3$ [pN, 20° C.]: | 20.0 |
| CCPC-35 | 3.0 | | |
| CDUQU-3-F | 2.0 | | |
| CLGIP-3-2 | 6.0 | | |
| CLPC-3-2 | 4.0 | | |
| DPGU-4-F | 2.0 | | |
| PGP-2-2V | 9.5 | | |
| PGUQU-3-F | 5.0 | | |
| PPGU-3-F | 0.5 | | |
| PUQU-3-F | 5.0 | | |
| Σ | 100.0 | | |

| Mixture Example M30 | | | |
|---|---|---|---|
| CGPC-5-3 | 1.0 | cl.p. [° C.]: | 118 |
| CC-3-V | 26.5 | Δn [589 nm, 20° C.]: | 0.1224 |
| CC-3-V1 | 6.0 | Δε [1 kHz, 20° C.]: | 4.1 |
| CCP-V-1 | 15.0 | $\gamma_1$ [mPa · s, 20° C.]: | 107 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-3-F | 0.5 | | |
| PUS-3-1(c5) | 13.0 | | |
| Σ | 100.0 | | |

Mixture Example M31

Mixture Example M31 consists of 99.975% of Mixture Example M1 and 0.025% of the compound ST-3d:

ST-3c

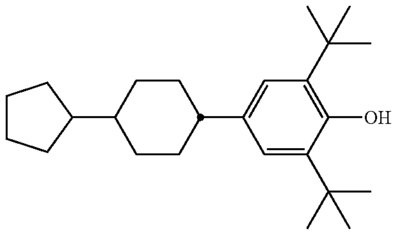

Mixture Example M32

The mixture example M32 consists of 99.98% of the Mixture example M1 and 0.02% of a compound of the formula ST-12b-1:

ST-12

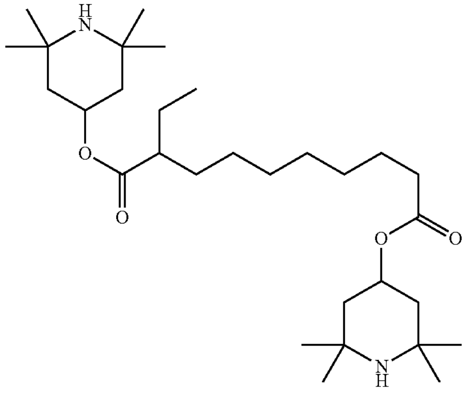

Mixture Example M33

The mixture example M33 consists of 99.985% of the Mixture example M1 and 0.015% of a compound of the formula S1-1a:

ST-19a

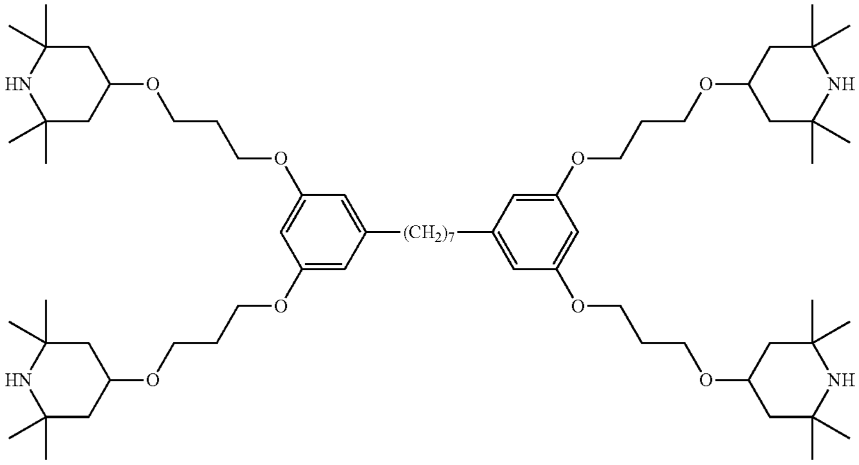

Mixture Example M34

The mixture example M34 consists of 99.995% of the Mixture example M2 and 0.005% of a compound of the formula ST-9-1:

ST-9-1

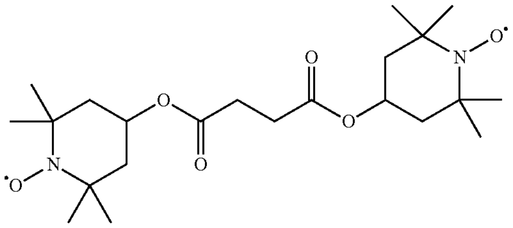

Mixture Example M35

Mixture Example M35 consists of 99.97% of Mixture Example 2 and 0.03% of the compound ST-3d:

ST-3d

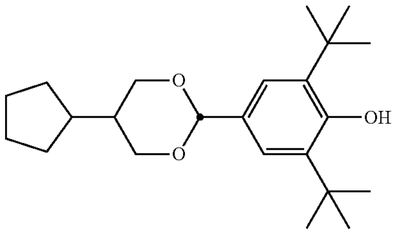

Mixture Example M36

Mixture Example M36 consists of 99.97% of Mixture Example M1 and 0.03% of the compound ST-3b-1:

ST-3b-1

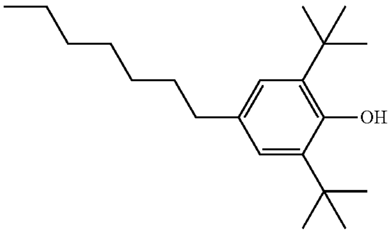

Mixture Example M37

| | | | |
|---|---|---|---|
| CGPC-5-3 | 2.0 | cl.p. [° C.]: | 120.4 |
| CC-3-V | 28.0 | Δn [589 nm, 20° C.]: | 0.1291 |
| CC-3-V1 | 5.0 | Δε [1 kHz, 20° C.]: | 4.4 |
| CCP-V-1 | 15.0 | $\gamma_1$ [mPa · s, 20° C.]: | 105 |
| CCP-V2-1 | 10.0 | | |
| CCVC-3-V | 6.0 | | |
| CDUQU-3-F | 2.0 | | |
| CLGIP-3-2 | 3.5 | | |
| CLPC-3-2 | 1.0 | | |
| DGUQU-4-F | 3.0 | | |
| PGP-2-2V | 4.0 | | |
| PGUQU-3-F | 3.0 | | |
| PGUQU-4-F | 2.0 | | |
| PGU-3-T | 2.0 | | |
| PGU-5-T | 2.0 | | |
| PPGU-3-F | 0.5 | | |
| PUS-3-2 | 11.0 | | |
| Σ | 100.0 | | |

Mixture Example M38

| | | | |
|---|---|---|---|
| CGPC-5-3 | 1.0 | cl.p. [° C.]: | 121 |
| CC-3-V | 26.5 | Δn [589 nm, 20° C.]: | 0.1293 |
| CC-3-V1 | 6.0 | Δε [1 kHz, 20° C.]: | 4.1 |
| CCP-V-1 | 15.0 | $\gamma_1$ [mPa · s, 20° C.]: | 103 |
| CCP-V2-1 | 10.0 | $K_1$ [pN, 20° C.]: | 19.3 |
| CCVC-3-V | 8.5 | $K_3$ [pN, 20° C.]: | 20.4 |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-(c5)-F | 0.5 | | |
| PUS-3-2 | 13.0 | | |
| Σ | 100.0 | | |

Mixture Example M39

| | | | |
|---|---|---|---|
| CGPC-5-3 | 1.0 | cl.p. [° C.]: | 122 |
| CC-3-V | 26.5 | Δn [589 nm, 20° C.]: | 0.1301 |
| CC-3-V1 | 6.0 | Δε [1 kHz, 20° C.]: | 4.2 |
| CCP-V-1 | 15.0 | $\gamma_1$ [mPa · s, 20° C.]: | 102 |
| CCP-1V-2 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PPGU-3-F | 0.5 | | |
| PUS-3-2 | 13.0 | | |
| Σ | 100.0 | | |

Mixture Example M40

| | | | |
|---|---|---|---|
| CGPC-5-3 | 1.0 | cl.p. [° C.]: | 120.7 |
| CC-3-V | 26.5 | Δn [589 nm, 20° C.]: | 0.1288 |
| CC-3-V1 | 6.0 | Δε [1 kHz, 20° C.]: | 4.1 |
| CCP-V-1 | 15.0 | $\gamma_1$ [mPa · s, 20° C.]: | 104 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-(c5)-F | 2.0 | | |
| PPGU-3-F | 0.5 | | |
| PUS-3-2 | 13.0 | | |
| Σ | 100.0 | | |

Mixture Example M41

| | | | |
|---|---|---|---|
| CGPC-5-3 | 1.0 | cl.p. [° C.]: | 121 |
| CC-3-V | 26.5 | Δn [589 nm, 20° C.]: | 0.1293 |
| CC-3-V1 | 6.0 | Δε [1 kHz, 20° C.]: | 4.0 |
| CCP-V-1 | 15.0 | $\gamma_1$ [mPa · s, 20° C.]: | 104 |
| CCP-V2-1 | 10.0 | | |
| CCVC-3-V | 8.5 | | |
| CDUQU-3-F | 2.0 | | |
| CLGIP-3-2 | 2.5 | | |
| DGUQU-4-F | 4.0 | | |
| CP-3-O2 | 0.5 | | |
| PGP-2-2V | 4.0 | | |
| PGUQU-3-F | 4.5 | | |
| PGUQU-4-F | 2.0 | | |
| PGPNp-5-0 | 0.5 | | |
| PUS-3-2 | 13.0 | | |
| Σ | 100.0 | | |

The invention claimed is:

1. A liquid crystal medium comprising:

one or more compounds of formula I:

I

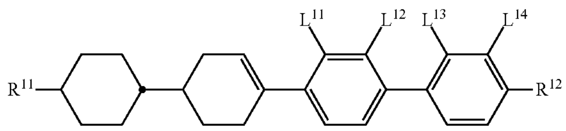

in which $R^{11}$ and $R^{12}$ identically or differently, denote H, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group having 3 to 15 C atoms, wherein one or more $CH_2$ groups are optionally replaced, independently of one another, by

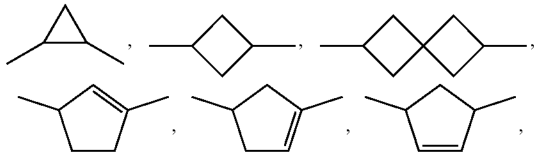

—CH═CH—, —C≡C—, —$CF_2O$—, —$OCF_2$—, —O—, —CO—O—, or —O—CO— in such a way that O atoms are not linked directly to one another, and in which one or more H atoms are optionally replaced by halogen; and $L^{11}$, $L^{12}$, $L^{13}$, and $L^{14}$ identically or differently, denote H, F, Cl, $CH_3$, $CF_3$, or $CHF_2$, wherein at least one of $L^{11}$, $L^{12}$, $L^{13}$, or $L^1$ denotes F, Cl, $CH_3$, $CF_3$, or $CHF_2$; and one or more compounds of formula VIII:

VIII

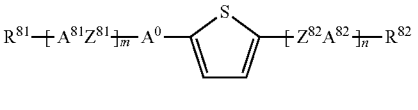

in which $R^{81}$ and $R^{82}$ identically or differently, denote H, halogen, CN, SCN, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group having 3 to 15 C atoms, where one or more $CH_2$ groups are optionally replaced, independently of one another, by

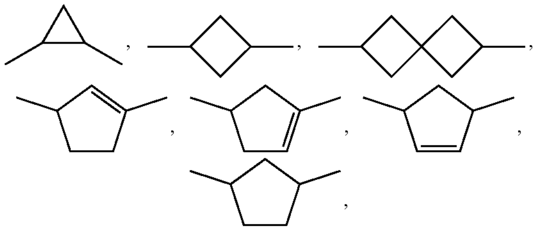

—C≡C—, —$CF_2O$—, —$OCF_2$—, —CH═CH—, —O—, —CO—O—, or —O—CO— in such a way that 0 atoms are not linked directly to one another, and in which one or more H atoms are optionally replaced by halogen;

$A^0$, $A^{81}$, and $A^{82}$ each, independently of one another, denote phenylene-1,4-diyl, in which one or two CH groups are optionally replaced by N and one or more H atoms are optionally replaced by halogen, CN, $CH_3$, $CHF_2$, $CH_2F$, $CF_3$, $OCH_3$, $OCHF_2$, or $OCF_3$, cyclohexane-1,4-diyl, in which one or two non-adjacent $CH_2$ groups are optionally replaced, independently of one another, by O and/or S and one or more H atoms are optionally replaced by F, cyclohexene-1,4-diyl, bicyclo[1.1.1]-pentane-1,3-diyl, bicyclo[2.2.2]octane-1,4-diyl, spiro[3.3]heptane-2,6-diyl, tetrahydropyran-2,5-diyl, or 1,3-dioxane-2,5-diyl;

$Z^{81}$ and $Z^{82}$ each, independently of one another, denote —$CF_2O$—, —$OCF_2$—, —$CH_2O$—, —$OCH_2$—, —CO—O—, —O—CO—, —$C_2H_4$—, —$C_2F_4$, —$CF_2CH_2$—, —$CH_2CF_2$—, —CFHCFH—, —$CFHCH_2$—, —$CH_2CFH$—, —$CF_2CFH$—, —$CFHCF_2$—, —CH═CH—, —CF═CH—, —CH═CF—, —CF═CF—, —C≡C—, or a single bond;

n denotes 0, 1, 2, or 3, and m denotes 0, 1, 2, or 3.

2. The liquid crystal medium according to claim 1, wherein the medium further comprises one or more compounds selected from formulae II and III:

II

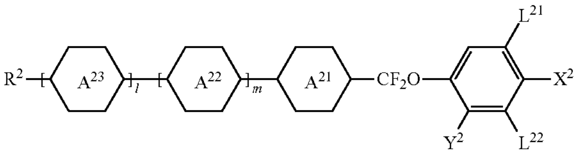

III

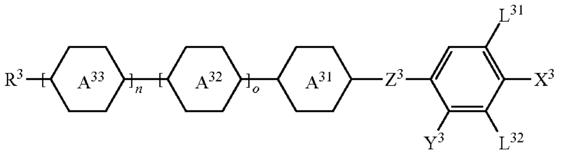

in which $R^2$ and $R^3$ independently of one another, denote H, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group having 3 to 15 C atoms, where one or more $CH_2$ groups in the straight-chain alkyl or alkoxy group having 1 to 15 C atoms, the straight-chain alkenyl or alkenyloxy group having 2 to 15 C atoms, or the branched alkyl, alkoxy, alkenyl, or alkenyloxy group having 3 to 15 C atoms are optionally replaced, independently of one another, by

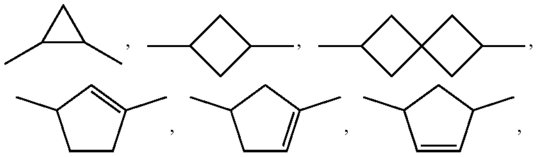

—CH═CH—, —C≡C—, —$CF_2O$—, —$OCF_2$—, —O—, —CO—O—, or —O—CO— in such a way that O atoms are not linked directly to one another, and in which one or more H atoms are optionally replaced by halogen;

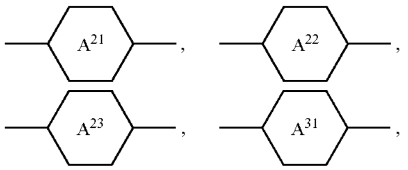

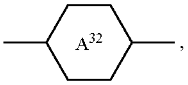

, and

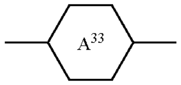

and independently of one another denote

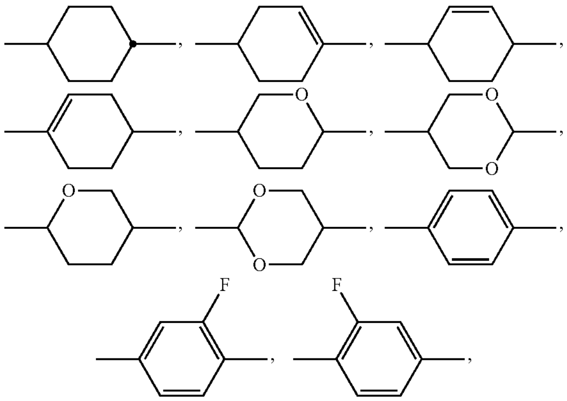

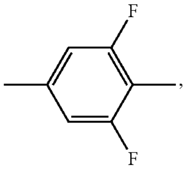

or

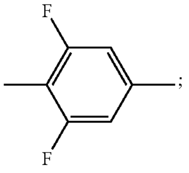

;

$L^{21}$, $L^{22}$, $L^{31}$, and $L^{32}$ independently of each other, denote H or F;

$Y^2$ and $Y^3$ identically or differently, denote H or $CH_3$;

$X^2$ and $X^3$ independently of each other, denote halogen, a halogenated alkyl or alkoxy group with 1 to 3 C atoms, or a halogenated alkenyl or alkenyloxy group with 2 or 3 C atoms;

$Z^3$ denotes —$CH_2CH_2$—, —$CF_2CF_2$—, —COO—, trans-—CH═CH—, trans- —CF═CF—, —$CH_2O$—, or a single bond; and l, m, n, and o are, independently of each other, 0 or 1.

3. The liquid crystal medium according to claim 1, wherein the medium further comprises one or more compounds selected from formulae II-1, II-2, and II-3:

II-1

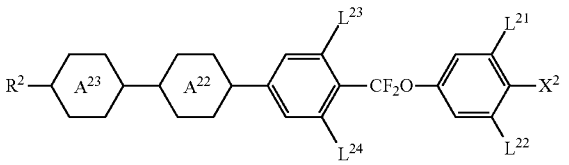

II-2

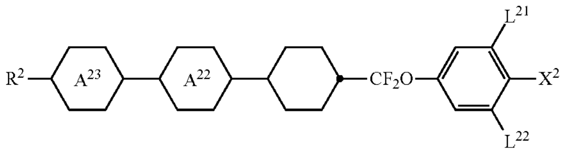

II-3

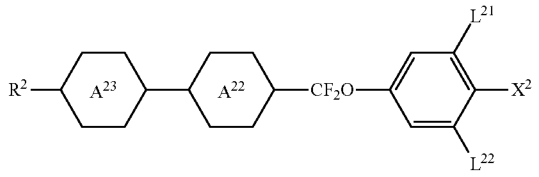

in which $L^{21}$, $L^{22}$, $L^{23}$, and $L^{24}$ independently of each other, denote H or F;

$R^2$ denotes H, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group having 3 to 15 C atoms, where one or more $CH_2$ are optionally replaced, independently of one another, by

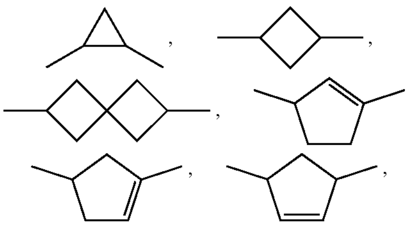

—CH═CH—, —C═C—, —$CF_2O$—, —$OCF_2$—, —O—, —CO—O—, or —O—CO— in such a way that O atoms are not linked directly to one another, and in which one or more H atoms are optionally replaced by halogen;

$X^2$ denotes halogen, a halogenated alkyl or alkoxy group with 1 to 3 C atoms, or a halogenated alkenyl or

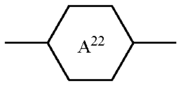

and

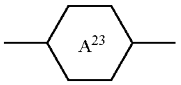

independently of one another, denote

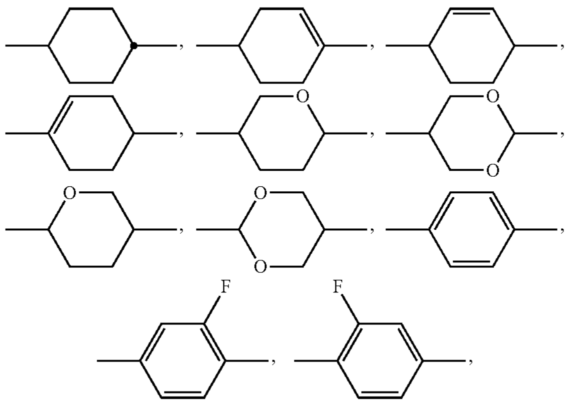

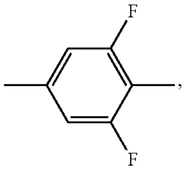

or

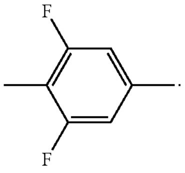

4. The liquid crystal medium according to claim 1, wherein the medium further comprises one or more compounds selected from formulae III-1 and III-2:

III-1

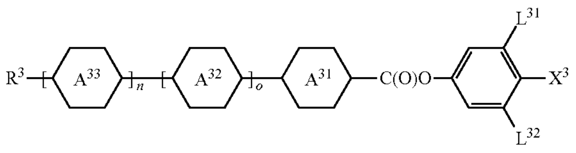

III-2

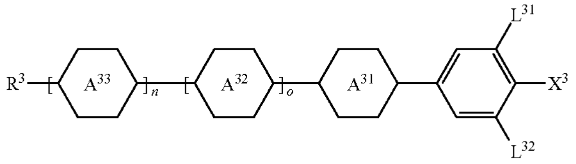

in which $R^3$ denotes H, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group having 3 to 15 C atoms, where one or more $CH_2$ groups are optionally replaced, independently of one another, by

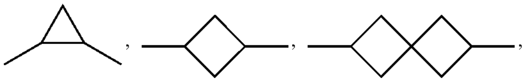

-continued

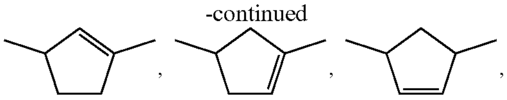

—CH═CH—, —C≡C—, —$CF_2O$—, —$OCF_2$—, —O—, —CO—O—, or —O—CO— in such a way that O atoms are not linked directly to one another, and in which one or more H atoms are optionally replaced by halogen;

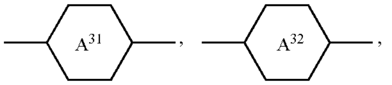

and

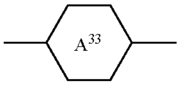

and independently of one another, denote

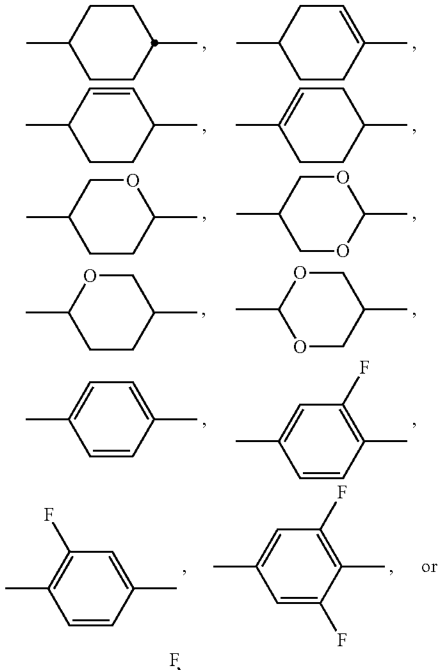

or

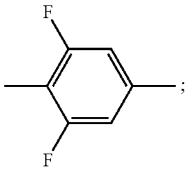

$L^{31}$ and $L^{32}$ independently of each other, denote H or F;

$X^3$ denotes halogen, a halogenated alkyl or alkoxy group with 1 to 3 C atoms, or a halogenated alkenyl or alkenyloxy group with 2 or 3 C atoms;

$Z^3$ denotes —$CH_2CH_2$—, —$CF_2CF_2$—, —COO—, trans-—CH═CH—, trans- —CF═CF—, —$CH_2O$—, or a single bond; and n and o are, independently of each other, 0 or 1.

5. The liquid crystal medium according to claim 1, wherein the medium further comprises one or more compounds selected from the group consisting of formulae Y, B, BC, CR, PH-1, and PH-2:

Y

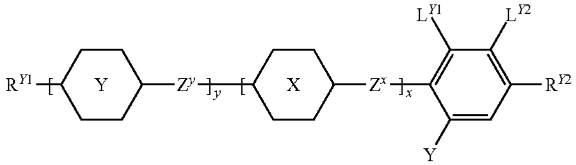

B

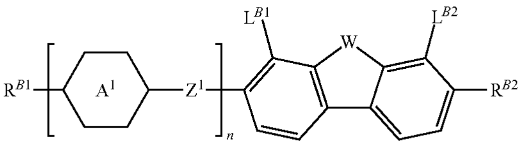

BC

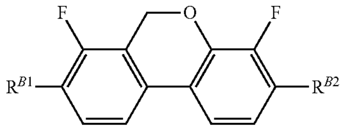

Y

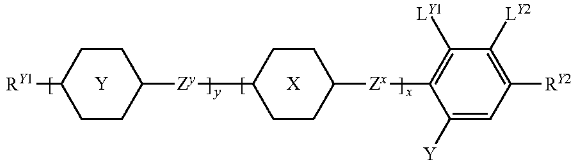

CR

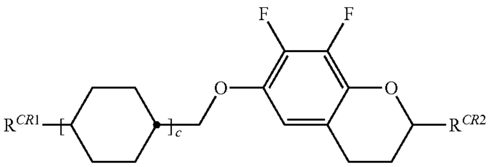

PH-1

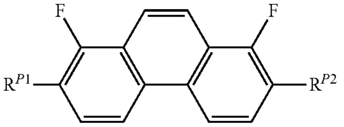

PH-2

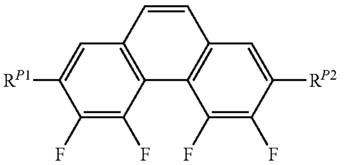

in which $R^{Y1}$, $R^{Y2}$, $R^{B1}$, $R^{B2}$, $R^{CR1}$, $R^{CR2}$, $R^{P1}$, and $R^{P2}$ each, independently of one another, denote H, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group having 3 to 15 C atoms, where one or more $CH_2$ groups in the straight-chain alkyl or alkoxy group having 1 to 15 C atoms, the straight-chain alkenyl or alkenyloxy group having 2 to 15 C atoms, or the branched alkyl, alkoxy, alkenyl, or alkenyloxy group having 3 to 15 C atoms are optionally replaced, independently of one another, by

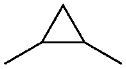, 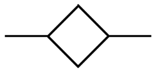,

-continued

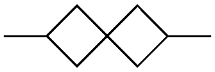, 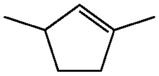,

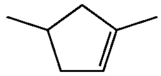, 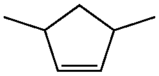,

—CH═CH—, —C≡C—, $—CF_2O—$, $—OCF_2—$, —O—, —CO—O—, or —O—CO— in such a way that O atoms are not linked directly to one another, and in which one or more H atoms are optionally replaced by halogen;

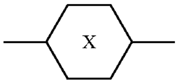, 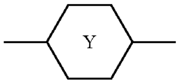, and

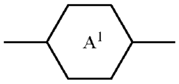

and on each occurrence, independently of one another, denote a) 1,4-cyclohexylene or 1,4-cyclohexenylene radical, in which one or two non-adjacent $CH_2$ groups are optionally replaced by —O— or —S—;

b) a 1,4-phenylene radical, in which one or two CH groups are optionally replaced by N; or c) a radical from the group spiro[3.3]heptane-2,6-diyl, 1,4-bicyclo[2.2.2]octylene, naphthalene-2,6-diyl, decahydronaphthalene-2,6-diyl, 1,2,3,4-tetrahydronaphthalene-2,6-diyl, phenanthrene-2,7-diyl, and fluorene-2,7-diyl, where the radicals a), b), and c) are optionally mono- or poly-substituted by halogen atoms;

$Z^x$ and $Z^y$ identically or differently, denote $—CH_2CH_2—$, —CH═CH—, $—CF_2O—$, $—OCF_2—$, $—CH_2O—$, $—OCH_2—$, —CO—O—, —O—CO—, $—C_2F_4—$, —CF═CF—, $—CH═CH—CH_2O—$, or a single bond;

$Z^1$ denotes —CO—O—, —O—CO—, $—CF_2O—$, $—OCF_2—$, $—CH_2O—$, $—OCH_2—$, $—CH_2—$, $—CH_2CH_2—$, $—(CH_2)_4—$, $—CH═CH—CH_2O—$, $—C_2F_4—$, $—CH_2CF_2—$, $—CF_2CH_2—$, —CF═CF—, —CH═CF—, —CF═CH—, —CH═CH—, —C≡C—, or a single bond;

$L^{Y1}$, $L^{Y2}$, $L^{B1}$, and $L^{B2}$ each, independently of one another, denote F, Cl, $CF_3$ or $CHF_2$;

W denotes O or S;

n is 0, 1, or 2;

c is 0, 1, or 2; and x and y independently, are 0, 1, or 2, where x+y≤3.

6. The liquid crystal medium according to claim 1, wherein the medium further comprises one or more compounds of formula VII:

VII

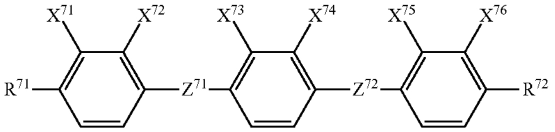

in which $R^{71}$ and $R^{72}$ denote H, F, a straight-chain alkyl or alkoxy group having 1 to 15 C atoms, a straight-chain alkenyl or alkenyloxy group having 2 to 15 C atoms, or a branched alkyl, alkoxy, alkenyl, or alkenyloxy group each having 3 to 15 C atoms, where one or more $CH_2$ groups in the straight-chain alkyl or alkoxy group having 1 to 15 C atoms, the straight-chain alkenyl or alkenyloxy group having 2 to 15 C atoms, or the branched alkyl, alkoxy, alkenyl, or alkenyloxy group each having 3 to 15 C atoms are optionally replaced, independently of one another, by

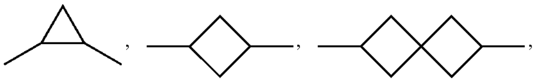

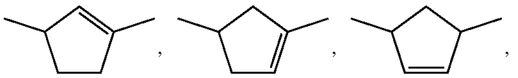

$-C{\equiv}C-$, $-CF_2O-$, $-OCF_2-$, $-CH{=}CH-$, $-O-$, $-CO-O-$, or $-O-CO-$ in such a way that O atoms are not linked directly to one another, and in which one or more H atoms are optionally replaced by halogen;

$X^{71}$, $X^{72}$, $X^{73}$, $X^{74}$, $X^{75}$ and $X^{76}$ identically or differently, denote H or F; and $Z^{71}$ and $Z^{72}$ identically or differently, denote $CH_2CH_2$ or a single bond.

7. The liquid crystal medium according to claim 1, wherein the medium comprises one or more compounds of formula IV:

IV

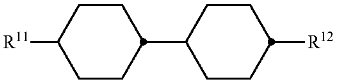

in which $R^{11}$ denotes a straight-chain alkyl or alkoxy radical having 1 to 12 C atoms, a branched or cyclic alkyl radical having 3 to 12 C atoms, a straight-chain alkenyl radical having 2 to 12 C atoms, a branched alkenyl radical having 3 to 12 C atoms, or a cyclic alkenyl radical having 5 to 12 C atoms, wherein one or more H atoms are optionally replaced by fluorine; and $R^{12}$ denotes a straight-chain alkyl or alkoxy radical having 1 to 12 C atoms, a branched or cyclic alkyl or alkoxy radical having 3 to 12 C atoms, a straight-chain alkenyl radical having 2 to 12 C atoms, a branched alkenyl radical having 3 to 12 C atoms, or a cyclic alkenyl radical having 5 to 12 C atoms, wherein one or more H atoms are optionally replaced by fluorine.

8. The liquid crystal medium according to claim 1, wherein the medium comprises one or more compounds of formulae IVa and/or IVb:

IVa

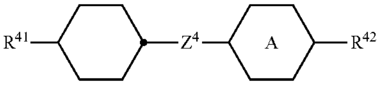

-continued

IVb

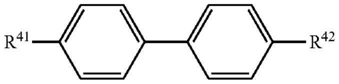

in which $R^{41}$ and $R^{42}$ each, independently of one another, denote a straight-chain alkyl, alkoxy, alkenyl, alkoxyalkyl, or alkenyloxy radical having up to 12 C atoms;

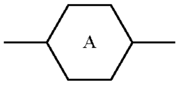

denotes

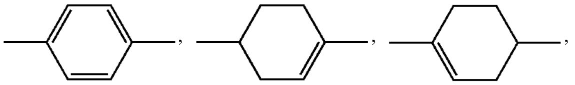

or

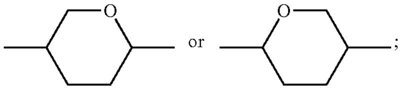

and $Z^4$ denotes a single bond, $-CH_2CH_2-$, $-CH{=}CH-$, $-CF_2O-$, $-OCF_2-$, $-CH_2O-$, $-OCH_2-$, $-COO-$, $-OCO-$, $-C_2F_4-$, $-C_4H_8-$, or $-CF{=}CF-$.

9. The liquid crystal medium according to claim 1, wherein the medium further comprises one or more compounds of formula V:

V

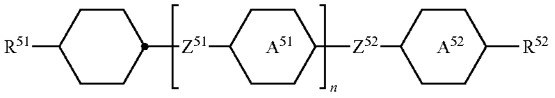

in which $R^{51}$ and $R^{52}$ denote an alkyl group having 1 to 7 C atoms, an alkoxy group having 1 to 7 C atoms, or an alkoxyalkyl, alkenyl, or alkenyloxy group having 2 to 7 C atoms;

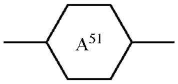

and

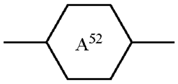

identically or differently, denote

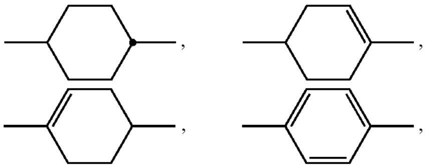

-continued

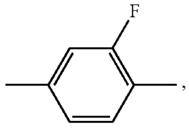

or

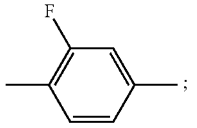

$Z^{51}$ and $Z^{52}$ each, independently of one another, denote $—CH_2—CH_2—$, $—CH_2—O—$, $—CH{=}CH—$, $—C{\equiv}C—$, $—COO—$, or a single bond; and n is 1 or 2.

10. The liquid crystal medium according to claim 1, wherein the medium further comprises one or more compounds of formula V-3:

V-3

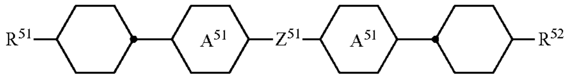

in which $R^{51}$ and $R^{52}$ denote an alkyl group having 1 to 7 C atoms, an alkoxy group having 1 to 7 C atoms, or an alkoxyalkyl, alkenyl, or alkenyloxy group having 2 to 7 C atoms;

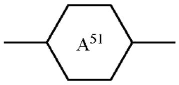

denotes

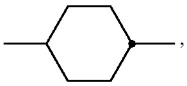

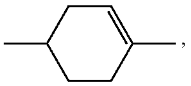

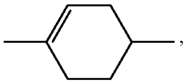

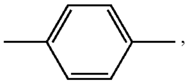

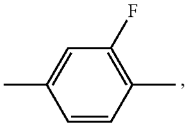

or

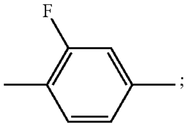

and $Z^{51}$ denotes $—CH_2—CH_2—$, $—CH_2—O—$, $—CH{=}CH—$, $—C{\equiv}C—$, $—COO—$, or a single bond.

11. A liquid crystal display comprising the liquid-crystal medium according to claim 1.

12. The liquid crystal display according to claim 11, wherein the display is configured to operate under IPS or FFS mode.

* * * * *